(12) United States Patent
Lamson et al.

(10) Patent No.: US 10,575,844 B2
(45) Date of Patent: Mar. 3, 2020

(54) DEVICES, SYSTEMS AND METHODS FOR TREATING BENIGN PROSTATIC HYPERPLASIA AND OTHER CONDITIONS

(71) Applicant: NeoTract, Inc., Pleasanton, CA (US)

(72) Inventors: Theodore Charles Lamson, Pleasanton, CA (US); Joshua Makower, Los Altos Hills, CA (US); Joseph Catanese, III, San Leandro, CA (US); Jacqueline Nemey Welch, Moraga, CA (US); Amrish Jayprakash Walke, Santa Clara, CA (US); Claude Vidal, Santa Barbara, CA (US); Russell J. Redmond, Goleta, CA (US); Michael Collinson, Goleta, CA (US)

(73) Assignee: NeoTract, Inc., Pleasanton, CA (US)

( * ) Notice: Subject to any disclaimer, the term of this patent is extended or adjusted under 35 U.S.C. 154(b) by 0 days.

(21) Appl. No.: 16/433,018

(22) Filed: Jun. 6, 2019

(65) Prior Publication Data

US 2019/0282225 A1    Sep. 19, 2019

Related U.S. Application Data

(60) Continuation of application No. 16/107,447, filed on Aug. 21, 2018, which is a continuation of application
(Continued)

(51) Int. Cl.
*A61B 17/04* (2006.01)
*A61B 17/06* (2006.01)
(Continued)

(52) U.S. Cl.
CPC ...... *A61B 17/0401* (2013.01); *A61B 17/0469* (2013.01); *A61B 17/0482* (2013.01);
(Continued)

(58) Field of Classification Search
CPC .... A61M 3/0291; A61M 29/02; A61M 29/00; A61B 17/00234; A61B 17/0218;
(Continued)

(56) References Cited

U.S. PATENT DOCUMENTS

| 659,422 | A | 10/1900 | Shidler |
|---|---|---|---|
| 780,392 | A | 1/1905 | Wanamaker et al. |

(Continued)

FOREIGN PATENT DOCUMENTS

| CA | 2477220 | 11/2007 |
|---|---|---|
| CN | 1697633 A | 11/2005 |

(Continued)

OTHER PUBLICATIONS

Bacharova, O.A., et al. "The Effect of Rhodiolae rosea Extract on Incidence Rate of Superficial Bladder Carcinoma Relapses", Kozin 1995.
(Continued)

*Primary Examiner* — Gregory A Anderson
(74) *Attorney, Agent, or Firm* — Christopher J. Buchko

(57) ABSTRACT

Devices, systems and methods for compressing, cutting, incising, reconfiguring, remodeling, attaching, repositioning, supporting, dislocating or altering the composition of tissues or anatomical structures to alter their positional or force relationship to other tissues or anatomical structures. In some applications, the invention may be used to used to improve patency or fluid flow through a body lumen or cavity (e.g., to limit constriction of the urethra by an enlarged prostate gland).

21 Claims, 59 Drawing Sheets

Related U.S. Application Data

No. 14/535,266, filed on Nov. 6, 2014, now Pat. No. 10,105,132, which is a continuation of application No. 13/844,020, filed on Mar. 15, 2013, now Pat. No. 8,900,252, which is a continuation of application No. 13/073,763, filed on Mar. 28, 2011, now Pat. No. 8,734,468, which is a division of application No. 11/838,036, filed on Aug. 13, 2007, now Pat. No. 7,914,542, which is a division of application No. 11/134,870, filed on May 20, 2005, now Pat. No. 7,758,594.

(51) Int. Cl.
| | | |
|---|---|---|
| *A61B 17/42* | (2006.01) | |
| *A61B 17/00* | (2006.01) | |
| *A61F 2/04* | (2013.01) | |
| *A61F 2/82* | (2013.01) | |
| *A61B 17/02* | (2006.01) | |
| *A61B 17/34* | (2006.01) | |
| *A61B 18/00* | (2006.01) | |

(52) U.S. Cl.
CPC .... *A61B 17/0487* (2013.01); *A61B 17/06109* (2013.01); *A61B 17/42* (2013.01); *A61F 2/82* (2013.01); *A61B 17/00234* (2013.01); *A61B 17/0218* (2013.01); *A61B 17/0467* (2013.01); *A61B 17/3468* (2013.01); *A61B 17/3478* (2013.01); *A61B 2017/00022* (2013.01); *A61B 2017/00274* (2013.01); *A61B 2017/00792* (2013.01); *A61B 2017/00796* (2013.01); *A61B 2017/00805* (2013.01); *A61B 2017/0404* (2013.01); *A61B 2017/0409* (2013.01); *A61B 2017/0417* (2013.01); *A61B 2017/0419* (2013.01); *A61B 2017/0451* (2013.01); *A61B 2017/0454* (2013.01); *A61B 2017/0456* (2013.01); *A61B 2017/0458* (2013.01); *A61B 2017/0462* (2013.01); *A61B 2017/0464* (2013.01); *A61B 2017/0488* (2013.01); *A61B 2017/06052* (2013.01); *A61B 2017/06176* (2013.01); *A61B 2018/00547* (2013.01); *A61F 2002/041* (2013.01)

(58) Field of Classification Search
CPC ............ A61B 17/0401; A61B 17/3468; A61B 2017/00274; A61B 2017/0409; A61B 2017/0417; A61B 2017/0419; A61B 2017/0464; A61B 2017/0488; A61B 2018/00547; A61F 2/82
See application file for complete search history.

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William et al. |
| 2,579,192 A | 12/1951 | Alexander |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Mckenzie |
| 3,326,586 A | 6/1967 | Frost et al. |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs et al. |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori et al. |
| 3,931,667 A | 1/1976 | Merser et al. |
| 3,976,079 A | 8/1976 | Samuels et al. |
| 4,006,747 A | 2/1977 | Kronenthal et al. |
| 4,137,920 A | 2/1979 | Bonnet |
| 4,164,225 A | 8/1979 | Johnson et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,419,094 A | 12/1983 | Patel |
| 4,452,236 A | 6/1984 | Utsugi |
| 4,493,323 A | 1/1985 | Albright et al. |
| 4,513,746 A | 4/1985 | Aranyi et al. |
| 4,621,640 A | 11/1986 | Mulhollan et al. |
| 4,655,771 A | 4/1987 | Wallsten |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,790,809 A * | 12/1988 | Kuntz ............... A61M 25/0045 600/434 |
| 4,823,794 A | 4/1989 | Pierce |
| 4,863,439 A | 9/1989 | Sanderson |
| 4,893,623 A | 1/1990 | Rosenbluth |
| 4,899,743 A | 2/1990 | Nicholson et al. |
| 4,926,860 A | 5/1990 | Stice et al. |
| 4,935,028 A | 6/1990 | Drews |
| 4,946,468 A | 8/1990 | Li |
| 4,955,859 A | 9/1990 | Zilber |
| 4,955,913 A | 9/1990 | Robinson |
| 4,968,315 A | 11/1990 | Gattuma |
| 4,994,066 A | 2/1991 | Voss |
| 5,002,550 A | 3/1991 | Li |
| 5,019,032 A | 5/1991 | Robertson |
| 5,041,129 A | 8/1991 | Hayhurst et al. |
| 5,046,513 A | 9/1991 | Gattuma et al. |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen et al. |
| 5,100,421 A | 3/1992 | Christoudias |
| 5,123,914 A | 6/1992 | Cope |
| 5,127,393 A | 7/1992 | McFarlin et al. |
| 5,129,912 A | 7/1992 | Noda et al. |
| 5,133,713 A | 7/1992 | Huang et al. |
| 5,159,925 A | 11/1992 | Neuwirth et al. |
| 5,160,339 A | 11/1992 | Chen et al. |
| 5,163,960 A | 11/1992 | Bonutti |
| 5,167,614 A | 12/1992 | Tessmann et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,237,984 A | 8/1993 | Williams et al. |
| 5,254,126 A | 10/1993 | Filipi et al. |
| 5,258,015 A | 11/1993 | Li et al. |
| 5,267,960 A | 12/1993 | Hayman et al. |
| 5,269,802 A | 12/1993 | Garber |
| 5,269,809 A | 12/1993 | Hayhurst et al. |
| 5,300,099 A | 4/1994 | Rudie |
| 5,306,280 A | 4/1994 | Bregen et al. |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,350,399 A | 9/1994 | Erlebacher et al. |
| 5,354,271 A | 10/1994 | Voda |
| 5,358,511 A | 10/1994 | Gatturna et al. |

(56) References Cited

U.S. PATENT DOCUMENTS

| | | |
|---|---|---|
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,370,661 A | 12/1994 | Branch |
| 5,372,600 A | 12/1994 | Beyar et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,409,453 A | 4/1995 | Lundquist et al. |
| 5,411,520 A | 5/1995 | Nash et al. |
| 5,417,691 A | 5/1995 | Hayhurst |
| 5,435,805 A | 7/1995 | Edwards et al. |
| 5,458,612 A | 10/1995 | Chin |
| 5,464,416 A | 11/1995 | Steckel |
| 5,470,308 A | 11/1995 | Edwards et al. |
| 5,470,337 A | 11/1995 | Moss |
| 5,472,446 A | 12/1995 | Torre |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,759 A | 7/1996 | Kensey et al. |
| 5,531,763 A | 7/1996 | Mastri et al. |
| 5,534,012 A | 7/1996 | Bonutti |
| 5,536,240 A | 7/1996 | Edwards et al. |
| 5,540,655 A | 7/1996 | Edwards et al. |
| 5,540,704 A | 7/1996 | Gordon et al. |
| 5,542,594 A | 8/1996 | McKean et al. |
| 5,545,171 A | 8/1996 | Sharkey et al. |
| 5,545,178 A | 8/1996 | Kensey et al. |
| 5,549,631 A | 8/1996 | Bonutti |
| 5,550,172 A | 8/1996 | Regula et al. |
| 5,554,162 A | 9/1996 | DeLange |
| 5,554,171 A | 9/1996 | Gatturna et al. |
| 5,562,688 A | 10/1996 | Riza |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,591,179 A | 1/1997 | Edelstein |
| 5,593,421 A | 1/1997 | Bauer |
| 5,611,515 A | 3/1997 | Benderev et al. |
| 5,620,461 A | 4/1997 | Moer et al. |
| 5,626,614 A | 5/1997 | Hart |
| 5,630,824 A | 5/1997 | Hart |
| 5,643,321 A | 7/1997 | McDevitt |
| 5,647,836 A | 7/1997 | Blake et al. |
| 5,653,373 A | 8/1997 | Green et al. |
| 5,665,109 A | 9/1997 | Yoon |
| 5,667,486 A | 9/1997 | Mikulich et al. |
| 5,667,488 A | 9/1997 | Lundquist et al. |
| 5,667,522 A | 9/1997 | Flomenblit et al. |
| 5,669,917 A | 9/1997 | Sauer et al. |
| 5,672,171 A | 9/1997 | Andrus et al. |
| 5,690,649 A | 11/1997 | Li |
| 5,690,677 A | 11/1997 | Schmieding et al. |
| 5,697,950 A | 12/1997 | Fucci et al. |
| 5,707,394 A | 1/1998 | Miller et al. |
| 5,716,368 A | 2/1998 | Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,749,889 A | 5/1998 | Bacich et al. |
| 5,752,963 A | 5/1998 | Allard et al. |
| 5,775,328 A | 7/1998 | Lowe et al. |
| 5,782,862 A | 7/1998 | Bonutti |
| 5,782,864 A | 7/1998 | Lizardi |
| 5,791,022 A | 8/1998 | Bohman |
| 5,800,445 A | 9/1998 | Ratcliff et al. |
| 5,807,403 A | 9/1998 | Beyar et al. |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus et al. |
| 5,830,221 A | 11/1998 | Stein et al. |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,908,447 A | 6/1999 | Schroeppel et al. |
| 5,919,198 A | 7/1999 | Graves et al. |
| 5,919,202 A | 7/1999 | Yoon |
| 5,921,982 A | 7/1999 | Lesh et al. |
| 5,921,986 A | 7/1999 | Bonutti |
| 5,928,252 A | 7/1999 | Steadman et al. |
| 5,931,844 A | 8/1999 | Thompson et al. |
| 5,941,439 A | 8/1999 | Kammerer et al. |
| 5,944,739 A | 8/1999 | Zlock et al. |
| 5,948,000 A | 9/1999 | Larsen et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Willard |
| 5,971,447 A | 10/1999 | Steck |
| 5,971,967 A | 10/1999 | Willard |
| 6,010,514 A | 1/2000 | Burney et al. |
| 6,011,525 A | 1/2000 | Piole |
| 6,015,428 A | 1/2000 | Pagedas |
| 6,024,751 A | 2/2000 | Lovato et al. |
| 6,030,393 A | 2/2000 | Corlew |
| 6,033,413 A | 3/2000 | Mikus et al. |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,053,935 A | 4/2000 | Brenneman et al. |
| 6,056,722 A | 5/2000 | Jayaraman |
| 6,056,772 A | 5/2000 | Bonutti |
| 6,066,160 A | 5/2000 | Colvin et al. |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li et al. |
| 6,120,539 A | 9/2000 | Eldridge et al. |
| 6,132,438 A | 10/2000 | Fleischman et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,156,044 A | 12/2000 | Kammerer et al. |
| 6,156,049 A | 12/2000 | Lovato et al. |
| 6,159,207 A | 12/2000 | Yoon |
| 6,159,234 A | 12/2000 | Bonutti et al. |
| 6,193,714 B1 | 2/2001 | McGaffigan et al. |
| 6,200,329 B1 | 3/2001 | Fung et al. |
| 6,203,565 B1 | 3/2001 | Bonutti et al. |
| 6,206,895 B1 | 3/2001 | Levinson |
| 6,206,907 B1 | 3/2001 | Marino et al. |
| 6,228,096 B1 | 5/2001 | Marchand |
| 6,235,024 B1 | 5/2001 | Tu |
| 6,258,124 B1 | 7/2001 | Darois et al. |
| 6,261,302 B1 | 7/2001 | Voegele et al. |
| 6,261,320 B1 | 7/2001 | Tam et al. |

(56) References Cited

U.S. PATENT DOCUMENTS

| | | |
|---|---|---|
| 6,270,530 B1 | 8/2001 | Eldridge et al. |
| 6,280,441 B1 | 8/2001 | Ryan |
| 6,280,460 B1 | 8/2001 | Bolduc et al. |
| 6,287,317 B1 | 9/2001 | Makower et al. |
| 6,290,711 B1 | 9/2001 | Caspari et al. |
| 6,306,158 B1 | 10/2001 | Bartlett |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,382,214 B1 | 5/2002 | Raz et al. |
| 6,387,041 B1 | 5/2002 | Harari et al. |
| 6,398,795 B1 | 6/2002 | McAlister et al. |
| 6,398,796 B2 | 6/2002 | Levinson |
| 6,425,900 B1 | 7/2002 | Knodel et al. |
| 6,425,919 B1 | 7/2002 | Lambrecht |
| 6,428,538 B1 | 8/2002 | Blewett et al. |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,672 B2 | 12/2002 | Slepian et al. |
| 6,491,707 B2 | 12/2002 | Makower et al. |
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,514,247 B1 | 2/2003 | McGaffigan et al. |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,544,230 B1 | 4/2003 | Flaherty et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,582,453 B1 | 6/2003 | Tran et al. |
| 6,592,609 B1 | 7/2003 | Bonutti |
| 6,595,911 B2 | 7/2003 | LoVuolo |
| 6,596,013 B2 | 7/2003 | Yang et al. |
| 6,599,311 B1 | 7/2003 | Biggs et al. |
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | Goar et al. |
| 6,638,275 B1 | 10/2003 | McGaffigan et al. |
| 6,641,524 B2 | 11/2003 | Kovac |
| 6,641,592 B1 | 11/2003 | Sauer et al. |
| 6,656,182 B1 | 12/2003 | Hayhurst |
| 6,660,008 B1 | 12/2003 | Foerster et al. |
| 6,660,023 B2 | 12/2003 | McDevitt et al. |
| 6,663,589 B1 | 12/2003 | Halevy |
| 6,663,633 B1 | 12/2003 | Pierson |
| 6,663,639 B1 | 12/2003 | Laufer et al. |
| 6,699,263 B2 | 3/2004 | Cope |
| 6,702,846 B2 | 3/2004 | Mikus et al. |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,790,223 B2 | 9/2004 | Reever |
| 6,802,838 B2 | 10/2004 | Loeb et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,921,361 B2 | 7/2005 | Suzuki et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,986,784 B1 | 1/2006 | Weiser et al. |
| 6,988,983 B2 | 1/2006 | Connors et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,004,965 B2 | 2/2006 | Gross |
| 7,008,381 B2 | 3/2006 | Janssens |
| 7,011,688 B2 | 3/2006 | Gryska et al. |
| 7,015,253 B2 | 3/2006 | Escandon et al. |
| 7,041,111 B2 | 5/2006 | Chu |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,063,715 B2 | 6/2006 | Onuki et al. |
| 7,065,325 B2 | 6/2006 | Zegelin et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,096,301 B2 | 8/2006 | Beaudoin et al. |
| 7,104,949 B2 | 9/2006 | Anderson et al. |
| 7,105,004 B2 | 9/2006 | DiCesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,220,274 B1 * | 5/2007 | Quinn .................. A61F 2/07 623/1.13 |
| 7,226,558 B2 | 6/2007 | Nieman et al. |
| 7,232,448 B2 | 6/2007 | Battles et al. |
| 7,255,675 B2 | 8/2007 | Gertner et al. |
| 7,261,709 B2 | 8/2007 | Swoyer et al. |
| 7,261,710 B2 | 8/2007 | Elmouelhi et al. |
| 7,282,020 B2 | 10/2007 | Kaplan |
| 7,288,063 B2 | 10/2007 | Petros et al. |
| 7,303,108 B2 | 12/2007 | Shelton |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines |
| 7,335,197 B2 | 2/2008 | Sage et al. |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,437,194 B2 | 10/2008 | Skwarek et al. |
| 7,463,934 B2 | 12/2008 | Tronnes et al. |
| 7,470,228 B2 | 12/2008 | Connors et al. |
| 7,481,771 B2 | 1/2009 | Fonseca et al. |
| 7,485,124 B2 | 2/2009 | Kuhns et al. |
| 7,553,317 B2 | 6/2009 | William et al. |
| 7,608,108 B2 | 10/2009 | Bhatnagar et al. |
| 7,632,297 B2 | 12/2009 | Gross |
| 7,645,286 B2 | 1/2010 | Catanese et al. |
| 7,658,311 B2 | 2/2010 | Boudreaux |
| 7,666,197 B2 | 2/2010 | Orban |
| 7,674,275 B2 | 3/2010 | Martin et al. |
| 7,682,374 B2 | 3/2010 | Foerster et al. |
| 7,695,494 B2 | 4/2010 | Foerster |
| 7,704,261 B2 | 4/2010 | Sakamoto et al. |

(56) References Cited

U.S. PATENT DOCUMENTS

| | | | |
|---|---|---|---|
| 7,727,248 B2 | 6/2010 | Smith et al. |
| 7,731,725 B2 | 6/2010 | Gadberry et al. |
| 7,736,374 B2 | 6/2010 | Vaughan et al. |
| 7,758,594 B2 | 7/2010 | Lamson et al. |
| 7,766,923 B2 | 8/2010 | Catanese et al. |
| 7,766,939 B2 | 8/2010 | Yeung et al. |
| 7,780,682 B2 | 8/2010 | Catanese et al. |
| 7,815,655 B2 | 10/2010 | Catanese et al. |
| 7,850,712 B2 | 12/2010 | Conlon et al. |
| 7,862,584 B2 | 1/2011 | Lyons et al. |
| 7,887,551 B2 | 2/2011 | Bojarski et al. |
| 7,896,891 B2 | 3/2011 | Catanese et al. |
| 7,905,889 B2 | 3/2011 | Catanese et al. |
| 7,905,904 B2 | 3/2011 | Stone et al. |
| 7,909,836 B2 | 3/2011 | McLean et al. |
| 7,914,542 B2 | 3/2011 | Lamson et al. |
| 7,922,645 B2 | 4/2011 | Kaplan |
| 7,951,158 B2 | 5/2011 | Catanese et al. |
| 8,007,503 B2 | 8/2011 | Catanese et al. |
| 8,043,309 B2 | 10/2011 | Catanese et al. |
| 8,114,070 B2 | 2/2012 | Rubinsky et al. |
| 8,145,321 B2 | 3/2012 | Gross |
| 8,152,804 B2 | 4/2012 | Elmouelhi et al. |
| 8,157,815 B2 | 4/2012 | Catanese et al. |
| 8,162,960 B2 | 4/2012 | Manzo |
| 8,167,830 B2 | 5/2012 | Noriega |
| 8,211,118 B2 | 7/2012 | Catanese et al. |
| 8,216,254 B2 | 7/2012 | McLean et al. |
| 8,236,011 B2 | 8/2012 | Harris et al. |
| 8,251,985 B2 | 8/2012 | Hoey et al. |
| 8,273,079 B2 | 9/2012 | Hoey et al. |
| 8,298,132 B2 | 10/2012 | Connors et al. |
| 8,303,604 B2 | 11/2012 | Stone et al. |
| 8,308,765 B2 | 11/2012 | Saadat et al. |
| 8,333,776 B2 | 12/2012 | Cheng et al. |
| 8,343,187 B2 | 1/2013 | Lamson et al. |
| 8,361,112 B2 | 1/2013 | Kempton et al. |
| 8,372,065 B2 | 2/2013 | Hoey et al. |
| 8,388,611 B2 | 3/2013 | Shadduck et al. |
| 8,388,653 B2 | 3/2013 | Nobis et al. |
| 8,394,110 B2 | 3/2013 | Catanese et al. |
| 8,394,113 B2 | 3/2013 | Wei et al. |
| 8,419,723 B2 | 4/2013 | Shadduck et al. |
| 8,425,535 B2 | 4/2013 | McLean et al. |
| 8,444,657 B2 | 5/2013 | Saadat et al. |
| 8,454,655 B2 | 6/2013 | Yeung et al. |
| 8,465,551 B1 | 6/2013 | Wijay et al. |
| 8,480,686 B2 | 7/2013 | Bakos et al. |
| 8,491,606 B2 | 7/2013 | Tong et al. |
| 8,496,684 B2 | 7/2013 | Crainich et al. |
| 8,521,257 B2 | 8/2013 | Whitcomb et al. |
| 8,529,584 B2 | 9/2013 | Catanese et al. |
| 8,529,588 B2 | 9/2013 | Ahlberg et al. |
| 8,562,646 B2 | 10/2013 | Gellman et al. |
| 8,585,692 B2 | 11/2013 | Shadduck et al. |
| 8,603,106 B2 | 12/2013 | Catanese et al. |
| 8,603,123 B2 | 12/2013 | Todd |
| 8,603,187 B2 | 12/2013 | Kilemnick et al. |
| 8,628,542 B2 | 1/2014 | Merrick et al. |
| 8,663,243 B2 | 3/2014 | Lamson et al. |
| 8,668,705 B2 | 3/2014 | Johnston et al. |
| 8,683,895 B2 | 4/2014 | Nash |
| 8,715,239 B2 | 5/2014 | Lamson et al. |
| 8,715,298 B2 | 5/2014 | Catanese et al. |
| 8,734,469 B2 | 5/2014 | Pribanic et al. |
| 8,790,356 B2 | 7/2014 | Darois et al. |
| 8,801,702 B2 | 8/2014 | Hoey et al. |
| 8,808,363 B2 | 8/2014 | Perry et al. |
| 8,814,856 B2 | 8/2014 | Elmouelhi et al. |
| 8,828,035 B2 | 9/2014 | Kim |
| 8,834,458 B2 | 9/2014 | Neuberger et al. |
| 8,880,195 B2 | 11/2014 | Azure |
| 8,900,293 B2 | 12/2014 | Forbes et al. |
| 8,920,437 B2 | 12/2014 | Harris et al. |
| 8,926,494 B1 | 1/2015 | Cook et al. |
| 8,945,114 B2 | 2/2015 | Elmouelhi et al. |
| 9,034,001 B2 | 5/2015 | Cheng et al. |
| 9,039,740 B2 | 5/2015 | Wales et al. |
| 9,089,320 B2 | 7/2015 | Spivey et al. |
| 9,150,817 B2 | 10/2015 | Furihata et al. |
| 9,179,991 B2 | 11/2015 | Gozzi et al. |
| 9,204,922 B2 | 12/2015 | Hooven |
| 9,211,155 B2 | 12/2015 | Fruland et al. |
| 9,220,874 B2 | 12/2015 | Pillai et al. |
| 9,272,140 B2 | 3/2016 | Gerber |
| 9,277,914 B2 | 3/2016 | Wales et al. |
| 9,345,507 B2 | 5/2016 | Hoey et al. |
| 9,345,867 B2 | 5/2016 | Browning |
| 9,393,007 B2 | 7/2016 | Darois et al. |
| 9,439,643 B2 | 9/2016 | Darois et al. |
| 9,459,751 B2 | 10/2016 | Weaver et al. |
| 9,526,555 B2 | 12/2016 | Hoey et al. |
| 9,549,739 B2 | 1/2017 | Catanese et al. |
| 9,561,025 B2 | 2/2017 | Stone et al. |
| 9,592,044 B2 | 3/2017 | Weir et al. |
| 9,597,145 B2 | 3/2017 | Nelson et al. |
| 9,668,803 B2 | 6/2017 | Bhushan et al. |
| 9,675,373 B2 | 6/2017 | Todd |
| 9,750,492 B2 | 9/2017 | Ziniti et al. |
| 2001/0021835 A1* | 9/2001 | Mitchell .................. A61F 2/07 |
| | | 604/385.17 |
| 2001/0041916 A1 | 11/2001 | Bonutti |
| 2001/0044639 A1 | 11/2001 | Levinson |
| 2002/0049453 A1 | 4/2002 | Nobles et al. |
| 2002/0095064 A1 | 7/2002 | Beyar |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0161382 A1 | 10/2002 | Neisz et al. |
| 2002/0177866 A1 | 11/2002 | Weikel et al. |
| 2002/0183740 A1 | 12/2002 | Edwards et al. |
| 2002/0193809 A1 | 12/2002 | Meade et al. |
| 2003/0023248 A1 | 1/2003 | Parodi |
| 2003/0040803 A1 | 2/2003 | Rioux et al. |
| 2003/0060819 A1 | 3/2003 | McGovern et al. |
| 2003/0078601 A1 | 4/2003 | Shikhman et al. |
| 2003/0109769 A1 | 6/2003 | Lowery et al. |
| 2003/0120309 A1 | 6/2003 | Colleran et al. |
| 2003/0130575 A1 | 7/2003 | Desai |
| 2003/0144570 A1 | 7/2003 | Hunter et al. |
| 2003/0176883 A1 | 9/2003 | Sauer et al. |
| 2003/0191479 A1* | 10/2003 | Thornton ........... A61B 17/0644 |
| | | 606/151 |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0236535 A1 | 12/2003 | Onuki et al. |
| 2004/0010301 A1 | 1/2004 | Kindlein et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0122456 A1 | 6/2004 | Saadat et al. |
| 2004/0122474 A1 | 6/2004 | Gellman et al. |
| 2004/0143343 A1 | 7/2004 | Grocela |
| 2004/0147958 A1 | 7/2004 | Lam et al. |
| 2004/0162568 A1 | 8/2004 | Saadat et al. |
| 2004/0167635 A1 | 8/2004 | Yachia et al. |
| 2004/0172046 A1 | 9/2004 | Hlavka et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0215181 A1 | 10/2004 | Christopherson et al. |
| 2004/0230316 A1 | 11/2004 | Cioanta et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0010203 A1 | 1/2005 | Edwards et al. |
| 2005/0033403 A1 | 2/2005 | Ward et al. |
| 2005/0055087 A1 | 3/2005 | Starksen |
| 2005/0059929 A1 | 3/2005 | Bolmsjo et al. |
| 2005/0065550 A1 | 3/2005 | Starksen et al. |
| 2005/0101982 A1 | 5/2005 | Ravenscroft et al. |

(56) References Cited

U.S. PATENT DOCUMENTS

| | | |
|---|---|---|
| 2005/0107811 A1 | 5/2005 | Starksen et al. |
| 2005/0107812 A1 | 5/2005 | Starksen et al. |
| 2005/0137716 A1 | 6/2005 | Gross |
| 2005/0154401 A1 | 7/2005 | Weldon et al. |
| 2005/0165272 A1 | 7/2005 | Okada et al. |
| 2005/0171522 A1 | 8/2005 | Christopherson |
| 2005/0177181 A1 | 8/2005 | Kagan et al. |
| 2005/0203344 A1 | 9/2005 | Orban et al. |
| 2005/0203550 A1 | 9/2005 | Laufer et al. |
| 2005/0216040 A1 | 9/2005 | Gertner et al. |
| 2005/0216078 A1 | 9/2005 | Starksen et al. |
| 2005/0222557 A1 | 10/2005 | Baxter et al. |
| 2005/0251157 A1 | 11/2005 | Saadat et al. |
| 2005/0251159 A1 | 11/2005 | Ewers et al. |
| 2005/0251177 A1 | 11/2005 | Saadat et al. |
| 2005/0251206 A1 | 11/2005 | Maahs et al. |
| 2005/0267405 A1 | 12/2005 | Shah |
| 2005/0273138 A1 | 12/2005 | To et al. |
| 2005/0283189 A1 | 12/2005 | Rosenblatt |
| 2005/0288694 A1 | 12/2005 | Solomon |
| 2006/0004410 A1 | 1/2006 | Nobis et al. |
| 2006/0020276 A1 | 1/2006 | Saadat et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0026750 A1 | 2/2006 | Ballance |
| 2006/0030884 A1 | 2/2006 | Yeung et al. |
| 2006/0058817 A1 | 3/2006 | Starksen et al. |
| 2006/0079880 A1 | 4/2006 | Sage et al. |
| 2006/0079881 A1 | 4/2006 | Christopherson et al. |
| 2006/0089646 A1 | 4/2006 | Bonutti |
| 2006/0095058 A1 | 5/2006 | Sivan et al. |
| 2006/0167477 A1 | 7/2006 | Arcia et al. |
| 2006/0178680 A1 | 8/2006 | Nelson et al. |
| 2006/0199996 A1 | 9/2006 | Caraballo et al. |
| 2006/0241694 A1 | 10/2006 | Cerundolo |
| 2006/0265042 A1 | 11/2006 | Catanese et al. |
| 2006/0271032 A1 | 11/2006 | Chin et al. |
| 2006/0276481 A1 | 12/2006 | Evrard et al. |
| 2006/0276871 A1 | 12/2006 | Lamson et al. |
| 2006/0282081 A1 | 12/2006 | Fanton et al. |
| 2007/0049929 A1 | 3/2007 | Catanese et al. |
| 2007/0049970 A1 | 3/2007 | Belef et al. |
| 2007/0060931 A1 | 3/2007 | Hamilton et al. |
| 2007/0073322 A1 | 3/2007 | Mikkaichi et al. |
| 2007/0073342 A1 | 3/2007 | Stone et al. |
| 2007/0088362 A1 | 4/2007 | Bonutti et al. |
| 2007/0100421 A1 | 5/2007 | Griffin |
| 2007/0112385 A1 | 5/2007 | Conlon |
| 2007/0112423 A1* | 5/2007 | Chu .................. A61B 17/064 623/2.11 |
| 2007/0142846 A1 | 6/2007 | Catanese et al. |
| 2007/0173888 A1 | 7/2007 | Gertner et al. |
| 2007/0179491 A1 | 8/2007 | Kratoska et al. |
| 2007/0179496 A1 | 8/2007 | Swoyer et al. |
| 2007/0198038 A1 | 8/2007 | Cohen et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0021485 A1 | 1/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039893 A1 | 2/2008 | McLean et al. |
| 2008/0039894 A1 | 2/2008 | Catanese et al. |
| 2008/0039921 A1 | 2/2008 | Wallsten et al. |
| 2008/0045978 A1 | 2/2008 | Kuhns et al. |
| 2008/0051810 A1 | 2/2008 | To et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0161852 A1 | 7/2008 | Kaiser et al. |
| 2008/0195145 A1 | 8/2008 | Bonutti et al. |
| 2008/0208220 A1 | 8/2008 | Shiono et al. |
| 2008/0228202 A1 | 9/2008 | Cropper et al. |
| 2008/0269737 A1 | 10/2008 | Elmouelhi et al. |
| 2009/0012537 A1 | 1/2009 | Green |
| 2009/0018553 A1 | 1/2009 | McLean et al. |
| 2009/0060977 A1 | 3/2009 | Lamson et al. |
| 2009/0112234 A1 | 4/2009 | Crainich et al. |
| 2009/0112537 A1 | 4/2009 | Okumura |
| 2009/0118762 A1 | 5/2009 | Crainch et al. |
| 2009/0177288 A1 | 7/2009 | Wallsten |
| 2009/0198227 A1 | 8/2009 | Prakash |
| 2010/0010631 A1 | 1/2010 | Otte et al. |
| 2010/0023022 A1 | 1/2010 | Zeiner et al. |
| 2010/0023024 A1 | 1/2010 | Zeiner et al. |
| 2010/0023025 A1 | 1/2010 | Zeiner et al. |
| 2010/0023026 A1 | 1/2010 | Zeiner et al. |
| 2010/0030262 A1 | 2/2010 | McLean et al. |
| 2010/0030263 A1 | 2/2010 | Cheng et al. |
| 2010/0049188 A1 | 2/2010 | Nelson et al. |
| 2010/0063542 A1 | 3/2010 | Burg et al. |
| 2010/0114162 A1 | 5/2010 | Bojarski et al. |
| 2010/0130815 A1 | 5/2010 | Gross et al. |
| 2010/0286106 A1 | 11/2010 | Gat et al. |
| 2010/0286679 A1 | 11/2010 | Hoey et al. |
| 2010/0298948 A1 | 11/2010 | Hoey et al. |
| 2010/0324669 A1 | 12/2010 | Hlavka et al. |
| 2011/0040312 A1 | 2/2011 | Lamson et al. |
| 2011/0046648 A1 | 2/2011 | Johnston et al. |
| 2011/0060349 A1 | 3/2011 | Cheng et al. |
| 2011/0077676 A1 | 3/2011 | Sivan et al. |
| 2011/0144423 A1 | 6/2011 | Tong et al. |
| 2011/0152839 A1 | 6/2011 | Cima et al. |
| 2011/0160747 A1 | 6/2011 | McLean et al. |
| 2011/0166564 A1 | 7/2011 | Merrick et al. |
| 2011/0190758 A1 | 8/2011 | Lamson et al. |
| 2011/0196393 A1 | 8/2011 | Eliachar et al. |
| 2011/0202052 A1 | 8/2011 | Gelbart et al. |
| 2011/0218387 A1 | 9/2011 | Lamson et al. |
| 2011/0245828 A1 | 10/2011 | Baxter et al. |
| 2011/0276081 A1 | 11/2011 | Kilemnik |
| 2011/0276086 A1 | 11/2011 | Al-Qbandi et al. |
| 2012/0010645 A1 | 1/2012 | Feld |
| 2012/0059387 A1 | 3/2012 | Schanz et al. |
| 2012/0165837 A1 | 6/2012 | Belman et al. |
| 2012/0203250 A1 | 8/2012 | Weir et al. |
| 2012/0245600 A1 | 9/2012 | McLean et al. |
| 2012/0265006 A1 | 10/2012 | Makower et al. |
| 2013/0096582 A1 | 4/2013 | Cheng et al. |
| 2013/0178871 A1 | 7/2013 | Koogle et al. |
| 2013/0211431 A1 | 8/2013 | Wei et al. |
| 2013/0253574 A1 | 9/2013 | Catanese et al. |
| 2013/0253662 A1 | 9/2013 | Lamson et al. |
| 2013/0261383 A1 | 10/2013 | Catanese et al. |
| 2013/0261665 A1 | 10/2013 | Yeung et al. |
| 2013/0267772 A1 | 10/2013 | Catanese et al. |
| 2013/0268001 A1 | 10/2013 | Catanese et al. |
| 2013/0274799 A1 | 10/2013 | Catanese et al. |
| 2013/0289342 A1 | 10/2013 | Tong et al. |
| 2013/0296639 A1 | 11/2013 | Lamson et al. |
| 2013/0296889 A1 | 11/2013 | Tong et al. |
| 2013/0296935 A1 | 11/2013 | McLean et al. |
| 2013/0325143 A1 | 12/2013 | Lamson et al. |
| 2014/0005473 A1 | 1/2014 | Catanese et al. |
| 2014/0005690 A1 | 1/2014 | Catanese et al. |
| 2014/0012192 A1 | 1/2014 | Bar-On et al. |
| 2014/0088587 A1 | 3/2014 | Merrick et al. |
| 2014/0221981 A1 | 8/2014 | Cima et al. |
| 2014/0236230 A1 | 8/2014 | Johnston et al. |
| 2014/0288637 A1 | 9/2014 | Clerc et al. |
| 2015/0112299 A1 | 4/2015 | Forbes et al. |
| 2015/0157309 A1 | 6/2015 | Bird |
| 2015/0257908 A1 | 9/2015 | Chao et al. |

(56) References Cited

U.S. PATENT DOCUMENTS

| | | |
|---|---|---|
| 2015/0335393 A1 | 11/2015 | Ciulla et al. |
| 2016/0000455 A1 | 1/2016 | Golan et al. |
| 2016/0038087 A1 | 2/2016 | Hunter |
| 2016/0051735 A1 | 2/2016 | Slepian |
| 2016/0081736 A1 | 3/2016 | Hoey et al. |
| 2016/0089140 A1 | 3/2016 | Kawaura et al. |
| 2016/0096009 A1 | 4/2016 | Feld |
| 2016/0120647 A1 | 5/2016 | Rogers et al. |
| 2016/0206370 A1 | 7/2016 | Fruland et al. |
| 2016/0242894 A1 | 8/2016 | Davis |
| 2016/0302904 A1 | 10/2016 | Ogdahl et al. |
| 2016/0317180 A1 | 11/2016 | Kilemnik |
| 2017/0000598 A1 | 1/2017 | Bachar |
| 2017/0128741 A1 | 5/2017 | Keltner et al. |
| 2017/0135830 A1 | 5/2017 | Harkin et al. |
| 2018/0353169 A1 | 12/2018 | Lamson et al. |

FOREIGN PATENT DOCUMENTS

| | | |
|---|---|---|
| CN | 101795641 A | 8/2010 |
| CN | 102112064 B | 6/2014 |
| CN | 105919695 A | 9/2016 |
| DE | 10159470 A1 | 6/2003 |
| EP | 0246836 B1 | 12/1991 |
| EP | 0464480 A1 | 1/1992 |
| EP | 0274846 B1 | 2/1994 |
| EP | 0632999 A1 | 1/1995 |
| EP | 0667126 A1 | 8/1995 |
| EP | 1016377 A2 | 7/2000 |
| EP | 1482841 A1 | 12/2004 |
| EP | 1082941 B1 | 3/2005 |
| EP | 1584295 A2 | 10/2005 |
| EP | 1006909 B1 | 1/2007 |
| EP | 1852071 A2 | 11/2007 |
| EP | 1584295 B1 | 2/2008 |
| EP | 1884198 A2 | 2/2008 |
| EP | 1884199 A1 | 2/2008 |
| EP | 1670361 B1 | 4/2008 |
| EP | 1331886 B1 | 12/2008 |
| EP | 1482840 B1 | 12/2008 |
| EP | 2243507 A1 | 10/2010 |
| EP | 1484023 B1 | 5/2011 |
| EP | 2345373 A1 | 7/2011 |
| EP | 2345374 A1 | 7/2011 |
| EP | 2049023 B1 | 12/2014 |
| EP | 3167845 A1 | 5/2017 |
| FR | 2750031 A1 | 12/1997 |
| JP | 5836559 A | 3/1983 |
| JP | 09122134 | 5/1997 |
| JP | 3370300 B2 | 1/2003 |
| JP | 2004344427 A | 12/2004 |
| JP | 2009521278 A | 6/2009 |
| JP | 2011529745 A | 12/2011 |
| JP | 2012143622 A | 8/2012 |
| KR | 20060009698 A | 2/2006 |
| RU | 2062121 C1 | 6/1996 |
| RU | 2112571 C1 | 6/1998 |
| RU | 2128012 C1 | 3/1999 |
| RU | 2221501 C2 | 1/2004 |
| SU | 825094 A1 | 4/1981 |
| WO | 1987001270 A1 | 3/1987 |
| WO | 1992010142 A1 | 6/1992 |
| WO | 1993004727 A1 | 3/1993 |
| WO | 1993015664 A1 | 8/1993 |
| WO | 1995000818 A1 | 1/1995 |
| WO | 2000040159 A1 | 7/2000 |
| WO | 2001026588 A2 | 4/2001 |
| WO | 2001028432 A1 | 4/2001 |
| WO | 2001039671 A1 | 6/2001 |
| WO | 2001049195 A1 | 7/2001 |
| WO | 2001095818 A1 | 12/2001 |
| WO | 2002028289 A1 | 4/2002 |
| WO | 2002030335 A2 | 4/2002 |
| WO | 2002032321 A1 | 4/2002 |
| WO | 2002058577 A1 | 8/2002 |
| WO | 2003039334 A2 | 5/2003 |
| WO | 2003077772 A1 | 9/2003 |
| WO | 2004000159 A2 | 12/2003 |
| WO | 2004017845 A1 | 3/2004 |
| WO | 2004019787 A2 | 3/2004 |
| WO | 2004019788 A2 | 3/2004 |
| WO | 2004030569 A2 | 4/2004 |
| WO | 2004066875 A1 | 8/2004 |
| WO | 2004080529 A2 | 9/2004 |
| WO | 2004103189 A1 | 12/2004 |
| WO | 2005034738 A2 | 4/2005 |
| WO | 2005065412 A2 | 7/2005 |
| WO | 2005094447 A2 | 10/2005 |
| WO | 2006127241 A2 | 11/2006 |
| WO | 2006127431 A2 | 11/2006 |
| WO | 2007048437 A1 | 5/2007 |
| WO | 2007053516 A2 | 5/2007 |
| WO | 2007064906 A2 | 6/2007 |
| WO | 2007075981 A2 | 7/2007 |
| WO | 2008002340 A2 | 1/2008 |
| WO | 2008006084 A2 | 1/2008 |
| WO | 2008014191 A2 | 1/2008 |
| WO | 2008043044 A2 | 4/2008 |
| WO | 2008043917 A2 | 4/2008 |
| WO | 2008097942 A1 | 8/2008 |
| WO | 2008132735 A1 | 11/2008 |
| WO | 2008142677 A2 | 11/2008 |
| WO | 2009009617 A1 | 1/2009 |
| WO | 2009072131 A2 | 6/2009 |
| WO | 2010011832 A1 | 1/2010 |
| WO | 2010014821 A2 | 2/2010 |
| WO | 2010014825 A1 | 2/2010 |
| WO | 2010065214 A2 | 6/2010 |
| WO | 2010086849 A1 | 8/2010 |
| WO | 2010106543 A2 | 9/2010 |
| WO | 2011084712 A1 | 7/2011 |
| WO | 2012018446 A2 | 2/2012 |
| WO | 2012079548 A1 | 6/2012 |
| WO | 2012079549 A2 | 6/2012 |
| WO | 2012091952 A2 | 7/2012 |
| WO | 2012091954 A2 | 7/2012 |
| WO | 2012091955 A2 | 7/2012 |
| WO | 2012091956 A2 | 7/2012 |
| WO | 2012123950 A2 | 9/2012 |
| WO | 2014003987 A1 | 1/2014 |
| WO | 2014035506 A2 | 3/2014 |
| WO | 2014145381 A1 | 9/2014 |
| WO | 2014153219 A1 | 9/2014 |
| WO | 2014200764 A1 | 12/2014 |
| WO | 2015101975 A1 | 7/2015 |
| WO | 2016134166 A1 | 8/2016 |
| WO | 2017017499 A1 | 2/2017 |
| WO | 2017112856 A1 | 6/2017 |

OTHER PUBLICATIONS

Berges, Richard, et al. "Alternative Minimalinvasive Therapien Beim Benignen Prostatasyndrom", Medizin, Jg. 104, Heft 37, Sep. 14, 2007.

Borzhievski, et al., "Tactics of the Surgical Treatment of Patients With Prostatic Adenoma and Acute Urinary Retention," Urologia Nefrol (Mosk), Jan.-Feb. 1987, (1):39-43.

European Search Report for EP Application No. 06770621.8, dated Sep. 20, 2012.

European Search Report for EP Application No. 06845991.6, dated Mar. 22, 2013.

European Search Report for EP Application No. 07840462.1, dated May 29, 2012.

European Search Report for EP Application No. 08729001.1, dated Feb. 4, 2014.

European Search Report for EP Application No. 08772483.7, dated Feb. 12, 2015.

European Search Report for EP Application No. 11154962.2, dated May 19, 2011.

European Search Report for EP Application No. 11154976.2, dated Jun. 6, 2011.

(56) References Cited

OTHER PUBLICATIONS

European Search Report for EP Application No. 11814950.9, dated Sep. 8, 2015.
European Search Report for EP Application No. 11852778.7, dated Nov. 19, 2015.
European Search Report for EP Application No. 11854148.1, dated Oct. 20, 2017.
European Search Report for EP Application No. 13810314.8, dated Apr. 6, 2016.
European Search Report for EP Application No. 17150545.6, dated Sep. 11, 2017.
Hartung, Rudolf, et al. "Instrumentelle Therapie der benignen Prostatahyperplasie", Medizin, Deutsches Arzteblatt 97, Heft 15, Apr. 14, 2000.
Hofner, Klaus, et al., "Operative Therapie des benignen Prostatasyndroms", Medizin, Dtsch Arztebl, 2007; 104(36): A 2424-9.
Hubmann, R. "Geschichte der transurethralen Prostataeingriffe", Geschichte der Medizin, Urologe [B], 2000, 40:152-160.
International Search Report for PCT Application No. PCT/US2006/019372, dated May 2, 2008.
International Search Report for PCT Application No. PCT/US2006/048962, dated Dec. 10, 2008.
International Search Report for PCT Application No. PCT/US2007/074019, dated Jul. 25, 2008.
International Search Report for PCT Application No. PCT/US2008/053001, dated Jun. 17, 2008.
International Search Report for PCT Application No. PCT/US2008/069560, dated Sep. 8, 2008.
International Search Report for PCT Application No. PCT/US2009/052271, dated Apr. 7, 2010.
International Search Report for PCT Application No. PCT/US2009/052275, dated Oct. 9, 2009.
International Search Report for PCT Application No. PCT/US2011/041200, dated Feb. 17, 2012.
International Search Report for PCT Application No. PCT/US2011/065348, dated Jun. 21, 2012.
International Search Report for PCT Application No. PCT/US2011/065358, dated Jun. 21, 2012.
International Search Report for PCT Application No. PCT/US2011/065377, dated Aug. 29, 2012.
International Search Report for PCT Application No. PCT/US2011/065386, dated Jun. 28, 2012.
International Search Report for PCT Application No. PCT/US2013/044035, dated Sep. 6, 2013.
Jonas, U., et al., "Benigne Prostatahyperplasie", Der Urologe 2006—[Sonderheft] 45:134-144.
Kruck, S., et al., "Aktuelle Therapiemoglichkeiten des Benignen Prostata-Syndroms", J Urol Urogynakol, 2009; 16(1): 19-22.
Miyake, Osamu. "Medical Examination and Treatment for BPH," Pharma Med, vol. 22, No. 3, 2004, p. 97-103.
Reich, O., et al., "Benignes Prostatasyndrom (BPS)," Der Urologe A Issue vol. 45, No. 6, Jun. 2006, p. 769-782.
Schauer, P., et al. "New applications for endoscopy: the emerging field of endoluminal and transgastric bariatric surgery", Surgical Endoscopy, (Apr. 24, 2006), 10 pgs.
Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.
Takashi, Daito. "Low-Invasive Treatment for BPH", Medico vol. 34, No. 10, p. 366-369, 2000.
Teruhisa, Ohashi. "Urinary Dysfunction by Lower Urinary Tract Obstruction in Male", Pharma Medica, vol. 8, No. 8, p. 35-39, 1990.
Tomohiko, Koyanagi, et al., "Surgery View of 21st Century," Urological Surgery, vol. 84, No. 1, p. 47-53, 2001.
Trapeznikov, et al., "New Technologies in the Treatment of Benign Prostatic Hyperplasia", Urologia Nefrol (Mosk), Jul.-Aug. 1996, (4):41-47.
Yeung, Jeff. "Treating Urinary Stress Incontenance Without Incision with Endoscopic Suture Anchor & Approximating Device," Aleeva Medical, Inc., 2007.

\* cited by examiner

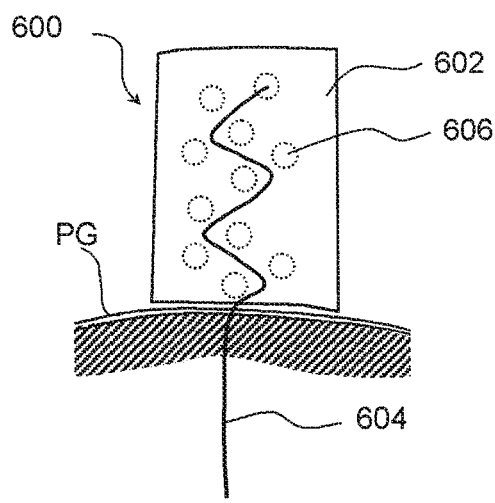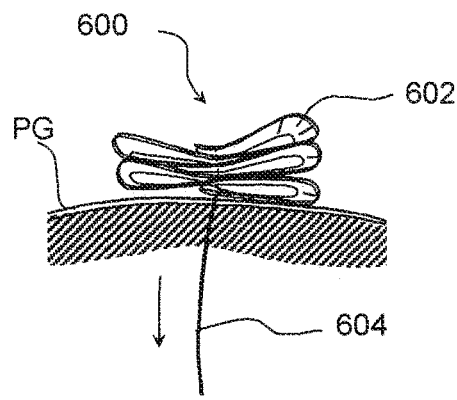
Fig. 6 A    Fig. 6 B
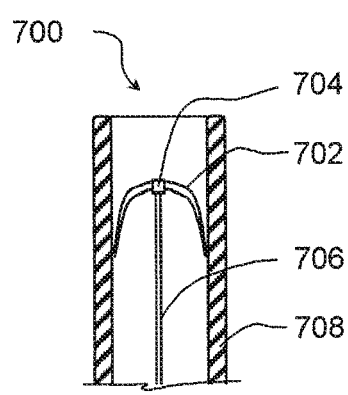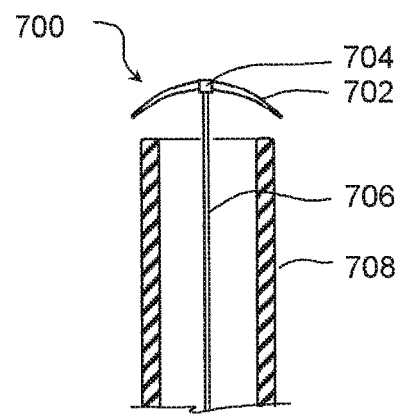
Fig. 7 A    Fig. 7 B
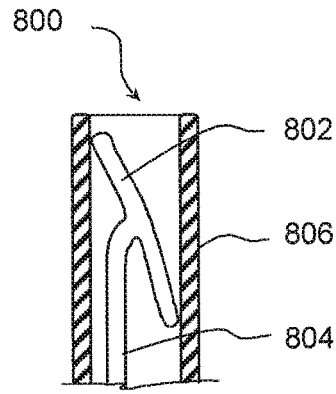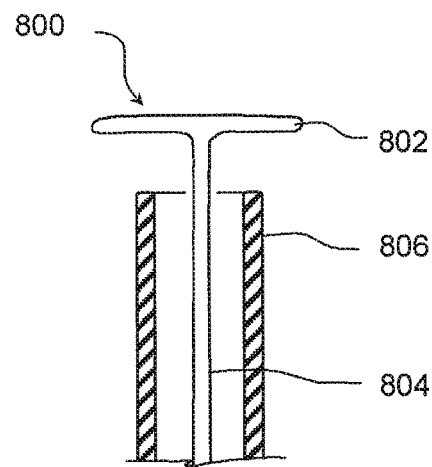
Fig. 8 A    Fig. 8 B

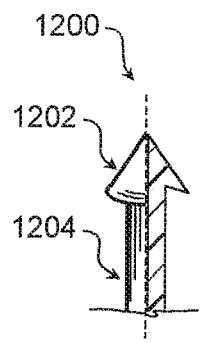
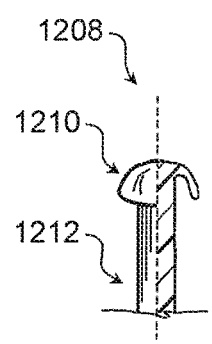
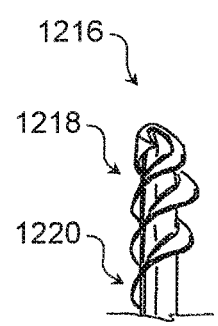
*Fig. 12 A*  *Fig. 12 B*  *Fig. 12 C*
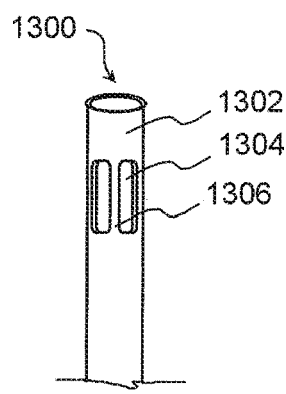
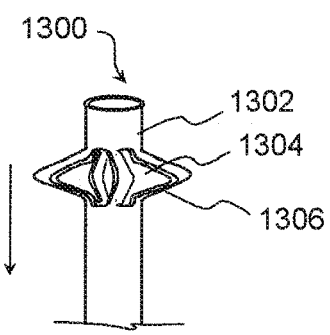
*Fig. 13 A*  *Fig. 13 B*
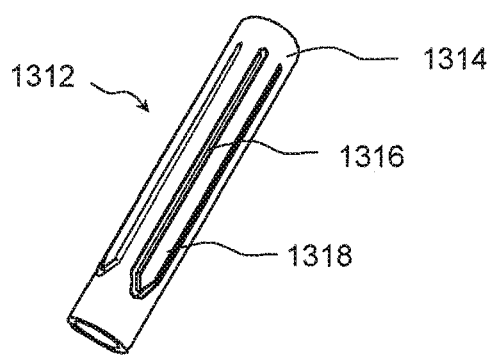
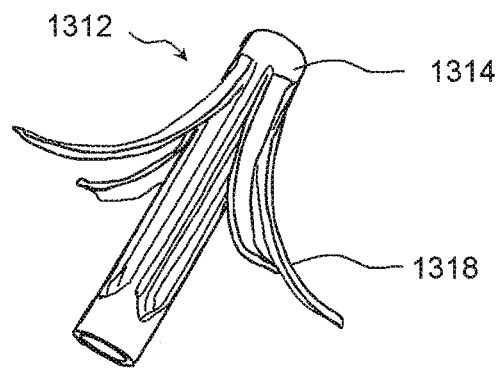
*Fig. 13 C*  *Fig. 13 D*

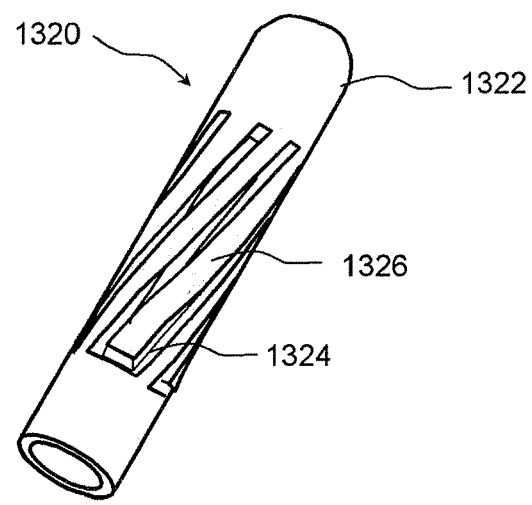
Fig. 13 E
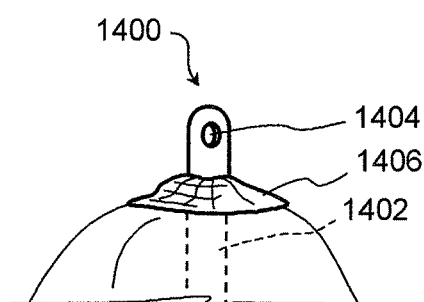 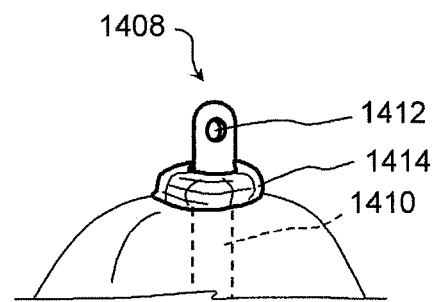
Fig. 14 A          Fig. 14 B

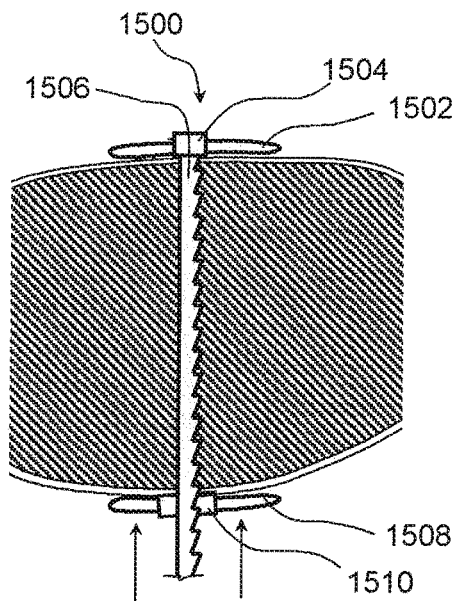
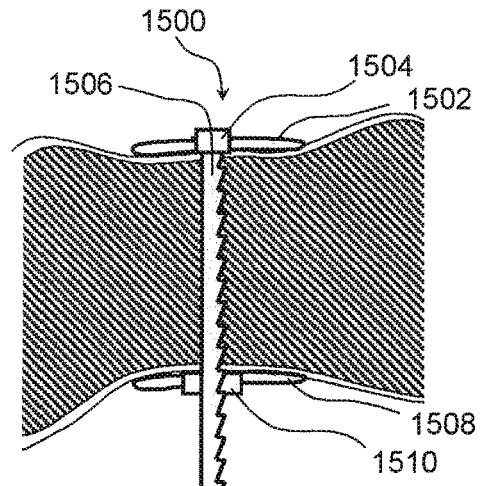
Fig. 15 A                Fig. 15 B
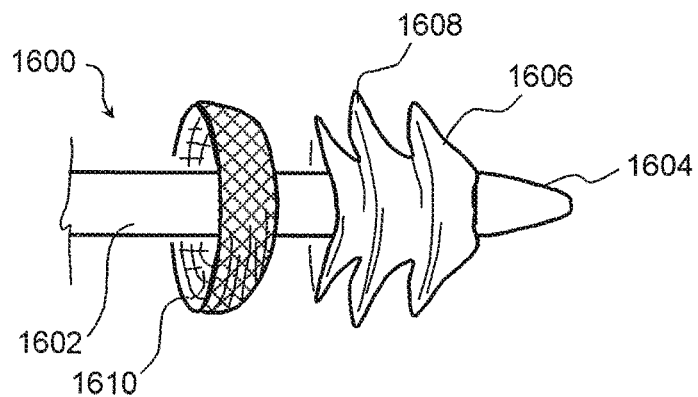
Fig. 16

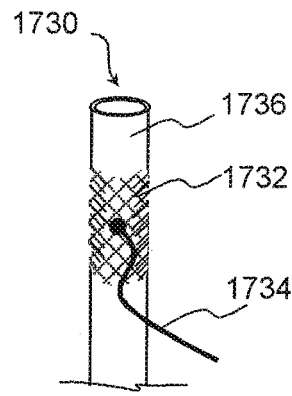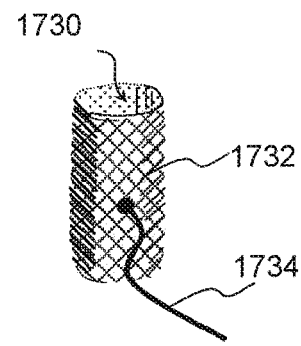
Fig. 17F        Fig. 17G
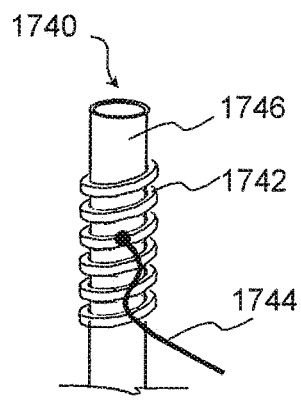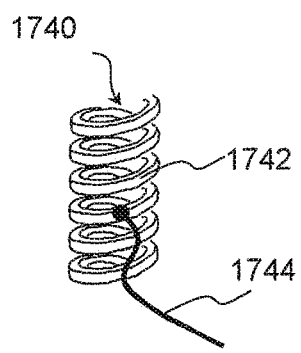
Fig. 17H        Fig. 17I

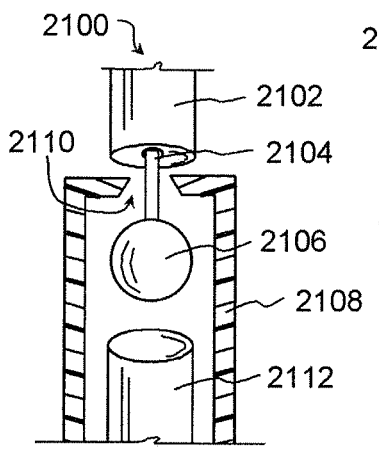
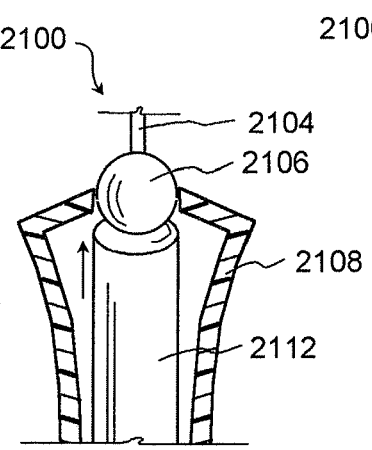
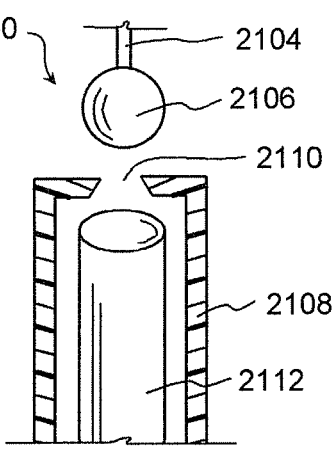
Fig. 21 A    Fig. 21 B    Fig. 21 C
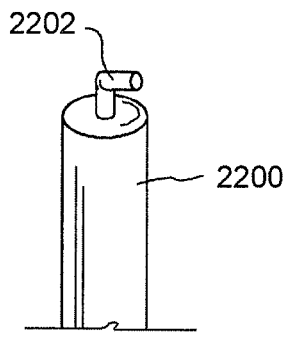
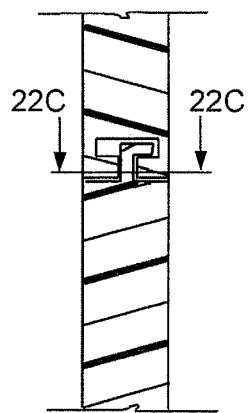
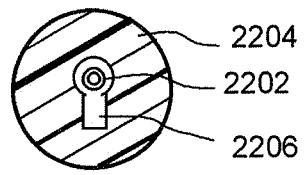
Fig. 22 A    Fig. 22 B    Fig. 22 C
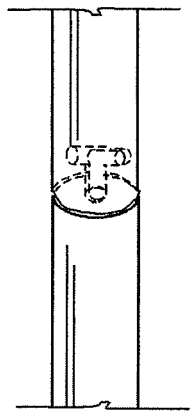
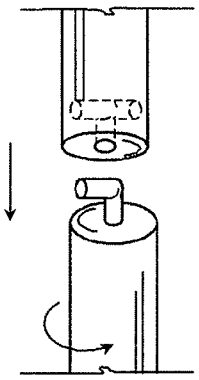
Fig. 22 D    Fig. 22 E

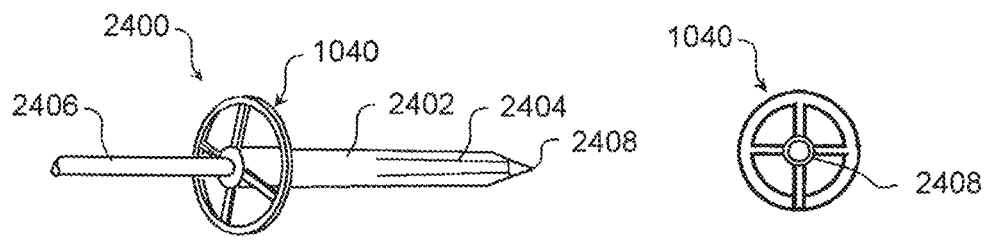
*Fig. 24 A*    *Fig. 24 A'*
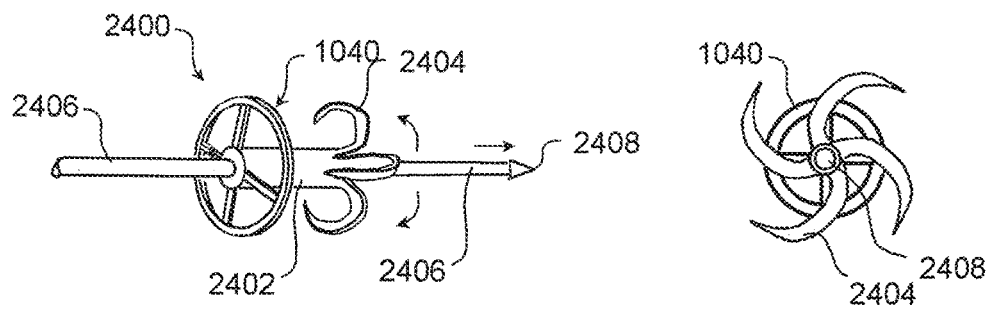
*Fig. 24 B*    *Fig. 24 B'*
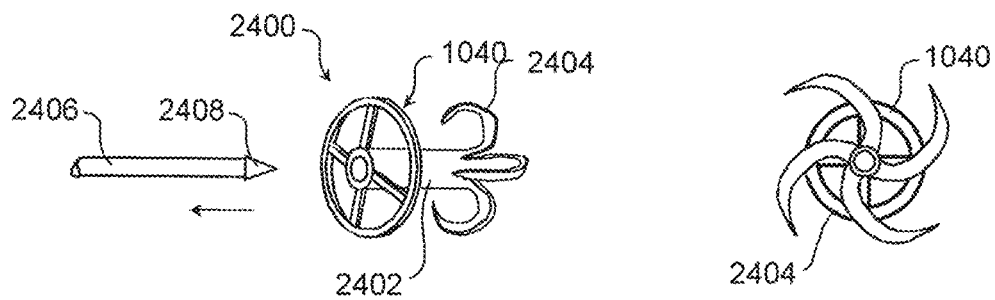
*Fig. 24 C*    *Fig. 24 C'*

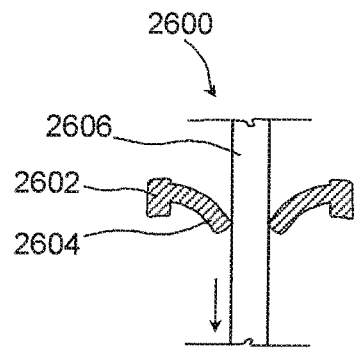
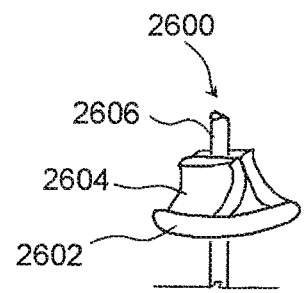
Fig. 26 A    Fig. 26 B
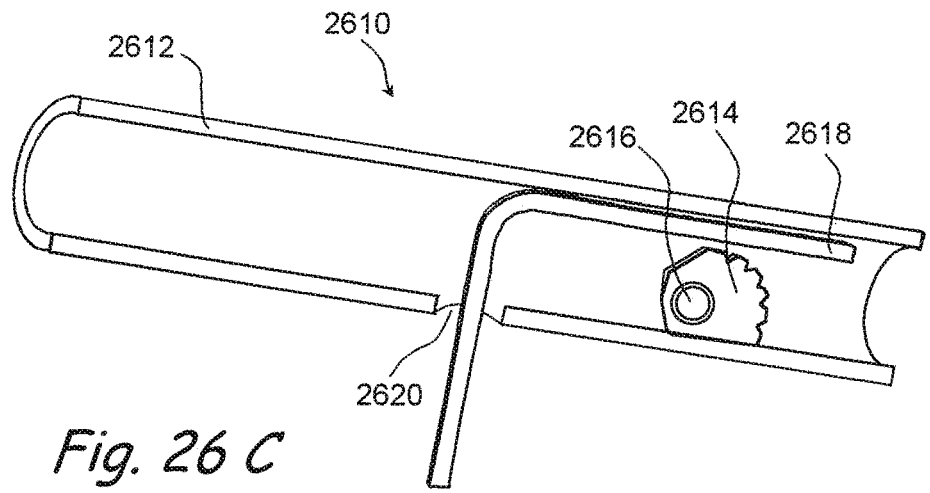
Fig. 26 C
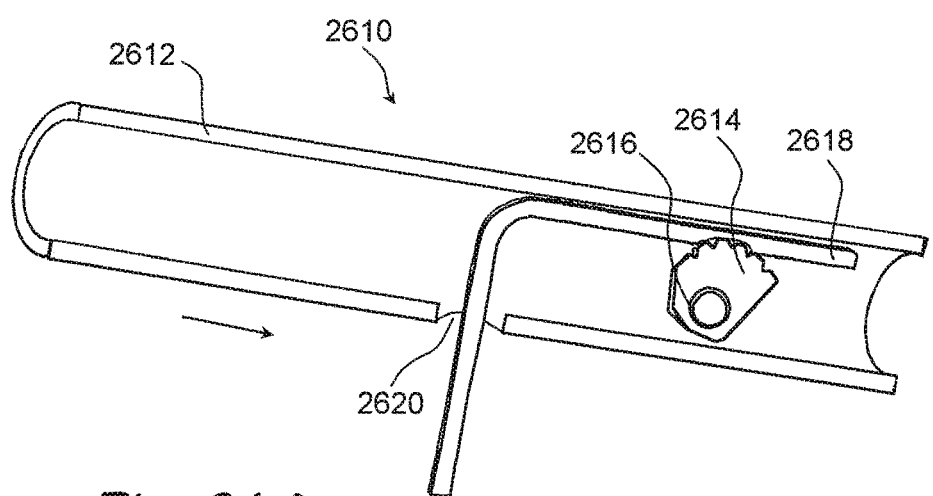
Fig. 26 D

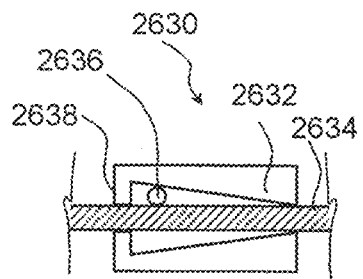
Fig. 26 E
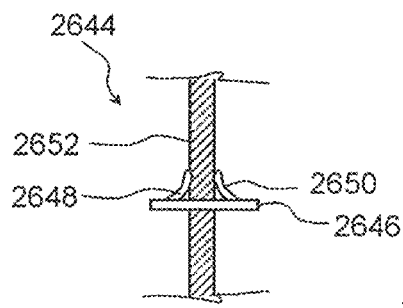
Fig. 26 F
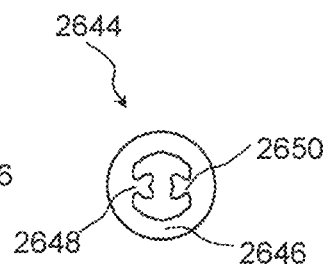
Fig. 26 G
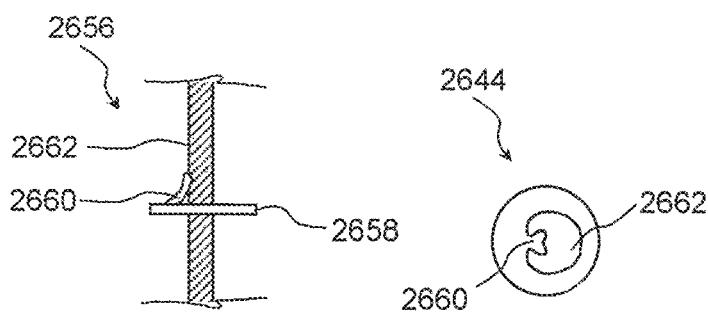
Fig. 26 H  Fig. 26 I  Fig. 26 J
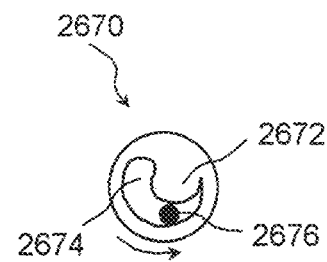
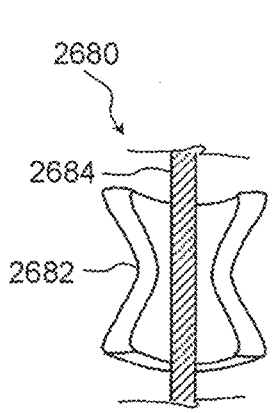
Fig. 26 K
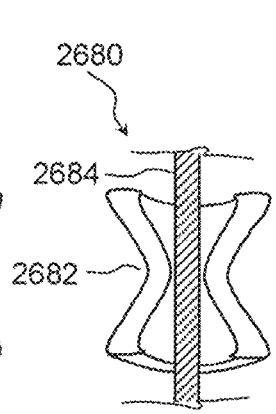
Fig. 26 L
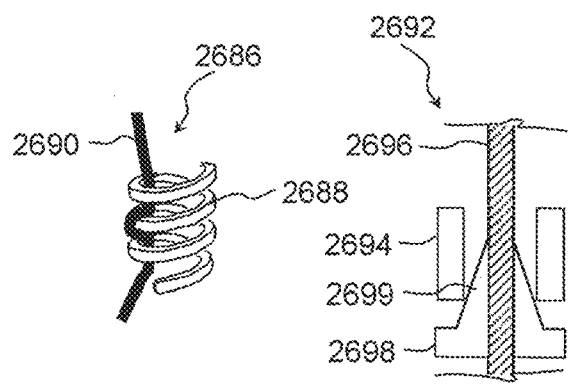
Fig. 26 M  Fig. 26 N

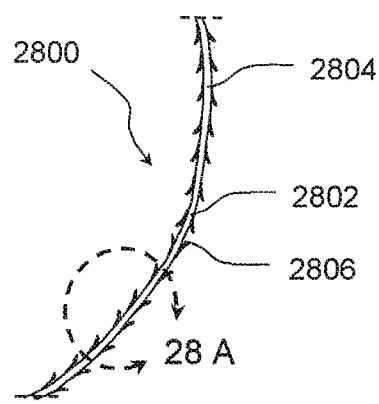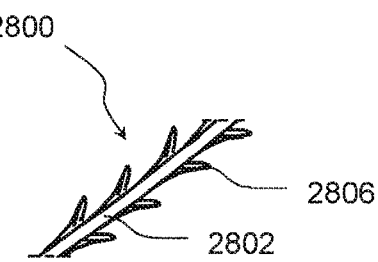
Fig. 28  Fig. 28 A
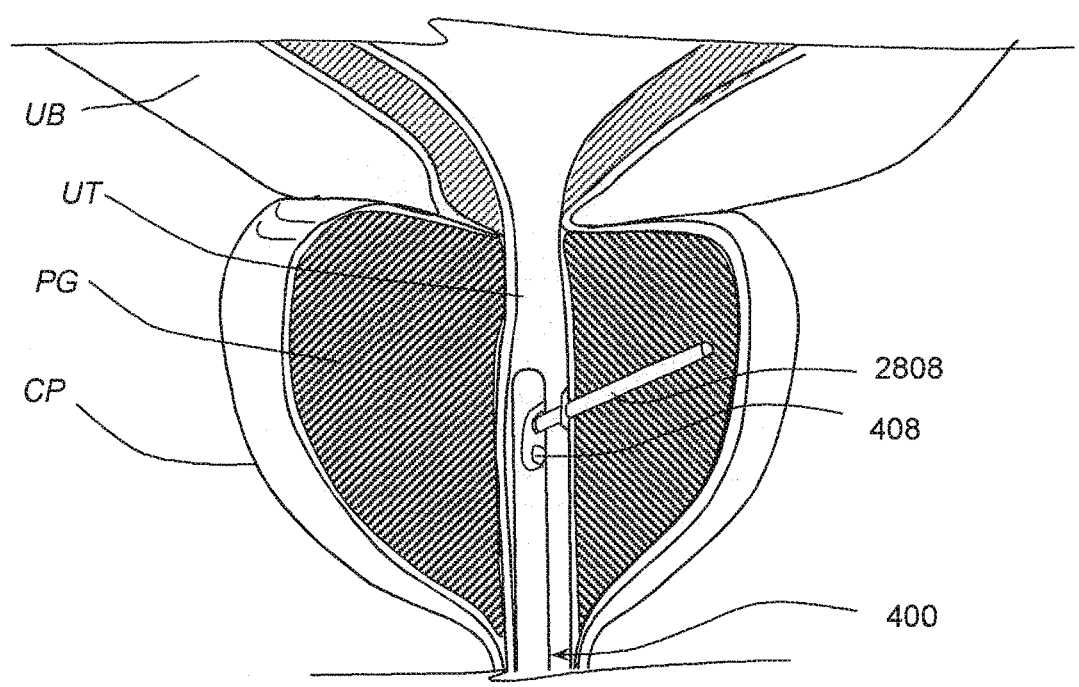
Fig. 28 B

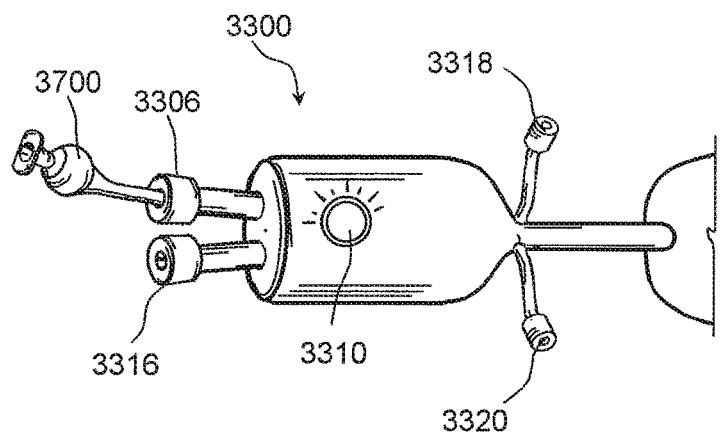
Fig. 37 C'
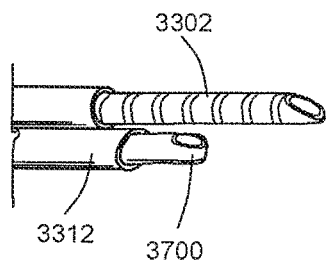
Fig. 37 C"
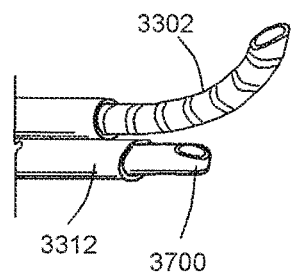
Fig. 37 C'''

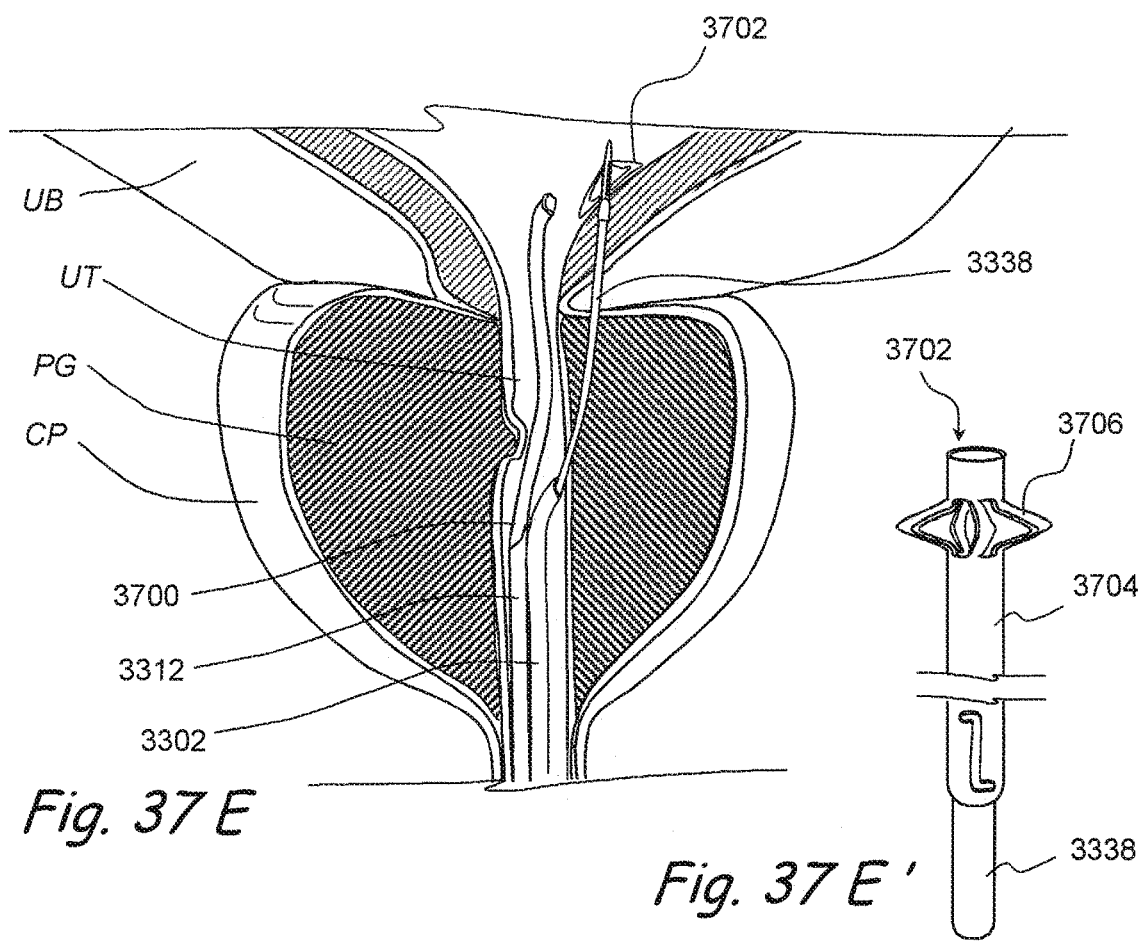
Fig. 37 E
Fig. 37 E'
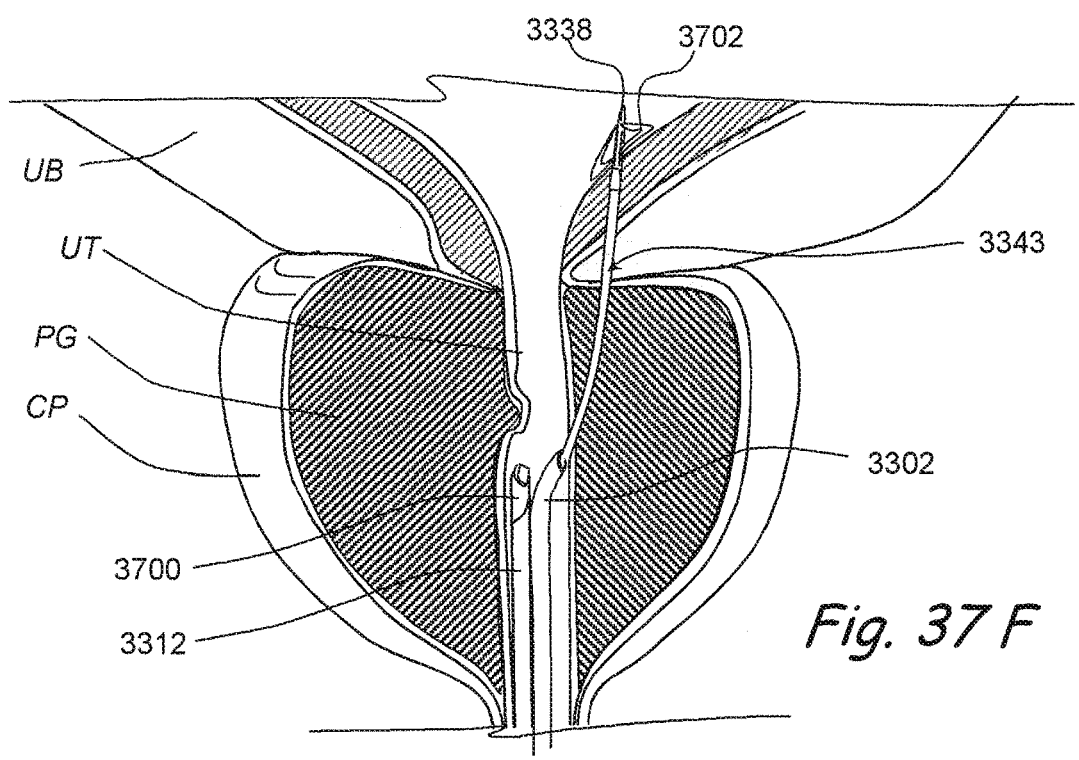
Fig. 37 F

DEVICES, SYSTEMS AND METHODS FOR TREATING BENIGN PROSTATIC HYPERPLASIA AND OTHER CONDITIONS

CROSS REFERENCE TO RELATED APPLICATIONS

This application is a continuation of U.S. patent application Ser. No. 16/107,447 filed Aug. 21, 2018, which is a continuation of U.S. patent application Ser. No. 14/535,266 filed Nov. 6, 2014, now U.S. Pat. No. 10,105,132, which is a continuation of U.S. patent application Ser. No. 13/844,020, filed Mar. 15, 2013, now U.S. Pat. No. 8,900,252, which is a continuation of U.S. patent application Ser. No. 13/073,763 filed Mar. 28, 2011, now U.S. Pat. No. 8,734,468, which is a division of U.S. patent application Ser. No. 11/838,036 filed Aug. 13, 2007, now U.S. Pat. No. 7,914,542, which is a division of U.S. patent application Ser. No. 11/134,870, filed May 20, 2005, now U.S. Pat. No. 7,758,594, the entire disclosures of each of which are expressly incorporated herein by reference.

FIELD OF THE INVENTION

The present invention relates generally to medical devices and methods and more particularly to devices, systems and methods for treating conditions wherein a tissue (e.g., the prostate gland) has a) become enlarged and/or b) undergone a change in form, position, structure, rigidity or force exertion with respect to another anatomical structure and/or c) has begun to impinge upon or compress an adjacent anatomical structure (e.g., the urethra).

BACKGROUND OF THE INVENTION

There are numerous pathological and nonpathological conditions in which a tissue (e.g., a gland, tumor, cyst, muscle, fascia, skin, adipose, mucous membrane, etc.) becomes enlarged, changed form or position and/or causes unwanted impingement, obstruction, occlusion, stretching, sagging, caving, expulsion and/or collapse of an adjacent body lumen or anatomical structure (e.g., the urethra). Examples of specific conditions which illustrate these medical problems include tissue relaxation or collapse (loose skin, fat or muscle folds, vaginal, rectal, or bladder prolapse, incontinence, etc.), tissue remodeling (scar formation, bladder stiffness secondary to chronic overexertion, infiltrative lung disease), traumatic injury, surgical manipulation (i.e. removal of supportive tissues, removal of tumors, reattachment of ligaments, etc.), tissue growth or enlargement (i.e. benign growths, cancers, angiomas, bone spurs, etc.), luminal obstruction or occlusion (coronary artery disease, peripheral vascular disease, stroke, non-communicating hydrocephalus, infertility secondary to non-patent fallopian tubes, urinary tract obstruction, etc.), tissue impingement (slipped spinal disks, degenerative joint disease, etc.), and ptosis.

In particular, Benign Prostatic Hyperplasia (BPH) is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner region of the prostate gland to squeeze the urethra. This compression of the urethra increases resistance to urine flow through the region of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Medications for treating BPH symptoms include phytotherapy and prescription medications. In phytotherapy, plant products such as Saw Palmetto, African Pygeum, *Serenoa repens* (sago palm) and South African star grass are administered to the patient. Prescription medications are prescribed as first line therapy in patients with symptoms that are interfering with their daily activities. Two main classes of prescription medications are alpha-1a-adrenergic receptors blockers and 5-alpha-reductase inhibitors. Alpha-1a-adrenergic receptors blockers block that activity of alpha-1a-adrenergic receptors that are responsible for causing constriction of smooth muscle cells in the prostate. Thus, blocking the activity of alpha-1a-adrenergic receptors causes prostatic smooth muscle relaxation. This in turn reduces urethral resistance thereby reducing the severity of the symptoms. 5-alpha-reductase inhibitors block the conversion of testosterone to dihydrotestosterone. Dihydrotestosterone causes growth of epithelial cells in the prostate gland. Thus 5-alpha-reductase inhibitors cause regression of epithelial cells in the prostate gland and hence reduce the volume of the prostate gland which in turn reduces the severity of the symptoms.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Transurethal Resection of Prostate (TURP) is the most commonly practiced surgical procedure implemented for the treatment of BPH. In this procedure, prostatic urethral obstruction is reduced by removing most of the prostatic urethra and a sizeable volume of the surrounding prostate gland. This is carried out under general or spinal anesthesia. In this procedure, a urologist visualizes the urethra by inserting a resectoscope, that houses an optical lens in communication with a video camera, into the urethra such that the distal region of the resectoscope is in the region of the urethra surrounded by the prostate gland. The distal region of the resectoscope consists of an electric cutting loop that can cut prostatic tissue when an electric current is applied to the device. An electric return pad is placed on the patient to close the cutting circuit. The electric cutting loop is used to scrape away tissue from the inside of the prostate gland. The tissue that is scraped away is flushed out of the urinary system using an irrigation fluid. Using a coagulation energy setting, the loop is also used to cauterize transected vessels during the operation.

Another example of a surgical procedure for treating BPH symptoms is Transurethral Electrovaporization of the Prostate (TVP). In this procedure, a part of prostatic tissue squeezing the urethra is desiccated or vaporized. This is carried out under general or spinal anesthesia. In this procedure, a resectoscope is inserted transurethrally such that the distal region of the resectoscope is in the region of the urethra surrounded by the prostate gland. The distal region of the resectoscope consists of a rollerball or a grooved roller electrode. A controlled amount of electric current is passed through the electrode. The surrounding tissue is rapidly heated up and vaporized to create a vaporized space. Thus the region of urethra that is blocked by the surrounding prostate gland is opened up.

Another example of a surgical procedure for treating BPH symptoms is Transurethral Incision of the Prostate (TUIP). In this procedure, the resistance to urine flow is reduced by making one or more incisions in the prostate gland in the region where the urethra meets the urinary bladder. This procedure is performed under general or spinal anesthesia. In this procedure, one or more incisions are made in the muscle of the bladder neck, which is the region where the urethra meets the urinary bladder. The incisions are in most cases are deep enough to cut the surrounding prostate gland tissue including the prostatic capsule. This releases any compression on the bladder neck and causes the bladder neck to spring apart. The incisions can be made using a resectoscope, laser beam etc.

Another example of a surgical procedure for treating BPH symptoms is Laser Prostatectomy. Two common techniques used for Laser Prostatectomy are Visual Laser Ablation of the Prostate (VLAP) and the Holmium Laser Resection/Enucleation of the Prostate (HoLEP). In VLAP, a neodymium:yttrium-aluminum-garnet (Nd:YAG) laser is used to ablate tissue by causing coagulation necrosis. The procedure is performed under visual guidance. In HoLEP, a holmium: Yttrium-aluminum-garnet laser is used for direct contact ablation of tissue. Both these techniques are used to remove tissue obstructing the urethral passage to reduce the severity of BPH symptoms.

Another example of a surgical procedure for treating BPH symptoms is Photoselective Vaporization of the Prostate (PVP). In this procedure, laser energy is used to vaporize prostatic tissue to relieve obstruction to urine flow in the urethra. The type of laser used is the Potassium-Titanyl-Phosphate (KTP) laser. The wavelength of this laser is highly absorbed by oxyhemoglobin. This laser vaporizes cellular water and hence is used to remove tissue that is obstructing the urethra.

Another example of a surgical procedure for treating BPH symptoms is Open Prostatectomy. In this procedure, the prostate gland is surgically removed by an open surgery. This is done under general anesthesia. The prostate gland is removed through an incision in the lower abdomen or the perineum. The procedure is used mostly in patients that have a large (greater than approximately 100 grams) prostate gland.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

In Transurethral Microwave Thermotherapy (TUMT), microwave energy is used to generate heat that destroys hyperplastic prostate tissue. This procedure is performed under local anesthesia. In this procedure, a microwave antenna is inserted in the urethra. A rectal thermosensing unit is inserted into the rectum to measure rectal temperature. Rectal temperature measurements are used to prevent overheating of the anatomical region. The microwave antenna is then used to deliver microwaves to lateral lobes of the prostate gland. The microwaves are absorbed as they pass through prostate tissue. This generates heat which in turn destroys the prostate tissue. The destruction of prostate tissue reduces the degree of squeezing of the urethra by the prostate gland thus reducing the severity of BPH symptoms.

Another example of a minimally invasive procedure for treating BPH symptoms is Transurethral Needle Ablation (TUNA). In this procedure, heat induced coagulation necrosis of prostate tissue regions causes the prostate gland to shrink. It is performed using local anesthetic and intravenous or oral sedation. In this procedure, a delivery catheter is inserted into the urethra. The delivery catheter comprises two radiofrequency needles that emerge at an angle of 90 degrees from the delivery catheter. The two radiofrequency needles are aligned are at an angle of 40 degrees to each other so that they penetrate the lateral lobes of the prostate. A radiofrequency current is delivered through the radiofrequency needles to heat the tissue of the lateral lobes to 70-100 degree Celsius at a radiofrequency power of approximately 456 KHz for approximately 4 minutes per lesion. This creates coagulation defects in the lateral lobes. The coagulation defects cause shrinkage of prostatic tissue which in turn reduces the degree of squeezing of the urethra by the prostate gland thus reducing the severity of BPH symptoms.

Another example of a minimally invasive procedure for treating BPH symptoms is Interstitial Laser Coagulation (ILC). In this procedure, laser induced necrosis of prostate tissue regions causes the prostate gland to shrink. It is performed using regional anesthesia, spinal or epidural anesthesia or local anesthesia (periprostatic block). In this procedure, a cystoscope sheath is inserted into the urethra and the region of the urethra surrounded by the prostate gland is inspected. A laser fiber is inserted into the urethra. The laser fiber has a sharp distal tip to facilitate the penetration of the laser scope into prostatic tissue. The distal tip of the laser fiber has a distal-diffusing region that distributes laser energy 360.degree. along the terminal 3 mm of the laser fiber. The distal tip is inserted into the middle lobe of the prostate gland and laser energy is delivered through the distal tip for a desired time. This heats the middle lobe and causes laser induced necrosis of the tissue around the distal tip. Thereafter, the distal tip is withdrawn from the middle lobe. The same procedure of inserting the distal tip into a lobe and delivering laser energy is repeated with the lateral lobes. This causes tissue necrosis in several regions of the prostate gland which in turn causes the prostate gland to shrink. Shrinkage of the prostate gland reduces the degree of squeezing of the urethra by the prostate thus reducing the severity of BPH symptoms.

Another example of a minimally invasive procedure for treating BPH symptoms is implanting Prostatic Stents. In this procedure, the region of urethra surrounded by the prostate is mechanically supported to reduce the constriction caused by an enlarged prostate. Prostatic stents are flexible devices that are expanded after their insertion in the urethra. They mechanically support the urethra by pushing the obstructing prostatic tissue away from the urethra. This reduces the constriction of the urethra and improves urine flow past the prostate gland thereby reducing the severity of BPH symptoms.

Although existing treatments provide some relief to the patient from symptoms of BPH, they have significant disadvantages. Alpha-1a-adrenergic receptors blockers have side effects such as dizziness, postural hypotension, lightheadedness, asthenia and nasal stuffiness. Retrograde ejaculation can also occur. 5-alpha-reductase inhibitors have minimal side effects, but only a modest effect on BPH symptoms and the flow rate of urine. In addition, anti-androgens, such as 5-alpha-reductase, require months of therapy before LUTS improvements are observed. Surgical treatments of BPH carry a risk of complications including erectile dysfunction; retrograde ejaculation; urinary incontinence; complications related to anesthesia; damage to the penis or urethra, need for a repeat surgery etc. Even TURP, which is the gold standard in treatment of BPH, carries a high risk of complications. Adverse events associated with this procedure are reported to include retrograde ejaculation (65% of patients), post-operative irritation (15%), erectile dysfunction (10%), need for transfusion (8%), bladder neck constriction (7%), infection (6%), significant hematuria (6%), acute urinary retention (5%), need for secondary procedure (5%), and incontinence (3%) Typical recovery from TURP involves several days of inpatient hospital treatment with an indwelling urethral catheter, followed by several weeks in which obstructive symptoms are relieved but there is pain or discomfort during micturition.

The reduction in the symptom score after minimally invasive procedures is not as large as the reduction in symptom score after TURP. Up to 25% of patients who receive these minimally invasive procedures ultimately undergo a TURP within 2 years. The improvement in the symptom score generally does not occur immediately after the procedure. For example, it takes an average of one month for a patient to notice improvement in symptoms after TUMT and 1.5 months to notice improvement after ILC. In fact, symptoms are typically worse for these therapies that heat or cook tissue, because of the swelling and necrosis that occurs in the initial weeks following the procedures. Prostatic stents often offer more immediate relief from obstruction but are now rarely used because of high adverse effect rates. Stents have the risk of migration from the original implant site (up to 12.5% of patients), encrustation (up to 27.5%), incontinence (up to 3%), and recurrent pain and discomfort. In published studies, these adverse effects necessitated 8% to 47% of stents to be explanted. Overgrowth of tissue through the stent and complex stent geometries have made their removal quite difficult and invasive.

Thus the most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry a lower risk of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

Thus there remains a need for the development of new devices, systems and methods for treating BPH as well as other conditions in which one tissue or anatomical structure impinges upon or compresses another tissue or anatomical structure.

SUMMARY OF THE INVENTION

The present invention provides devices, systems and methods for compressing, cutting, incising, reconfiguring, remodeling, attaching, repositioning, supporting, dislocating or altering the composition of tissues or anatomical structures to alter their positional or force relationship to other tissues or anatomical structures. In some applications, the invention may be used to improve patency or fluid flow through a body lumen or cavity. Examples of body lumens through which flow may be facilitated using the present invention include the urethra, ureter, trachea, bronchus, bronchiole, other respiratory passageway, stomach, duodenum, small intestine, jejunum, illium, colon, cystic duct, hepatic duct, common bile duct, pancreatic duct, the alimentary canal, an endocrine passageway, a lymphatic, etc. Examples of tissues and anatomical structures that may be compressed, cut, incised, reconfigured, remodeled, attached, repositioned, supported, dislocated or compositionally altered by the present invention include the prostate gland, other glands and organs, neoplasms, benign growths, cancerous growths, tumors, cysts, other masses, congenital deformities, structures that have become enlarged due to hypertrophy, hyperplasia, edema, fluid build up, fluid retention, excess fluid production, impeded fluid outflow, etc.

In accordance with the invention there are provided devices, systems and methods for implanting devices within the body to compress tissue in a manner that relieves pressure exerted on or interference with an adjacent anatomical structure. The implantable devices useable for this purpose generally comprising anchoring elements and tensioning elements that extend between the anchoring elements. The anchoring elements are implanted at selected locations and the tensioning elements then draw or pull the anchoring elements toward one another, thereby compressing tissue between the anchoring elements. In applications where these devices are implanted to treat prostatic enlargement, anchoring and tensioning element(s) are implanted and tensioned to compress or reposition prostatic tissue thereby lessening prostate induced constriction of the urethra. In at least some applications, this invention may be used to treat prostatic enlargement without causing substantial damage to the urethra (e.g., forming an opening in the urethra no larger than about 2 mm in its greatest cross-dimension). As used herein, the term "compress" includes not only actual compression of the tissue but also any application of pressure or force upon the tissue that causes the intended therapeutic effect by reconfiguring, remodeling, repositioning or altering the tissue.

Still further in accordance with the invention there are provided devices, systems and methods for cutting tissue(s) of the body in a manner that relieves pressure exerted on or interference with an adjacent anatomical structure. In some applications of the invention, one or more working devices may be inserted into the body and used to incise the capsule of an encapsulated organ, tumor, mass or other structure, thereby relieving the capsule's constraint of the encapsulated organ, tumor, mass or other structure and allowing the encapsulated organ, tumor, mass or other structure to expand, herniate, evulse, splay, spread apart, reconfigure or move in a way that results in decreased pressure on, or decreased interference with, the adjacent anatomical structure. In applications where the invention is used to treat prostatic enlargement, a cutting device may be anchoring and tensioning element(s) are implanted and tensioned to compress or reposition prostatic tissue thereby lessening prostate induced constriction of the urethra.

Additional and more specific aspects, elements, steps, applications, embodiments and examples of the invention will be understood by those of skill in the art upon reading of the detailed description and claims set forth herebelow.

BRIEF DESCRIPTION OF THE DRAWINGS

FIG. 3A shows the perspective view of an introducer device.

FIG. 3B shows a perspective view of an injecting needle that may be used for injecting one or more diagnostic or therapeutic agents in the anatomy.

FIG. 3C shows a perspective view of an introducing sheath.

FIG. 3D shows a perspective view of a trocar.

FIG. 3E shows a perspective view of an anchor delivery device.

FIG. 3F shows an enlarged view of the distal region of the device in FIG. 3E.

FIG. 3G shows a perspective view of deployed anchors showing radially expanded splayable arms of proximal anchor and distal anchor.

FIG. 3H shows a perspective view from the proximal direction of a particular embodiment of the attachment mechanism of FIG. 99E.

FIG. 4A shows a first step of a method of treating prostate gland disorders.

FIG. 4B shows a second step of a method of treating prostate gland disorders.

FIG. 4C shows a third step of a method of treating prostate gland disorders.

FIG. 4D shows a fourth step of a method of treating prostate gland disorders.

FIG. 4E shows a fifth step of a method of treating prostate gland disorders.

FIG. 4F shows a sixth step of a method of treating prostate gland disorders.

FIG. 4G shows a seventh step of a method of treating prostate gland disorders.

FIG. 4H shows an eighth step of a method of treating prostate gland disorders.

FIGS. 4G' through 4H' show the final steps of an embodiment of method of treating prostate gland disorders by deploying a proximal anchor in the urethra.

FIG. 4H" shows a coronal section through the prostate gland showing a final deployed configuration of an embodiment of bone anchoring devices for treating prostate gland disorders by compressing a region of the prostate gland.

FIG. 5A shows a perspective view of a tension element comprising a single strand of an untwisted material.

FIG. 5B shows a perspective view of a tension element comprising one or more serrations or notches.

FIG. 5C shows a perspective view of a tension element comprising multiple filaments of a material twisted together.

FIG. 5D shows a perspective view of a tension element comprising a flexible, elastic, spiral or spring element.

FIG. 5E shows a perspective view of a tension element comprising a screw threading on the outer surface of tension element.

FIG. 5F shows a perspective view of a tension element comprising a hollow shaft comprising one or more collapsible regions.

FIG. 5G shows a perspective view of an anchoring device 522 comprising a tension element and two anchors.

FIG. 5H shows a perspective view of a tensioning element device comprising a detachable region.

FIG. 5I shows a perspective view of a tensioning element comprising telescoping tubes.

FIGS. 6A through 11A show various examples of anchor designs and/or anchoring device designs.

FIGS. 6A and 6B show perspective views of two states of a crumpling anchor.

FIGS. 7A and 7B show sectional views of an undeployed configuration and a deployed configuration respectively of a deployable anchor.

FIGS. 8A and 8B show sectional views of an undeployed configuration and a deployed configuration respectively of a "T" shaped deployable anchor.

FIG. 9A shows a first alternative configuration of the anchor arms.

FIG. 9B shows a second alternative configuration of the anchor arms.

FIG. 9C shows a third alternative configuration of the anchor arms.

FIG. 9D shows a fourth alternative configuration of the anchor arms.

FIG. 10D shows a perspective view of an embodiment of an anchoring device comprising an outer ring.

FIG. 10E shows a partial perspective view of an anchoring device comprising a hemostatic element.

FIG. 11A shows a perspective view of a device having a set of anchors comprising a curved sheet.

FIGS. 12A through 17I show further examples of anchor designs and/or anchoring device designs. FIG. 12A shows a perspective view of an anchor comprising an arrowhead.

FIG. 12B shows a crossectional view of an anchor comprising a cup-shaped element that encloses a cavity.

FIG. 12C shows a perspective view of an anchor comprising a screw.

FIGS. 13A and 13B show perspective views of an uncollapsed state and a collapsed state respectively of an anchor comprising a collapsible region.

FIGS. 13C and 13D show perspective views of an undeployed state and a deployed state respectively of an anchor comprising radially spreading arms.

FIG. 13E shows perspective views of an alternate embodiment of an undeployed state of an anchor comprising radially spreading arms.

FIGS. 14A and 14B show perspective views of anchoring devices comprising an adhesive delivering element.

FIGS. 15A and 15B show two configurations of an anchoring device comprising a ratcheted tension element.

FIG. 16 shows a perspective view of an anchor comprising a trocar lumen.

FIGS. 17F and 17G show perspective views of an undeployed and deployed configuration of an anchor comprising a stent.

FIGS. 17H and 17I show perspective views of an undeployed and deployed configuration of an anchor comprising a spring.

FIGS. 18A through 22E show various embodiments of mechanisms to deploy one or more anchors. FIGS. 18A and 18B show a crossection of an anchor deploying mechanism comprising a screw system.

FIGS. 19A and 19B show a crossectional view of an anchor deploying system comprising an electrolytic detachment element.

FIG. 20 shows a perspective view of an anchor deploying system comprising a looped ribbon.

FIG. 21A shows a crossectional view of an anchor deploying system comprising a locked ball.

FIGS. 21B and 21C show a method of deploying an anchor comprising a locked ball.

FIGS. 22A through 22C show various views of an anchor deploying system comprising two interlocking cylinders.

FIG. 22A shows a first view of an anchoring system.

FIG. 22B shows a second view of an anchoring system.

FIG. 22C shows a third view of an anchoring system.

FIGS. 22D and 22E show the steps of a method of unlocking the two interlocking cylinders from the anchor deploying systems of FIGS. 22A through 22C.

FIGS. 24A and 24A' show a first step of a method of compressing an anatomical region using a device with deploying arms deployed through a trocar.

FIG. 24C' shows a fourth step of a method of compressing an anatomical region using a device with deploying arms deployed through a trocar.

FIG. 25B shows a first step of a method of spreading anatomical region or regions.

FIG. 25C shows a second step of a method of spreading anatomical region or regions.

FIG. 25D shows a third step of a method of spreading anatomical region or regions.

FIG. 25E shows a fourth step of a method of spreading anatomical region or regions.

FIG. 25F shows a fifth step of a method of spreading anatomical region or regions.

FIG. 27A shows a first configuration of an anchoring device.

FIG. 27B shows a second configuration of an anchoring device.

FIG. 27C shows a third configuration of an anchoring device.

FIG. 27D shows a fourth configuration of an anchoring device.

FIGS. 28 and 28A show perspective views of an embodiment of an anchoring device comprising an elongate element comprising multiple barbs or anchors.

FIGS. 28B through 28E show a coronal section through the prostate gland showing various steps of a method of treating the prostate gland using the device of FIG. 28.

FIG. 28B shows a first step of a method of treating the prostate gland.

FIG. 28C shows a second step of a method of treating the prostate gland.

FIG. 28D shows a third step of a method of treating the prostate gland.

FIG. 28E shows a fourth step of a method of treating the prostate gland.

FIG. 29A shows an axial section of the prostate gland showing a pair of implanted magnetic anchors.

FIGS. 29B through 29D show a coronal section through the prostate gland showing the steps of a method of implanting magnetic anchors of FIG. 29A.

FIG. 29B shows a first step of a method of implanting.

FIG. 29C shows a second step of a method of implanting.

FIG. 29D shows a third step of a method of implanting.

FIG. 30A is a coronal sectional view of a portion of the male urogenital system showing a transurethral approach that may be used to perform a prostate cutting procedure of the present invention.

FIG. 30B is a coronal sectional view of a portion of the male urogenital system showing another transurethral approach that may be used to perform a prostate cutting procedure of the present invention.

FIG. 30C is a coronal sectional view of a portion of the male urogenital system showing a transurethral/transvesicular approach that may be used to perform a prostate cutting procedure of the present invention.

FIG. 30D is a coronal sectional view of a portion of the male urogenital system showing another transurethral approach that may be used to perform a prostate cutting procedure of the present invention, wherein a device advances from the urethra, through the prostate gland, and thereafter accesses the prostate capsule from its outer surface.

FIG. 31 is a coronal sectional view of a portion of the male urogenital system showing a percutaneous/infrapubic approach that may be used to perform a prostate cutting procedure of the present invention.

FIG. 32 is a coronal sectional view of a portion of the male urogenital system showing a percutaneous/transvesicular approach that may be used to perform a prostate cutting procedure of the present invention.

FIGS. 33A-33E shows perspective views of various devices that may be included in a system for performing a prostate cutting procedure in accordance with the present invention.

FIG. 33A shows a perspective view of an introducer device comprising a first tubular element having a working device lumen.

FIG. 33B shows a perspective view of an injecting needle that may be used for injecting one or more diagnostic or therapeutic substances.

FIG. 33C shows a perspective view of a guiding device comprising an elongate body comprising a sharp distal tip.

FIGS. 33D and 33D' show a perspective view of a RF cutting device in two different configurations.

FIG. 33E shows a perspective view of an embodiment of a plugging device to plug an opening created during a procedure.

FIGS. 33F through 33N show various alternate embodiments of the electrosurgical cutting device in FIG. 33D.

FIGS. 33F and 33G show perspective views of the distal region of a first alternate embodiment of an electrosurgical cutting device in the undeployed and deployed states respectively.

FIGS. 33H and 33I show perspective views of the distal region of a second alternate embodiment of an electrosurgical cutting device in the undeployed and deployed states respectively.

FIGS. 33J through 33L show perspective views of the distal region of a second alternate embodiment of an electrosurgical cutting device showing the steps of deploying the electrosurgical cutting device.

FIGS. 33M through 33N show perspective views of the distal region of a third alternate embodiment of an electrosurgical cutting device showing the steps of deploying the electrosurgical cutting device.

Figure 34:
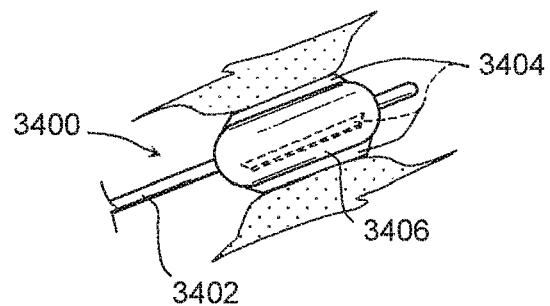

FIG. 34 shows a perspective view of the distal region of a balloon catheter comprising a balloon with cutting blades.

Figure 35:
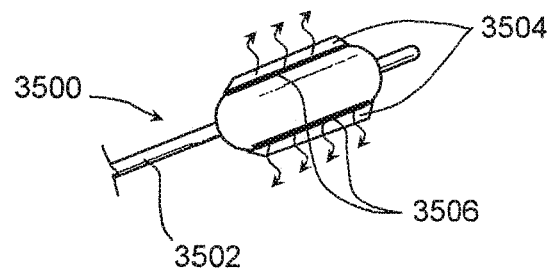

FIG. 35 shows a perspective view of the distal region of a balloon catheter comprising a balloon with cutting wires.

Figure 36:
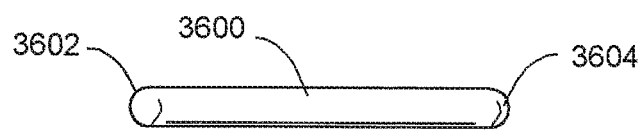
Figure 36:
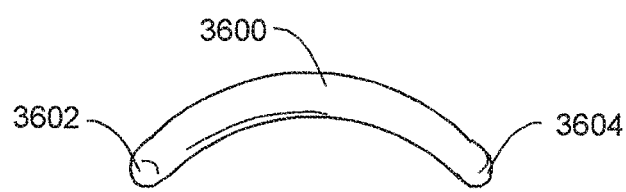
Figure 36:
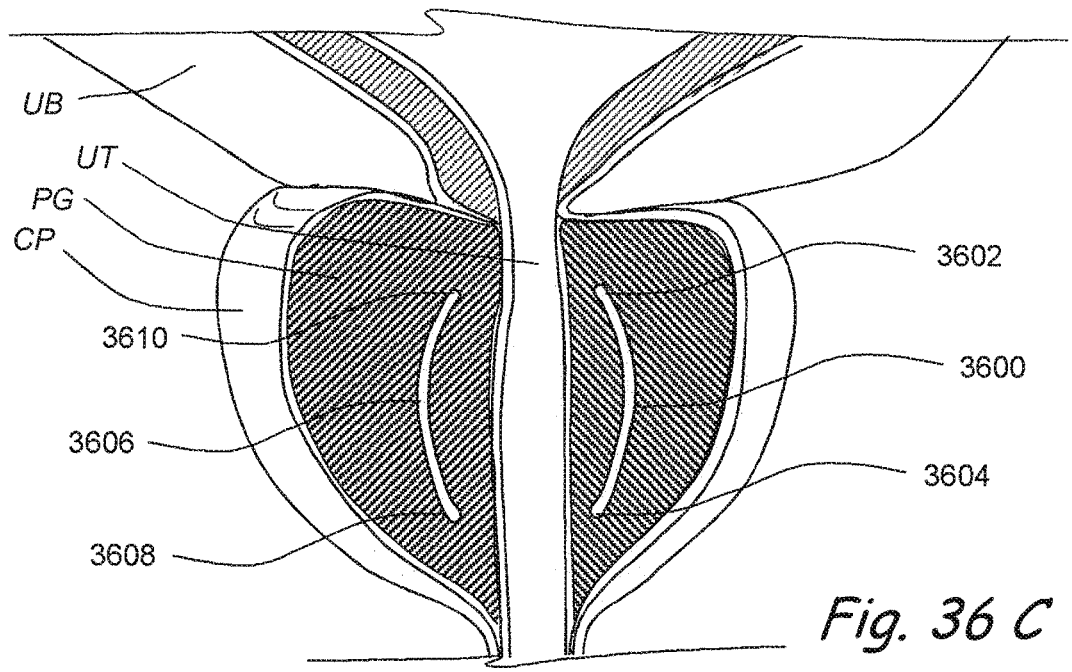
Figure 36:
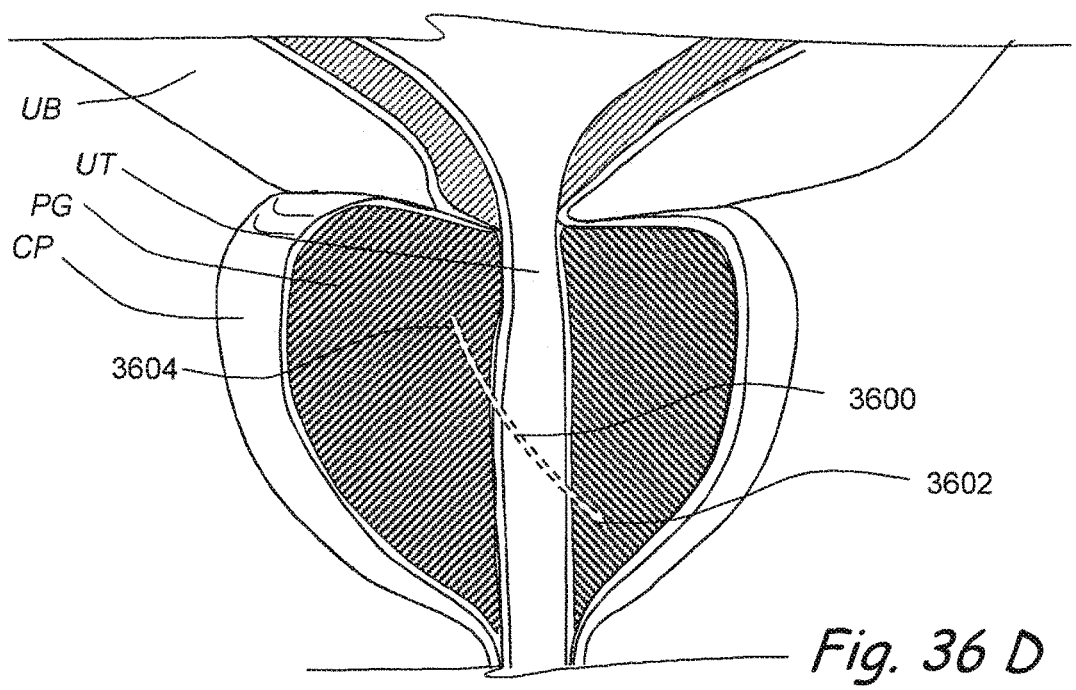
Figure 36:
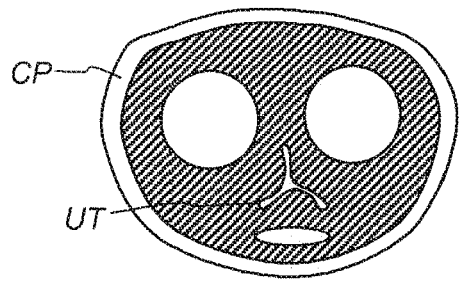
Figure 36:
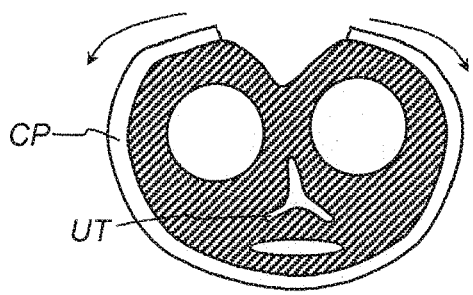
Figure 36:
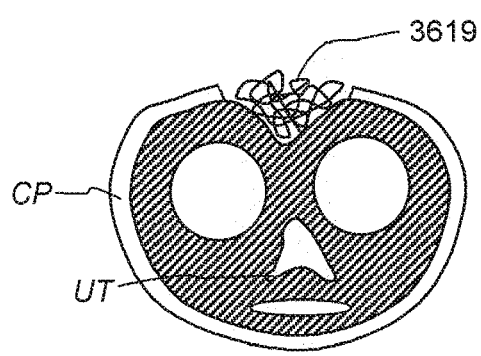
Figure 36:
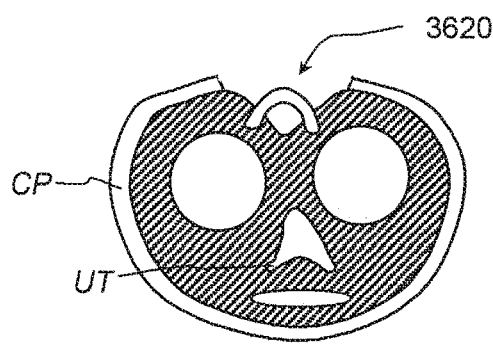

FIGS. 36A and 36B series show perspective views of an undeployed state and a deployed state respectively of a tissue displacement device.

FIGS. 36C and 36D show a coronal view and a lateral view respectively of a pair of deployed tissue displacement devices of FIGS. 36A and 36B implanted in the prostate gland.

FIGS. 36E through 36H show an axial section through a prostate gland showing the various steps of a method of cutting or puncturing the prostate gland and lining or plugging the cut or puncture.

FIG. 36E shows a first step of a method of cutting or puncturing.

FIG. 36F shows a second step of a method of cutting or puncturing.

FIG. 36G shows a third step of a method of cutting or puncturing.

FIG. 36H shows a fourth step of a method of cutting or puncturing.

FIGS. 37A through 37K show an embodiment of a method of treating prostate gland disorders by cutting a region of the prostate gland using the devices described in FIG. 33A through 33E.

Figure 37A:
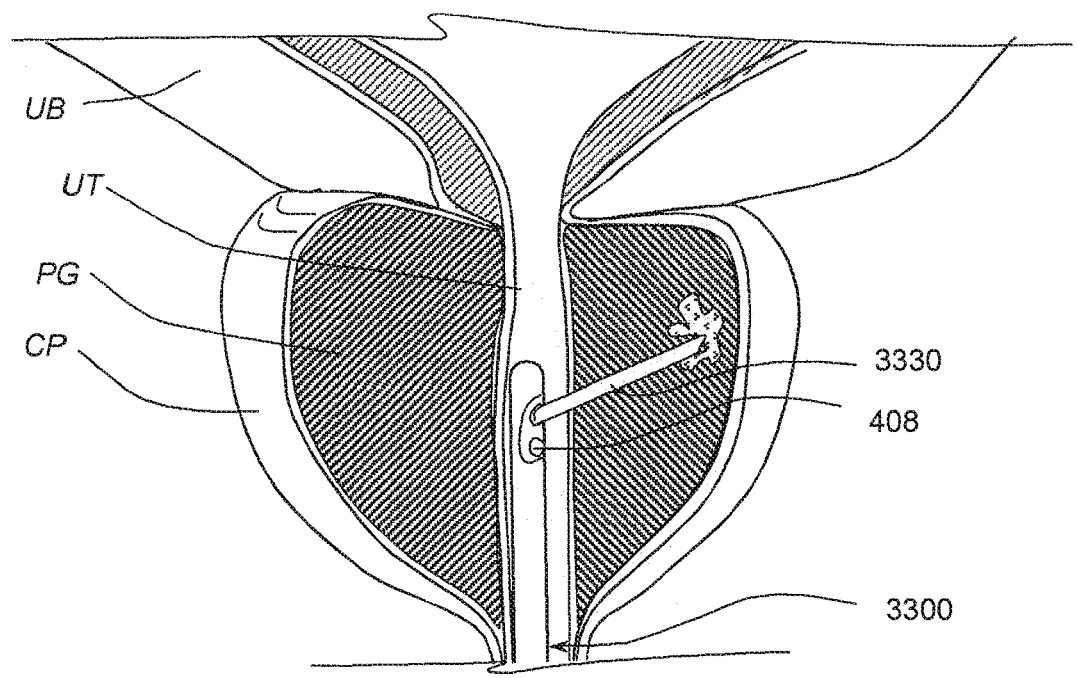

FIG. 37A shows a first step of a method of treating a prostate gland.

Figure 37B:
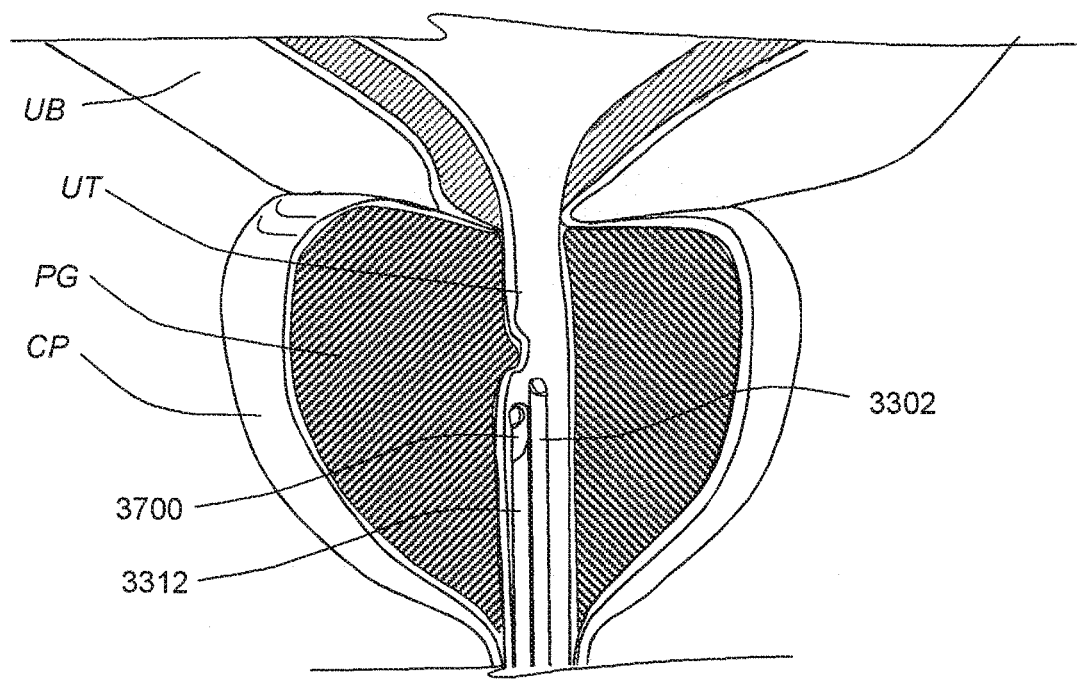

FIG. 37B shows a second step of a method of treating a prostate gland.

Figure 37C:
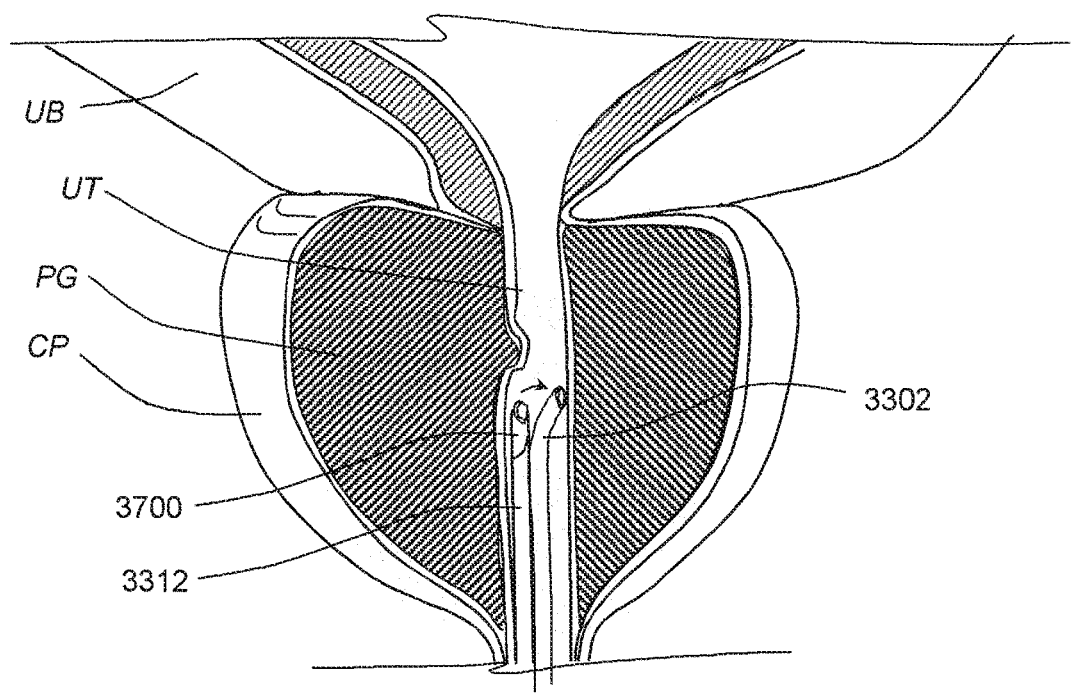

FIGS. 37C, 37C', 37C", and '37C'" show a third step of a method of treating a prostate gland.

Figure 37D:
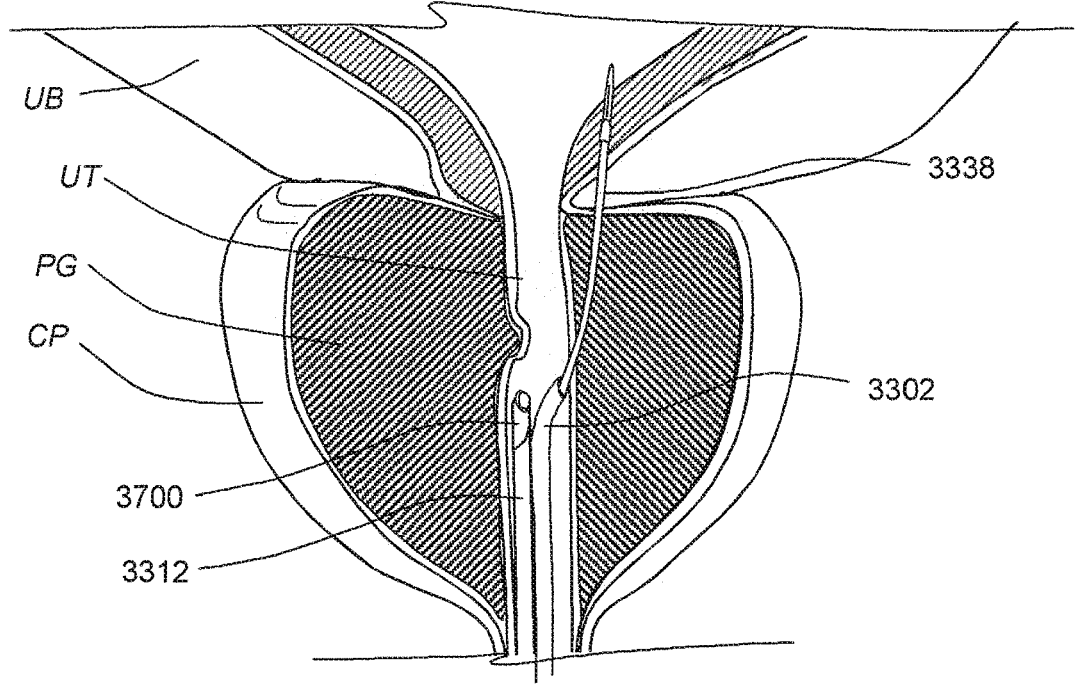

FIG. 37D shows a fourth step of a method of treating a prostate gland.

FIGS. 37E and 37E' show a fifth step of a method of treating a prostate gland.

FIG. 37F shows a sixth step of a method of treating a prostate gland.

Figure 37G:
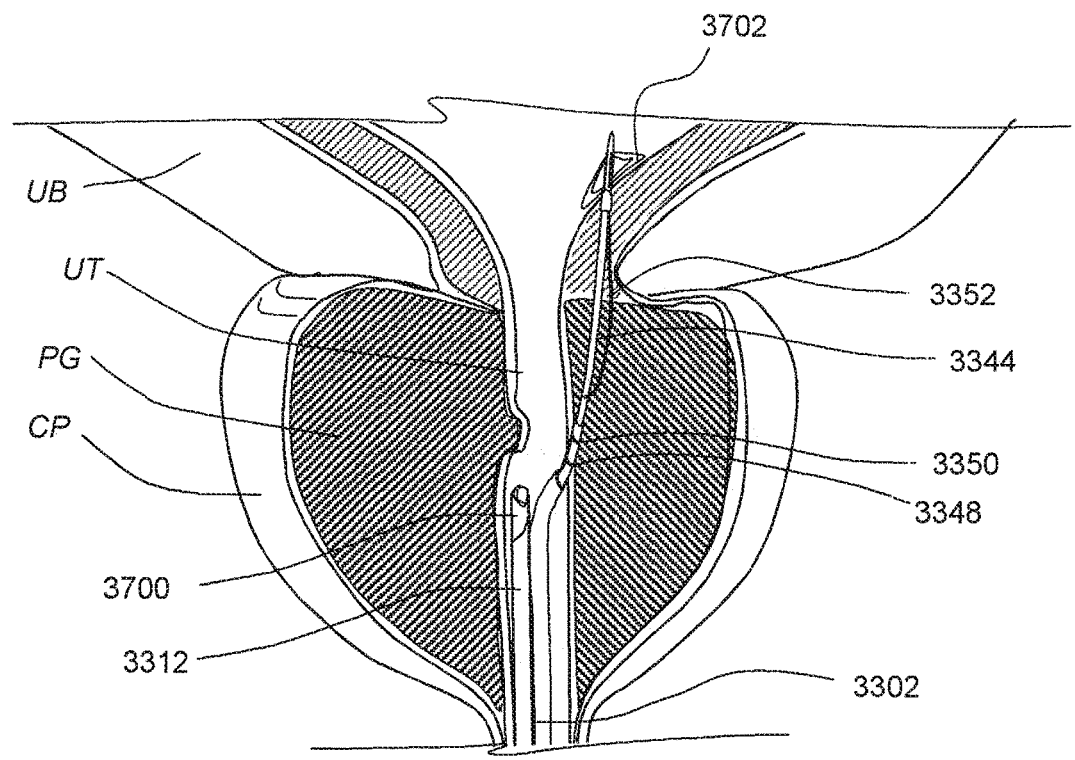

FIG. 37G shows a seventh step of a method of treating a prostate gland.

Figure 37H:
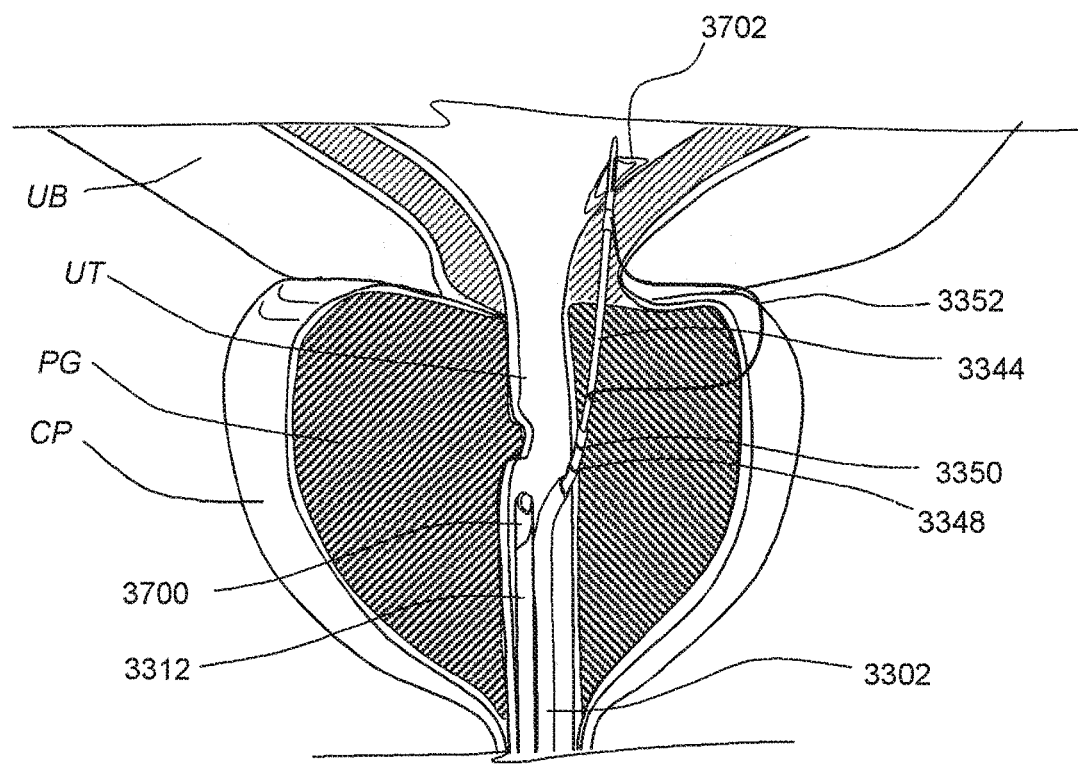
Figure 37:
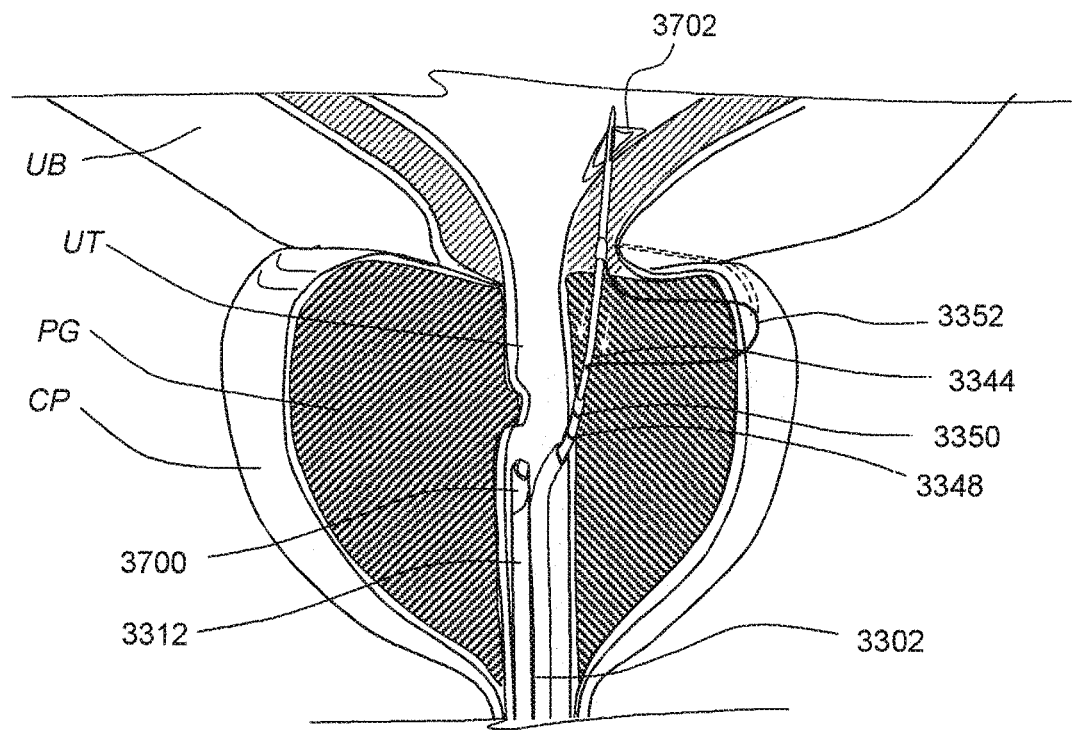
Figure 37:
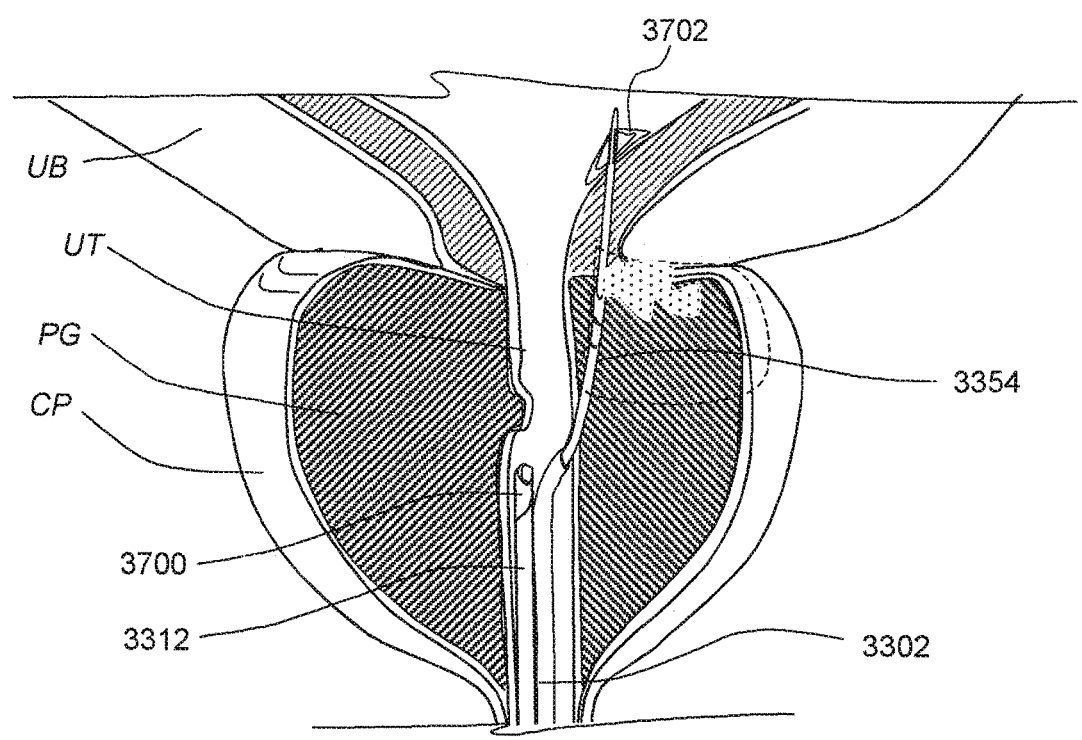

FIG. 37H shows an eighth step of a method of treating a prostate gland.

FIG. 37I shows a ninth step of a method of treating a prostate gland.

FIG. 37J shows a tenth step of a method of treating a prostate gland.

Figure 37K:
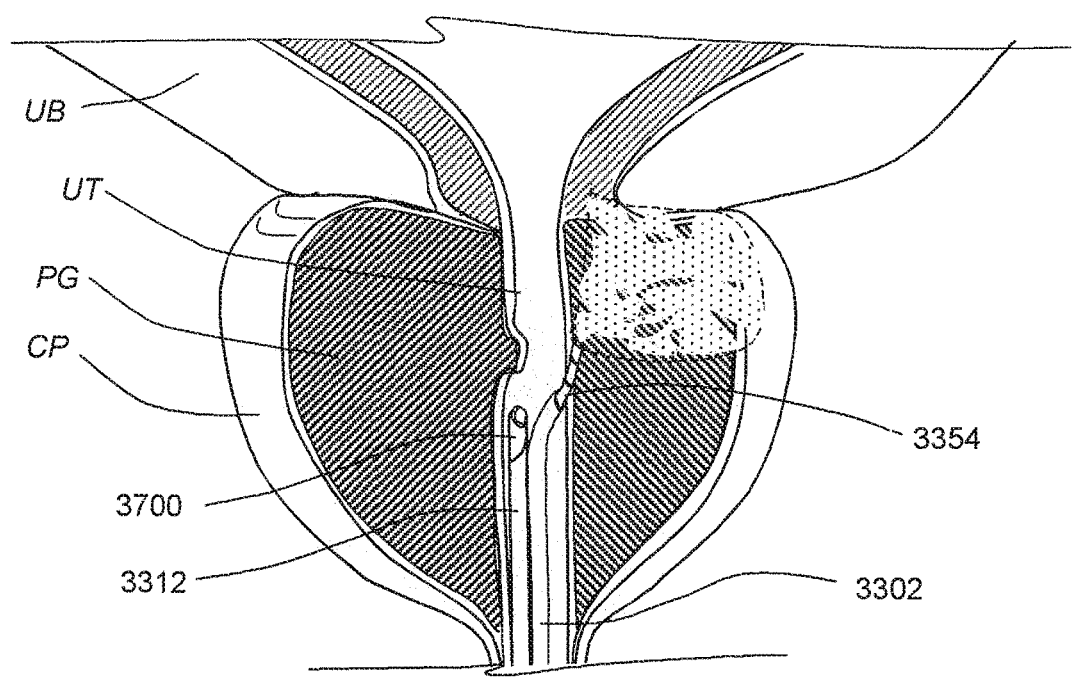

FIG. 37K shows an eleventh step of a method of treating a prostate gland.

Figure 38A:
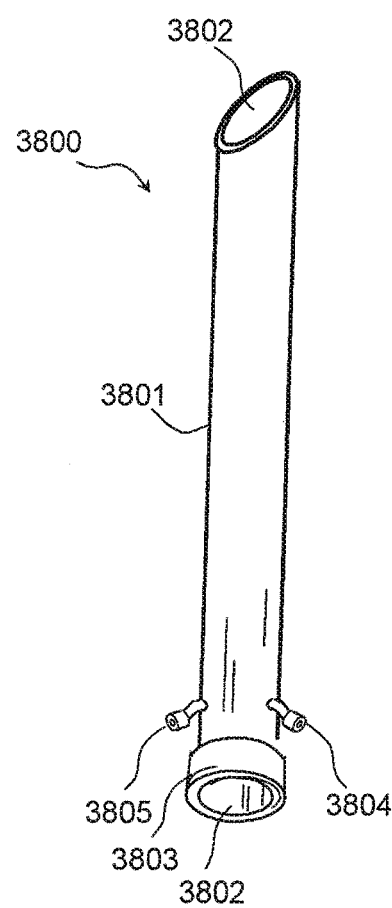
Figure 38:
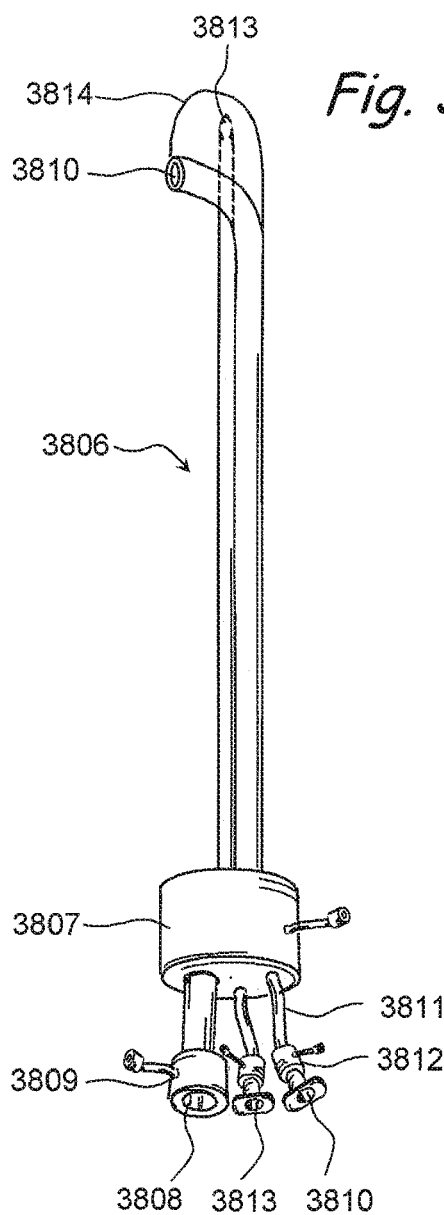
Figure 38:
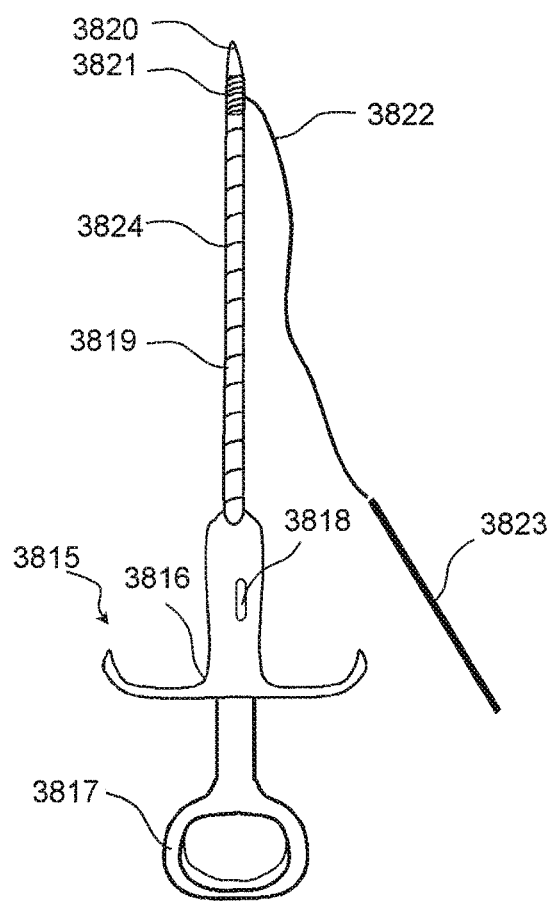
Figure 38:
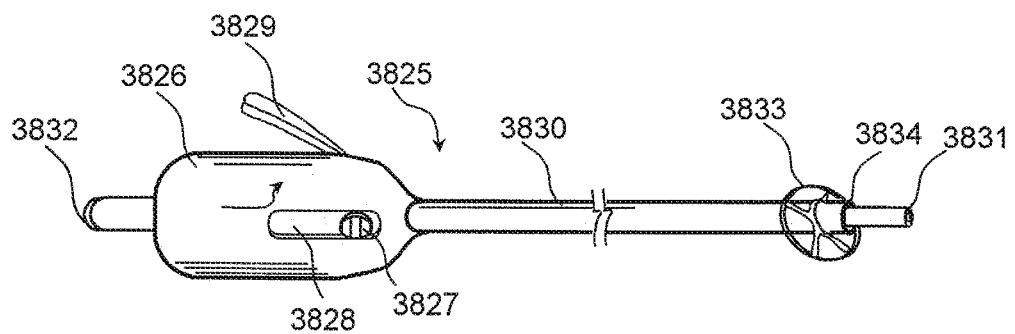
Figure 38:
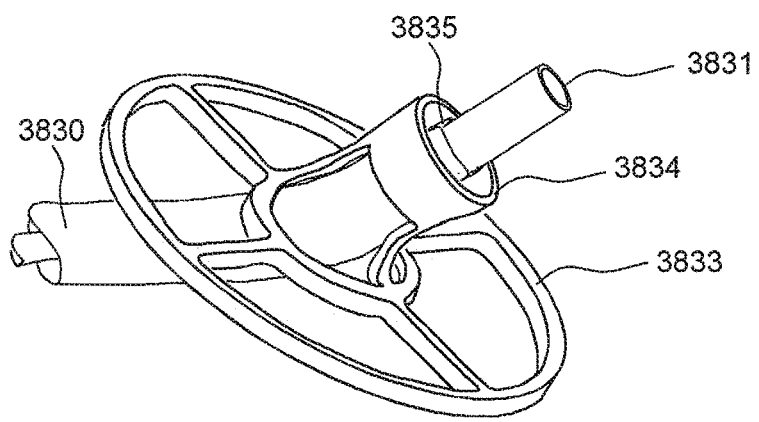

FIGS. 38A to 38D show various components of a kit for treating prostate gland disorders by compressing a region of the prostate gland. FIG. 38A shows the perspective view of an introducer device.

FIG. 38B shows a perspective view of a bridge device

FIG. 38C shows a perspective view of a distal anchor deployment device

FIG. 38D shows the proximal anchor delivery tool

FIG. 38E shows a close-up perspective view of proximal anchor 3833 mounted on proximal anchor delivery tool of FIG. 38D.

DETAILED DESCRIPTION

The following detailed description and the accompanying drawings are intended to describe some, but not necessarily all, examples or embodiments of the invention only and does not limit the scope of the invention in any way.

The following detailed description and the accompanying drawings are intended to describe some, but not necessarily all, examples or embodiments of the invention only and does not limit the scope of the invention in any way.

A number of the drawings in this patent application show anatomical structures of the male reproductive and/or urinary system. In general, these anatomical structures are labeled with the following reference letters:

TABLE 1

| | |
|---|---|
| Urethra | UT |
| Urethral Lumen | UL |
| Urethral Opening | UO |
| Urinary Bladder | UB |
| Ureters | UR |
| Prostate Gland | PG |
| Capsule of Prostate Gland | CP |
| Testis | TS |
| Vas Deferens | VD |

Figure 1:
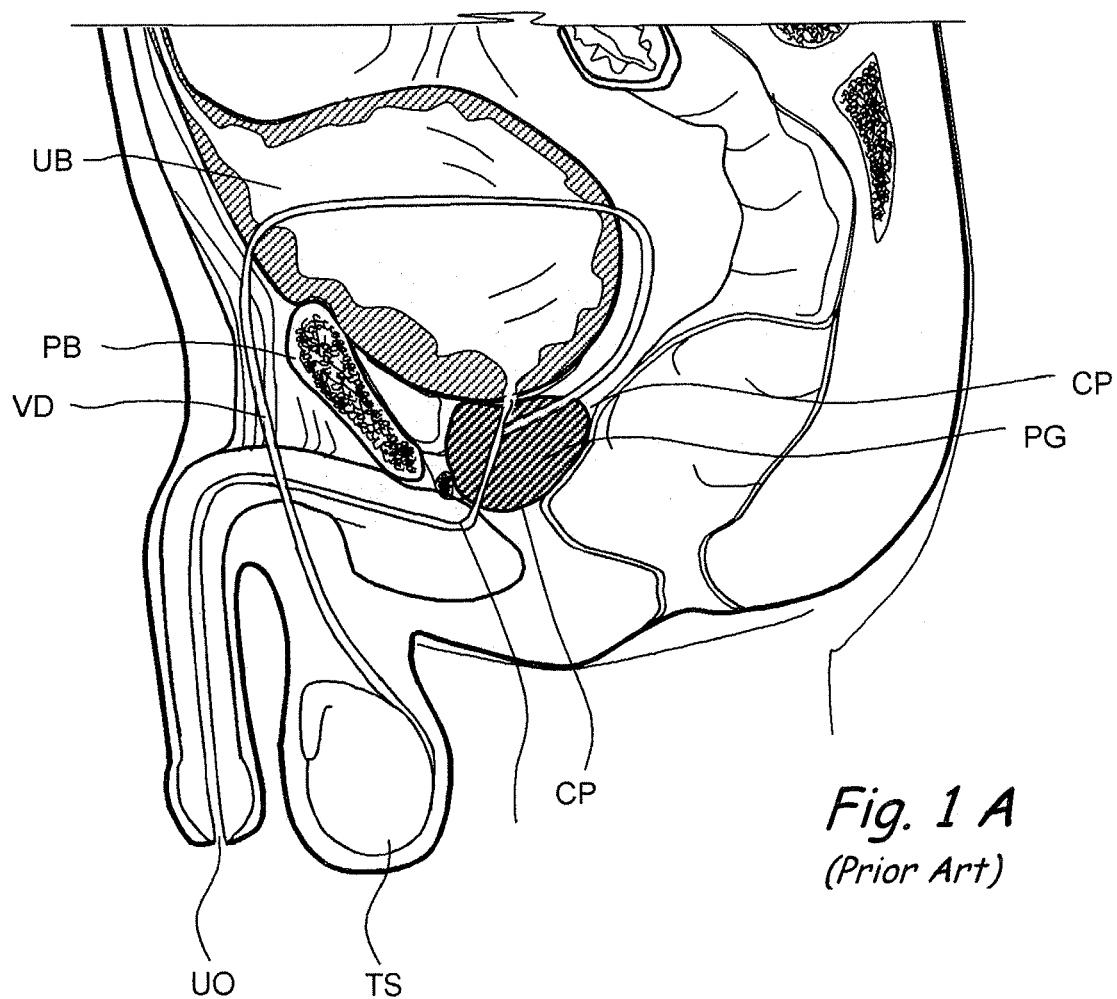
FIG. 1A is a sagittal sectional view of a male human body through the lower abdomen showing the male urinary tract.
FIG. 1B is a coronal sectional view through the lower abdomen of a human male showing a region of the male urogenital system.
Figure 1:
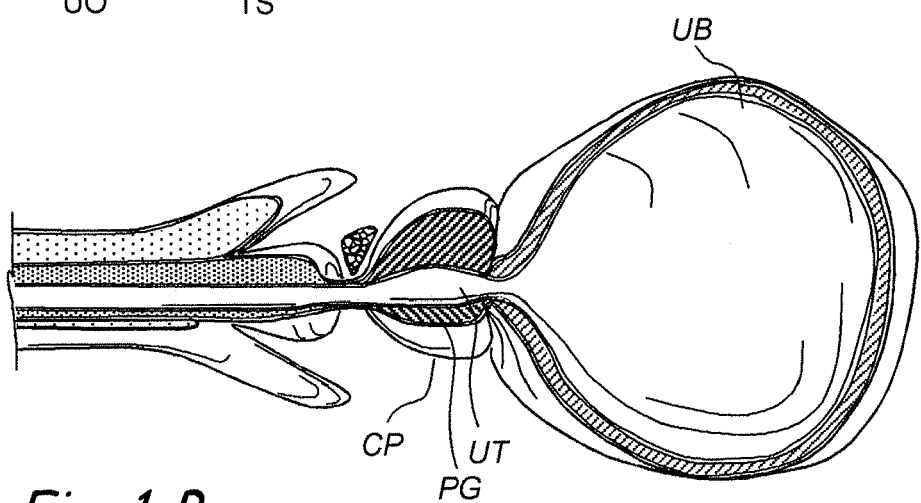

FIG. 1A shows a sagittal section of a male human body through the lower abdomen showing the male urinary tract. The male urinary tract comprises a pair of tubular organs called ureters (UR) that conduct urine produced by the kidneys. The ureters empty into the urinary bladder. The urinary bladder is a hollow muscular organ that temporarily stores urine. It is situated posterior to the pubic bone. The inferior region of the urinary bladder has a narrow muscular opening called the bladder neck which opens into a soft, flexible, tubular organ called the urethra. The muscles around the bladder neck are called the internal urethral sphincter. The internal urethral sphincter is normally contracted to prevent urine leakage. The urinary bladder gradually fills with urine until full capacity is reached, at which point the sphincter relaxes. This causes the bladder neck to open, thereby releasing the urine stored in the urinary bladder into the urethra. The urethra begins at the bladder neck, terminates at the end of the penis, and allows for urine to exit the body.

The region of the urethra just inferior to the urinary bladder is completely surrounded by the prostate gland. The prostate gland is part of the male reproductive system and is usually walnut shaped. Clinically, the prostate is divided into lobes. The lateral lobes are located lateral to the urethra; the middle lobe is located on the dorsal aspect of the urethra, near the bladder neck. Most commonly in BPH, the lateral lobes become enlarged and act like curtains to close the urethral conduit. Less commonly, the middle lobe grows in size and becomes problematic. Because of its superior location near the bladder neck with respect to the urethra, an enlarged middle lobe acts like a ball valve and occludes fluid passage.

FIG. 1B shows a coronal section through the lower abdomen of a human male showing a region of the male urinary system. The prostate gland (PG) is located around the urethra at the union of the urethra and the urinary bladder.

FIGS. 2A through 2H show various alternate approaches to deploy implantable tissue compression device(s) (e.g., one or more clips, anchoring elements, tensioning members, etc.) to compress the prostate gland PG, thereby relieving constriction of the urethra. Specific examples of implantable tissue compression device(s) (e.g., one or more clips, anchoring elements, tensioning members, etc.) useable in this invention are shown in other figures of this patent application and are described more fully herebelow.

Figure 2A:
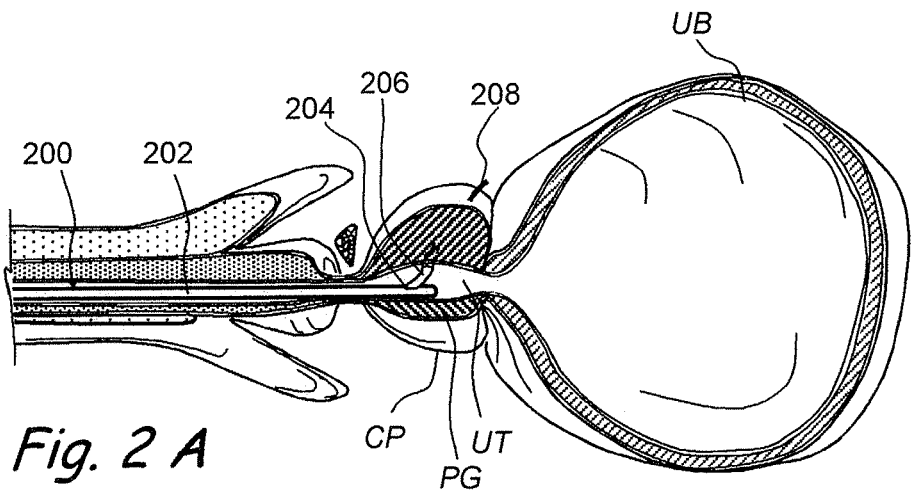
FIG. 2A is a coronal sectional view through the prostate gland and adjacent structures showing a first trans-urethral approach that may be used to implant tissue compression devices(s) (e.g., clips, compression elements, anchoring elements, etc.) to compress or modify the shape of the prostate gland.

FIG. 2A shows a first trans-urethral approach that may be used to implant tissue compression devices(s) to compress the prostate gland PG. In FIG. 2A, an introducing device 200 is introduced in the urethra through the urethral opening of the penis. Introducing device 200 comprises an elongate body 202 comprising a lumen that terminates distally in a distal opening 204. One or more working device(s) 206 is/are then introduced through distal opening 204 into the urethra. The working device(s) 206 penetrate the urethral wall and thereafter one or more lobes of the prostate gland. In some applications of the method, working device(s) 206 may further penetrate the prostate capsule and enters the pelvic cavity. Working device(s) 206 are also used to deploy and implant implantable tissue compression device(s) (e.g., one or more clips, anchoring elements, tensioning members, etc.) to compress the prostate gland PG, thereby relieving constriction of the urethra.

Figure 2B:
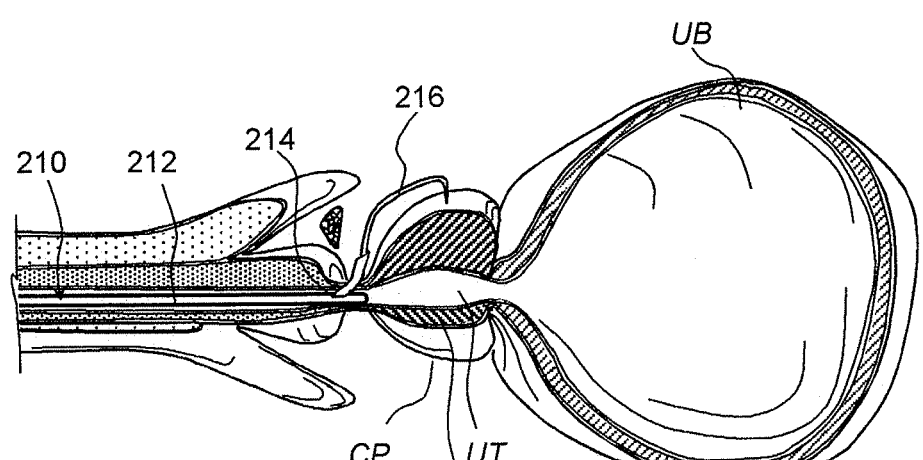
FIG. 2B is a coronal sectional view through the prostate gland and adjacent structures showing a second trans-urethral approach that may be used to implant tissue compression devices(s) (e.g., clips, compression elements, anchoring elements, etc.) to compress or modify the shape of the prostate gland.

FIG. 2B shows a second trans-urethral approach that may be used to implant tissue compression devices(s) to compress the prostate gland PG. In FIG. 2B, an introducing device 210 is introduced in the urethra through the urethral opening UO of the penis. Introducing device 210 comprises an elongate body 212 comprising a lumen that terminates distally in a distal opening 214. One or more working device(s) 216 is/are insertable through distal opening 214 into the urethra. Working device(s) 216 penetrate(s) the urethral wall inferior to the prostate gland and enters the pelvic cavity. Thereafter, working device(s) 216 penetrate(s) the prostate capsule CP and thereafter one or more lobes of the prostate gland. In some applications of the method the working device(s) 216 may further penetrate the urethral wall enclosed by the prostate gland EG and enters the urethral lumen. Working device(s) 216 may then be used to deploy and implant implantable tissue compression device(s) (e.g., one or more clips, anchoring elements, tensioning members, etc.) to compress the prostate gland PG, thereby relieving constriction of the urethra.

Figure 2C:
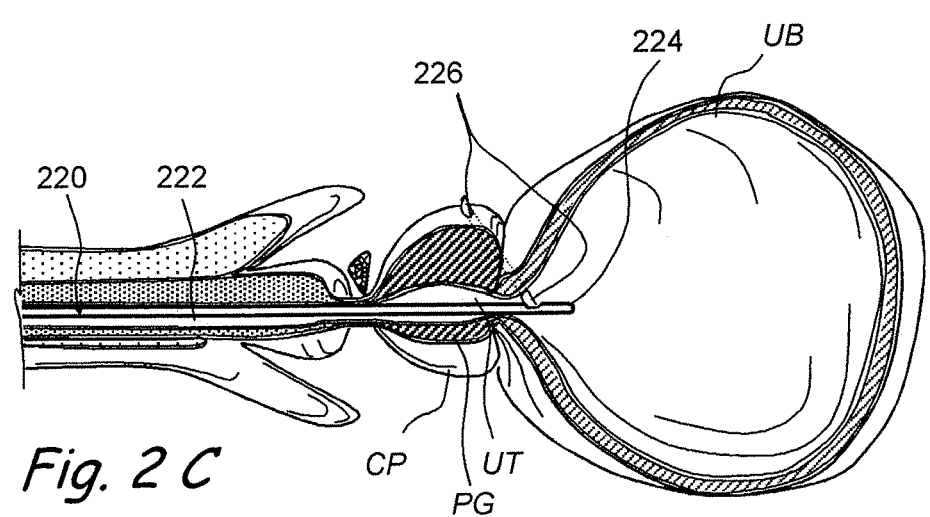
FIG. 2C is a coronal sectional view through the prostate gland and adjacent structures showing a third trans-urethral approach that may be used to implant tissue compression devices(s) (e.g., clips, compression elements, anchoring elements, etc.) to compress or modify the shape of the prostate gland.

FIG. 2C shows a third trans-urethral approach that may be used to implant tissue compression devices(s) to compress the prostate gland PG. In FIG. 2C, an introducing device 220 is introduced in the urethra through the urethral opening UO of the penis. Introducing device 220 comprises an elongate body 222 comprising a lumen that terminates distally in a distal opening 224. Introducing device 220 is positioned such that distal opening 224 is located in the urinary bladder UB. Thereafter, a one or more working device(s) 226 is/are introduced through distal opening 224 into the urinary bladder UB. Working device(s) 226 penetrate(s) the wall of the urinary bladder UB and thereafter penetrate(s) one or more lobes of the prostate gland PG. In some applications of the method, the working device(s) 226 may further penetrate the prostate capsule and enter the pelvic cavity. Working device(s) 226 may then be used to deploy and implant implantable tissue compression device(s) (e.g., one or more clips, anchoring elements, tensioning members, etc.) to compress the prostate gland PG, thereby relieving constriction of the urethra.

Figure 2D:
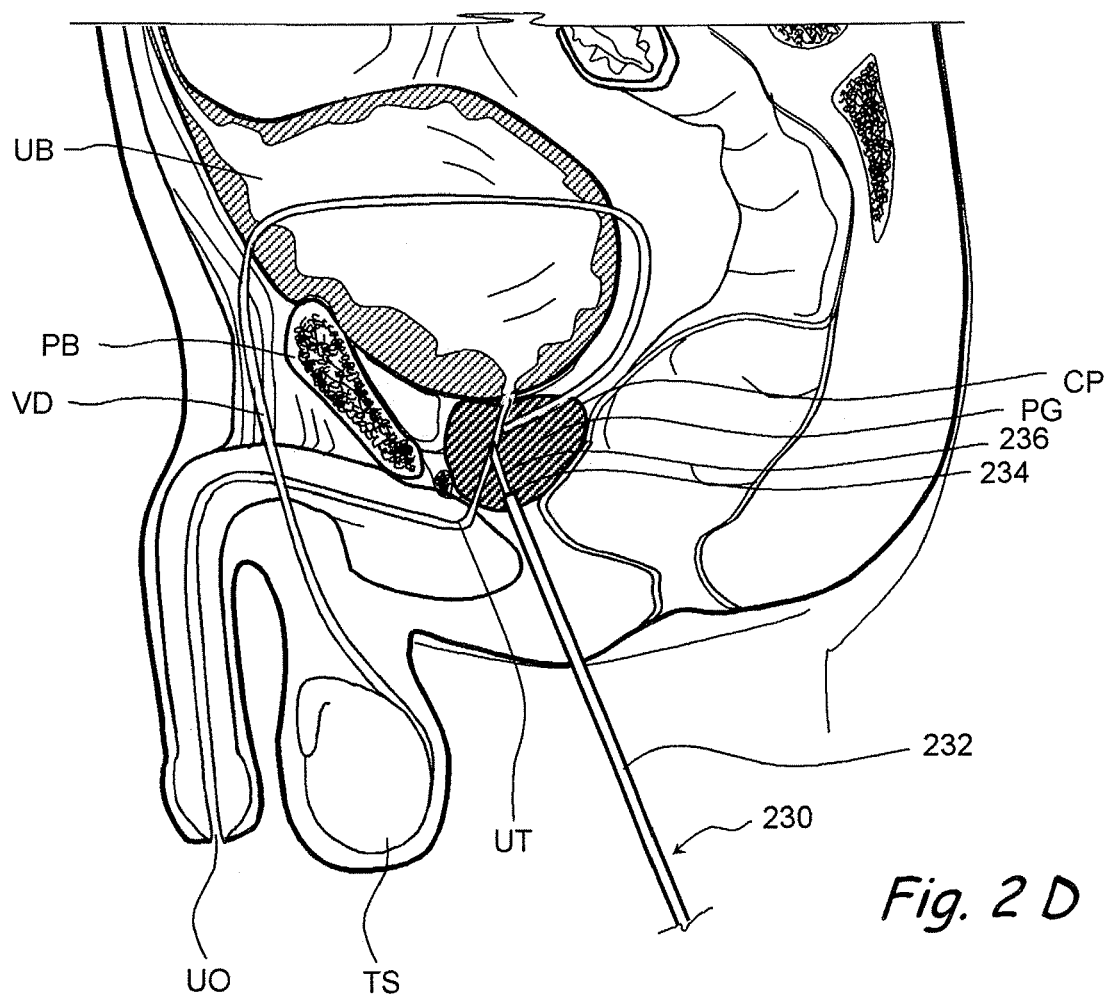
FIG. 2D is a coronal sectional view through the prostate gland and adjacent structures showing a transperineal approach that may be used to implant tissue compression devices(s) (e.g., clips, compression elements, anchoring elements, etc.) to compress or modify the shape of the prostate gland.

FIG. 2D shows a transperineal approach that may be used to implant tissue compression devices(s) to compress the prostate gland PG. In FIG. 2D, an introducing device 230 is introduced in the pelvic cavity percutaneously through the perineum. Introducing device 230 comprises an elongate body 232 comprising a lumen that terminates distally in a distal opening 234. Introducing device 230 is positioned such that distal opening 234 is located in the pelvic cavity adjacent to prostate gland. Thereafter, one or more working device(s) 236 is/are introduced through distal opening 234 into the prostate gland PG. Working device(s) 236 penetrate(s) the prostate capsule CP and thereafter penetrate(s) one or more lobes of the prostate gland PG. In some applications of the method, the working device(s) 236 may further penetrate the urethral wall surrounded by the prostate gland PG and enter the urethral lumen. Working device 236 may then be used to deploy and implant implantable tissue compression device(s) (e.g., one or more clips, anchoring elements, tensioning members, etc.) to compress the prostate gland PG, thereby relieving constriction of the urethra.

Figure 2E:
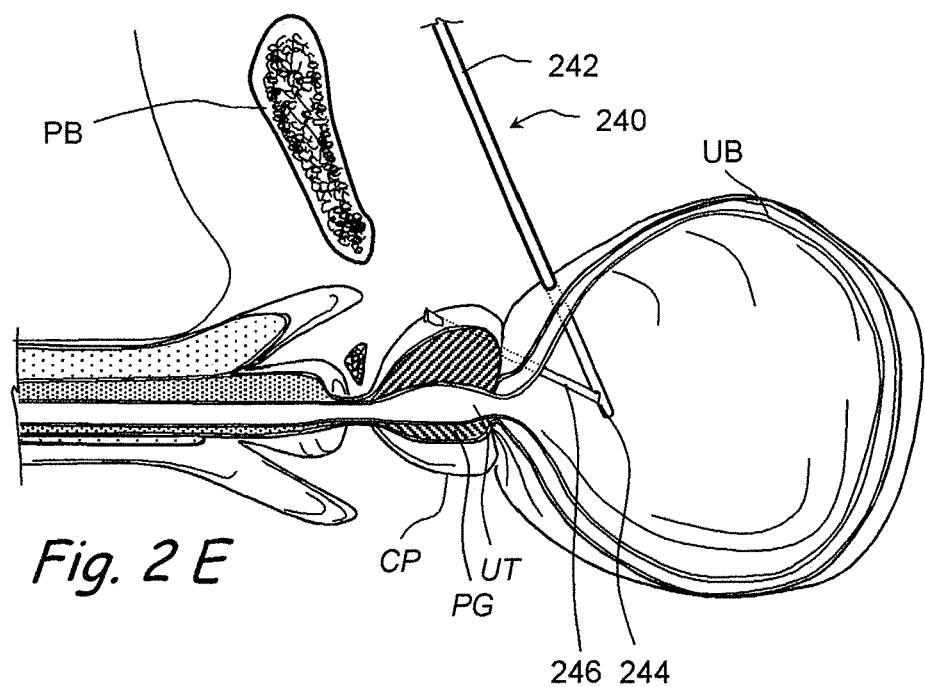
FIG. 2E is a coronal sectional view through the prostate gland and adjacent structures showing a percutaneous approach that may be used to implant tissue compression devices(s) (e.g., clips, compression elements, anchoring elements, etc.) to compress or modify the shape of the prostate gland.

FIG. 2E shows a percutaneous/transvesicular approach that may be used to implant tissue compression devices(s) to compress the prostate gland PG. In FIG. 2E, an introducing device 240 is introduced percutaneously through the abdominal wall. Introducing device 240 comprises an elongate body 242 comprising a lumen that terminates distally in a distal opening 244. After passing through the abdominal wall, introducing device 240 is advanced through the wall of the urinary bladder UB such that distal opening 244 is located in the urinary bladder UB. Thereafter, one or more working device(s) 246 is/are introduced through distal opening 244 into the urinary bladder UB. One ore more working device(s) 246 are advanced through the wall of the urinary bladder UB and into the prostate gland PG. In some applications of the method, working device(s) 246 may further penetrate through the prostate gland capsule and enter the pelvic cavity. Working device(s) 246 is/are then used to deploy and implant implantable tissue compression device(s) (e.g., one or more clips, anchoring elements, tensioning members, etc.) to compress the prostate gland PG, thereby relieving constriction of the urethra.

Figure 2F:
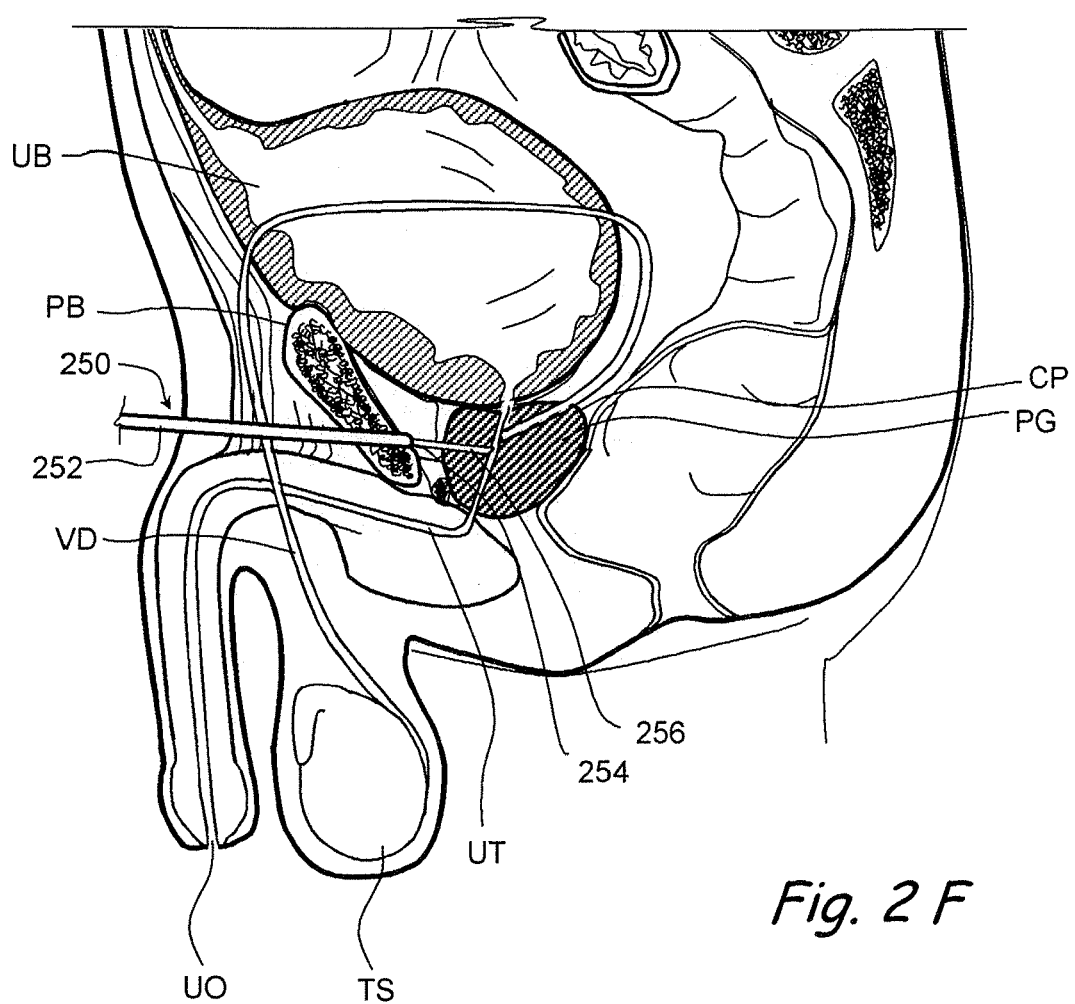
FIG. 2F is a coronal sectional view through the prostate gland and adjacent structures showing a percutaneous trans-osseus approach that may be used to implant tissue compression devices(s) (e.g., clips, compression elements, anchoring elements, etc.) to compress or modify the shape of the prostate gland.

FIG. 2F shows a percutaneous trans-osseus approach that may be used to implant tissue compression devices(s) to compress the prostate gland PG. In FIG. 2F, an introducing device 250 is introduced percutaneously through the abdominal wall. Introducing device 250 comprises an elongate body 252 comprising a lumen that terminates distally in a distal opening 254. Introducing device 250 is used to penetrate a pelvic bone (e.g. the pubic bone PB). Thereafter, introducing device 250 is positioned such that distal opening 254 is located adjacent to the prostate gland PG. Thereafter, one or more working device(s) 256 is/are introduced through distal opening 254 into the prostate gland PG. Working device(s) 256 penetrate the prostate capsule and thereafter penetrate one or more lobes of the prostate gland PG. In some applications of the method, working device(s) 256 may further penetrate the urethral wall surrounded by the prostate gland and enter the urethral lumen. Working device(s) 256 is/are then used to deploy and implant implantable tissue compression device(s) (e.g., one or more clips, anchoring elements, tensioning members, etc.) to compress the prostate gland PG, thereby relieving constriction of the urethra.

Figure 2G:
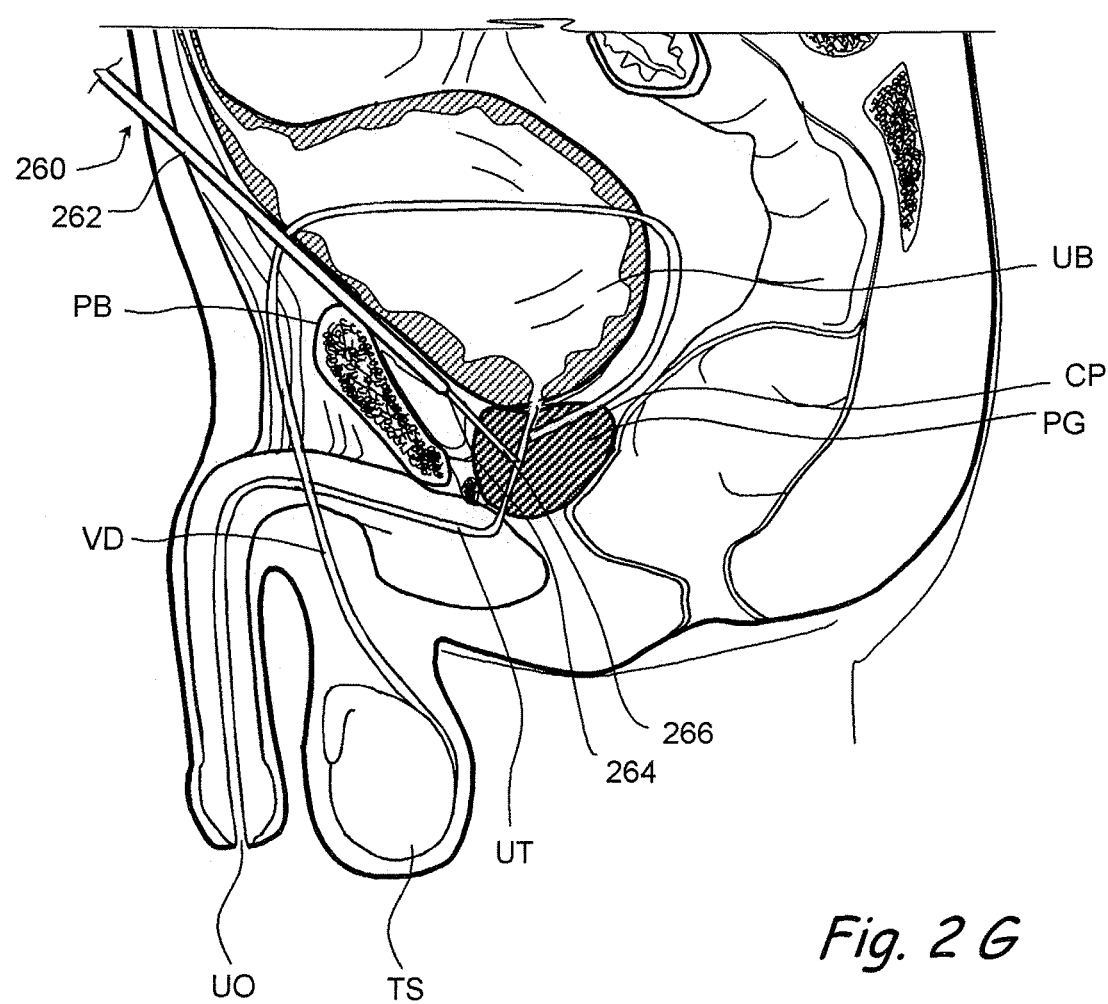
FIG. 2G is a coronal sectional view through the prostate gland and adjacent structures showing a percutaneous suprapubic approach that may be used to implant tissue compression devices(s) (e.g., clips, compression elements, anchoring elements, etc.) to compress or modify the shape of the prostate gland.
Figure 2H:
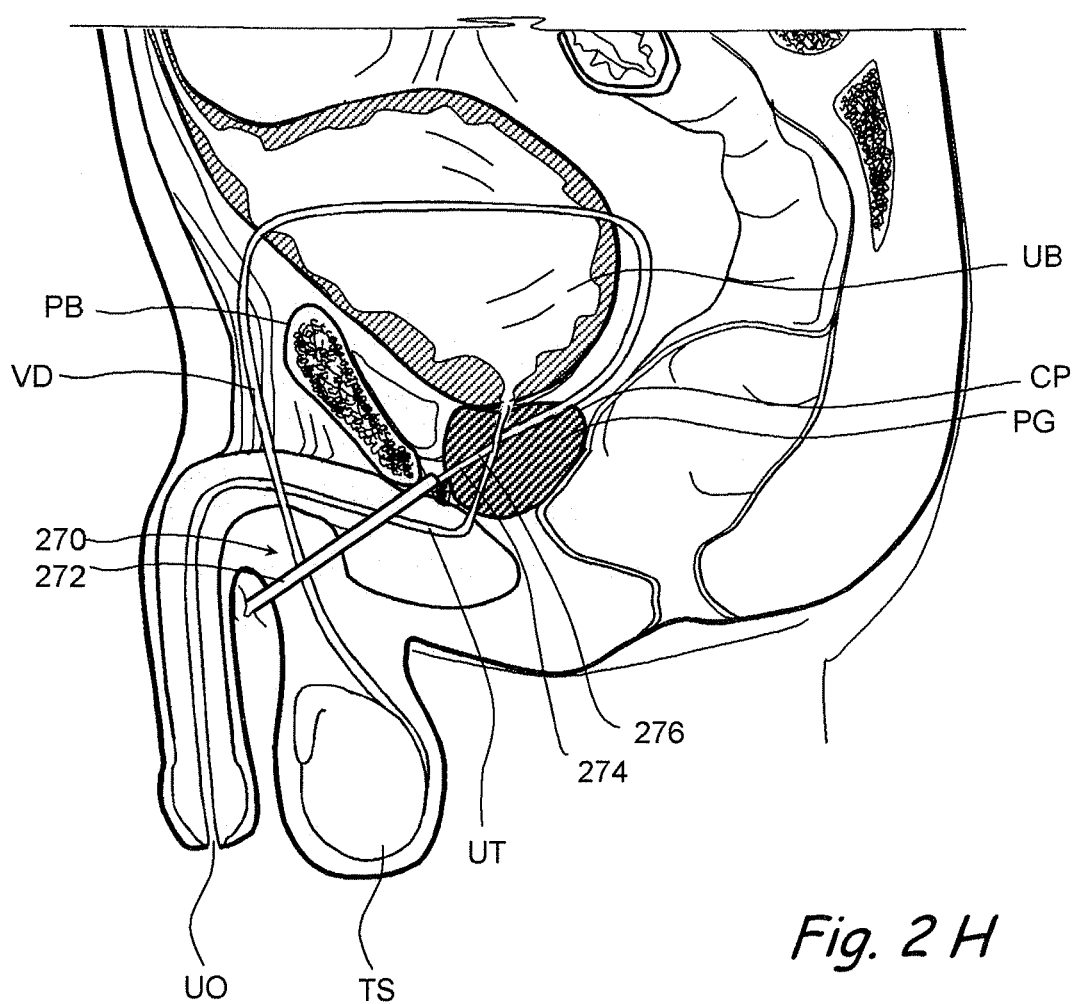
FIG. 2H is a sagittal sectional view through the prostate gland and adjacent structures showing a percutaneous infrapubic approach that may be used to implant tissue compression devices(s) (e.g., clips, compression elements, anchoring elements, etc.) to compress or modify the shape of the prostate gland.
Figure 2:
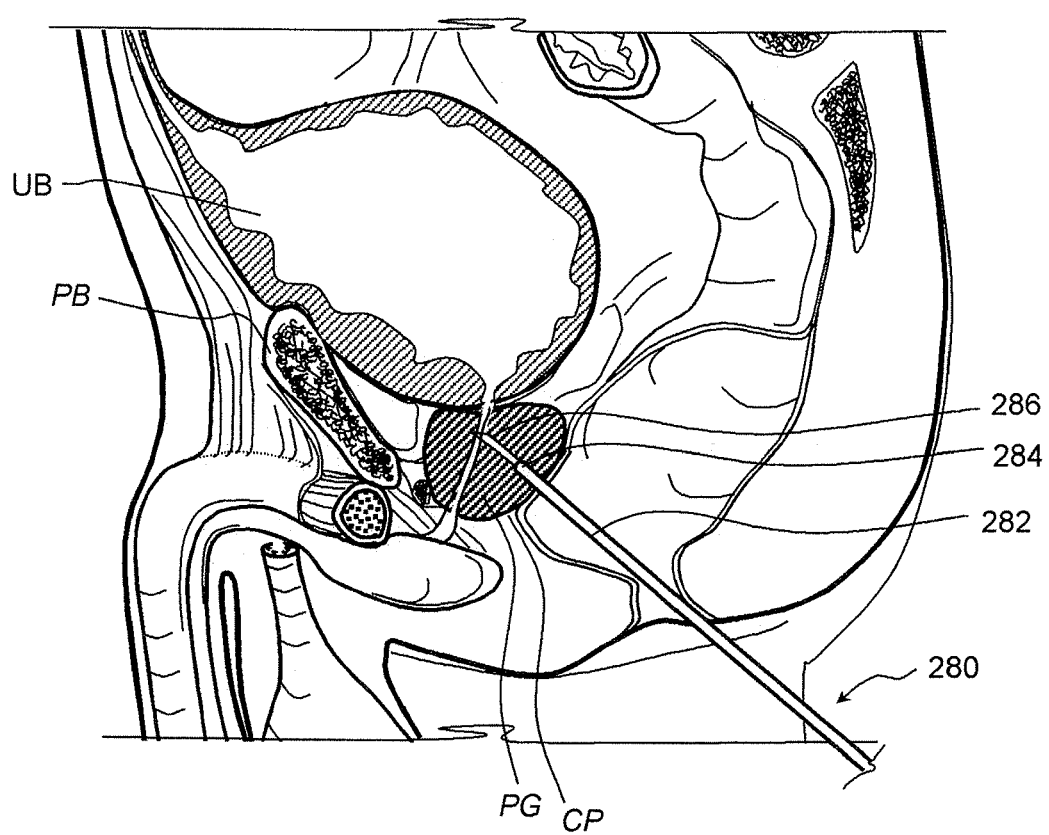
FIG. 2I is a sagittal sectional view through the prostate gland and adjacent structures showing a trans-rectal approach that may be used to implant tissue compression devices(s) (e.g., clips, compression elements, anchoring elements, etc.) to compress or modify the shape of the prostate gland.

FIG. 2G shows a percutaneous suprapubic approach that may be used to implant tissue compression devices(s) to compress the prostate gland PG. In FIG. 2G, an introducing device 260 is introduced in the pelvic cavity percutaneously in a trajectory that passes superior to the pubis bone. Introducing device 260 comprises an elongate body 262 comprising a lumen that terminates distally in a distal opening 264. Introducing device 260 is then positioned such that distal opening 264 is located in the pelvic cavity adjacent to prostate gland. Thereafter, one or more working device(s) 266 is/are introduced through distal opening 264 into the prostate gland PG. Working device(s) 266 penetrate the prostate capsule CP and thereafter penetrate one or more lobes of the prostate gland PG. In some applications of the method, working device(s) 266 may further penetrate the urethral wall surrounded by the prostate gland and enter the urethral lumen. Working device(s) 266 is/are then used to deploy and implant implantable tissue compression device(s) (e.g., one or more clips, anchoring elements, tensioning members, etc.) to compress the prostate gland PG, thereby relieving constriction of the urethra. FIG. 2H shows a percutaneous infrapubic approach that may be used to implant tissue compression devices(s) to compress the prostate gland. In FIG. 2H, an introducing device 270 is introduced in the pelvic cavity percutaneously in a trajectory that passes inferior to the pubis bone. Introducing device 270 comprises an elongate body 272 comprising a lumen that terminates distally in a distal opening 274. Introducing device 270 is introduced percutaneously in the pelvic cavity in a trajectory that passes inferior to the pubic bone. Introducing device 270 is then positioned such that distal opening 274 is located in the pelvic cavity adjacent to prostate gland. Thereafter, one or more working device(s) 276 is/are introduced through distal opening 274 into the prostate gland PG. Working device(s) 276 penetrate the prostate capsule CP and thereafter penetrate one or more lobes of the prostate gland PG. In some applications of the method, working device(s) 276 may further penetrate the urethral wall surrounded by the prostate gland PG and enter the urethral lumen. Working device(s) 276 is/are then used to deploy and implant implantable tissue compression device(s) (e.g., one or more clips, anchoring elements, tensioning members, etc.) to compress the prostate gland PG, thereby relieving constriction of the urethra.

FIG. 2I shows a trans-rectal approach that may be used to implant tissue compression devices(s) to compress the prostate gland PG. In FIG. 2I, an introducing device 280 is introduced in the rectum. Introducing device 280 comprises an elongate body 282 comprising a lumen that terminates distally in a distal opening 284. Introducing device is then advanced such that it penetrates the rectal wall and enters the pelvic cavity. Introducing device 280 is then positioned such that distal opening 284 is located in the pelvic cavity adjacent to prostate gland. Thereafter, one or more working device(s) 286 is/are introduced through distal opening 284 into the prostate gland PG. Working device(s) 286 penetrate the prostate capsule CP and thereafter penetrate one or more lobes of the prostate gland. In some applications of the method, working device(s) 286 may further penetrate the urethral wall surrounded by the prostate gland and enter the urethral lumen. Working device(s) 286 is/are then used to deploy and implant implantable tissue compression device(s) (e.g., one or more clips, anchoring elements, tensioning members, etc.) to compress the prostate gland PG, thereby relieving constriction of the urethra.

FIGS. 3A to 3F show various examples of devices and systems that are useable to treat conditions where the prostate gland PG is compressing a region of the urethra such that the urethra does not expand normally during micturition and urine outflow is impeded.

Figure 3A:
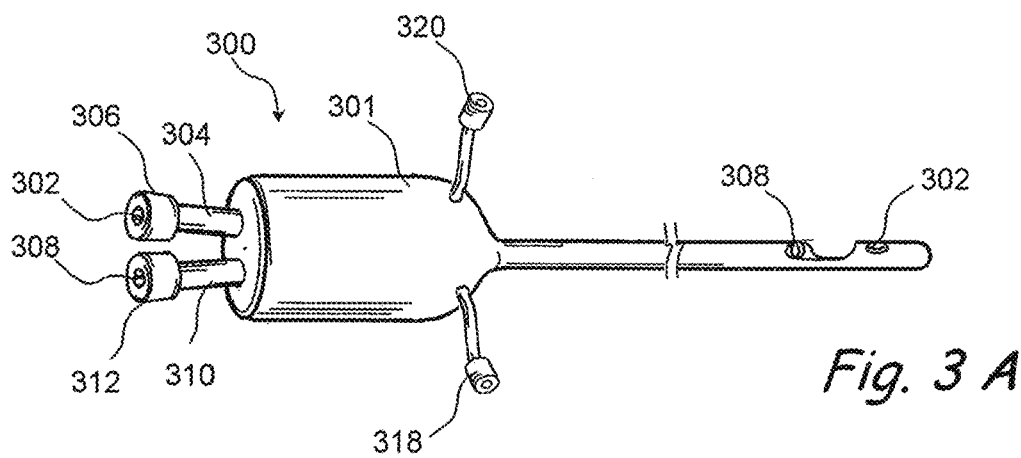
FIGS. 3A to 3H show various components of a system for treating prostate gland disorders by compressing a region of the prostate gland.

FIG. 3A shows the perspective view of an introducer device 300. Introducer device 300 comprises an outer body 301 constructed from suitable biocompatible materials including, but not limited to Pebax, Polyimide, Braided Polyimide, Polyurethane, Nylon, PVC, Hytrel, HDPE, PEEK, metals like stainless steel and fluoropolymers like PTFE, PFA, FEP, EPTFE etc. Body 301 comprises a working device lumen 302. Distal end of working device lumen 302 emerges out of the distal end of body 301. In one embodiment, distal end of working device lumen 302 has a bent or curved region. Proximal end of working device lumen 302 emerges out of a first flexible tube 304. The proximal end of first flexible tube 304 comprises a stasis valve 306. Body 301 further comprises a cystoscope lumen 308. Distal end of cystoscope lumen 308 emerges out of the distal end of body 301. Proximal end of cystoscope lumen 308 emerges out of a second flexible tube 310. The proximal end of second flexible tube 310 comprises a stasis valve 312. Cystoscope lumen 308 may comprise one or more side ports e.g. a first side port 318 for the introduction or removal of one or more fluids. Working device lumen 302 may comprise one or more side ports e.g. a second side port 320 for the introduction or removal of one or more fluids.

Figure 3B:
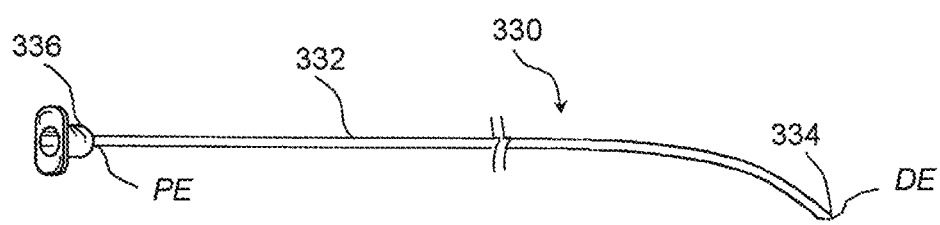

FIG. 3B shows a perspective view of an injecting needle. Injecting needle 330 is used for injecting one or more diagnostic or therapeutic substances. In some applications of the invention, the injecting needle 330 may be used to inject local anesthetic in the urethra, prostate gland and/or tissues near the prostate gland. Specific examples of target areas for injecting local anesthetics are the neurovascular bundles, the genitourinary diaphragm, the region between the rectal wall and prostate, etc. Examples of local anesthetics that can be injected by injecting needle 330 are anesthetic solutions e.g. 1% lidocaine solution; anesthetic gels e.g. lidocaine gels; combination of anesthetic agents e.g. combination of lidocaine and bupivacaine; etc. Injecting needle 330 comprises a hollow shaft 332 made of suitable biocompatible materials including, but not limited to stainless steel 304, stainless steel 306, Nickel-Titanium alloys, titanium etc. In this example, the distal end of hollow shaft 332 comprises a sharp tip 334. The proximal end of hollow shaft 332 has a needle hub 336 made of suitable biocompatible materials including, but not limited to metals e.g. stainless steel 304, stainless steel 306, Nickel-Titanium alloys, titanium etc.; polymers e.g. polypropylene, Pebax, Polyimide, Braided Polyimide, Polyurethane, Nylon, PVC, Hytrel, HDPE, PEEK, PTFE, PFA, FEP, EPTFE etc. In one embodiment, needle hub 336 comprises a luer lock.

Figure 3C:
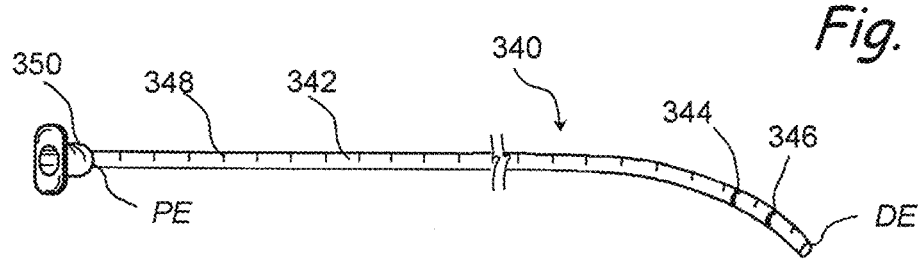

FIG. 3C shows an example of an introducing device or introducing sheath 340. Introducing sheath 340 comprises a hollow, tubular body 342 made of suitable biocompatible materials including, but not limited to metals e.g. stainless steel 304, stainless steel 306, Nickel-Titanium alloys, titanium etc. or polymers e.g. Pebax, Polyimide, Braided Polyimide, Polyurethane, Nylon, PVC, Hytrel, HDPE, PEEK, PTFE, PFA, FEP, EPTFE etc. Tubular body 342 further comprises two marker bands: a proximal marker band 344 and a distal marker band 346. The marker bands can be seen by a cystoscope. In one embodiment, proximal marker band 344 and distal marker band 346 are radiopaque. The position of proximal marker band 344 and distal marker band 346 is such that after introducing sheath 340 is placed in an optimum location in the anatomy, proximal marker band 344 is located in the urethra where it can be seen by a cystoscope and distal marker band 346 is located in the prostrate gland or in the wall of the urethra where it cannot be seen by a cystoscope. Tubular body 342 further comprises a series of distance markers 348 on the outer surface of tubular body 342. The proximal end of tubular body 342 further comprises a hub 350 made of suitable biocompatible materials including, but not limited to metals e.g. stainless steel 304, stainless steel 306, Nickel-Titanium alloys, titanium etc. or polymers e.g. Pebax, Polyimide, Braided Polyimide, Polyurethane, Nylon, PVC, Hytrel, HDPE, PEEK, PTFE, PFA, FEP, EPTFE etc. In one embodiment, hub 350 comprises a luer lock.

Figure 3D:
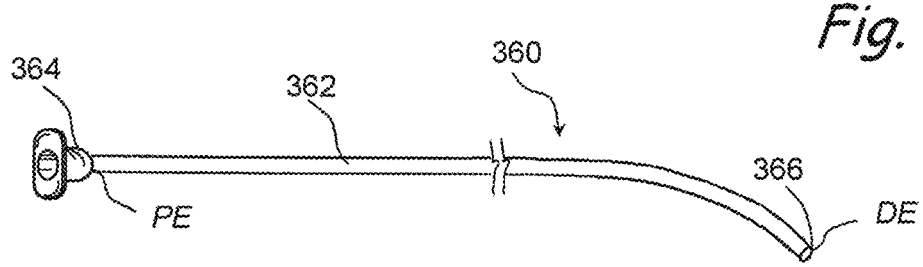

FIG. 3D shows a perspective view of a trocar. Trocar 360 comprises a tubular trocar body 362. The proximal end of trocar body 362 comprises a hub 364. Trocar body 362 and hub can be constructed from suitable biocompatible materials including, but not limited to metals e.g. stainless steel 304, stainless steel 306, Nickel-Titanium alloys, titanium etc. or polymers e.g. Pebax, Polyimide, Braided Polyimide, Polyurethane, Nylon, PVC, Hytrel, HDPE, PEEK, PTFE, PFA, FEP, EPTFE etc. Distal end of trocar body 362 ends in a sharp trocar tip 366.

Figure 3E:
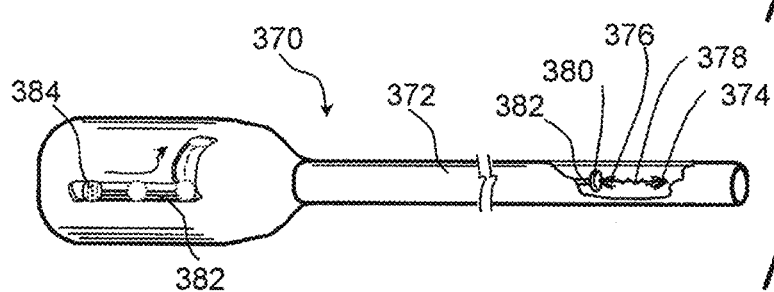
Figure 3:
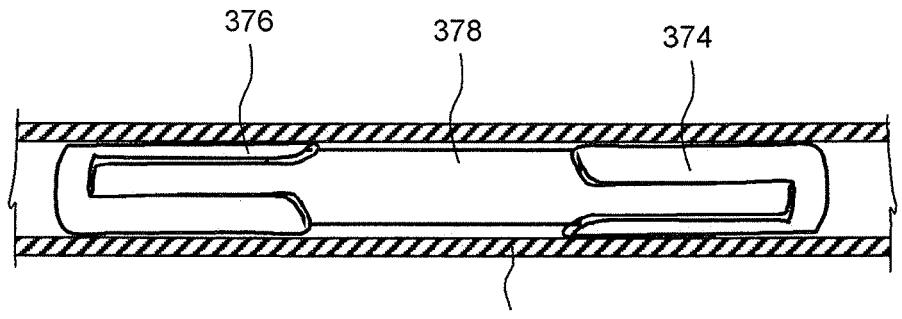
Figure 3:
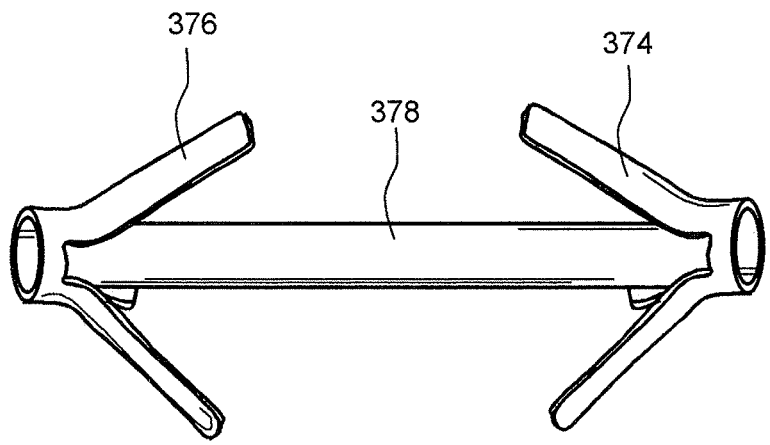
Figure 3:
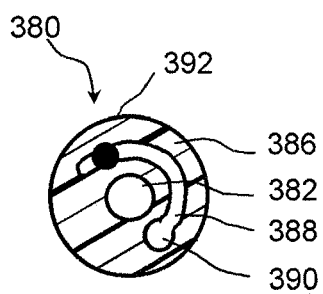

FIG. 3E shows a perspective view of an anchor delivery device. Anchor delivery device 370 comprises a body 372 having a distal opening 373. A section of the distal region of body 372 has been removed to show a view of the anchor assembly. Body 372 encloses a distal anchor 374 and a proximal anchor 376. Proximal anchor 376 and distal anchor 374 can have a variety of designs including, but not limited to the designs disclosed elsewhere in this patent application. Proximal anchor 376 and distal anchor 374 can be constructed from suitable biocompatible materials including, but not limited to metals e.g. stainless steel 304, stainless steel 306, Nickel-Titanium alloys, titanium etc. or polymers e.g. Pebax, Polyimide, Braided Polyimide, Polyurethane, Nylon, PVC, Hytrel, HDPE, PEEK, PTFE, PFA, FEP, EPTFE etc. In one embodiment, shown in FIGS. 3F and 3G, proximal anchor 9976 and distal anchor 9974 comprise splayable elements that expand in a radially outward direction when a radial compression force, as enacted by body lumen 9972, on proximal anchor 9976 and distal anchor 9974 is removed. The splayable elements can be made of suitable super-elastic materials such as Nickel-Titanium alloys etc. Proximal anchor 9976 and distal anchor 9974 are connected to each other by a tension element 9978. Tension element 9978 can be made of suitable elastic or non-elastic materials including, but not limited to metals e.g. stainless steel 304, stainless steel 306, Nickel-Titanium alloys, suture materials, titanium etc. or polymers such as silicone, nylon, polyamide, polyglycolic acid, polypropylene, Pebax, PTFE, ePTFE, silk, gut, or any other braided or mono-filament material. Tension element 9978 can have a variety of designs including the designs shown in FIGS. 5A through 5F. As shown in FIG. 3E, the proximal end of proximal anchor 9976 is connected by an attachment mechanism 9980 to a torquable shaft 9982. The proximal end of torquable shaft 9982 is attached to a control button 9984. Control button 9984 can be used to deploy proximal anchor 9976 by sliding control button 9984 along groove 9985 in the distal direction. Control button 9984 is then used to deploy distal anchor 9974 by turning control button 9984 in the circumferential direction along groove 9985.

FIG. 3H shows a perspective view from the proximal direction of a particular embodiment of the attachment mechanism of FIG. 3E. Attachment mechanism 380 comprises a circular plate 386 made from suitable biocompatible materials including, but not limited to metals e.g. stainless steel 304, stainless steel 306, Nickel-Titanium alloys, titanium etc. or polymers e.g. Polycarbonate, PVC, Pebax, Polyimide, Polyurethane, Nylon, Hytrel, HDPE, PEEK, PTFE, PFA, FEP etc. The proximal face of circular plate 386 is connected to torquable shaft 382. Circular plate 386 further comprises a semicircular groove 388. One end of semicircular groove 388 comprises an enlarged region 390. A knob 392 located on the proximal portion of proximal anchor 376 slides on semicircular groove 388. The size of knob 322 is larger than the size of semicircular groove 388 but smaller than size of enlarged region 390. This keeps proximal anchor 376 attached to circular plate 386. When control button 384 is turned in the circumferential direction along groove 385, torquable shaft 382 is turned. This turns circular plate 386 causing knob 392 to slide on the groove 388. Ultimately, knob 392 reaches enlarged region 390. This releases knob 392 from circular plate 386 thereby releasing proximal anchor 376 from anchor delivery device 370.

Figure 4A:
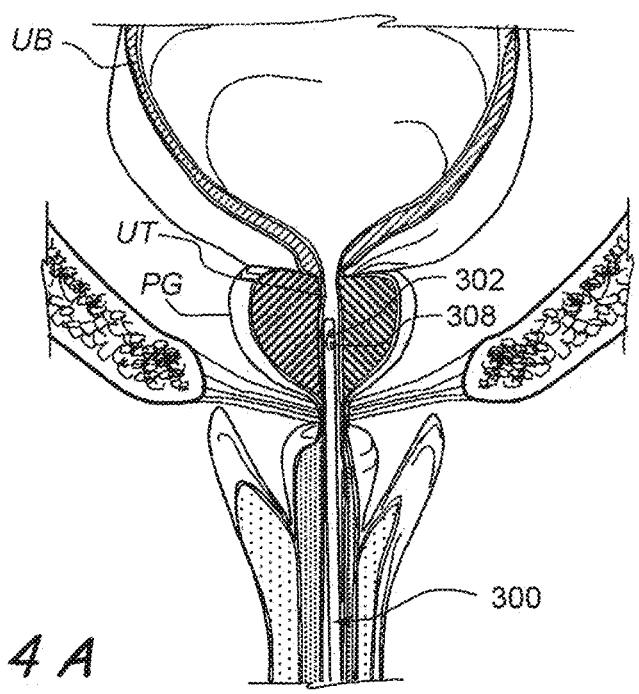
FIGS. 4A through 4H show a coronal section through the prostate gland showing the various steps of a method of treating prostate gland disorders by compressing a region of the prostate gland using the kit shown in FIGS. 3A through 3H.
Figure 4B:
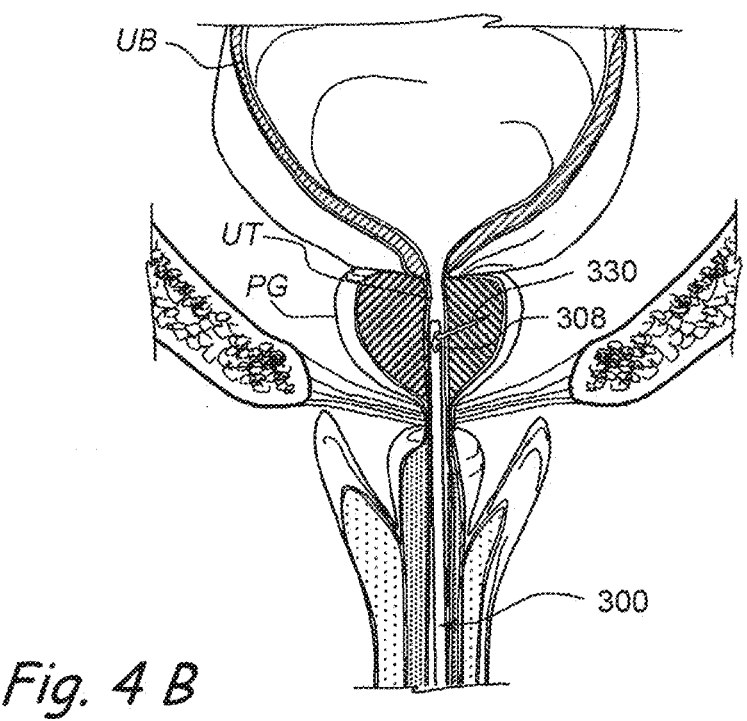
Figure 4C:
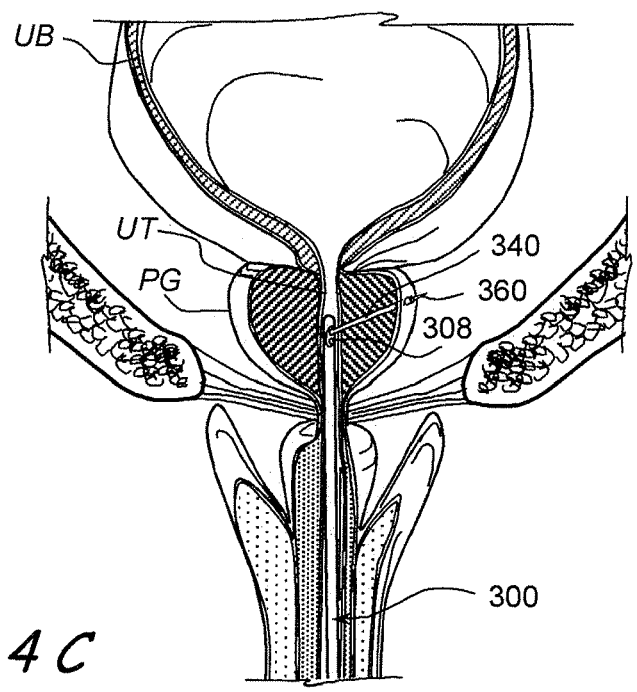

FIGS. 4A through 4H show a coronal section through the prostate gland showing the various steps of a method of treating prostate gland disorders by compressing a region of the prostate gland using the kit shown in FIGS. 3A through 3F. In FIG. 4A, introducer device 300 is introduced in the urethra through the urethral opening at the tip if the penis. A cystoscope is inserted in introducer device 300 through cystoscope lumen 308 such that the lens of the cystoscope is located in the distal opening of cystoscope lumen. The cystoscope is used to navigate introducer device 300 through the urethra such that the distal region of introducer device 300 is located in a target region in the prostatic urethra. Thereafter in FIG. 4B, injecting needle 330 is advanced through working device lumen 302 such that the distal tip of injecting needle 330 penetrates into a region of the urethral wall or the prostate gland. Injecting needle 330 is then used to inject one or more diagnostic or therapeutic agents into the urethral wall or the prostate gland. This step may be repeated one or more times to inject one or more diagnostic or therapeutic agents in one or more regions of the urethral wall and/or the prostate gland. In one method embodiment, injecting needle 330 is used to inject an anesthetic in one or more regions of the urethral wall and/or the prostate gland. In another embodiment, injecting needle 330 is used to deliver energy in the form of radiofrequency energy, resistive heating, laser energy, microwave energy etc. In another embodiment, injecting needle 330 is used to deliver alpha antagonist agents, such as phenoxybenzamine, prazosin, doxazosin, terazosin, tamsulosin, alfuzosin etc. In another embodiment, injecting needle 330 is used to deliver antiandrogen, such as flutamide or 5-alpha reductase inhibitors, such as finasteride, dutasteride, 3-oxosteroid compounds, 4-aza-3-oxosteroid derivatives of testosterone etc. In another embodiment, injecting needle 330 is used to deliver anti-inflammatory agents, such as rapamycin, paclitaxel, ABT-578, everolimus, taxol etc. In another embodiment, injecting needle 330 is used to deliver ablative agents such as methyl alcohol etc.

In another embodiment, injecting needle 330 is used to deliver energy in the form of radiofrequency energy, resistive heating, laser energy, microwave energy etc. In another embodiment, injecting needle 330 is used to deliver alpha antagonist agents, such as phenoxybenzamine, prazosin, doxazosin, terazosin, tamsulosin, alfuzosin etc. In another embodiment, injecting needle 330 is used to deliver anti-androgen, such as flutamide or 5-alpha reductase inhibitors, such as finasteride, dutasteride, 3-oxosteroid compounds, 4-aza-3-oxosteroid derivatives of testosterone etc. In another embodiment, injecting needle 330 is used to deliver anti-inflammatory agents, such as rapamycin, paclitaxel, ABT-578, everolimus, taxol etc. In another embodiment, injecting needle 330 is used to deliver ablative agents such as methyl alcohol etc.

Figure 4D:
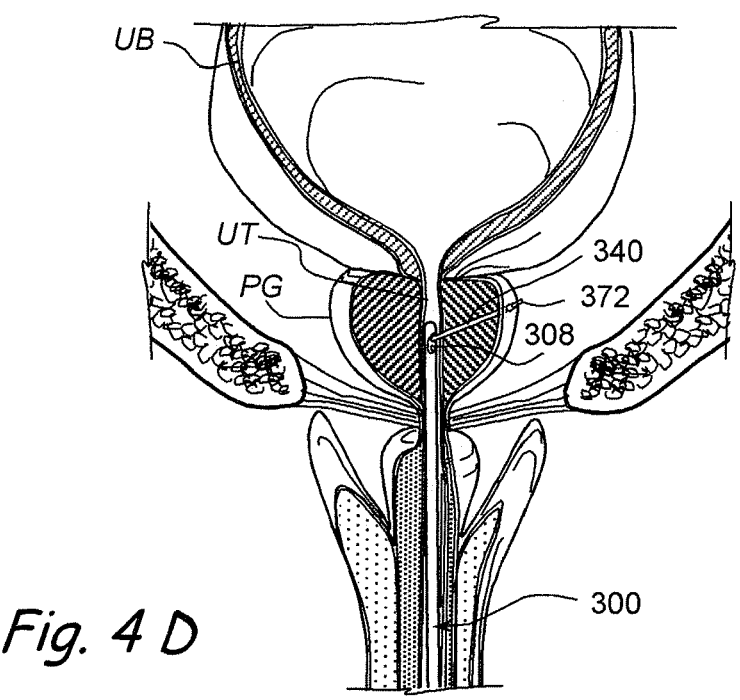
Figure 4:
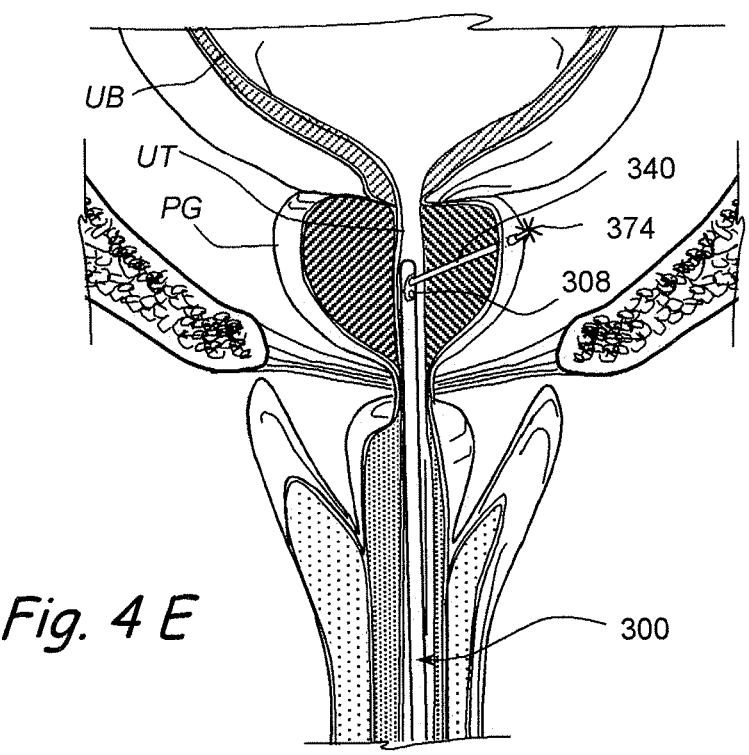
FIGS. 4I and 4J is a crossectional view through the prostatic urethra (i.e., the portion of the urethra that passes through the prostate gland) showing the appearance of the urethral lumen before and after performing the method shown in FIGS. 4A through 4H.
Figure 4:
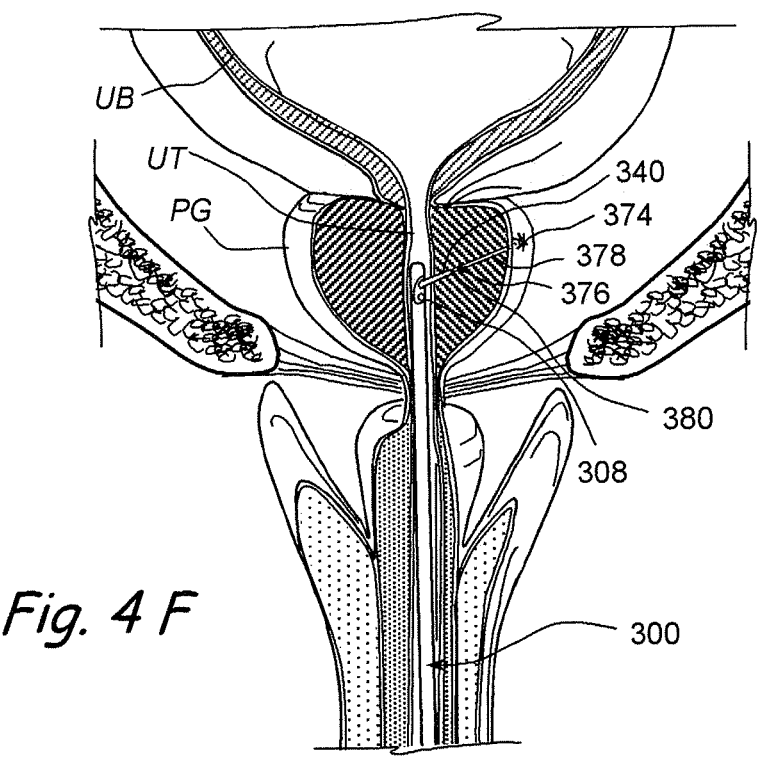
Figure 4G:
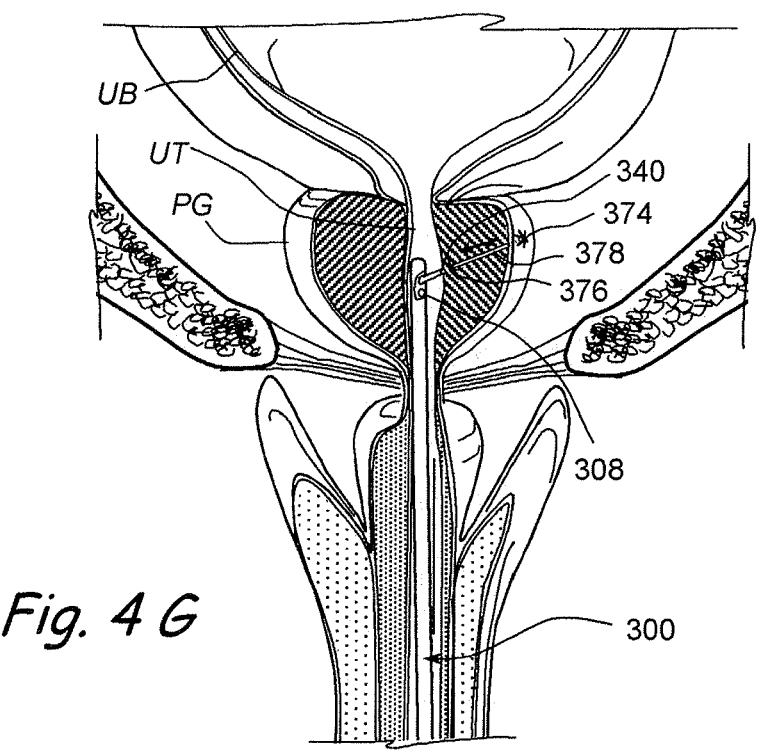
Figure 4H:
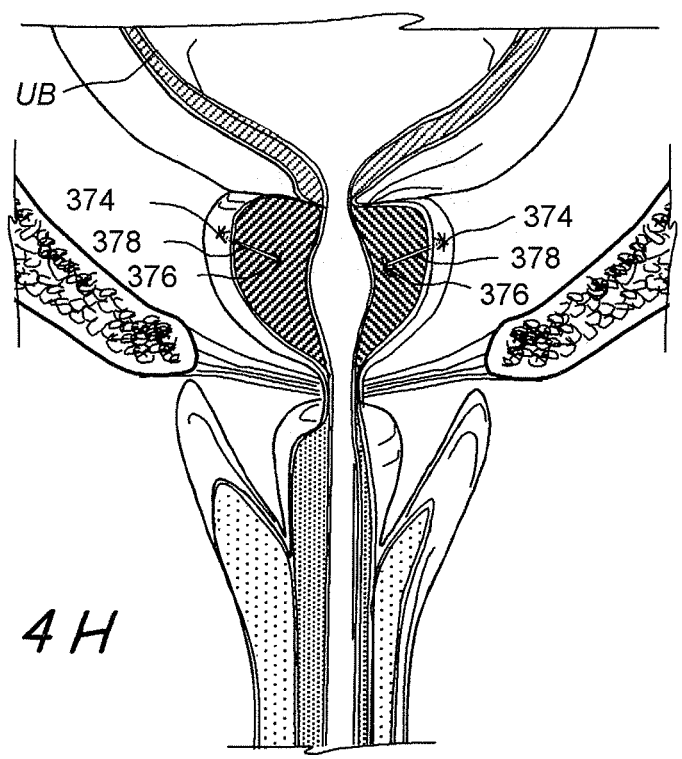
Figure 4:
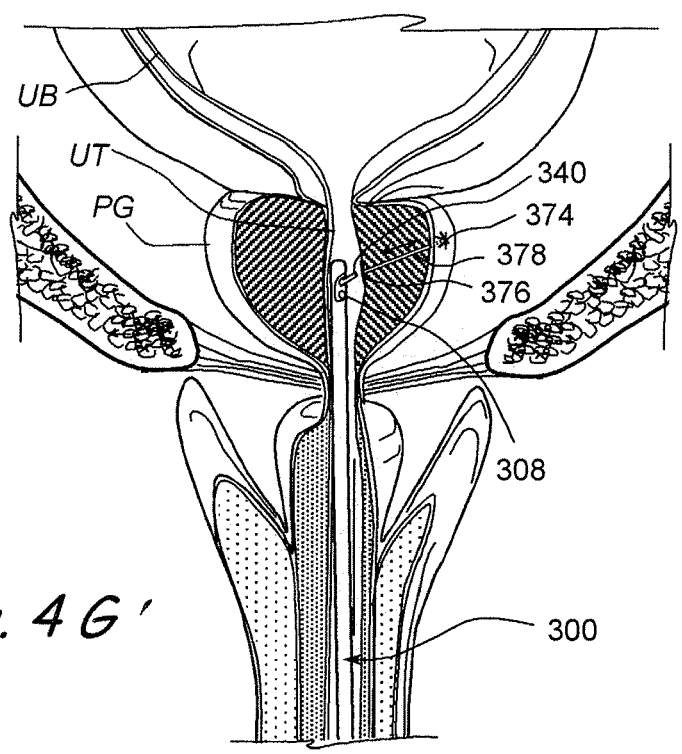
Figure 4:
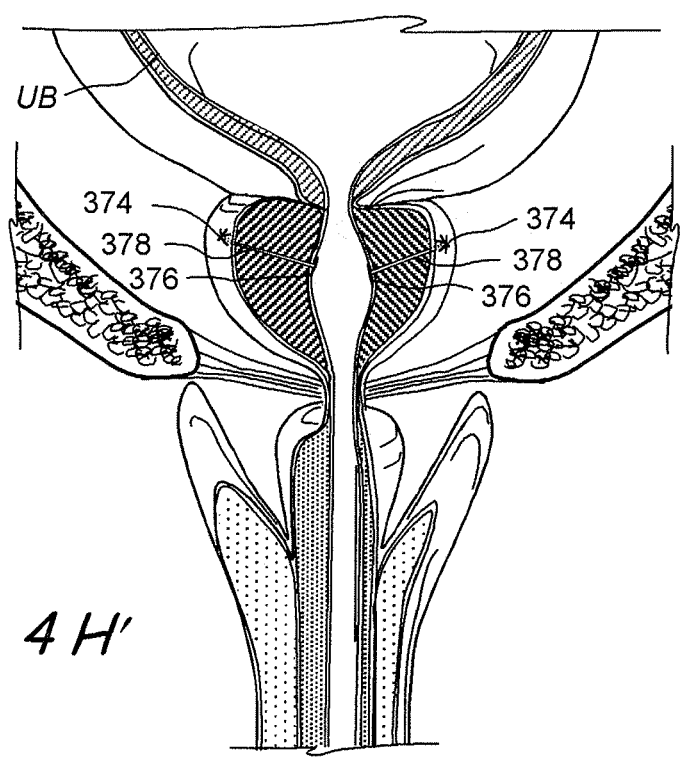
Figure 4:
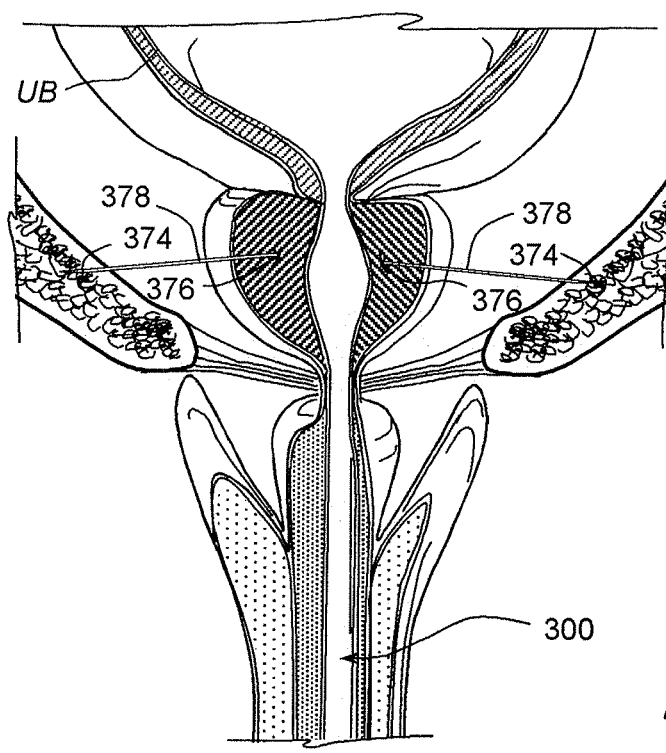
Figure 4:
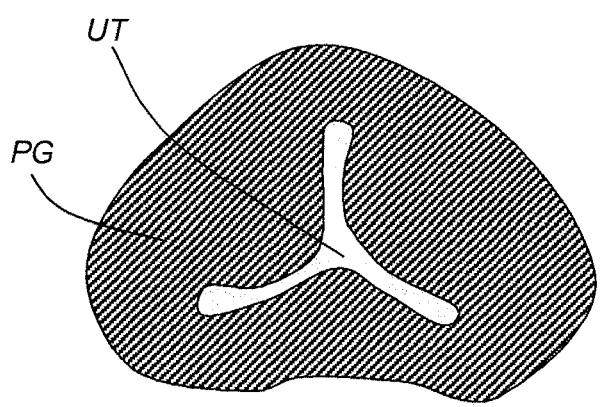
Figure 4:
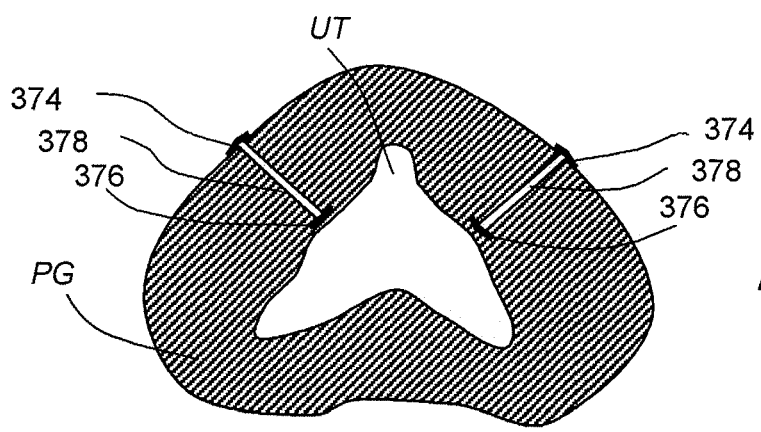

In step 4C, injecting needle 330 is withdrawn from introducer device 300. Thereafter, introducer sheath 340 and trocar 360 are advanced through working device lumen 302. In the example shown, introducer sheath 340 and trocar 360 are advanced till the distal tip of trocar 360 penetrates the capsule of the prostate gland and the distal end of introducer sheath 340 is located outside the prostate gland in the pelvic cavity. Thereafter, trocar 360 is withdrawn from working device lumen 302 leaving introducer sheath 340 in place. In FIG. 4D, anchor delivery device 370 is introduced through the lumen of introducer sheath 340 till the distal end of body 372 protrudes through the distal tip of introducer sheath 340. In step E, distal anchor 374 is deployed. It should be noted that the anchor may be carried to the site and deployed from within an introducer, on the outside of an introducer, or it may be the distal tip of the introducer itself. Thereafter, anchor deliver device 370 is pulled in the proximal direction along with introducer sheath 340 so that distal anchor 374 is anchored on the outer surface of the prostate capsule. This step may be used to create tension in the tension element 378. In one method embodiment, anchor deliver device 370 is pulled in the proximal direction along with introducer sheath 340 such that the distal end of anchor delivery device 370 is located in the prostate gland. In another method embodiment, anchor deliver device 370 is pulled in the proximal direction along with introducer sheath 340 till the distal end of anchor delivery device 370 is located in the urethral wall or the urethral lumen. In step 4F, proximal anchor 376 is deployed. Proximal anchor 376 may be deployed in the prostate gland, in the urethral wall or in the urethral lumen. Proximal anchor 376 is still attached by attachment mechanism 380 to anchor delivery device 370. The proximal anchor may be pre-loaded on the tension element, or may subsequently be loaded by the operator on the tension element. FIGS. 4G through 4H show the steps of deploying proximal anchor 376 in the prostate gland. In FIG. 4G, proximal anchor 376 is separated from anchor delivery device 370. This separation may be achieved via numerous means including cutting, melting, un-locking a link, or breaking the tensioning element at a desired location. Ideally this residual end of the tensioning element will not protrude substantially into the lumen of the urethra. Thus proximal anchor 376 and distal anchor 374 are anchored in the anatomy. Thereafter, anchor delivery device 370 and introducer sheath 340 are both pulled in the proximal direction and are withdrawn into introducer device 300. Thereafter, introducer device 300 is pulled in the proximal direction to pull it out of the urethra. In FIG. 4H, the steps from FIG. 4A through 4G are repeated in a second region of the prostate gland if desired to implant two or more sets of anchoring devices.

Alternatively, FIGS. 4G' through 4H' show the steps of deploying proximal anchor 376 in the urethra. After the step in FIG. 4F, in FIG. 4G', proximal anchor 376 is separated from anchor delivery device 370 in the urethra. Thus proximal anchor 376 and distal anchor 374 are anchored in the urethra and the prostate capsule respectively. Thereafter, anchor delivery device 370 and introducer sheath 340 are both pulled in the proximal direction and are withdrawn into introducer device 300. Thereafter, introducer device 300 is pulled in the proximal direction to pull it out of the urethra. In FIG. 4H', the steps from FIG. 4A through 4G' are repeated optionally in a second region of the prostate gland to implant two or more sets of anchoring devices. It should be understood that this method and devices may be applied to any lobe (middle or lateral lobes) of the prostate and further more may be used multiple times in the same lobe to achieve the desired effect.

FIG. 4H" shows a coronal section through the prostate gland showing the final deployed configuration of an embodiment of bone anchoring devices for treating prostate gland disorders by compressing a region of the prostate gland. In the method of deploying this device, introducer sheath 340 and trocar 360 are advanced till the distal tip of trocar 360 penetrates a bone in the abdomen (e.g. the pelvic bone, etc.) and the distal end of introducer sheath 340 is located outside the bone. Thereafter, trocar 360 is withdrawn from working device lumen 302 leaving introducer sheath 340 in place. Thereafter, anchor delivery device 370 is introduced through the lumen of introducer sheath 340 until the distal end of body 372 touches the bone through the distal tip of introducer sheath 340. Thereafter, distal anchor 374 is implanted in the bone. Distal anchor 374 may comprise a variety of designs including, but not limited to designs of distal tips of Kirschner wires. Examples of such Kirschner wire distal tips are spiral drill tips, lancer tips, threaded trocar tips, lengthwise knurled tips, 3-sided trocar tips, 4-sided trocar tips, Thereafter, anchor deliver device 370 is pulled in the proximal direction along with introducer sheath 340. This step creates tension in the tension element 378. In another method embodiment, anchor deliver device 370 is pulled in the proximal direction along with introducer sheath 340 till the distal end of anchor delivery device 370 is located in the urethral wall or the urethral lumen. The remaining method steps are similar to steps 4F through 4H.

One or more anchors disclosed in this patent application may be implanted in anatomical locations that include, but are not limited to:
  a location within prostatic lobe;
  a location within peripheral zone of prostate;
  a location within prostatic capsule;
  a location between prostatic capsule and pubic fascia;
  a location within the pubic fascia;
  a location within the levator ani muscle;
  a location within the obturator internus muscle;
  a location within the pelvic bone;
  a location within the periostium of pelvic bone;
  a location within the pubic bone;
  a location within the periostium of pubic bone;
  a location within the symphysis pubica;
  a location within the urinary bladder wall;
  a location within the ischiorectal fossa;

a location within the urogenital diaphragm; and
a location within the abdominal fascia.

FIGS. 4I and 4J show a crossection of the urethra through the prostate gland PG showing the appearance of the urethral lumen before and after performing the method shown in FIGS. 4A through 4H. FIG. 4I shows a crossection of the urethra through the prostate gland showing the appearance of the urethral lumen in a patient with BPH. FIG. 4J shows a crossection of the urethra through the prostate gland PG showing the appearance of the urethral lumen after performing the procedure shown in FIGS. 4A through 4H. The urethral lumen shown in FIG. 4I is larger than the urethral lumen in FIG. 4J.

Figure 5:
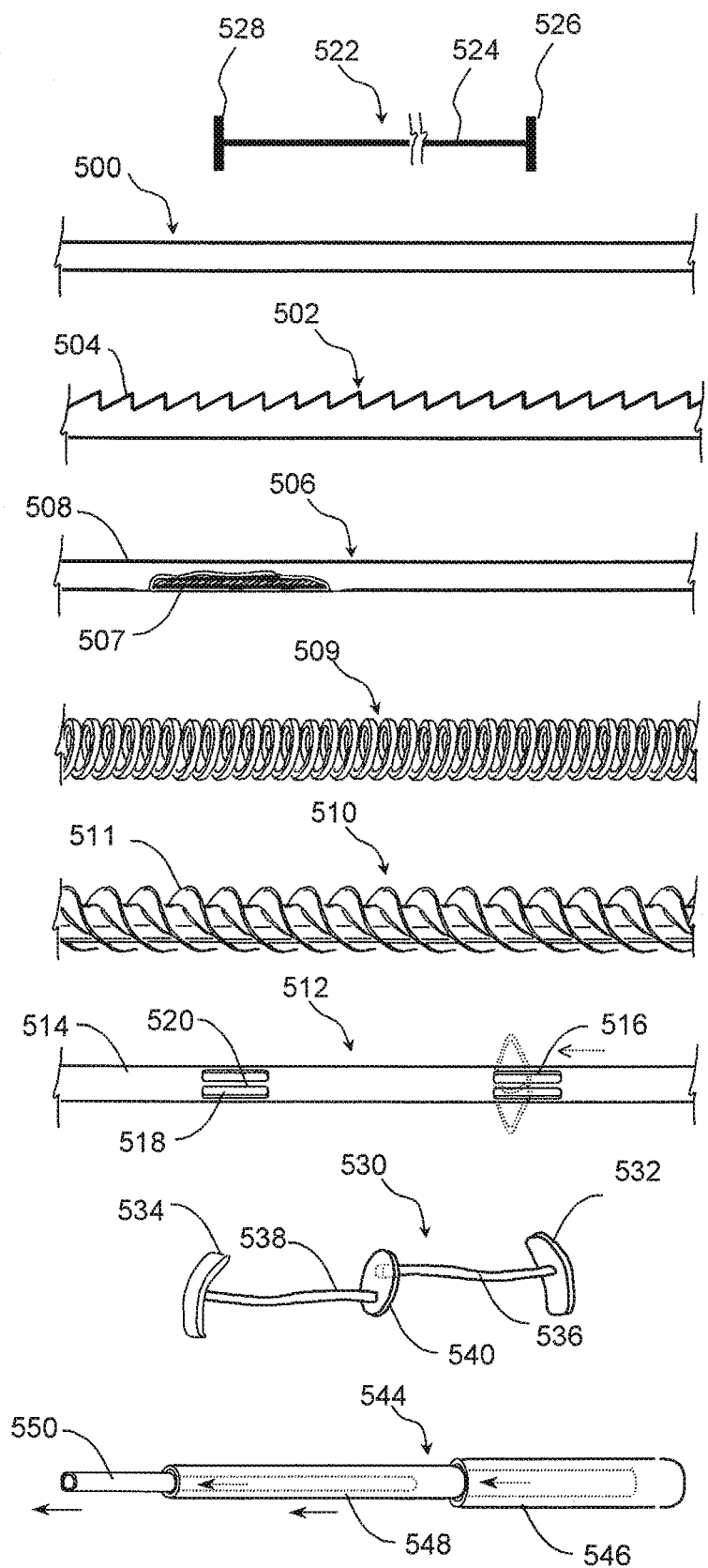
FIGS. 5A through 5I show perspective views of some designs of the tension elements that can be used in the embodiments disclosed elsewhere in this patent application.

FIGS. 5A through 5F show perspective views of some designs of the tension elements that can be used in the embodiments disclosed elsewhere in this patent application. FIG. 5A shows a perspective view of a tension element 500 comprising a single strand of an untwisted material. Examples of materials that can be used to manufacture tension element 500 include but are not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. FIG. 5B shows a perspective view of a tension element 502 comprising one or more serrations 504 or notches. Serrations 504 may be aligned in a particular direction to allow relatively easy movement of an outer body along tension element 502 in one direction and offer significant resistance to movement of the outer body along the tension element in the other direction. FIG. 5C shows a perspective view of a tension element 506 comprising multiple filaments 507 of a material twisted together. Examples of materials that can be used include to manufacture multiple filaments 507 include but are not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. multiple filaments 507 may be coated with a coating 508 including, but not limited to a lubricious coating, antibiotic coating, etc. It is also possible for the tension element to comprise a composite braided structure in a plastic/metal or plastic/plastic configuration to reduce profile and increase strength. Such materials could have preset levels of elasticity and non-elasticity. FIG. 5D shows a perspective view of a tension element 509 comprising a flexible, elastic, spiral or spring element. Examples of materials that can be used include to manufacture tension element 509 include but are not limited to metals e.g. various grades of stainless steel, titanium, nickel-titanium alloys, cobalt-chromium alloys, tantalum etc. FIG. 5E shows a perspective view of a tension element 510 comprising a screw threading 511 on the outer surface of tension element 510. Screw threading 511 enables tension element 510 to be screwed through an outer element to advance or withdraw tension element through the outer element. FIG. 5F shows a perspective view of a tension element 512 comprising a hollow shaft 514 comprising one or more collapsible regions 516. A collapsible region 516 comprises one or more windows 518. Windows 518 are cut in hollow shaft 514 in such a way that several thin, collapsible struts 520 are created between adjacent windows 518. When tension element 512 is compresses along its length, collapsible struts 520 are deformed in the radially outward direction to create one or more anchoring regions.

FIG. 5G shows a perspective view of an anchoring device 522 comprising a tension element and two anchors. Distal end of a tension element 524 is attached to a distal anchor 526. Proximal end of tension element 524 is attached to a proximal anchor 528.

FIG. 5H shows a perspective view of a tensioning element device comprising a detachable region. Anchoring device 530 comprises a first anchor 532 and a second anchor 534. First anchor 532 and second anchor 534 may comprise a variety of anchor designs disclosed elsewhere in this patent application. In one embodiment, one or both of first anchor 532 and second anchor 534 comprise a substantially flat plate. The substantially flat plate may be made from various materials including, but not limited to metals e.g. various grades of stainless steel, titanium, nickel-titanium alloys, cobalt-chromium alloys, tantalum etc.; polymers e.g. polypropylene, Teflon etc.; synthetic fibers e.g. various grades of Nylon, polyethylene, polypropylene, polyester, Aramid etc.; natural fibers e.g. cotton, silk etc.; rubber materials e.g. various grades of silicone rubber etc. First anchor 532 and second anchor 534 are connected to a tensioning element. The tensioning element comprises two flexible members: a first tensioning member 536 and a second tensioning member 538. The distal end of first tensioning member 536 is connected to first anchor 532 and the proximal end of second tensioning member 538 is connected to second anchor 534. Proximal end of first tensioning member 536 and distal end of second tensioning member 538 are connected to a releasable member 540. Releasable member 540 can be releasably connected to a deploying device. In one embodiment of a method using anchoring device 530, first anchor 532 is deployed out of an anatomical tissue (e.g. the prostate gland) into a first anatomical cavity (e.g. the pelvic cavity). Thereafter, second anchor 534 is deployed into a second anatomical cavity (e.g. the urethral lumen). Thereafter, releasable member 540 is released from the deploying device to deliver anchoring device 530 in a target region.

FIG. 5I shows a perspective view of a tensioning element comprising telescoping tubes. Tensioning element 544 may comprise two or more telescoping tubes. In this example, tensioning element 544 comprises three telescoping tubes: a first telescoping tube 546, a second telescoping tube 548 and a third telescoping tube 550. Second telescoping tube 548 slidably fits into a lumen of first telescoping tube 546. Similarly third telescoping tube 550 slidably fits into a lumen of second telescoping tube 548. The telescoping tubes have a locking mechanism to prevent a telescoping tube from completely disengaging from another telescoping tube. The telescoping tubes may be made from a variety of biocompatible materials including, but not limited to plastics, metals etc.

All the components of the systems disclosed herein (including but not limited to the tensioning elements, inner and outer anchor members) may be coated or embedded with therapeutic or diagnostic substances (e.g., drugs or therapeutic agents) or such therapeutic or diagnostic substances may be introduced into or near the prostate or adjacent tissue through a catheter, cannula needles, etc. Examples of therapeutic and diagnostic substances that may be introduced or eluted include but are not limited to: hemostatic agents; antimicrobial agents (antibacterials, antibiotics, antifungals, antiprotozoals; antivirals; antimicrobial metals (e.g., silver, gold, etc.); hemostatic and/or vasoconstricting agents (e.g., pseudoephedrine, xylometazoline, oxymetazoline, phenylephrine, epinephrine, cocaine, etc.); local anesthetic agents (lidocaine, cocaine, bupivacaine); hormones; anti-inflammatory agents (steroidal and non-steroidal); hormonally active agents; agents to enhance potency; substances to dissolve, degrade, cut, break, weaken, soften, modify or remodel connective tissue or other tissues; (e.g., enzymes or other agents such as collagenase (CGN), trypsin, trypsin/EDTA, hyaluronidase, and tosyllysylchloromethane (TLCM)); chemotherapeutic or antineoplastic agents; substances that prevent adhesion formation (e.g., hyaluronic acid gel); substances that promote desired tissue ingrowth into an anchoring device or other implanted device; substances that promote or facilitate epithelialization of the urethra or other areas; substances that create a coagulative lesion which is subsequently resorbed causing the tissue to shrink; substances that cause the prostate to decrease in size; phytochemicals that cause the prostate to decrease in size; alpha-1a-adrenergic receptor blocking agents; 5-alpha-reductase inhibitors; smooth muscle relaxants; agents that inhibit the conversion of testosterone to dihydrotestosterone, etc. Specific examples of antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) that may be delivered in accordance with the present invention include but are not limited to; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (*vinca*) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, macrophages or giant cells that modify or soften tissue when so desired, cells that participate in or effect the growth of tissue.

FIGS. 6A through 11A show various examples of anchor designs and/or anchoring device designs. FIGS. 6A and 6B show examples of a crumpling anchor 600. In FIG. 6A, crumpling anchor 600 comprises a substantially flattened body 602. Body 602 can be made of a variety of materials including, but not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. Further, in any of the implantable tissue compression devices, any or all of the anchors, the tensioning element(s) and any other components may be coated, impregnated, embedded or otherwise provided with substance(s) (e.g., drugs, biologics, cells, etc.) to reduce the likelihood of infection, inflammation, treat the prostatic adenoma directly or enhance the likelihood of endothelialization, deter adhesion formation, promote healing or otherwise improve the likelihood or degree of success of the procedure. Such substance(s) may be released primarily at the time of delivery or may be released over a sustained period. Examples of such substances are listed above and include but are not limited to certain metals with bacteriostatic action (i.e. silver, gold, etc.), antibiotics, antifungals, hemostatic agents (i.e. collagen, hyaluronic acid, gelfoam, cyano-acrylate, etc.), anti-inflammatory agents (steroidal and non-steroidal), hormonally active agents, stem cells, endothelial cells, genes, vectors containing genes, etc. Body 602 may be non-woven or woven. Body 602 may have a variety of shapes including, but not limited to square, rectangular, triangular, other regular polygonal, irregular polygonal, circular etc. Body 602 may have a substantially one dimensional, two dimensional or three dimensional shape. The material chosen for this device may have hemostatic properties to reduce bleeding from the implantation tract or site. Distal end of body 602 is connected to the distal end of tension element 604. Body 602 further comprises one or more attachment means 606. Attachment means are used to create a channel in the body 602 through which tension element 604 passes. Crumpling anchor 600 is introduced through a region of tissue (e.g. through prostate gland tissue) into a cavity or lumen e.g. pelvic cavity, urethral lumen etc. In FIG. 6B, tension element 604 is pulled in the proximal direction. The causes crumpling (e.g., collapsing) of the crumpling anchor 600 between the tissue and the distal end of tension element 604. This process prevents tension element 604 in the tissue and prevents further movement of tension element 604 in the proximal direction.

FIGS. 7A and 7B show an example of a deployable anchor 700 in an undeployed configuration and a deployed configuration, respectively. This deployable anchor 700 comprises one or more anchoring arms 702. Anchoring arms 702 may be made from a variety of elastic, super-elastic or shape memory materials etc. Typical examples of such materials include but are not limited to metals e.g. stainless steel, titanium, nickel-titanium alloys, cobalt-chromium alloys, tantalum etc. Anchoring arms 702 are connected to a central hub 704. Central hub in turn is connected to the distal end of a tension element 706. In FIG. 7A, anchoring arms 702 are folded inside a hollow deploying sheath 708. This reduces the undeployed diameter of anchoring arms 702 and also prevents unwanted anchoring of anchoring arms 702. In FIG. 7B, deploying sheath 708 is pulled in the proximal direction. This releases anchoring arms 702 from the distal end of deploying sheath 702. This causes anchoring arms 702 to open in the radially outward direction. Anchor 700 can then anchor to tissue and resist movement of tension element 706 in the proximal direction.

FIGS. 8A and 8B show sectional views of an undeployed configuration and a deployed configuration respectively of a "T" shaped deployable anchor. Anchor 8110 comprises an elongate region 802. Elongate region 802 may be made from a variety of elastic, super-elastic or shape memory materials etc. Typical examples of such materials include but are not limited to metals e.g. stainless steel, titanium, nickel-titanium alloys, cobalt-chromium alloys, tantalum etc; polymers e.g. polypropylene, Teflon etc. Middle section of elongate region 802 is connected to the distal end of a tension element 804 to form a "T" shaped anchor. In one embodiment, middle section of elongate region 802 is connected to the distal end of a tension element 804 by a hinge. In FIG. 8A, elongate region 802 is folded inside a hollow deploying sheath 806. This reduces the undeployed diameter of the distal region of anchor 8110 and also prevents unwanted anchoring of elongate region 802 to tissue. In FIG. 8B, deploying sheath 806 is pulled in the proximal direction. This releases elongate region 802 from the distal end of deploying sheath 806. This in turn causes elongate region 802 to twist and orient itself perpendicular to the distal end of a tension element 804. Anchor 800 can then anchor to tissue and resist movement of tension element 804 in the proximal direction.

Figures 9A, 9B, 9C, 9D:
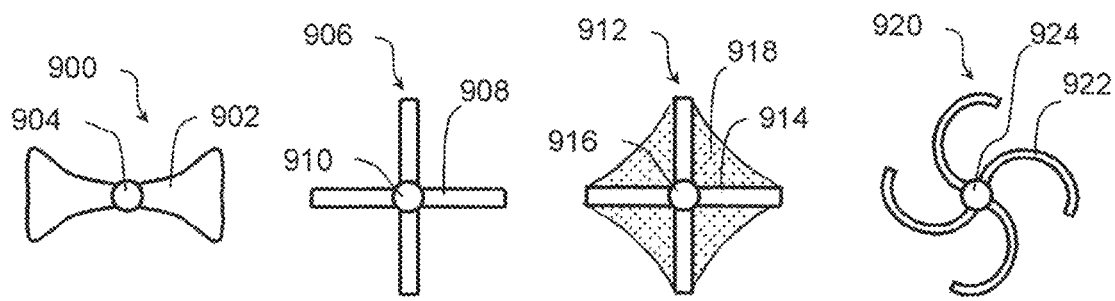
FIGS. 9A through 9D show various alternate configurations of the anchoring arms in FIGS. 7A and 7B.

Anchoring arms 702 in FIGS. 7A and 7B can have a variety of configurations including, but not limited to configurations shown in FIGS. 9A through 9D. FIG. 9A shows a distal end view of an embodiment of an anchor comprising two triangular arms. Anchor 900 comprises two anchor arms 902. Anchor arms 902 can be made of a variety of materials including, but not limited to metals e.g. stainless steel, titanium, nickel-titanium alloys, cobalt-chromium alloys, tantalum etc; polymers e.g. polypropylene, Teflon etc. Anchor arms 902 are connected to a tension element 904. In one embodiment, anchor arms 902 are connected to a central hub, which in turn is connected to tension element 904. The arms in each of these devices may be folded or contained prior to deployment through the use of a sheath or grasping or mounting device. FIG. 9B shows a distal end view of an embodiment of an anchor comprising four rectangular arms. Anchor 906 comprises four anchor arms 908. Anchor arms 908 can be made of a variety of materials including, but not limited to metals e.g. stainless steel, titanium, nickel-titanium alloys, cobalt-chromium alloys, tantalum etc; polymers e.g. polypropylene, Teflon etc. Anchor arms 908 are connected to a tension element 910. In one embodiment, anchor arms 908 are connected to a central hub, which in turn is connected to tension element 910. FIG. 9C shows a distal end view of an embodiment of an anchor comprising a mesh or a woven material. Anchor 912 comprises four anchor arms 914. Anchor arms 914 can be made of a variety of materials including, but not limited to metals e.g. stainless steel, titanium, nickel-titanium alloys, cobalt-chromium alloys, tantalum etc; polymers e.g. polypropylene, Teflon etc. Anchor arms 914 are connected to a tension element 916. In one embodiment, anchor arms 914 are connected to a central hub, which in turn is connected to tension element 916. A layer of porous material 918 is located between anchor arms 914. Porous material 918 comprises a plurality of pores that allow for tissue ingrowth. Porous material 918 may also help to distribute the pressure on anchor arms 914 over a wider area. Porous material 918 can be made of variety of materials including, but not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. Porous material 918 may be non-woven or woven. Any of the arms or struts in one or more anchoring devices may comprise bent or curved regions. For example, FIG. 9D shows a distal end view of an embodiment of an anchor comprising four curved arms. Anchor 920 comprises four curved anchor arms 922. Curved anchor arms 922 can be made of a variety of materials including, but not limited to metals e.g. stainless steel, titanium, nickel-titanium alloys, cobalt-chromium alloys, tantalum etc; polymers e.g. polypropylene, Teflon etc. Curved anchor arms 922 are connected to a tension element 924. In one embodiment, curved anchor arms 922 are connected to a central hub which in turn is connected to tension element 924.

Figures 10A, 10B, 10C:
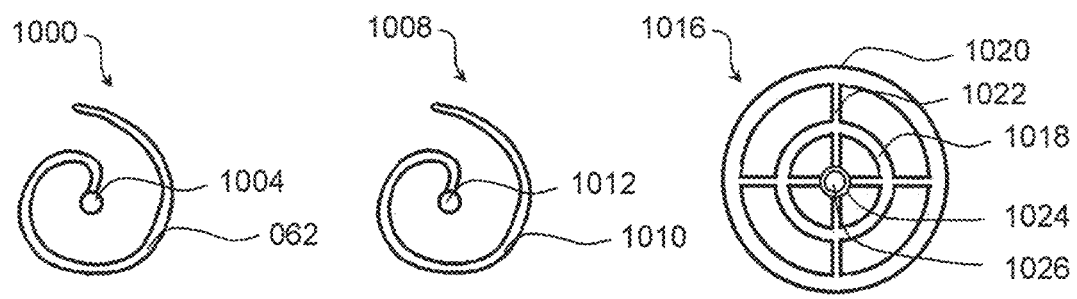
FIGS. 10A and 10A' show a distal view and a perspective view respectively of an anchor comprising a spiral element having a three dimensional shape.
FIGS. 10B and 10B' show a distal view and a side view respectively of an anchor comprising a spiral element having a two dimensional shape.
FIGS. 10C and 10C' show a distal view and a perspective view respectively of an anchor comprising one or more circular elements.
Figures 10A, 10B, 10C:
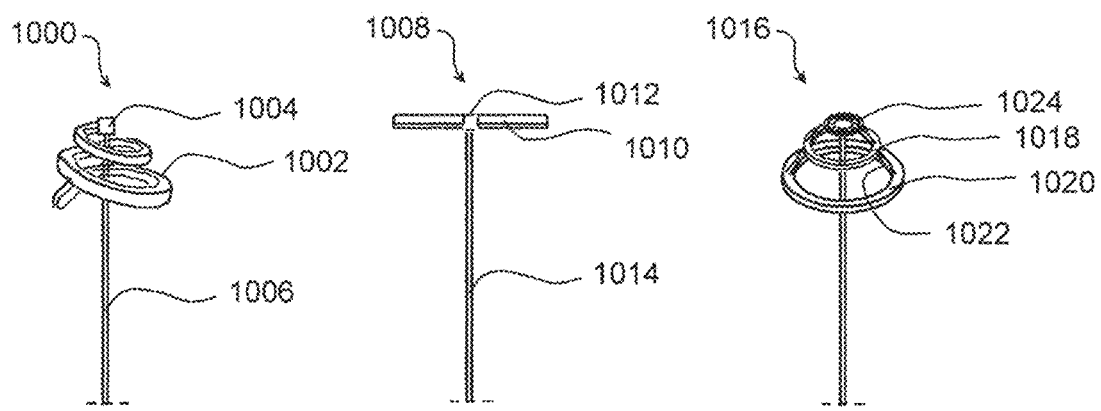
Figure 10:
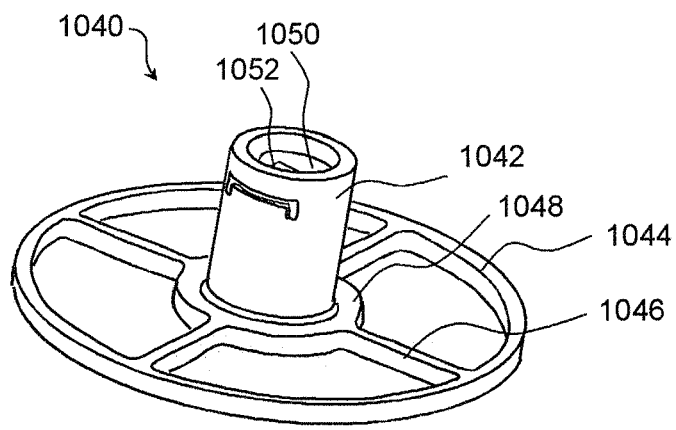
Figure 10:
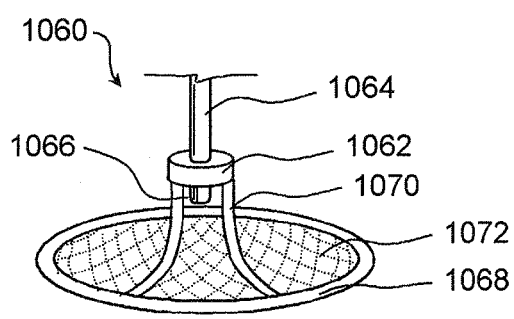
Figure 11:
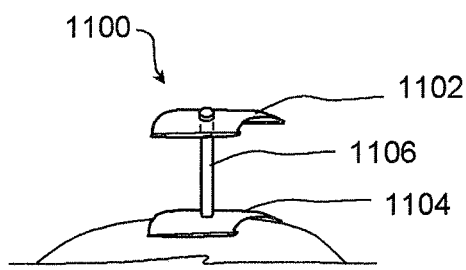

FIG. 10A shows a distal end view of an anchor comprising a spiral element having a three dimensional shape. Anchor 1000 comprises a three dimensional spiral element 1002. Diameter of spiral element 1002 may be substantially constant or may substantially vary along the length of spiral element 1002. Spiral element 1002 may be made of an elastic, super-elastic or shape memory materials. Spiral element 1002 may be made of a variety of materials including, but not limited to metals e.g. various grades of stainless steel, titanium, nickel-titanium alloys, cobalt-chromium alloys, tantalum etc.; polymers e.g. polypropylene, Teflon etc.; synthetic fibers e.g. various grades of Nylon, polyethylene, polypropylene, polyester, Aramid etc.; natural fibers e.g. cotton, silk etc.; rubber materials e.g. various grades of silicone rubber etc. Spiral element 1002 is connected to a central hub 1004, which in turn is connected to a tension element. In one embodiment, spiral element 1002 is directly connected to a tension element without using central hub 1004. FIG. 10A' shows a side view of the anchor in FIG. 10A. FIG. 10A' shows anchor 1000 comprising spiral element 1002 connected to central hub 1004 which in turn is connected to a tension element 1006. FIG. 10B shows a distal end view of an anchor comprising a spiral element having a two dimensional shape. Anchor 1000 comprises a two dimensional spiral element 1010. Spiral element 1010 may be made of an elastic, super-elastic or shape memory materials. Spiral element 1010 may be made of a variety of materials including, but not limited to metals e.g. various grades of stainless steel, titanium, nickel-titanium alloys, cobalt-chromium alloys, tantalum etc.; polymers e.g. polypropylene, Teflon etc.; synthetic fibers e.g. various grades of Nylon, polyethylene, polypropylene, polyester, Aramid etc.; natural fibers e.g. cotton, silk etc.; rubber materials e.g. various grades of silicone rubber etc. Spiral element 1010 is connected to a central hub 1012 which in turn is connected to a tension element. In one embodiment, spiral element 1010 is directly connected to a tension element without using central hub 1012. FIG. 10B' shows a side view of the anchor in FIG. 10B. FIG. 10B' shows anchor 1008 comprising spiral element 1010 connected to central hub 1012 which in turn is connected to a tension element 1014. FIG.

10C shows a distal end view of an anchor comprising one or more circular elements. In FIG. 10C, anchor 1016 comprises an inner circular element 1018 and an outer circular element 1020. A series of radial arms or struts 1022 connect inner circular element 1018 to outer circular element 1020 and to a central hub 1024. Central hub 1024 may have a lumen 1026. Anchor 1016 may be substantially two dimensional or three dimensional. FIG. 10C' shows a perspective view of the anchor in FIG. 10C. FIG. 10C' shows an anchor 1016 comprising an inner circular element 1018, an outer circular element 1020 and series of radial arms or struts 1022 connecting inner circular element 1018 to outer circular element 1020 and to a central hub 1024. Central hub 1024 is connected to a tension element.

FIG. 10D shows a perspective view of an embodiment of an anchoring device comprising an outer ring. Anchor 1040 comprises a central hub 1042 and an outer ring 1044. In one embodiment, central hub 1042 acts as a plug to plug an opening in the anatomy to reduce or prevent bleeding or leakage of fluids. Central hub 1042 is connected to outer ring 1044 by one or more bars or struts 1046. In one embodiment, central hub 1042 is connected to an inner ring 1048 which in turn is connected to outer ring 1044 by one or more bars or struts 1046. Central hub 1042 further comprises a locking element 1050. Locking element 1050 comprises a lumen 1052 through which a tension element can slide. After positioning anchor 1040 in a desired position with respect to the tension element, locking element 1050 is used to securely attach anchor 1040 on the tension element. Locking element 1050 may comprise a design disclosed including various locking designs disclosed elsewhere in this patent application. Anchor 1040 may be made from a variety of materials including, but not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc.

FIG. 10E shows a partial perspective view of an anchoring device comprising a hemostatic element. Anchor 1060 comprises a central hub 1062. In one embodiment, central hub 1062 acts as a plug to plug an opening in the anatomy to reduce or prevent bleeding or leakage of fluids. Central hub 1062 comprises a cinching mechanism to allow central hub 1062 to cinch on to a tension element 1064 passing through central hub 1062. The free end 1066 of tension element 1064 is severed to minimize the presence of tension element 1064 in the anatomy. Anchor 1060 further comprises an outer ring 1068. Central hub 1062 is connected to outer ring 1068 by one or more struts 1070. Anchor 1060 further comprises a mesh or porous element 1072 between outer ring 1068 and struts 1070. The mesh or porous element 1072 may be concave shaped as shown in FIG. 10E. Mesh or porous element 1072 allows for tissue ingrowth over a period of time thus providing additional securing of anchor 1060 to tissue.

FIG. 11A shows a perspective view of a device having a set of anchors comprising a curved sheet. Anchoring device 1100 may comprise one or more anchors comprising a curved sheet. In this example, anchoring device 1100 comprises a first anchor 1102 and a second anchor 1104. First anchor 1102 and second anchor 1104 may comprise elastic, super elastic or shape memory materials. First anchor 1102 and second anchor 1104 may be made from various materials including, but not limited to metals e.g. various grades of stainless steel, titanium, nickel-titanium alloys, cobalt-chromium alloys, tantalum etc.; polymers e.g. polypropylene, Teflon etc.; synthetic fibers e.g. various grades of Nylon, polyethylene, polypropylene, polyester, Aramid etc.; natural fibers e.g. cotton, silk etc.; rubber materials e.g. various grades of silicone rubber etc. The concave surface of first anchor 1102 is connected to a first end of a tension element 1106. Second end of tension element 1106 is connected to the convex surface of second anchor 1104. In one embodiment of a method to deploy anchoring device 1106, first anchor 1102 is deployed out of an anatomical tissue (e.g. the prostate gland) into a first anatomical cavity (e.g. the pelvic cavity). Thereafter, second anchor 1104 is deployed into a second anatomical cavity (e.g. the urethral lumen). This method embodiment has the advantage of using the natural curvature of first anchor 1102 and second anchor 1104 to distribute pressure on first anchor 1102 and second anchor 1104 over a large area.

FIGS. 12A through 17I show further examples of anchor designs and/or anchoring device designs. FIG. 12A shows a perspective view of an anchor comprising an arrowhead. Anchor 1200 comprises an arrowhead 1202. Arrowhead 1202 may be made from various materials including, but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. Arrowhead 1202 may comprise a sharp distal tip. Arrowhead 1202 may have a three dimensional or a substantially two dimensional design. Proximal region of arrowhead 1202 is wider that the distal region of arrowhead 1202 to resist motion of arrowhead 1202 along the proximal direction after it is deployed in a tissue. Proximal region of arrowhead 1202 is connected to a tension element 1204. FIG. 12B shows a crossectional view of an anchor comprising a cup-shaped element that encloses a cavity. Anchor 1208 comprises a cup-shaped element 1210. Proximal, concave surface of cup-shaped element 1210 encloses a cavity. Cup-shaped element 1210 may be made from various materials including, but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. Proximal region of cup-shaped element 1210 is connected to a tension element 1212. FIG. 12C shows a perspective view of an anchor comprising a screw. Anchor 1216 comprises a screw 1218. Screw 1218 may be made from various materials including, but not limited to metals e.g. various grades of stainless steel, titanium, nickel-titanium alloys, cobalt-chromium alloys, tantalum etc.; polymers e.g. polypropylene, Teflon etc. Screw 1218 may comprise a sharp distal tip. Proximal region of screw 1218 may be wider that the distal region of screw 1218 to resist motion of screw 1218 along the proximal direction after it is deployed in a tissue. Screw 1218 comprises a thread rolled thread including, but not limited to wood screw style thread, double lead thread, tapping style thread, tapered wood thread etc. Proximal region of arrowhead 1202 is connected to a tension element 1204.

FIGS. 13A and 13B show perspective views of an uncollapsed state and a collapsed state respectively of an anchor comprising a collapsible region. In FIG. 13A, anchor element 1300 is in an uncollapsed state. Anchor element 1300 comprises a hollow shaft 1302 comprising one or more collapsible regions. A collapsible region comprises one or more windows 1304. Windows 1304 are cut in hollow shaft 1302 in such a way that several thin, collapsible struts 1306 are created between adjacent windows 1304. In FIG. 13B, anchor element 1300 is in a collapsed state. When anchor element 1300 is compresses along its length, collapsible struts 1306 are deformed in the radially outward direction to create one or more anchoring regions.

FIGS. 13C and 13D show perspective views of an undeployed state and a deployed state respectively of an anchor comprising radially spreading arms. In FIG. 13C, anchor 1312 comprises a hollow tube 1314. Hollow tube 1314 is made from suitable elastic, super-elastic or shape memory materials such as metals including, but not limited to titanium, stainless steel, Nitinol etc.; suitable elastic polymers etc. U-shaped slots 1316 are cut in hollow tube 1314 in such a way that arms 1318 are created within U-shaped slots 1316. In this embodiment, U-shaped slots are substantially parallel to the axis of hollow tube 1314. In absence of an external force, arms 1318 tend to spread in a radially outward direction. Anchor 1312 is kept in an undeployed state by enclosing anchor 1312 in a sheath. Anchor 1312 is deployed by removing the sheath to allow arms 1318 to spread in a radially outward direction as shown in FIG. 13D.

Hollow tube 1314 may comprise one or more cinching elements. Cinching elements may be located on the proximal region, distal region or a middle region of hollow tube 1314. The cinching element or elements may comprise cinching mechanisms including, but not limited to cinching mechanisms disclosed in FIGS. 26A through 29P.

FIG. 13E shows perspective views of an alternate embodiment of an undeployed state of an anchor comprising radially spreading arms. In FIG. 13C, anchor 1320 comprises a hollow tube 1322. Hollow tube 1322 is made from suitable elastic, super-elastic or shape memory materials such as metals including, but not limited to titanium, stainless steel, Nitinol etc.; suitable elastic polymers etc. U-shaped slots 1324 are cut in hollow tube 1322 in such a way that arms 1326 are created within U-shaped slots 1324. In this embodiment, U-shaped slots are at an angle to the axis of hollow tube 1322 as shown in FIG. 13E.

FIGS. 14A and 14B show perspective views of anchoring devices comprising an adhesive delivering element. FIG. 14A shows a perspective view of an anchoring device 1400 comprising a hollow shaft 1402 with a shaft lumen. Hollow shaft 1402 can be made of suitable biocompatible materials including, but not limited to Pebax, Polyimide, Braided Polyimide, Polyurethane, Nylon, PVC, Hytrel, HDPE, PEEK, metals like stainless steel and fluoropolymers like PTFE, PFA, FEP and EPTFE etc. Distal end of shaft lumen ends in a delivery opening 1404. When an adhesive is injected through the shaft lumen, it emerges out of anchoring device 1400 through delivery opening 1404. Hollow shaft 1402 may also comprise an attachment element 1406 such as a porous woven or non-woven circular sleeve securely attached to hollow shaft 1402. The circular sleeve may be made of a variety of materials including, but not limited to metals e.g. various grades of stainless steel, titanium, nickel-titanium alloys, cobalt-chromium alloys, tantalum etc.; polymers e.g. polypropylene, Teflon etc.; synthetic fibers e.g. various grades of Nylon, polyethylene, polypropylene, polyester, Aramid etc.; natural fibers e.g. cotton, silk etc.; rubber materials e.g. various grades of silicone rubber etc. The adhesive flowing out through delivery opening comes into contact with attachment element 1406 and securely attaches attachment element 1406 to surrounding tissue. FIG. 14B shows a perspective view of an anchoring device 1408 comprising a hollow shaft 1410 with a shaft lumen. Hollow shaft 1410 can be made of suitable biocompatible materials including, but not limited to Pebax, Polyimide, Braided Polyimide, Polyurethane, Nylon, PVC, Hytrel, HDPE, PEEK, metals like stainless steel and fluoropolymers like PTFE, PFA, FEP and EPTFE etc. Distal end of shaft lumen ends in a delivery opening 1412. When an adhesive is injected through the shaft lumen, it emerges out of anchoring device 1408 through delivery opening 1412. Hollow shaft 1410 may also comprise an attachment element 1414 such as porous foam securely attached to hollow shaft 1410. The porous foam may be made of a variety of materials including, but not limited to polymers e.g. polypropylene, Teflon etc.; synthetic fibers e.g. various grades of Nylon, polyethylene, polypropylene, polyester, Aramid etc.; rubber materials e.g. various grades of silicone rubber etc. The adhesive flowing out through delivery opening comes into contact with attachment element 1414 and securely attaches attachment element 1414 to surrounding tissue. Typical examples of adhesives that can be used with anchoring device 1400 and anchoring device 1408 include but are not limited to cyanoacrylates, marine adhesive proteins, fibrin-based sealants etc.

FIGS. 15A and 15B show two configurations of an anchoring device comprising a ratcheted tension element. Anchoring device 1500 comprises a distal anchor. Distal anchor may comprise a design selected from the variety of designs disclosed elsewhere in this document. In this particular example, distal anchor comprises a series of radial arms 1502 connected to a central hub 1504. The proximal end of central hub is attached to a ratcheted tension element 1506. A proximal anchor is located on ratcheted tension element 1506 proximal to the distal anchor. Proximal anchor may comprise a design selected from the variety designs disclosed elsewhere in this document. In this particular example, distal anchor comprises a series of radial arms 1508 connected to a central hub 1510. Central hub 8368 has a central lumen through which ratcheted tension element 1506 can slide. Ratcheted tension element 1506 has ratchets arranged such that proximal anchor can slide easily over ratcheted tension element 1506 in the distal direction but cannot slide easily in the proximal direction. In FIG. 15B, proximal anchor slides over ratcheted tension element 1506 in the distal direction. This causes a compression of tissue between distal anchor and proximal anchor. The compression of tissue can be maintained since proximal anchor cannot slide easily in the proximal direction. In one embodiment of a method using anchoring device 1500, distal anchor is introduced via an anatomical lumen (e.g. the urethral lumen) and through a tissue (e.g. the prostate gland) into an anatomical cavity (e.g. the pelvic cavity). Thereafter, proximal anchor is advanced along ratcheted tension element 1506 till it encounters a wall (e.g. the urethral wall) of the anatomical lumen. Anchoring device 1500 may be made from various materials including, but not limited to metals e.g. various grades of stainless steel, titanium, nickel-titanium alloys, cobalt-chromium alloys, tantalum etc.; polymers e.g. polypropylene, Teflon etc.

FIG. 16 shows a perspective view of an anchor comprising a trocar lumen. Anchor 1600 comprises a hollow shaft 1602 comprising a lumen. A trocar 1604 or a penetrating device can pass through hollow shaft 1602 such that the distal tip of trocar 1604 emerges out through the distal end of hollow shaft 1602. Distal end of hollow shaft 1602 comprises a tapering region 1606 with a smaller distal diameter and a larger proximal diameter. Tapering region 1606 further comprises a series of sharp projections 1608 located on the proximal end of tapering region 1606. Projections 1608 may be projecting in the proximal direction, radially outward direction etc. Projections 1608 prevent the movement of anchor 1600 in the proximal direction after it has penetrated through a tissue. Anchor 1600 may also comprise a sleeve 1610 located proximal to tapering region 1606. Sleeve 1610 is made of a porous material that has a plurality of pores that allow for tissue ingrowth thus anchoring sleeve 1610 firmly in tissue. Sleeve 1610 may also help to distribute the pressure on tapering region 1606 over a wider area. Sleeve 1610 may be non-woven or woven. Sleeve 1610 can be made of variety of materials including, but not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc.

Figure 17A:
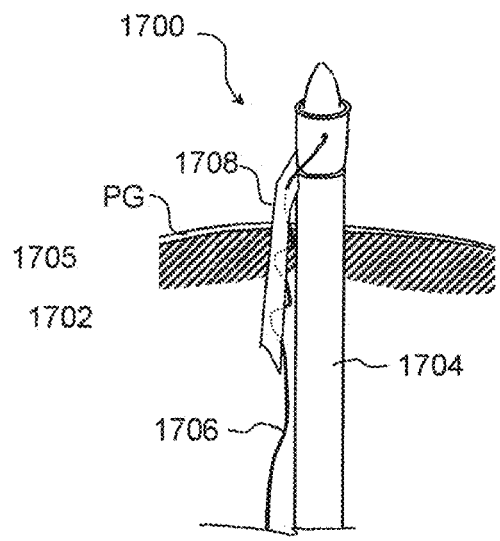
FIG. 17A shows a perspective view in the undeployed state of an anchor comprising a rigid or partially flexible T element and a crumpling element.
Figure 17B:
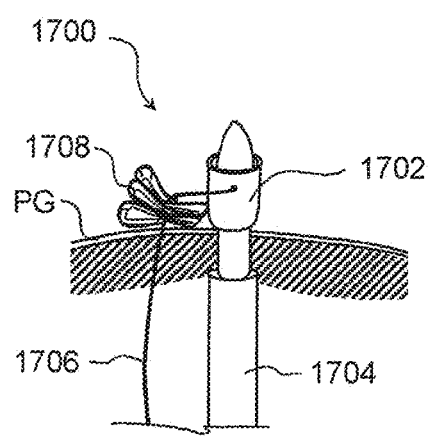
FIGS. 17B and 17C show various steps of a method to deploy the anchoring device shown in FIG. 17A.
Figure 17C:
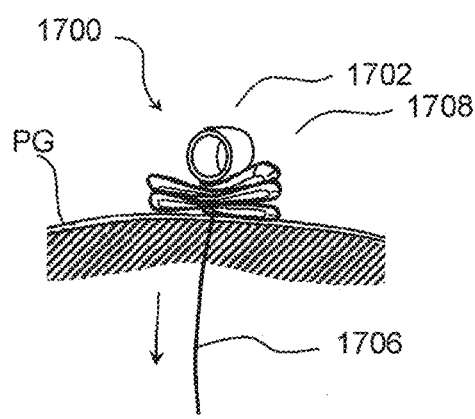

FIG. 17A shows a perspective view in the undeployed state of an anchor comprising a rigid or partially flexible T element and a crumpling element. In FIG. 17A, anchoring device 1700 comprises a distal, T element 1702. The T element 1702 may be made of a variety of materials including, but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. Further it may be a composite material or have cut out sections to allow it to be flexible in certain dimensions but rigid in other dimensions. In this example, T element 1702 is in the form of a hollow cylinder. The proximal end of T element 1702 is in contact with the distal end of a delivery rod 1704. Delivery rod 1704 is hollow and is used to deliver T element 8266 in a target anatomical region. A trocar 1705 can pass through delivery rod 1704 and through T element 1702 such that the distal tip of trocar emerges through the distal end of rigid element 1702. The T-element could also be contained within a lumen of the trocar or may be the trocar itself of the T element 1702 is connected to the distal end of a flexible tension element 1706. Various connection means are possible such as the tension element being tied or crimped to the T element, or passing through a loop in the T element, or being adhered by adhesive or weld, or by being made of a continuous material which becomes the T element. Although the T element is shown as a T, any shape which is larger in at least one dimension compared to its other dimensions could appropriately be released and cause to change it's orientation to produce an anchoring effect. Examples of materials that can be used to manufacture tension element 1706 include but are not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. A substantially flattened body 1708 is located on the distal region of tension element 1706. Tension element 1706 is threaded through body 1708 in such a way that tension element 1706 can slide through body 1708. Body 1708 may be non-woven or woven. Body 1708 can be made of a variety of materials including, but not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. Body 1708 may have a variety of shapes including, but not limited to square, rectangular, triangular, other regular polygonal, irregular polygonal, circular etc. Body 1708 may have a substantially one dimensional, two dimensional or three dimensional shape. FIGS. 17B and 17C show various steps of a method to deploy the anchoring device shown in FIG. 17A. In FIG. 17B, anchoring device 1700 is introduced in an anatomical cavity (e.g. the pelvic cavity) through a tissue (e.g. the prostate gland). Thereafter, trocar 1705 is withdrawn by pulling trocar 1705 in the proximal direction. Thereafter, delivery rod 1704 is withdrawn by pulling delivery rod 1704 in the proximal direction. Thereafter, tension element 1706 is pulled in the proximal direction. Tension element 1706 in turn pulls T element 1702 in the proximal direction. In FIG. 17C, rigid element 1702 is pulled against a wall of the tissue (e.g. the prostate gland) but is unable to penetrate the tissue because of its size. This causes body 1708 to crumple because of compression of body 1708 between the wall of the tissue and rigid element 1702. Crumpled body 1708 may be designed to cause tissue ingrowth or epithelialization in body 1708 as well as healing, hemostasis or a more even force distribution.

Figure 17D:
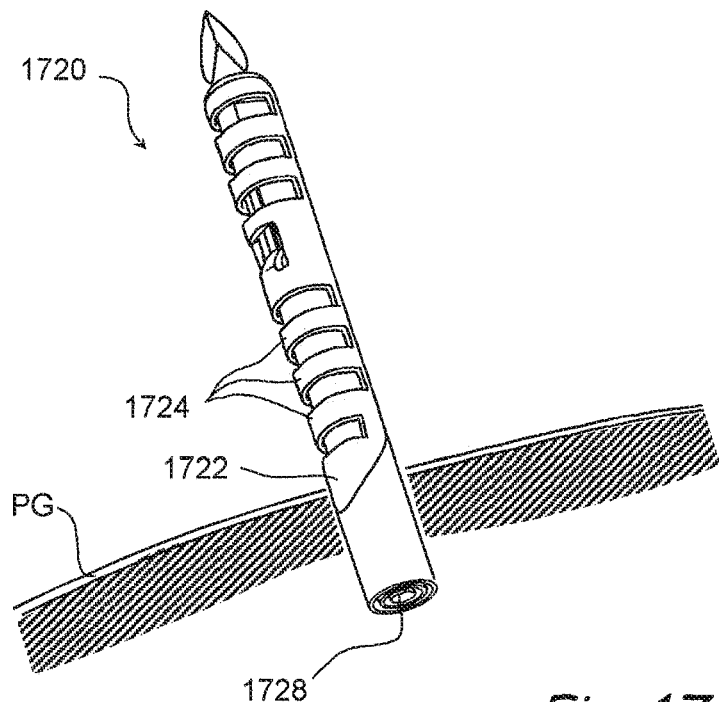
FIGS. 17D and 17E show perspective views of an undeployed and deployed configuration of an anchor comprising a rigid or partially flexible T element with one or more openings or perforations.
Figure 17E:
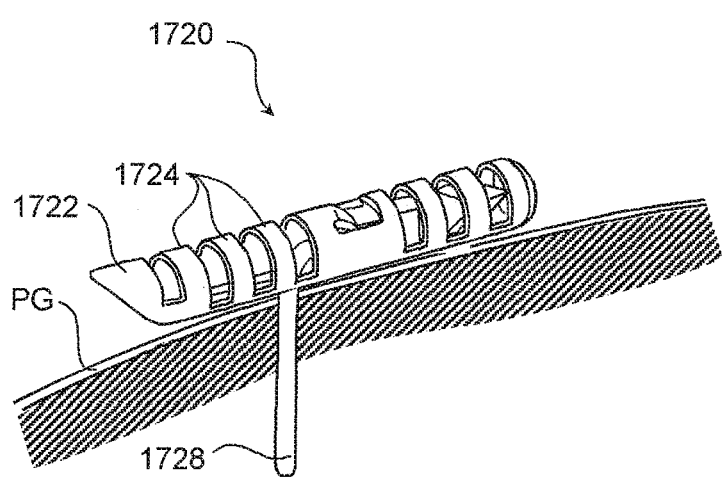

FIGS. 17D and 17E show perspective views of an undeployed and deployed configuration of an anchor comprising a rigid or partially flexible T element with one or more openings or perforations. FIG. 17D shows a perspective view of an anchoring device 1720 comprising an anchor 1722. Anchor 1722 comprises a tubular body. The tubular body may comprise one or more openings or perforations 1724 in the tubular body. Openings or perforations 1724 increase the flexibility of anchor 1722. This makes it easier to navigate anchoring device 1720 through the anatomy before reaching its target location. Further it enables anchoring device 1720 to be passed through a tight bend in the anatomy or through a delivery device. Within tubular body of anchor 1722 is trocar tip 1727 that is fixedly attached to tensioning element 1728. In the embodiment shown in FIG. 17D, anchor 1722 comprises a lumen. A length of the distal end of deployment element 1726 passes through the proximal end of the lumen and abuts trocar tip 1727 that enables anchor 1722 to puncture tissue. In an alternate embodiment trocar tip is fixedly attached to elongate deployment element 1726 and is retracted fully into element 1729 upon anchor deployment. In an alternate embodiment, distal tip of deployment device 1726 is not exposed through the distal end of anchor 1722. Distal end of anchor 1722 comprises a sharp tip to enable anchor 1722 to puncture tissue. Anchoring element 1720 further comprises a tension element 1728 attached to tubular body 1722. In this embodiment, distal end of tension element 1728 attached to the inner surface of the trocar tip 1727. Proximal region of tension element 1728 passes through deployment element 1726. Anchor 1722 is deployed by pushing in a distal direction one elongate deployment element 1726, that runs within lumen of anchor 1722 abutting trocar tip 1727 distally, in tandem with another elongate deployment element 1729 that abuts the proximal end of anchor 1722. Anchoring device 1720 punctures tissue to transport anchor 1722 through a first anatomical location (e.g. a prostate gland) to a second anatomical location (e.g. the pelvic cavity, urethra etc.). Thereafter, deployment element 1726 is withdrawn by pulling deployment element 1726 in the proximal direction. Thereafter, tension element 1728 is pulled in the proximal direction. This causes anchor 1722 to anchor in tissue as shown in FIG. 17E. Proximal portion of tension element 1728 emerges out of anchor 1722 through a lengthwise groove in anchor 1722 to create a T shaped anchor as shown in FIG. 17E. Tension on tensioning element 1728 causes trocar tip 1727 to retract into lumen 1722. In the example shown, the first anatomical location is the prostate gland PG and the second anatomical location is the pelvic cavity. Anchoring device 1720 can be made from a variety of materials including, but not limited to metals such as synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. Tension element 1728 may then be connected to any one of the other anchoring elements such as anchor 10D.

FIGS. 17F and 17G show perspective views of an undeployed and deployed configuration of an anchor comprising a stent. Anchor 1730 comprises a self-expanding stent and a tension element 1734. Distal end of tension element 1734 is attached to stent 1732. In one embodiment, distal end of tension element 1734 is attached on the mid section of stent 1732. Stent 1732 may comprise various designs including, but not limited to metallic tube designs, polymeric tube designs, spiral designs, chain-linked designs, rolled sheet designs, single wire designs etc. Stent 1732 may have an open celled or closed celled structure. A variety of fabrication methods can be used for fabricating stent 1732 including but not limited to laser cutting a metal or polymer element, welding metal elements etc. A variety of materials can be used for fabricating stent 1732 including but not limited to metals, polymers, foam type materials, super elastic materials etc. A variety of features can be added to stent 1732 including but not limited to radiopaque coatings, drug elution mechanisms etc. Anchor 1730 is introduced through a sheath 1736 into a target anatomy. Thereafter, sheath 1736 is withdrawn. This causes stent 1732 to revert to its natural shape as shown in FIG. 17G and act as an anchor.

FIGS. 17H and 17I show perspective views of an undeployed and deployed configuration of an anchor comprising a spring. Anchor 1740 comprises an elastic spring 1742 and a tension element 1744. Distal end of tension element 1744 is attached to spring 1742. In one embodiment, distal end of tension element 1744 is attached on the mid section of spring 1742. A variety of materials can be used for fabricating spring 1742 including but not limited to metals, polymers, foam type materials, super elastic materials etc. A variety of features can be added to spring 1742 including but not limited to radiopaque coatings, drug elution mechanisms etc. Anchor 1740 is introduced through a sheath 1746 into a target anatomy to reduce the profile of spring 1742. Thereafter, sheath 1746 is withdrawn. This causes spring 1742 to revert to its natural shape as shown in FIG. 17I and act as an anchor.

Figure 18:
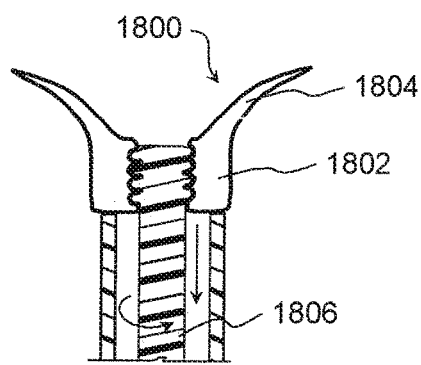
Figure 18:
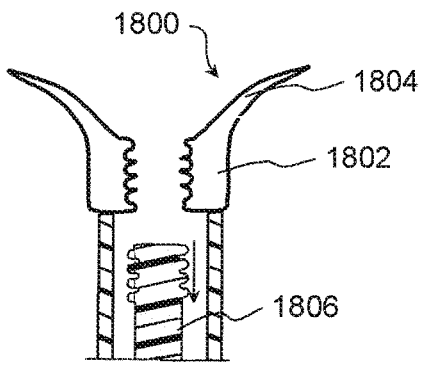
Figure 19:
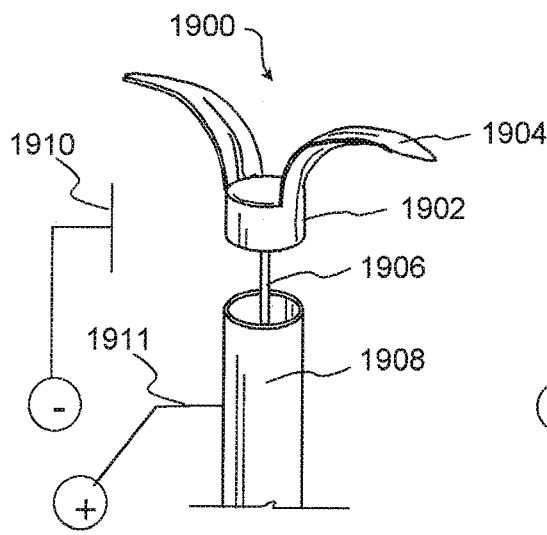
Figure 19:
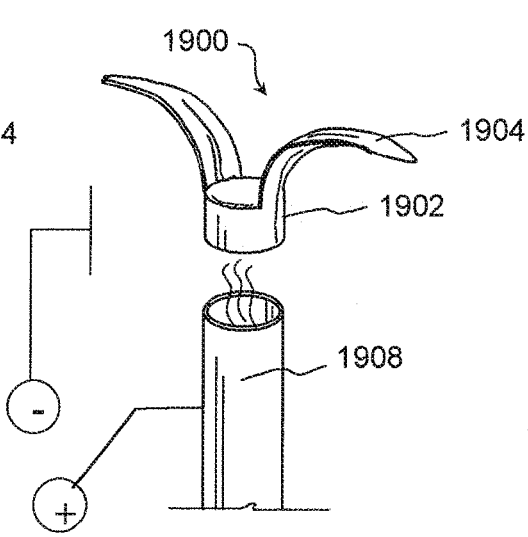

FIGS. 18A through 22E show various embodiments of mechanisms to deploy one or more anchors. FIG. 18A shows a crossection of an anchor deploying mechanism comprising a screw system. FIG. 18A shows an anchor deploying mechanism comprising an anchor 1800 comprising an anchor body 1802 and anchoring elements 1804 attached to anchor body 1802. Anchor body 1802 comprises an inner lumen. Inner lumen of anchor body 1802 comprises screw threading. Anchoring elements 1804 may have various designs including, but not limited to anchor designs disclosed elsewhere in this document. Anchor body 1802 and anchoring elements 1804 may be made of a variety of materials including but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. The anchor deploying mechanism further comprises a deploying shaft 1806. Distal region of deploying shaft 1806 comprises a screw threading such that deploying shaft 1806 can be screwed into anchor body 1802. FIG. 18B shows the method of deploying an anchor comprising a screw mechanism. Deploying shaft 1806 is rotated to release the distal region of deploying shaft 1806 from anchor body 1802 after positioning anchor 1800 in a desired location. Such a mechanism can be used to deploy one or more anchors. In one embodiment, more than one anchors are located on deploying shaft 1806. The anchors can be sequentially deployed by rotating deploying shaft 1806. Deploying shaft 1806 may be made of a variety of materials including, but not limited to metals e.g. various grades of stainless steel, titanium, nickel-titanium alloys, cobalt-chromium alloys, tantalum etc.; polymers e.g. polypropylene, Teflon etc. In one embodiment, the anchor deploying mechanism is located inside an outer sheath.

FIGS. 19A and 19B show a crossectional view of an anchor deploying system comprising an electrolytic detachment element. FIG. 19A shows a crossection of an anchor deploying mechanism comprising a deployable anchor 1900. Deployable anchor 1900 comprises an anchor body 1902 and anchoring elements 1904 attached to anchor body 1902. Anchoring elements 1904 may have various designs including, but not limited to anchor designs disclosed elsewhere in this document. Anchor body 8402 and anchoring elements 8404 may be made of a variety of materials including, but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. Proximal region of deployable anchor 1900 further comprises an electrolyzable element 1906. Electrolyzable element 1906 is made of a length of metallic wire e.g. steel wire. Proximal region of electrolyzable element 1906 is electrically connected to a deploying shaft 1908. Proximal region of deploying shaft 1908 is further connected to a first electrode. The anchor deploying system further comprises a second electrode 1910 connected to a bodily region of the patient to be treated. In FIG. 19B, the first electrode is connected to a positive terminal of a power supply and the second electrode is connected to the negative terminal of the power supply to form an electrical circuit. Electrical current flowing between electrolyzable element 1906 and second electrode 1910 causes metallic ions from electrolyzable element 1906 to dissolve into surrounding anatomy. This causes electrolyzable element 1906 to detach from deploying shaft 1908.

Figure 20:
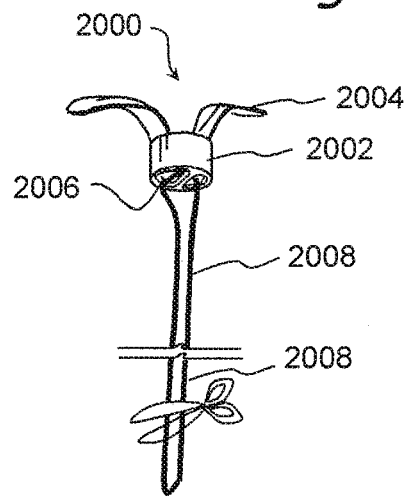

FIG. 20 shows a perspective view of an anchor deploying system comprising a looped ribbon. The anchor deploying system comprises a deployable anchor 2000. Deployable anchor 2000 comprises an anchor body 2002 and anchoring elements 2004 attached to anchor body 2002. Anchoring elements 2004 may have various designs including, but not limited to anchor designs disclosed elsewhere in this document. Anchor body 2002 and anchoring elements 2004 may be made of a variety of materials including, but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. Proximal region of deployable anchor 2000 further comprises a looping lumen 2006. A looped ribbon 2008 is looped through looping lumen 2006. Looped ribbon 2008 may be made of a variety of materials including, but not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. looped ribbon 2008 extends to a proximal region where it can be cut by a user. In a method of deploying deployable anchor 2000, a single cut is made in looped ribbon 2008 at a proximal region. This turns looped ribbon 2008 into a straight ribbon. The straight ribbon can then be pulled in the proximal direction to remove it from deployable anchor 2000. Looped ribbon 2008 may also be in the form of a looped monofilament or multifilament wire or suture.

FIG. 21A shows a crossectional view of an anchor deploying system comprising a locked ball. The anchor deploying system comprises a deployable anchor 2100. Deployable anchor 2100 comprises an anchor body 2102. Deployable anchor 2100 may have various designs including, but not limited to anchor designs disclosed elsewhere in this document. Proximal end of anchor body 2102 is connected to a thin shaft 2104. Proximal end of thin shaft 2104 comprises a locking ball 2106. Anchor body 8428, thin shaft 2104 and locking ball 2106 may be made of a variety of materials including, but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. The anchor deploying system further comprises an outer locking sheath 2108. Distal end of locking sheath 2108 comprises an opening 2110. Diameter of opening 2110 is greater than the diameter of thin shaft 2104 but greater than diameter of locking ball 2106. Thus, locking ball 2106 is locked in locking sheath 2108. The anchor deploying system further comprises a deploying shaft 2112 located within locking sheath 2108. Deploying shaft 2112 can be pushed in the distal direction within locking sheath 2108 by a user. Locking sheath 2108 and deploying shaft 2112 may be made of a variety of materials including, but not limited to metals e.g. various grades of stainless steel, titanium, nickel-titanium alloys, cobalt-chromium alloys, tantalum etc.; polymers e.g. polypropylene, Teflon etc. In one embodiment, distal region of locking sheath 2108 comprises one or more longitudinal grooves or windows to allow distal region of locking sheath 2108 to expand easily in the radial direction. FIGS. 21B and 21C show a method of deploying an anchor comprising a locked ball. In FIG. 21B, deploying shaft 2112 is pushed in the distal direction by a user. This causes distal end of deploying shaft 2112 to push locking ball 2106 in the distal direction. This in turn causes locking ball 2106 to exert a force on the distal end of locking sheath 2108. This force causes opening 2110 to enlarge and release locking ball 2106. In FIG. 21C, locking ball 2106 is released by locking sheath 2108 thus releasing deployable anchor 2100.

FIGS. 22A through 22C show various views of an anchor deploying system comprising two interlocking cylinders. The anchor deploying system comprises a proximal interlocking cylinder and a distal interlocking cylinder. The distal interlocking cylinder is located on an anchor to be deployed. FIG. 22A shows a perspective view of a proximal interlocking cylinder 2200 comprising a locking element 2202 located on the distal end of proximal interlocking cylinder 2200. In this example, locking element 2202 comprises a solid cylinder with a ninety degree bend. Proximal interlocking cylinder 2200 and locking element 2202 may be made of a variety of materials including, but not limited to metals e.g. various grades of stainless steel, titanium, nickel-titanium alloys, cobalt-chromium alloys, tantalum etc.; polymers e.g. polypropylene, Teflon etc. FIG. 22B shows a crossectional view of the anchor deploying system comprising proximal interlocking cylinder 2200 interlocked with a distal interlocking cylinder 2204. Distal interlocking cylinder 2204 comprises a groove 2206 which locks locking element 2202. Locking element 2202 can be unlocked from distal interlocking cylinder 2204 by turning proximal interlocking cylinder 2200. distal interlocking cylinder 2204 may be made of a variety of materials including, but not limited to metals e.g. various grades of stainless steel, titanium, nickel-titanium alloys, cobalt-chromium alloys, tantalum etc.; polymers e.g. polypropylene, Teflon etc.; rubber materials e.g. various grades of silicone rubber etc. FIG. 22C shows a crossectional view through plane A-A in FIG. 22B. FIG. 22C shows distal interlocking cylinder comprising groove 2206. Also shown is locking element 2202 located in groove 2206. Turning proximal interlocking cylinder 2200 turns locking element 2202. At a particular orientation, distal region of locking element 2202 can pass easily through groove 2206 unlocking proximal interlocking cylinder 2200 from distal interlocking cylinder 2204.

FIGS. 22D and 22E show the steps of a method of unlocking the two interlocking cylinders from the anchor deploying systems of FIGS. 22A through 22C. In FIG. 22D, locking element 2202 of proximal interlocking cylinder 2200 is locked in groove 2206 of distal interlocking cylinder 2204. In FIG. 22E, proximal interlocking cylinder 2200 is turned in a clockwise or counterclockwise direction to unlock locking element 2202 from groove 2206. Thereafter, proximal interlocking cylinder 2200 is pulled in the proximal direction to separate proximal interlocking cylinder 2200 from distal interlocking cylinder 2204.

Figure 23:
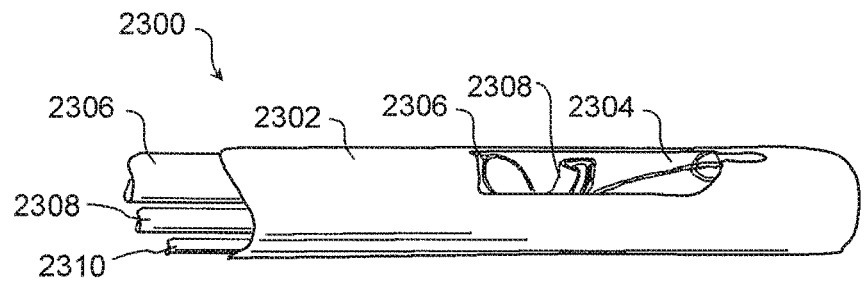
FIG. 23A shows a perspective view of a distal end of an anchoring device that has an imaging modality.
FIGS. 23B through 23G show various steps of a method for compressing an anatomical region using the anchoring device of FIG. 23A.
Figure 23:
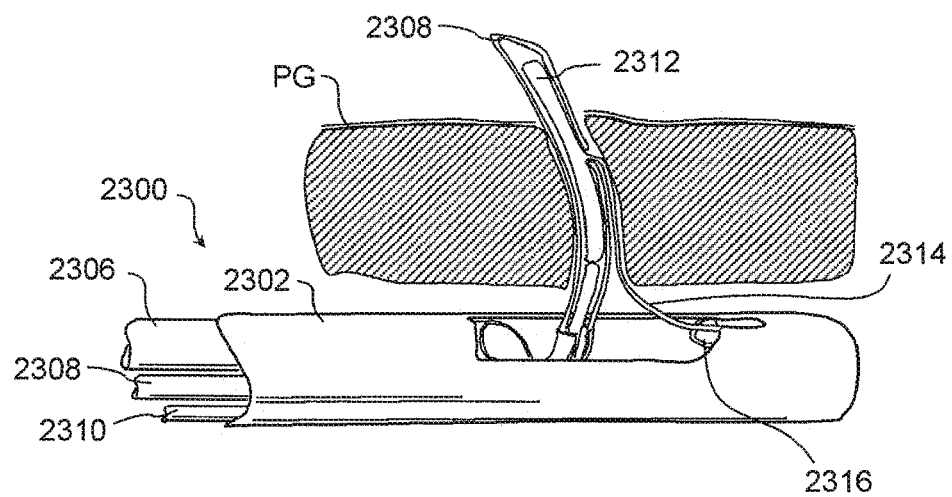
Figure 23:
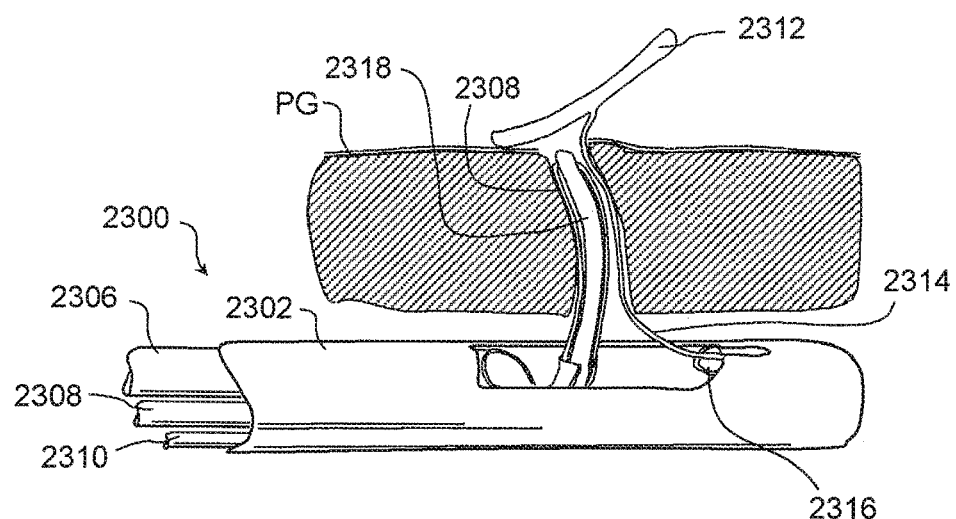
Figure 23:
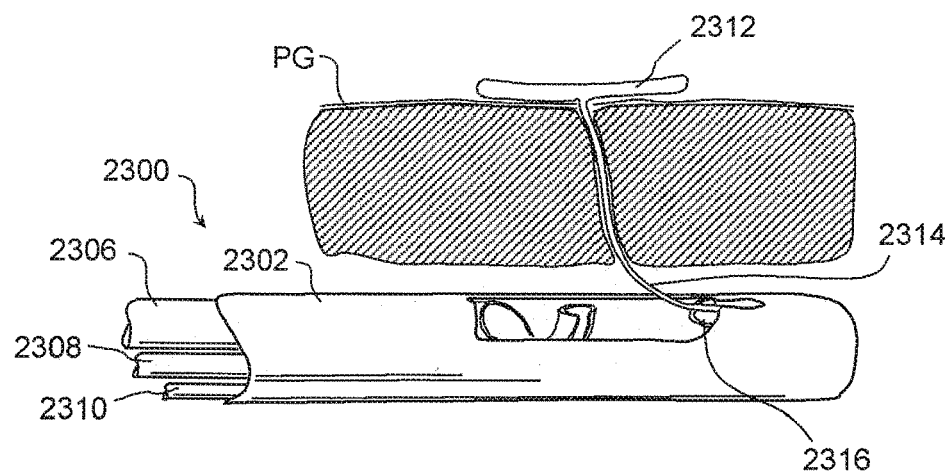
Figure 23:
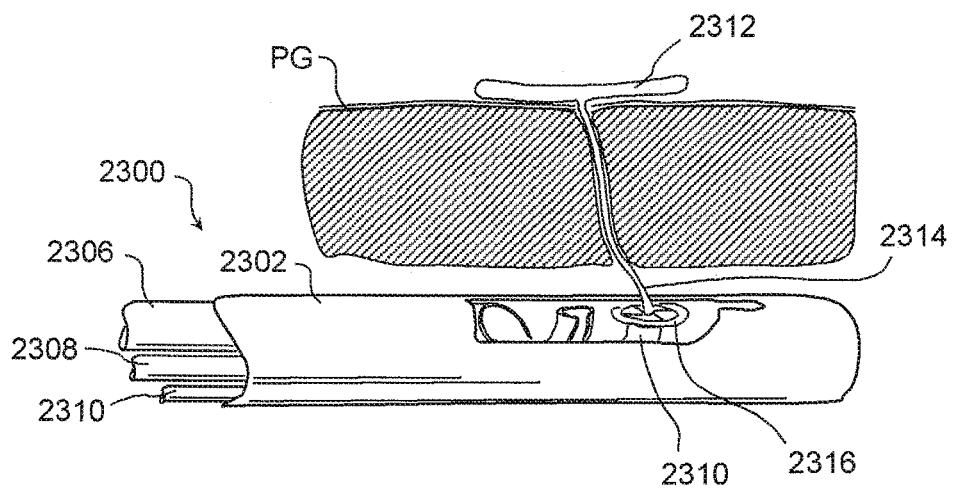
Figure 23:
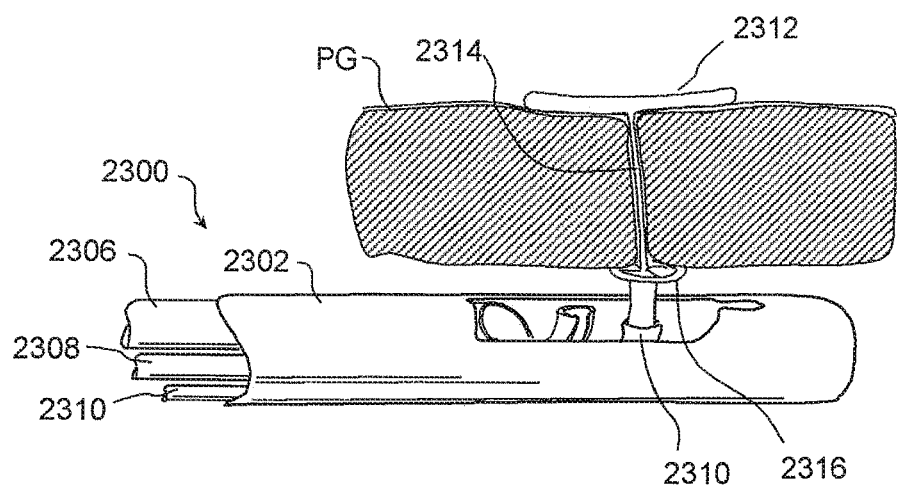
Figure 23:
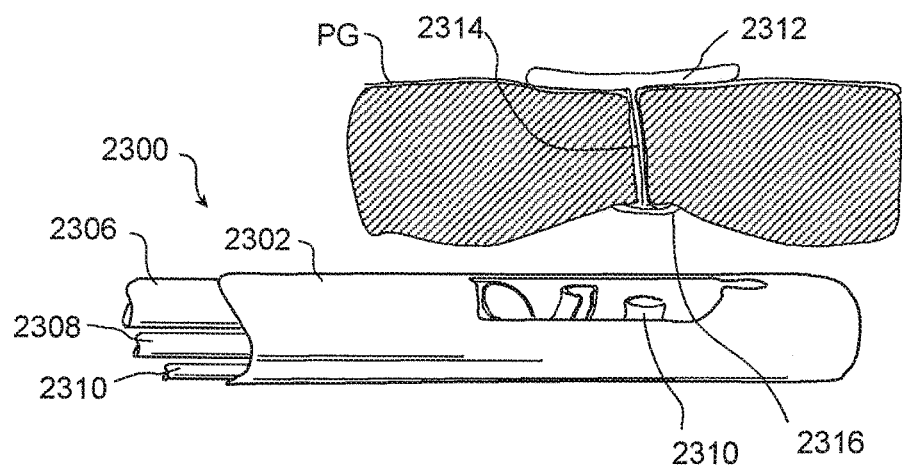

FIG. 23A shows a perspective view of a distal end of an anchoring device that has an imaging modality. Anchoring device 2300 comprises an elongate shaft 2302 comprising a lumen. Elongate shaft 2302 can be made of suitable biocompatible materials such as metals, polymers etc. The lumen of shaft 2302 terminates in a window 2304 located on the distal region of shaft 2302. Anchoring device further comprises an imaging modality such as a cystoscope, an ultrasound imaging system etc. In this example, the imaging modality is a cystoscope 2306. Distal end of cystoscope 2306 is located in window 2304 to allow visualization of the anatomy adjacent to window 2304. In one embodiment, cystoscope 2306 is permanently fixed to anchoring device 2300. In another embodiment, cystoscope 2306 can be introduced through the proximal region of anchoring device 2300. Anchoring device 2300 further comprises a puncturing device 2308. Puncturing device 2308 comprises a sharp distal tip and a lumen that holds an anchor. Anchoring device 2300 further comprises an anchor deployment device 2310. Distal end of anchor deployment device 2310 is detachably attached to the anchor.

FIGS. 23B through 23G show various steps of a method for compressing an anatomical region using the anchoring device of FIG. 23A. In FIG. 23B, Anchoring device 2300 is introduced in an anatomical region such that distal end of anchoring device 2300 is located adjacent to a target anatomical region to be treated. In one method embodiment, anchoring device 2300 is introduced transurethrally into the prostatic urethra. Thereafter, puncturing device 2308 is advanced to puncture the anatomical region. In this example, puncturing device 2308 punctures the prostate gland PG such that distal end of puncturing device 2308 is located in the pelvic cavity. Puncturing device comprises an anchor located in the lumen of puncturing device 2308. The anchor comprises a distal anchor 2312, a tension element 2314 connected at one end to distal anchor 2312 and a proximal anchor 2316 that can slide over tension element 2314. Puncturing device 2308 comprises a groove at the distal end such that tension element exits puncturing device 2308 through the groove. Puncturing device 2308 further comprises a pusher 2318 that can push distal anchor 2312 out of puncturing device 2308. Proximal anchor 2316 is detachably attached to the distal region of anchor deployment device 2310. Proximal anchor 2312, distal anchor 2316 and tension element 2314 may comprise designs including, but not limited to the designs disclosed elsewhere in this patent application. The imaging modality may be used to verify the accurate placement and working of anchoring device 2300. In FIG. 23C, pusher 2318 is pushed in the distal direction to push distal anchor 2312 out of puncturing device 2308. Distal anchor 2312 is thus deployed in the anatomy e.g. in the pelvic cavity surrounding the prostate gland PG. Thereafter, in step 23D, Puncturing device 2308 is withdrawn by pulling it in the proximal direction. In step 23E, tension element 2314 is pulled in the proximal direction through anchor deployment device 2310. Thereafter, in step 23F, tension element 2314 is pulled further in the proximal direction such that the anatomical region between proximal anchor 2316 and distal anchor 2312 is compressed. Thereafter, in step 23G, proximal anchor 2316 is securely locked on to tension element 2314. Further in step 23G, proximal anchor 2316 is detached from anchor deployment device 2310. The detachment can be performed by a variety of mechanisms including, but not limited to the anchor detachment mechanisms disclosed elsewhere in this patent application. Further in step 23G, excess length of tension element 2314 is removed. This removal can be done using a variety of methods including, but not limited to the methods disclosed elsewhere in this patent application such as cutting, delinking, melting, and breaking. Thereafter, anchoring device 2300 is withdrawn from the anatomy. It should be understood that these deployment steps may be repeated in the same, opposing or neighboring tissues to essentially tack up the encroaching tissue (i.e. prostatic tissue, tumor, relaxed tissue, expanded tissue or growth). It may be desired that over time both anchors become completely embedded within the tissue and covered to prevent encrustation, clotting or other tissue or body-fluid interaction—this may be facilitated by the processes, therapeutic agents and coatings described elsewhere in the application. Although these anchors are shown on either side of the tissue, it may be possible to deploy either or both of them within the body of the tissue itself to help bury them and eliminate the possibility that they may interact with other parts of the body. It should further be noted that in the case of application to the prostate, that this technique may be used on any of the lateral or middle lobes to compress or hold the prostate gland PG away from the lumen of the urethra.

If removal of the intra or para luminal anchor is required, it may be possible to resect that region completely, capturing the anchor embedded within the tissue and removing it en-bloc, severing the tether in the process. In the case of prostate applications, such removal may be accomplished with a standard resectoscope system. In other regions, and energized RF or sharp curette or blade may be used to resect the anchor minimally invasively. Alternatively if engagement with the locking mechanism is still achievable, it may be possible to simply unlock the tether, releasing the anchor. Lastly, if applying additional tension at some point after the procedure is required, it may be possible to engage and grasp the tether as it exits the locking device in the anchor and apply additional tension.

Figure 24:
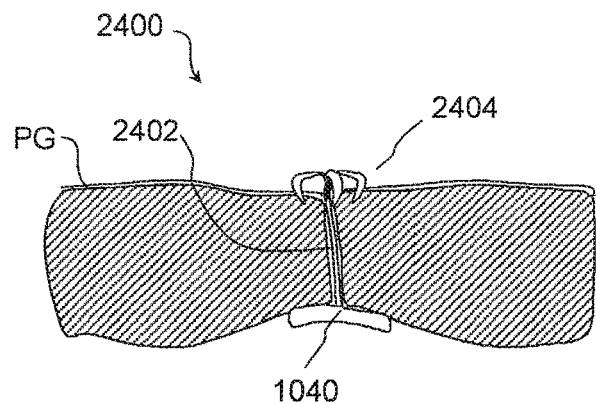
FIGS. 24A, 24A', 24B, 24B', 24C, and 24C' show the device and various steps of a method of compressing an anatomical region using a device with deploying arms deployed through a trocar.
FIGS. 24B and 24B' show a second step of a method of compressing an anatomical region using a device with deploying arms deployed through a trocar.
FIG. 24C shows a third step of a method of compressing an anatomical region using a device with deploying arms deployed through a trocar.
FIG. 24D shows a crossection through the deployed anchoring device of FIG. 24A.

FIGS. 24A through 24C' show various steps of a method of compressing an anatomical region using a device with deploying arms deployed through a trocar. In FIG. 24A, an anchoring device 2400 is introduced in an anatomical region. Anchoring device 2400 comprising a distal anchor 2402 is introduced in the anatomy. Distal anchor 2402 comprises a hollow shaft. Distal end of distal anchor 2402 comprises one ore more outwardly curling or spreading arms 2404. Curling or spreading arms 2404 are made of an elastic, springy, super-elastic or shape memory material such that they tend to curl or spread in a radially outward direction in absence of an external force. Anchoring device 2400 further comprises a proximal anchor comprising a variety of designs including, but not limited to the designs disclosed elsewhere in this patent application. In this example, proximal anchor is designed similar to anchor 1040 in FIG. 10D. Anchor 1040 can slide along proximal region of distal anchor 2402. Anchor 1040 can also be attached to distal anchor 2402 after a desired positioning between anchor 1040 and distal anchor 2402 is achieved. Anchoring device 2400 is delivered through a trocar 2406. Trocar 2406 comprises a sharp distal tip 2408 that can penetrate through tissue. The proximal region of distal tip 2408 comprises one ore more grooves or notches such that distal ends of curling or spreading arms 2404 can be temporarily held together by distal tip 2408 to allow for easy introduction into a target anatomy. Anchoring device 2400 is introduced into a target tissue to be compressed such that curling or spreading arms 2404 are distal to the target tissue and anchor 1040 is proximal to the target tissue. FIG. 24A' shows the distal end view of the anchoring device 2400. In FIG. 24B, trocar 2406 is pushed in the distal direction relative to proximal anchor 2402. As shown in FIG. 24B' this releases the distal ends of curling or spreading arms 2404 causing them to curl or spread outwards. FIG. 24A' shows the distal end view of the anchoring device 2400 with released curling or spreading arms 2404. In FIG. 24C, anchor 1040 is pushed in the distal direction over distal anchor 2402 to compress tissue between anchor 1040 and distal anchor 2402. Thereafter, anchor 1040 is attached to the hollow shaft of distal anchor 2402. Thereafter trocar 2406 is withdrawn from the anatomy. In the above embodiment, the tethering function is performed by the shaft of the distal anchor, and the force is created by the curling arms. This tension may be pre-set into the arms through heat forming. It should be noted that any mechanism capable of expanding from within a tubular shape and capable of applying retrograde forces on the tissue are within the scope of this invention such as expandable flanges, balloons, cages, molly-bolt-like structures, stent-like structures and springs.

FIG. 24D shows a crossection through the deployed anchoring device 2400 of FIG. 24A.

In one anchoring device embodiment, anchoring device 2400 comprises a distal anchor such as the distal anchor described in FIG. 17A instead of distal anchor 2412.

FIG. 25A shows a perspective view of a spring clip that can be used to spread the anatomy. Clip 2500 comprises two or more spreading arms 2502. Spreading arms 2502 may be curved or straight. Distal ends of spreading arms 2502 may comprise a flattened region. The proximal ends or curved arms 2502 are connected to each other by a heel region 2504. Heel region 2504 may be made from the same material as curved arms 2502. In an undeployed configuration, spreading arms 2502 are held close to each other. When clip 2500 is deployed, spreading arms 2502 tend to expand away from each other thus spreading the anatomical region or regions between spreading arms 2502. Clip 2500 can be made of suitable elastic, super-elastic or shape memory biocompatible materials including, but not limited to synthetic fibers e.g. various grades of Nylon, polyethylene, polypropylene, polyester, Aramid etc.; metals e.g. various grades of stainless steel, titanium, nickel-titanium alloys, etc.

FIGS. 25B through 25F show various steps of a method of spreading an anatomical region or regions using the spring clip of FIG. 25A. In FIG. 25B, a delivery tool 2506 comprising a clip 2500 is introduced in the anatomy and positioned near the target anatomy to be spread. Delivery tool 2506 comprises an elongate hollow body 2508 comprising a lumen. Distal end of body 2508 may comprise a blunt, atraumatic end. Distal region of body 2508 comprises a slot 2510 that is in fluid communication with the lumen of body 2508. Delivery tool may further comprise an outer sheath 2512 and an imaging modality 2514. Imaging modality 2514 may be permanently attached to delivery tool 2506 or may be introduced into delivery tool 2506 by a user. In this example, imaging modality 2514 is a cystoscope. In FIG. 25C, clip 2500 is introduced into the anatomy by pushing clip 2500 out of slot 2510 such that the distal ends of spreading arms 2502 emerge first. Slot 2510 is designed such that spreading arms 2504 are biased towards each other as they emerge out of slot 2510. In FIG. 25D, clip 2500 is further advanced such that distal tips of spreading arms 2502 penetrate into the tissue to be spread. In FIG. 25E, clip 2500 is advanced further such that the biasing forces on spreading arms 2502 are removed. Spreading arms 2502 tend to spread away from each other thus spreading the tissue between them. Clip 2500 is detachably attached to delivery tool 2506 by a detaching mechanism 2516 including, but not limited to the several detaching mechanisms disclosed elsewhere in this patent application. In FIG. 25F, detaching mechanism 2516 is used to detach clip 2500 from delivery tool 2506 or deploy clip 2500 in the target anatomy. In this example, distal region of delivery tool 2506 is inserted transurethrally into the prostatic urethra. Clip 2500 is then delivered into the anterior commissure to spread the two lateral lobes of the prostate gland PG apart. In one method embodiment, an opening in the commissure is made prior to the method of FIGS. 25B through 25G. In another embodiment, the spreading force exerted by spreading arms 2502 cause cutting of the anterior commissure. Clip 2500 may be placed completely sub-urethrally or a small amount of heel region 2504 remains in the urethra.

Figure 26:
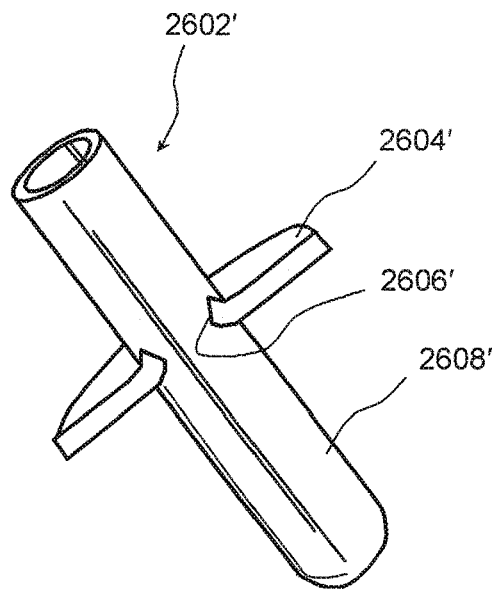
FIGS. 26A and 26B show a crossectional view and a perspective view respectively of a mechanism of cinching a tension element or tether to an anchor.
FIGS. 26C and 26D show a partial section through a cinching mechanism comprising a cam element.
FIG. 26E shows a sectional view of an embodiment of a cinching mechanism comprising a locking ball.
FIG. 26F shows a side view of an embodiment of a cinching mechanism comprising multiple locking flanges.
FIG. 26G shows an end view of body of FIG. 26F.
FIG. 26H shows a side view of an embodiment of a cinching mechanism comprising a single locking flange.
FIG. 26I shows an end view of body of FIG. 26H.
FIG. 26J shows an end view of a cinching mechanism comprising a crimping lumen.
FIGS. 26K and 26L show crossections of an embodiment of a cinching mechanism comprising a crimping anchor in the undeployed and deployed configurations respectively.
FIG. 26M shows a perspective view of an embodiment of a cinching mechanism comprising an element providing a tortuous path to a tension element.
FIG. 26N shows a crossectional view of an embodiment of a locking mechanism comprising a space occupying anchor securely attached to a tension element.
FIGS. 26O and 26P shows a partial sectional view and a perspective view of an embodiment of a cinching mechanism comprising a punched disk.
FIGS. 26Q and 26R show a perspective view of a first embodiment of a cutting device before and after cutting an elongate element.
FIG. 26S show a crossectional view of a second embodiment of a cutting device for cutting an elongate element.
Figure 26:
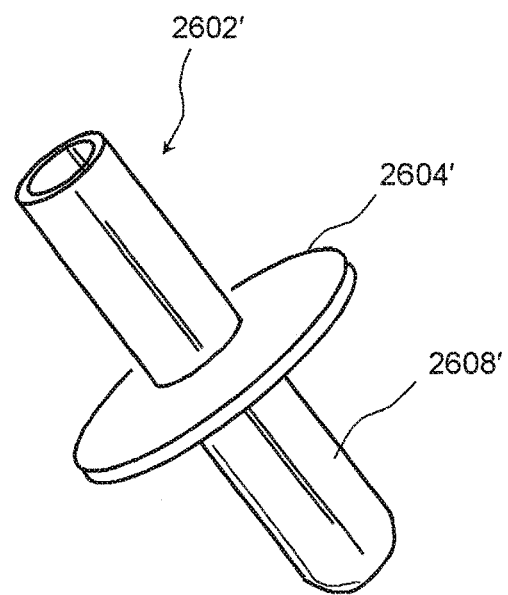
Figure 26:
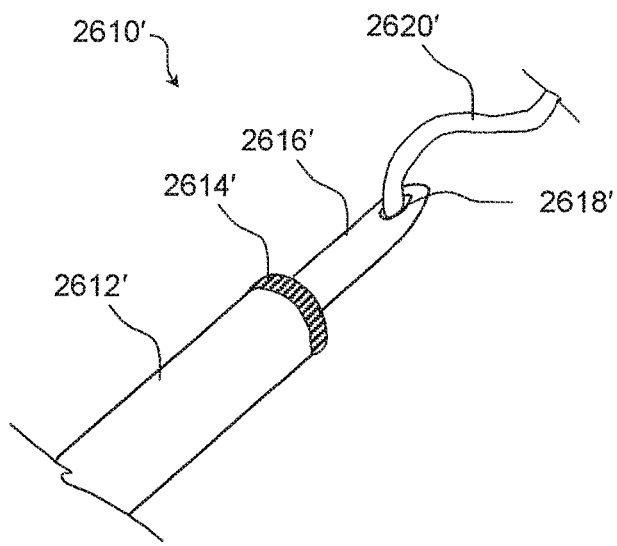
Figure 26:
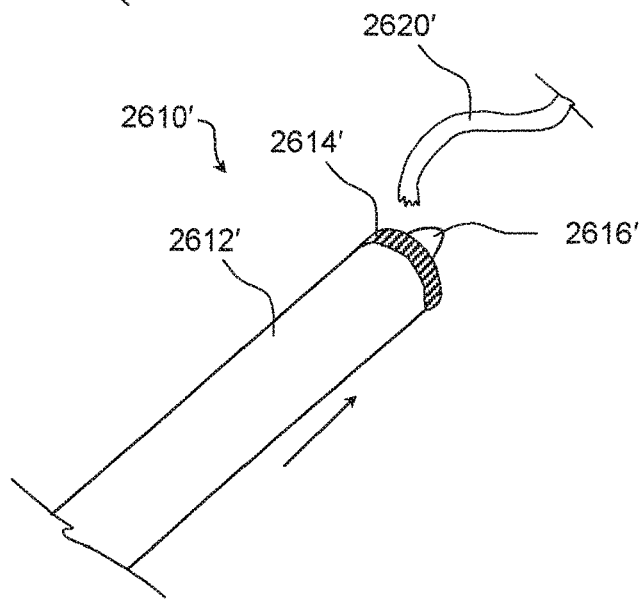
Figure 26:
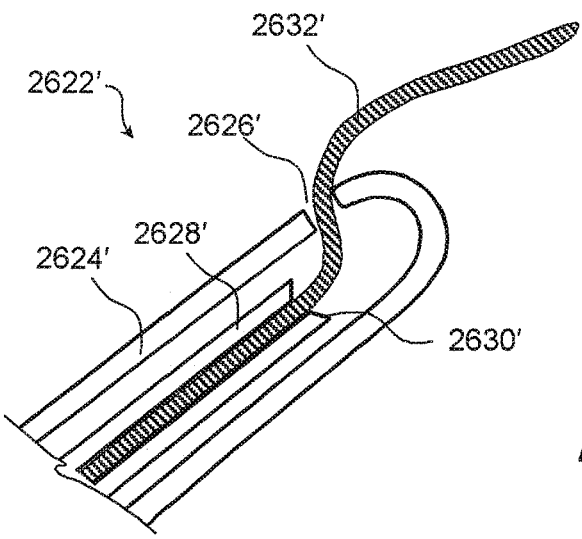
Figure 27:
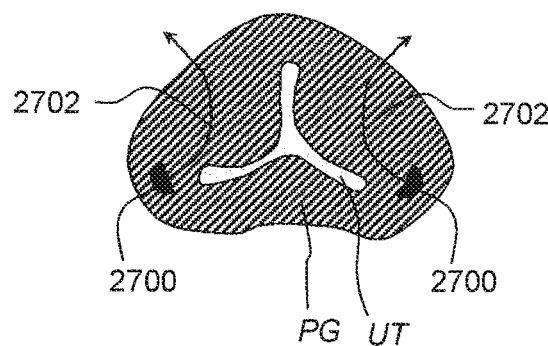
FIGS. 27A through 27D show axial sections through the prostate gland showing various configurations of anchoring devices comprising distal anchors and a tension element.
Figure 27:
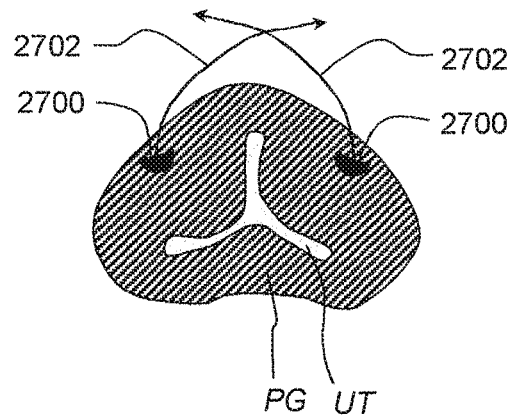
Figure 27:
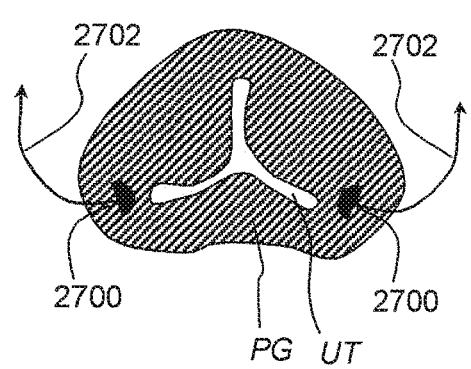
Figure 27:
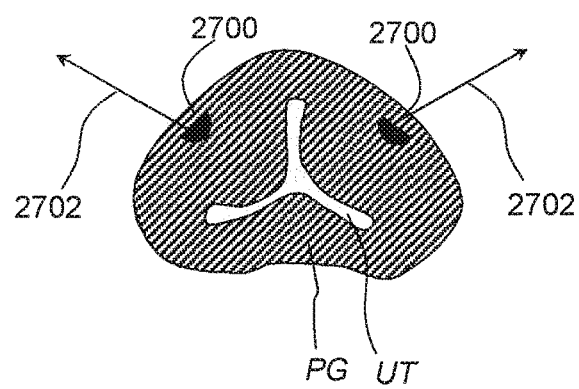

The embodiments of anchoring devices wherein a sliding anchor is slid over a tension element may comprise one or more cinching elements. These cinching elements may be present on the sliding anchors, on the tension elements etc. A cinching element may be a separate device that cinches to a tension element. In doing so, it increases the effective diameter of that region of the tension element and prevents the tension element from sliding through a sliding anchor. Cinching elements may allow only unidirectional motion of the sliding anchor over the tension element or may prevent any substantial motion of the sliding anchor over the tension element. Typical examples of such cinching mechanisms include, but are not limited to mechanisms described in the FIG. 26 series. For example, FIGS. 26A and 26B show a crossectional view and a perspective view respectively of a mechanism of cinching a tension element or tether to an anchor. In FIG. 26A, cinching mechanism 2600 comprises an outer base 2602. Outer base 2602 comprises one or more grooves created by the presence of two or more leaflets 2604. Leaflets 2604 are biased along a first axial direction as shown in FIG. 26A. When a tension element 2606 is located in the one or more grooves, cinching mechanism 2600 allows motion of tension element 2606 only along the first axial direction and prevents substantial movement of tension element 2606 in the opposite direction.

FIGS. 26C and 26D show a partial section through a cinching mechanism comprising a cam element. In FIG. 26C, cinching mechanism 2610 comprises an outer body 2612 made of suitable biocompatible metals, polymers etc. Body 2162 comprises a cam 2614 located on a pivot 2616. Cam 2614 may comprise a series of teeth to grip a tension element 2618 passing through body 2612. In one embodiment, body 2162 comprises an opening 2620 located proximal to cam 2614. Proximal region of tension element 2618 passes out of body 2612 through opening 2620. Cinching mechanism 2610 allows movement of body 2162 over tension element 2618 in the proximal direction. In FIG. 26D, body 2162 is moved over tension element 2618 in the distal direction. Motion of tension element 2618 over cam 2614 causes cam 2614 to turn in the anti-clockwise direction. This causes tension element 2618 to be pinched between cam 2614 and body 2612. This in turn prevents further motion of body 2162 over tension element 2618.

FIG. 26E shows a sectional view of an embodiment of a cinching mechanism comprising a locking ball. Cinching mechanism 2630 comprises an outer body 2632 comprising a lumen. A tension element 2634 passes through the lumen of outer body 2632. The lumen of outer body gradually reduces in the proximal direction as shown in FIG. 26E. A locking ball 2636 is present in the lumen. Motion of outer body 2632 over tension element 2634 in the distal direction pushes locking ball 2636 in the proximal region of outer body 2632. A proximal end region 2638 of a small diameter prevents locking ball 2636 from falling out of outer body 2632. The large lumen diameter in the proximal region of outer body 2632 allows free motion of locking ball 2636. Thus, presence of locking ball 2636 does not hinder the motion of outer body 2632 over tension element 2634 in the proximal direction. When outer body 2632 is moved over tension element 2634 in the proximal direction, locking ball 2636 is pushed in the distal region of outer body 2632. The small lumen diameter in the proximal region of outer body 2632 constricts motion of locking ball 2636. This causes a region of tension element 2634 to be pinched between anchoring ball 2636 and outer body 2632. This in turn prevents further motion of outer body 2632 over tension element 2634 in the proximal direction. This mechanism thus allows unidirectional motion of outer body 2632 is over tension element.

FIG. 26F shows a side view of an embodiment of a cinching mechanism comprising multiple locking flanges. In this embodiment, cinching mechanism 2644 comprises a body 2646 comprising a lumen lined by a first locking flange 2648 and a second locking flange 2650. First locking flange 2648 and second locking flange 2650 are biased in the proximal direction as shown. A tension element 2652 passes through the lumen of body 2646. First locking flange 2648 and second locking flange 2650 together allow the movement of body 2646 over tension element 2652 in the distal direction, but prevent movement of body 2646 over tension element 2652 in the proximal direction. Similar cinching mechanisms may be designed comprising more than two locking flanges. FIG. 26G shows an end view of body 2646 comprising a lumen lined by first locking flange 2648 and second locking flange 2650. Body 2646 may be made of suitable biocompatible metals, polymers etc.

FIG. 26H shows a side view of an embodiment of a cinching mechanism comprising a single locking flange. In this embodiment, cinching mechanism 2656 comprises a body 2658 comprising a lumen lined by a locking flange 2660. Locking flange 2660 is biased in the proximal direction as shown. A tension element 2662 passes through the lumen of body 2658. Locking flange 2660 allows the movement of body 2658 over tension element 2662 in the distal direction, but prevents movement of body 2658 over tension element 2662 in the proximal direction. FIG. 26I shows an end view of body 2658 comprising a lumen 2662 lined by locking flange 2660. Body 2658 may be made of suitable biocompatible metals, polymers etc.

FIG. 26J shows an end view of a cinching mechanism comprising a crimping lumen. Cinching mechanism 2670 comprises a body 2672 comprising a crimping lumen 2674. Crimping lumen 2674 is in the form of an arc with a gradually reducing size as shown in FIG. 26J. A tension element 2676 passes through crimping lumen 2674. In FIG. 26J, tension element 2676 is locked in a region of crimping lumen 2674 of a diameter smaller than the diameter of tension element 2676. Tension element 2676 can be unlocked from crimping lumen 2674 by rotating body 2672 in the anti-clockwise direction. Similarly, rotating body 2672 in the clockwise direction causes an unlocked tension element 2676 to be locked into crimping lumen 2674.

In an alternate embodiment, cinching mechanism comprises a disk shaped body comprising a central lumen. Central lumen is large enough to allow a tension element to slide easily through the central lumen. One or more radially oriented slits emerge from the central lumen. The radially oriented slits have a diameter that is of the same size or is slightly smaller than the diameter of the tension element. To lock cinching mechanism to the tension element, the tension element is forced through one of the radially oriented slits. The friction between the disk shaped body and the tension element prevents or resists sliding of tension element through the disk shaped body. To unlock cinching mechanism from the tension element, the tension element is moved back to the central lumen.

In another alternate embodiment, cinching mechanism comprises a disk shaped body comprising a small central lumen. The central region of the body comprises three or more triangular flaps biased together out of the plane of the body. The ends of the triangular flaps together form the central lumen that is of the same size or is slightly smaller than the diameter of the tension element. Tension element can pass easily through the central lumen in the direction of the bias of the triangular flaps. But, tension element cannot pass or encounters substantial resistance when the tension element is pulled through the central lumen in the opposite direction.

FIGS. 26K and 26L show crossections of an embodiment of a cinching mechanism comprising a crimping anchor in the undeployed and deployed configurations respectively. Cinching mechanism 2680 comprises a crimping anchor 2680 comprising a lumen. Crimping anchor 2680 can be made of a variety of biocompatible materials including, but not limited to metals e.g. various grades of stainless steel, titanium, nickel-titanium alloys, cobalt-chromium alloys, tantalum etc., polymers, etc. A tension element 2684 passes through the lumen of crimping anchor 2680. The lumen of an undeployed crimping anchor 2680 is larger than the diameter of tension element 2684. In FIG. 26L, crimping anchor 2680 is deployed by compressing the middle section of crimping anchor 2680 such that crimping anchor 2680 compresses tension element 2684. Friction between crimping anchor 2680 and tension element 2684 prevents relative motion between crimping anchor 2680 and tension element 2684. Crimping anchor 2680 may be a component of a sliding anchor or may be a stand-alone device used to prevent or restrict motion of a sliding anchor over a tension element.

FIG. 26M shows a perspective view of an embodiment of a cinching mechanism comprising an element providing a tortuous path to a tension element. In this example, cinching mechanism 2686 comprises a spring 2688. A tension element 2690 is passed through spring 2688 such that the path of tension element 2690 through spring 2688 is tortuous. When spring 2688 is moved over tension element, motion of tension element 2690 through the tortuous path generates high frictional forces that prevent or reduce motion of spring 2688 over tension element 2690. The frictional forces are strong enough to resist motion of spring 2688 over tension element 2690 after deploying cinching mechanism 2686 in the anatomy. A user can move spring 2688 over tension element 2690 by applying a force that overcomes the resistive frictional forces that prevent movement of spring 2688 over tension element 2690. Similarly, other cinching mechanisms comprising a tortuous path can be used instead of spring 2688. Examples of such mechanisms are solid elements comprising tortuous lumens, elements comprising multiple struts or bars that provide a tortuous path etc. In another embodiment the cinching mechanism comprises a knot on one or more tensioning element. Said knot can be advanced fully tightened or can be loose when advanced and tightened in situ.

FIG. 26N shows a crossectional view of an embodiment of a locking mechanism comprising a space occupying anchor securely attached to a tension element. Locking mechanism 2692 comprises a hollow element 2694 comprising a lumen. Hollow element 2694 is a component of a sliding anchor that slides over tension element 2696. Tension element 2696 comprises a space occupying anchor 2698 comprising a tapering distal end 2699. Anchor 2698 is securely attached to tension element 2696. Diameter of anchor 2698 is larger than the diameter of the lumen of hollow element. Due to this, anchor 2698 cannot pass through hollow element 2694 effectively locking the position of tension element 2696 with respect to the position of hollow element 2694.

FIGS. 26O and 26P shows a partial sectional view and a perspective view of an embodiment of a cinching mechanism comprising a punched disk. Cinching mechanism 2602' comprises a disk 2604' comprising a punched hole 2606'. Punched hole 2606' is made by punching disk 2604' along the proximal direction such that the punching action leaves an edge that is biased along the proximal direction as shown in FIG. 26O. Disk 2604' can slide over a tension element 2608' along the distal direction. However, motion of disk 2604' over tension element 2608' along the proximal direction is substantially resisted by the proximally biased edges of punched hole 2606'.

Excess lengths of tension elements or other severable regions of one or more devices disclosed in this patent application may be cut, severed or trimmed using one or more cutting devices. For example, FIGS. 26Q and 26R show a perspective view of a first embodiment of a cutting device before and after cutting an elongate element. In FIG. 26Q, cutting device 2610' comprises an outer sheath 2612' comprising a sharp distal edge 2614'. Outer sheath 2612' encloses an inner sheath 2616'. Inner diameter of outer sheath 2612' is slightly larger than outer diameter of inner sheath 2616' such that inner sheath 2616' can slide easily through outer sheath 2612'. Inner sheath 2616' comprises a lumen that terminates distally in an opening 2618'. An elongate severable device passes through the lumen and emerges out of opening 2618'. An example of an elongate severable device is a tension element 2620'. In the method of cutting or trimming tension element 2620' the desired area of tension element 2620' to be cut or severed is positioned near opening 2618' by advancing or withdrawing cutting device 2610' over tension element 2620'. Thereafter, outer sheath 2612' is advanced over inner sheath 2616' to cut tension element 2620' between sharp distal edge 2614' and an edge of opening 2618'. Inner sheath 2616' and outer sheath 2612' may be substantially rigid or flexible. They may be made of suitable materials including, but not limited to Pebax, Polyimide, Braided Polyimide, Polyurethane, Nylon, PVC, Hytrel, HDPE, PEEK, metals like stainless steel and fluoropolymers like PTFE, PFA, FEP and EPTFE etc.

FIG. 26S show a crossectional view of a second embodiment of a cutting device for cutting an elongate element. Cutting device 2622' comprises an outer sheath 2624' comprising a lumen that opens in an opening 2626' in outer sheath 2624'. Outer sheath 2624' encloses an inner sheath 2628' that comprises a lumen and a sharp distal edge 2630'. Inner diameter of outer sheath 2624' is slightly larger than outer diameter of inner sheath 2628' such that inner sheath 2628' can slide easily through outer sheath 2624'. An elongate severable device passes through the lumen of inner sheath 2628' and emerges out of distal end of inner sheath 2628' and out of outer sheath 2624' through opening 2626'. An example of an elongate severable device is a tension element 2632'. In the method of cutting or trimming tension element 2632' the desired area of tension element 2632' to be cut or severed is positioned near opening 2626' by advancing or withdrawing cutting device 2622' over tension element 2632'. Thereafter, inner sheath 2628' is advanced through outer sheath 2624' to cut tension element 2632' between sharp distal edge 2630' and an edge of opening 2626'. Inner sheath 2628' and outer sheath 2624 may be substantially rigid or flexible. They may be made of suitable materials including, but not limited to Pebax, Polyimide, Braided Polyimide, Polyurethane, Nylon, PVC, Hytrel, HDPE, PEEK, metals like stainless steel and fluoropolymers like PTFE, PFA, FEP and EPTFE etc.

In a third embodiment of a cutting device for cutting an elongate element, the cutting device comprises an outer hollow sheath. Outer hollow sheath has a distal end plate comprising a window. An elongate severable device passes through the window. An example of an elongate severable device is a tension element. An inner shaft can slide and rotate within outer hollow sheath. Distal end of inner shaft comprises a blade that is usually located away from the window and adjacent to the distal end plate of the outer hollow sheath. In the method of cutting or trimming tension element the elongate severable device, the desired area of the elongate severable device to be cut or severed is positioned near the window. This is done by advancing or withdrawing the cutting device over the elongate severable device. Thereafter, the inner shaft is rotated within outer hollow sheath such that the blade cuts the elongate severable device between a sharp edge of the blade and an edge of the window. Inner shaft and outer hollow sheath may be substantially rigid or flexible. They may be made of suitable materials including, but not limited to Pebax, Polyimide, Braided Polyimide, Polyurethane, Nylon, PVC, Hytrel, HDPE, PEEK, metals like stainless steel and fluoropolymers like PTFE, PFA, FEP and EPTFE etc. The end plate and the blade are preferentially rigid. They may be made of suitable materials including, but not limited to metals like stainless steel, polymers like Polycarbonate, Polyimide, PVC, Hytrel, HDPE, PEEK and fluoropolymers like PTFE, PFA, FEP etc.

The anchoring devices disclosed herein may be used in a variety of configurations depending on the location of the disease process, ease of procedure etc. FIGS. 27A through 27D show axial sections through the prostate gland PG showing various configurations of anchoring devices comprising distal anchors 2700 and a tension element 2702 that is anchored at a suitable location such that a sufficient tension exists in tension element 2702.

Figure 25:
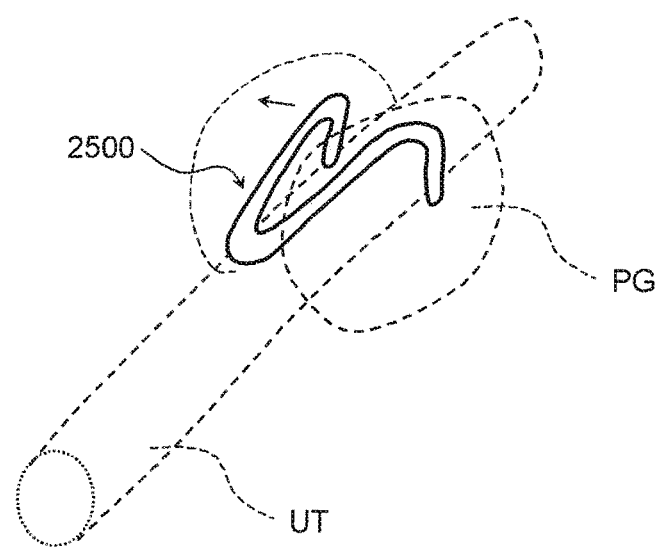
FIG. 25A shows a perspective view of a spring clip that can be used to spread the anatomy.
FIGS. 25B through 25F show various steps of a method of spreading an anatomical region or regions using the spring clip of FIG. 25A.
Figure 25:
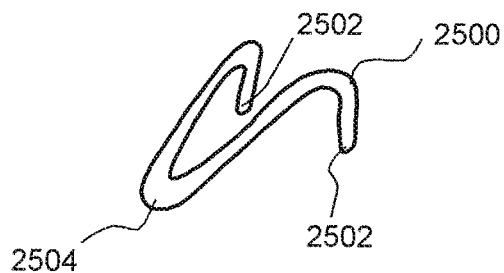
Figure 25:
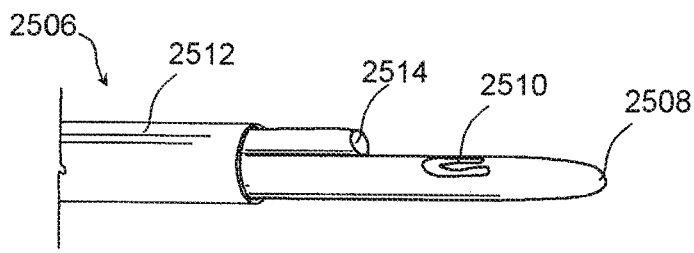
Figure 25:
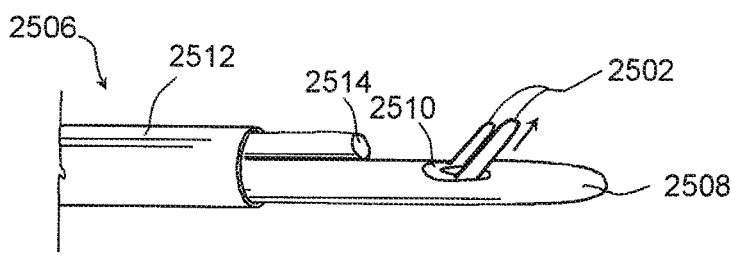
Figure 25:
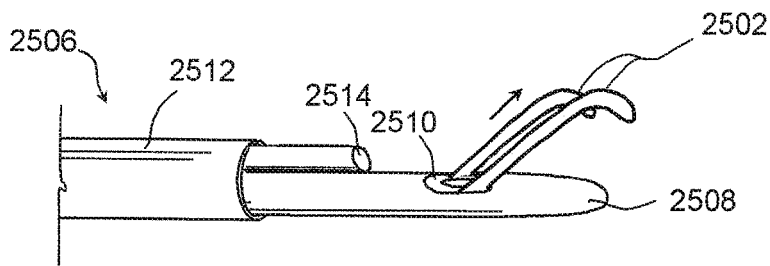
Figure 25:
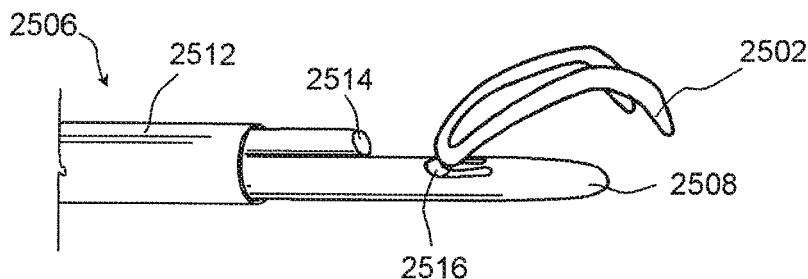
Figure 28:
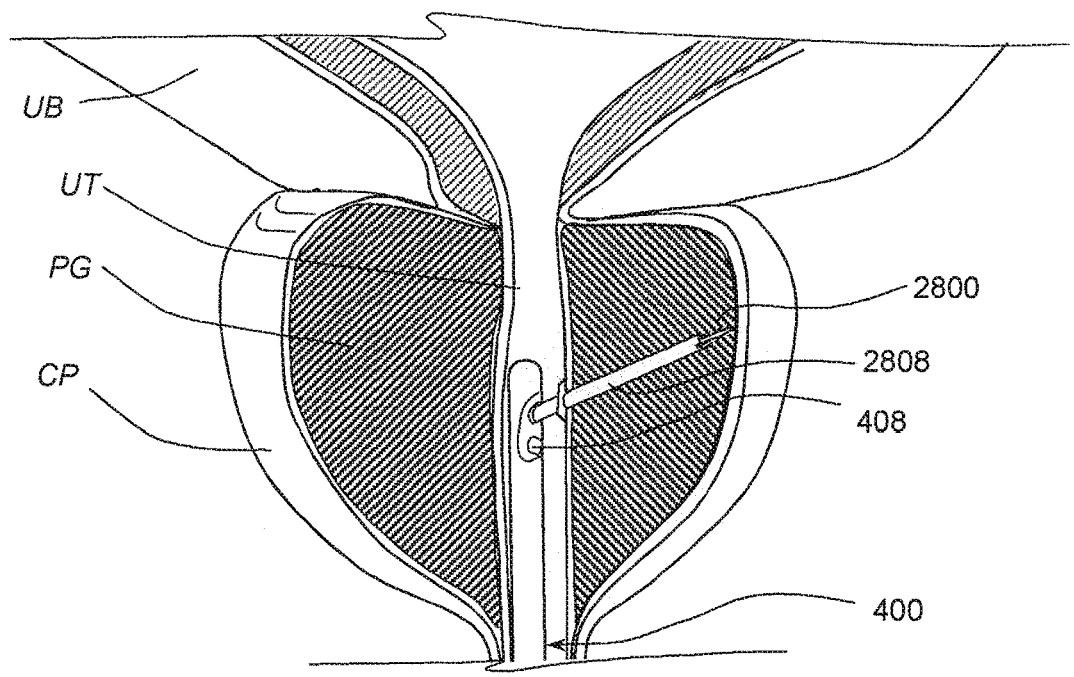
Figure 28:
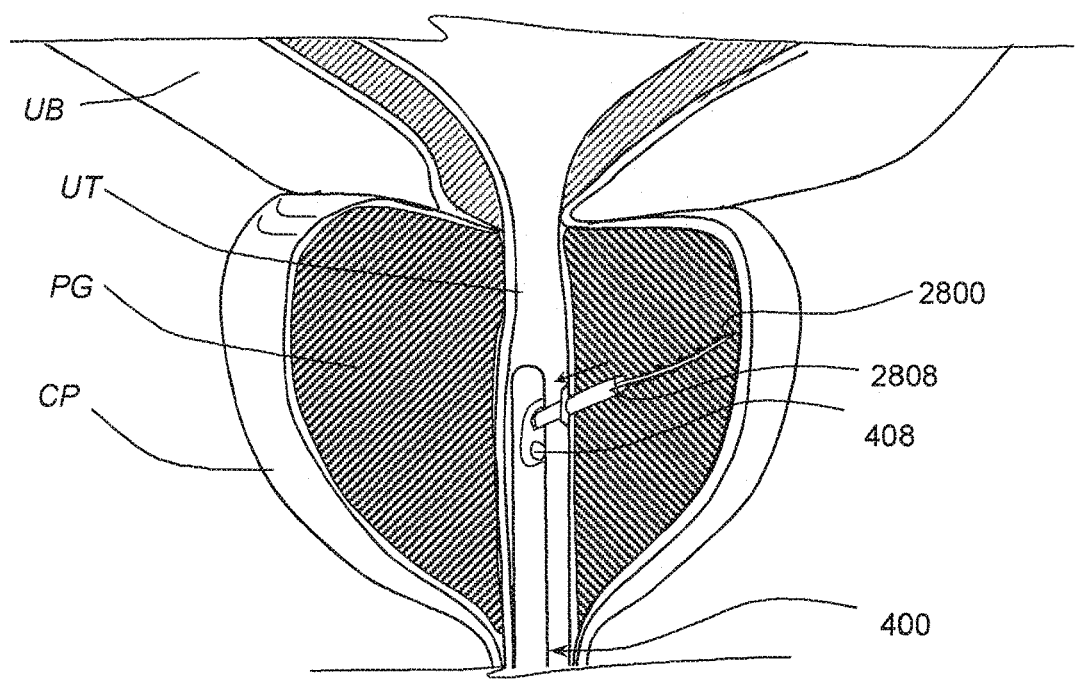
Figure 28:
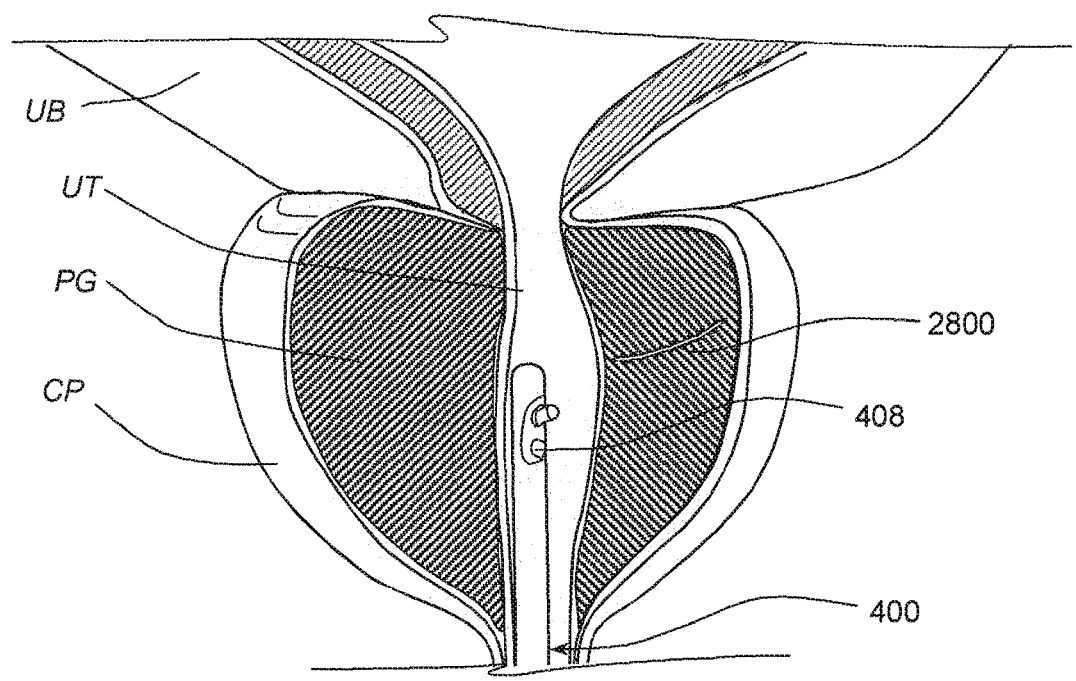
Figure 29:
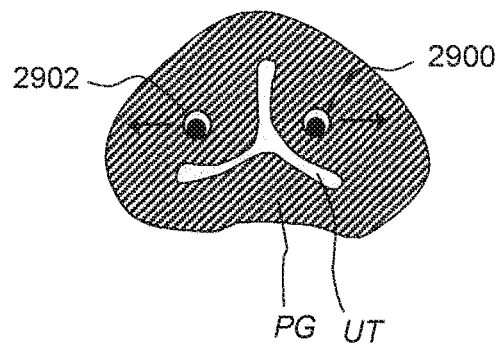
Figure 29:
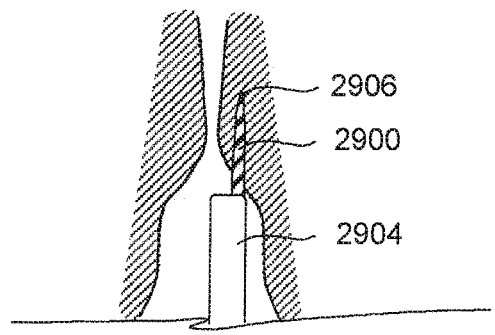
Figure 29:
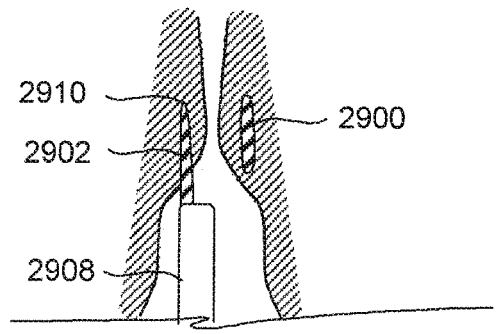
Figure 29:
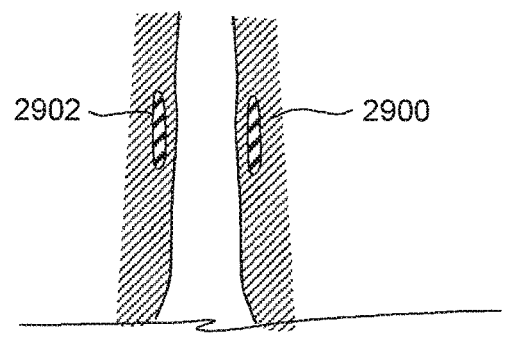

FIGS. 28 and 28A show perspective views of an embodiment of an anchoring device comprising an elongate element comprising multiple barbs or anchors. FIG. 28 shows a perspective view of anchoring device 2800 comprising an elongate element 2802. Elongate element 2802 can be made of several biocompatible materials including, but not limited to synthetic fibers e.g. various grades of Nylon, polyethylene, polypropylene, polyester, Aramid etc.; metals e.g. various grades of stainless steel, titanium, nickel-titanium alloys, cobalt-chromium alloys, tantalum etc.; natural fibers e.g. cotton, silk etc.; rubber materials e.g. various grades of silicone rubber etc. Elongate element 2802 may comprise natural or artificial suture materials. Examples of such materials include but are not limited to Polyamide (Nylon), Polypropylene, Polyglycolic Acid (PGA), polylactic acid (PLA) and copolymers of polylactic acid, polyglycolic acid and copolymers of polyglycolic acid, copolymers of PLA and PGA, Silk, Polyester, silicone, collagen, Polymers of Glycolide and Lactide. A particular example of a suture is the Nordstrom suture which is a highly elastic silicone suture. In one embodiment, the suture material is bioabsorbable. Elongate element 2802 comprises two sets of projections such as barbs, anchors or hooks. In the example shown, elongate element 2802 comprises a set of distal barbs 2804 and a set of proximal barbs 2806. Distal barbs 2804 are oriented in the proximal direction and proximal barbs 2806 are oriented in the distal direction as shown in FIG. 25. FIG. 28A shows a magnified view of the region 28A of anchoring device 2800 showing proximal barbs 2806.

FIGS. 28B through 28E show a coronal section through the prostate gland PG showing various steps of a method of treating the prostate gland PG using the device of FIG. 28. In FIG. 28B, introducer device 300 of FIG. 3A comprising a working device lumen and a cystoscope lumen 308 is introduced into the urethra such that the distal end of introducer device 300 is located in the prostatic urethra. Thereafter, a hollow puncturing device 2808 is inserted in the working device lumen of introducer device. Puncturing device 2808 is advanced such that distal end of puncturing device 2808 penetrates the prostate gland PG. In FIG. 28C, anchoring device 2800 is introduced through puncturing device 2808 into the prostate gland PG. Thereafter, puncturing device 2808 is pulled in the proximal direction. Simultaneously, anchoring device 2800 is pulled in the proximal direction to anchor distal barbs 2804 in the anatomy. In FIG. 28D, puncturing device 2808 is pulled further in the proximal direction to expose the entire anchoring device 2800. Thereafter, in step 28E, the proximal end of anchoring device 2800 is detached to deploy anchoring device 2800 in the anatomy. Thus, tissue between distal barbs 2804 and proximal barbs 2806 is anchored to anchoring device 2800.

FIG. 29A shows an axial section of the prostate gland PG showing a pair of implanted magnetic anchors. In FIG. 29A, a first magnetic anchor 2900 and a second magnetic anchor 2902 are implanted in the prostate gland PG on either side of the urethra. Like poles of first magnetic anchor 2900 and second magnetic anchor 2902 face each other such that there is magnetic repulsion between first magnetic anchor 2900 and second magnetic anchor 2902. This causes the urethral lumen to widen potentially reducing the severity of BPH symptoms.

FIGS. 29B through 29D show a coronal section through the prostate gland PG showing the steps of a method of implanting magnetic anchors of FIG. 29A. In FIG. 29B, a deployment device 2904 is advanced trans-urethrally. Deployment device 2904 comprises a sharp distal tip 2906 and first magnetic anchor 2900. Distal tip 2906 of deployment device 2904 penetrates prostatic tissue and implants first magnetic anchor 2900 in the prostate gland PG. Similarly, another deployment device 2908 comprising a sharp distal tip 2920 is used to implant second magnetic anchor 2902 in the prostate gland PG. First magnetic anchor 2900 and second magnetic anchor 2902 are implanted on opposite sides of the urethra such that like poles of first magnetic anchor 2900 and second magnetic anchor 2902 face each other. This causes magnetic repulsion between first magnetic anchor 2900 and second magnetic anchor 2902. This causes the urethral lumen to widen potentially reducing the severity of BPH symptoms. In one embodiment, deployment device 2904 can be used to deploy multiple magnetic anchors.

Figure 30:
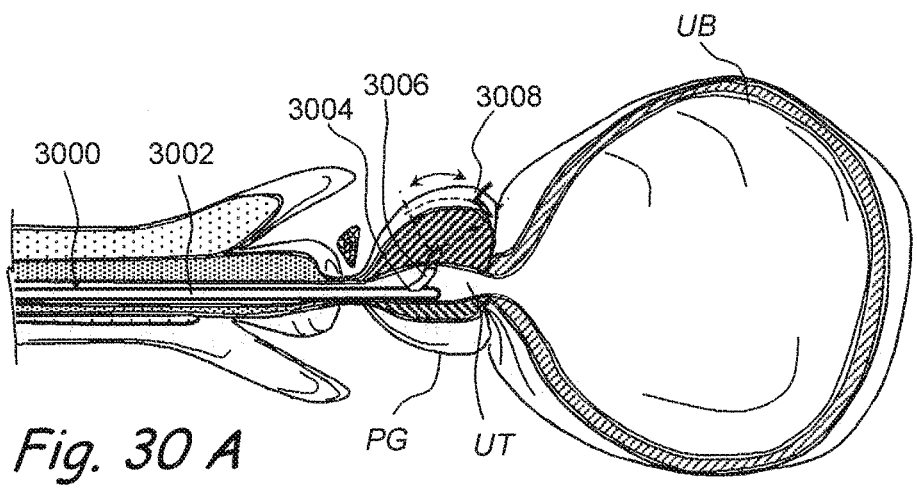
Figure 30:
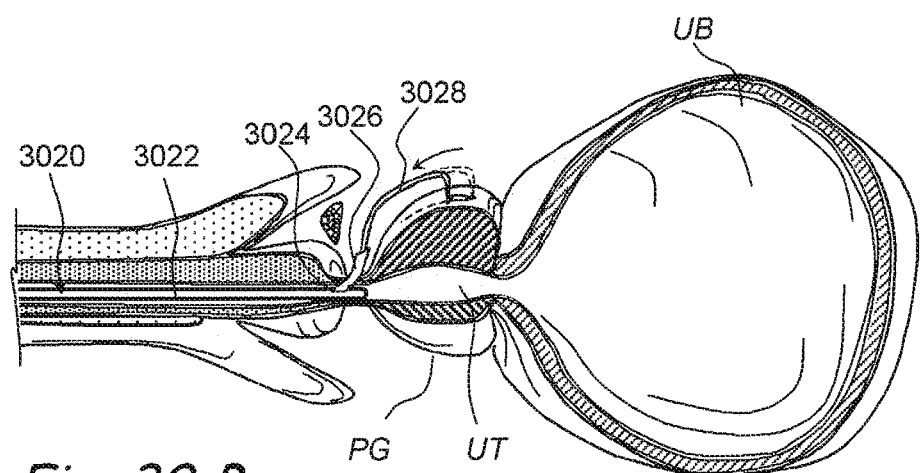
Figure 30:
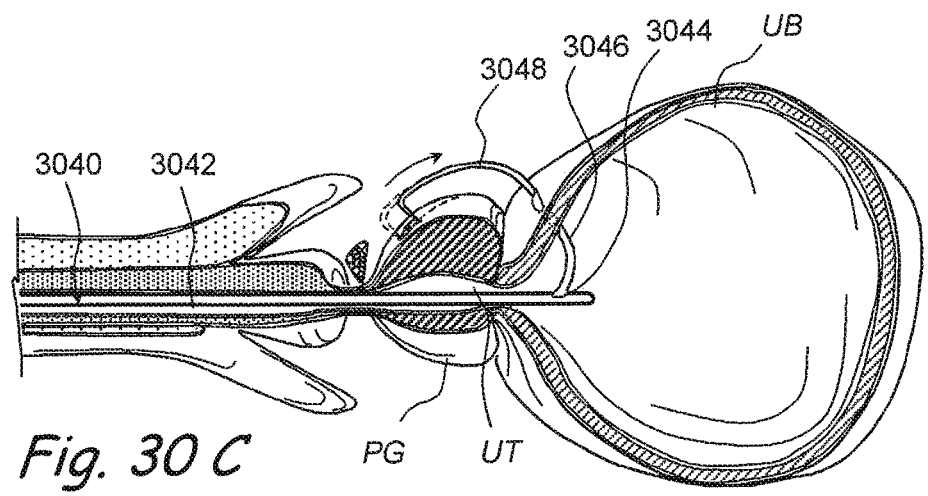
Figure 30:
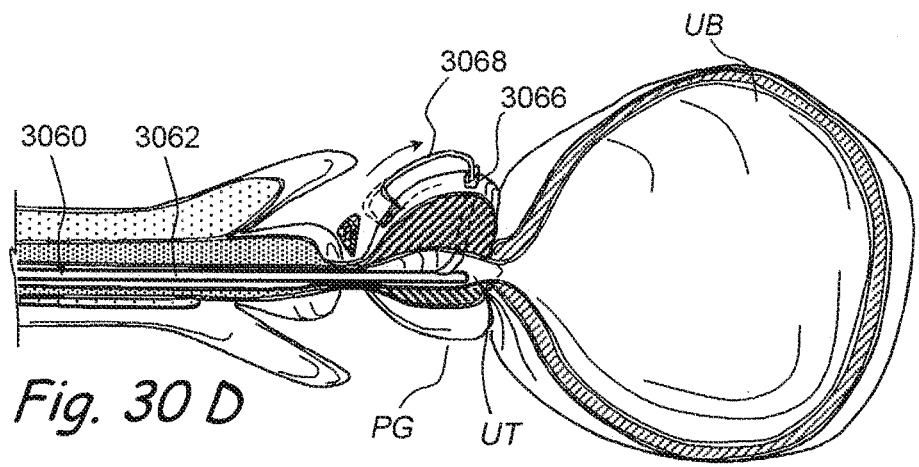

FIG. 30A shows a coronal section of a region of the male urinary system showing the general working environment of a method of treating prostate disorders by cutting prostrate tissue using a device inserted into the prostate gland PG from the urethra. Cutting device 3000 comprises an outer body 3002 comprising a side port 3004. Outer body 3002 can be made of suitable biocompatible materials including, but not limited to metals e.g. stainless steel, Nickel-Titanium alloys, titanium etc.; polymers e.g. etc. Cutting device 3000 further comprises an access device 3006 that can be deployed out of side port 3004. Access device 3006 can be retracted back into side port 3004. Typical examples of elements that can be used as access device 3006 are needles, trocars etc. Access device 3006 may be made from suitable biocompatible materials including, but not limited to metals e.g. stainless steel, Nickel-Titanium alloys, titanium etc.; polymers e.g. etc. Access device 3006 penetrates the walls of the urethra and enters the prostate gland PG by creating an access channel in the prostate gland PG. Cutting device 3000 further comprises a cutting element 3008 that is introduced into the prostate gland PG through the access channel in the prostate gland PG. In one embodiment, cutting element 3008 enters the prostate gland PG through access device 3006. Cutting element 3008 comprises one or more cutting modalities such as electrosurgical cutter, Laser cutter, mechanical cutter e.g. a knife edge etc. Cutting element 3008 may be moved through prostate tissue by several mechanisms including one or more deflecting or bending elements located on cutting element 3008; one or more articulating elements located on cutting element 3008; motion of cutting device 3000 along the urethra etc. Cutting element 3008 is used to cut one or more regions of the prostate gland PG including peripheral zone, transition zone, central zone or prostatic capsule. After the desired region or regions of the prostate gland PG are cut, cutting element 3008 and access device 3006 are withdrawn into cutting device 3000. Thereafter, cutting device 3000 is withdrawn from the urethra. In one device embodiment, cutting device 3000 comprises an endoscope or means for inserting an endoscope.

FIG. 30B shows a coronal section of a region of the male urinary system showing the general working environment of a method of treating prostate disorders by cutting prostrate tissue using a device that accesses outer surface of the prostate gland PG by passing through the walls of the urethra distal to the prostate gland PG. Cutting device 3020 comprises an outer body 3022 comprising a side port 3024. Outer body 3022 can be made of suitable biocompatible materials including, but not limited to metals e.g. stainless steel, Nickel-Titanium alloys, titanium etc.; polymers e.g. etc. Cutting device 3020 is advanced into the urethra such that side port 3024 is located distal to the prostate gland PG. Cutting device 3020 further comprises an access device 3026 that can be deployed out of side port 3024. Access device 3026 can be retracted back into side port 3024. Typical examples of elements that can be used as access device 3026 are needles, trocars etc. Access device 3026 may be made from suitable biocompatible materials including, but not limited to metals e.g. stainless steel, Nickel-Titanium alloys, titanium etc.; polymers e.g. etc. Access device 3026 is deployed from side port 3024 in a desired orientation such that access device 3026 penetrates the wall of the urethra. Access device 3026 is advanced further such that distal end of access device 3026 is located near the prostate gland PG. Thereafter, a cutting element 3028 is introduced through access device 3026 to the outer surface of the prostate gland PG. Cutting element 3028 comprises one or more cutting modalities such as electrosurgical cutter, Laser cutter, mechanical cutter e.g. a knife edge etc. Cutting element 3028 is used to cut one or more regions of the prostate gland PG including prostatic capsule, peripheral zone, transition zone or central zone. Cutting element 3028 may be moved relative to prostate tissue by several mechanisms including one or more deflecting or bending elements located on cutting element 3028; motion of cutting element 3028 along access device 3026 etc. In one method embodiment, cutting element 3028 cuts prostatic capsule while being withdrawn into access device 3026. After the desired region or regions of the prostate gland PG are cut, cutting element 3028 and access device 3026 are withdrawn into cutting device 3020. Thereafter, cutting device 3020 is withdrawn from the urethra. In one device embodiment, cutting device 3020 further comprises an endoscope or means for inserting an endoscope.

FIG. 30C shows a coronal section of a region of the male urinary system showing the general working environment of a method of treating prostate disorders by cutting prostrate tissue using a device that accesses outer surface of the prostate gland PG by passing through the wall of the urinary bladder. Cutting device 3040 comprises an outer body 3042 comprising a side port 3044. Outer body 3042 can be made of suitable biocompatible materials including, but not limited to metals e.g. stainless steel, Nickel-Titanium alloys, titanium etc.; polymers e.g. etc. Cutting device 3040 is advanced into the urethra such that side port 3044 is located inside the urinary bladder. Cutting device 3040 further comprises an access device 3046 that can be deployed out of side port 3044. Access device 3046 can be retracted back into side port 3044. Typical examples of elements that can be used as access device 3046 are needles, trocars etc. Access device 3046 may be made from suitable biocompatible materials including, but not limited to metals e.g. stainless steel, Nickel-Titanium alloys, titanium etc.; polymers e.g. etc. Access device 3046 is deployed from side port 3044 in a desired orientation such that access device 3046 penetrates the wall of the urinary bladder. Access device 3046 is advanced further such that distal end of access device 3046 is located near the prostate gland PG. Thereafter, a cutting element 3048 is introduced through access device 3046 to the outer surface of the prostate gland PG. Cutting element 3048 comprises one or more cutting modalities such as electrosurgical cutter, Laser cutter, mechanical cutter e.g. a knife edge etc. Cutting element 3048 is used to cut one or more regions of the prostate gland PG including prostatic capsule, peripheral zone, transition zone or central zone. Cutting element 3048 may be moved relative to prostate tissue by several mechanisms including one or more deflecting or bending elements located on cutting element 3048; motion of cutting element 3048 along access device 3046 etc. In one method embodiment, cutting element 3048 cuts prostatic capsule while being withdrawn into access device 3046. After the desired region or regions of the prostate gland PG are cut, cutting element 3048 and access device 3046 are withdrawn into cutting device 3040. Thereafter, cutting device 3040 is withdrawn from the urethra. In one device embodiment, cutting device 3040 further comprises an endoscope or means for inserting an endoscope.

FIG. 30D shows a coronal section of a region of the male urinary system showing the general working environment of a method of treating prostate disorders by cutting prostrate tissue using a device that accesses outer surface of the prostate gland PG by passing through the walls of the urethra enclosed to the prostate gland PG. Cutting device 3060 comprises an outer body 3062 comprising a side port 3064. Outer body 3062 can be made of suitable biocompatible materials including, but not limited to metals e.g. stainless steel, Nickel-Titanium alloys, titanium etc.; polymers e.g. etc. Cutting device 3060 is advanced into the urethra such that side port 3064 is located in the region of the urethra enclosed by the prostate gland PG. Cutting device 3060 further comprises an access device 3066 that can be deployed out of side port 3064. Access device 3066 can be retracted back into side port 3064. Typical examples of elements that can be used as access device 3066 are needles, trocars etc. Access device 3066 may be made from suitable biocompatible materials including, but not limited to metals e.g. stainless steel, Nickel-Titanium alloys, titanium etc.; polymers e.g. etc. Access device 3066 is deployed from side port 3064 in a desired orientation such that access device 3066 penetrates the prostate. Thereafter, a cutting element 3068 is introduced through access device 3066 such that the distal region of cutting element can access the outer surface of the prostate gland PG. Cutting element 3068 comprises one or more cutting modalities such as electrosurgical cutter, Laser cutter, mechanical cutter e.g. a knife edge etc. Cutting element 3068 is used to cut one or more regions of the prostate gland PG including prostatic capsule, peripheral zone, transition zone or central zone. Cutting element 3068 may be moved relative to prostate tissue by several mechanisms including one or more deflecting or bending elements located on cutting element 3068; motion of cutting element 3068 along access device 3066 etc. In one method embodiment, cutting element 3068 cuts prostatic capsule while being withdrawn into access device 3066. After the desired region or regions of the prostate gland PG are cut, cutting element 3068 and access device 3066 are withdrawn into cutting device 3060. Thereafter, cutting device 3060 is withdrawn from the urethra. In one device embodiment, cutting device 3060 further comprises an endoscope or means for inserting an endoscope.

Figure 31:
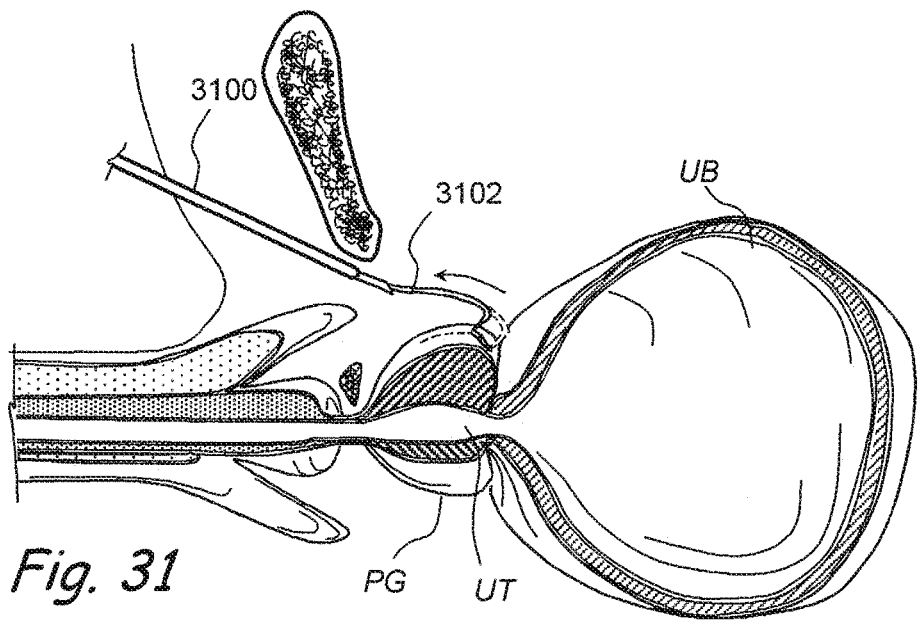

FIG. 31 shows a coronal section of a region of the male urinary system showing the general working environment of a method of treating prostate disorders by cutting prostrate tissue by a percutaneous device that accesses the prostate gland PG through an incision in the abdomen. In this method, a cannula 3100 is introduced percutaneously into the lower abdomen. Cannula 3100 can be made of suitable biocompatible materials including, but not limited to metals e.g. stainless steel, Nickel-Titanium alloys, titanium etc.; polymers etc. Cannula 3100 is advanced into the abdomen such that it passes below the pubic bone. The distal end of cannula 3100 is positioned near the prostate gland PG. Thereafter, a cutting device 3102 is advanced through distal end of cannula 3100 to the outer surface of the prostate gland PG. Cutting device 3102 can be retracted back into cannula 3100. Cutting device 3102 comprises one or more cutting modalities such as electrosurgical cutter, Laser cutter, mechanical cutter e.g. a knife edge etc. Cutting device 3102 is used to cut one or more regions of the prostate gland PG including prostatic capsule, peripheral zone, transition zone or central zone. Cutting device 3102 may be moved relative to prostate tissue by several mechanisms including one or more deflecting or bending elements located on cutting device 3102; motion of cutting device 3102 along cannula 3100 etc. In one method embodiment, cutting device 3102 cuts prostatic capsule while being withdrawn into cannula 3100. After the desired region or regions of the prostate gland PG are cut, cutting device 3102 is withdrawn into cannula 3100. Thereafter, cannula 3100 is withdrawn from the urethra. In one device embodiment, cannula 3100 further comprises an endoscope or means for inserting an endoscope.

Figure 32:
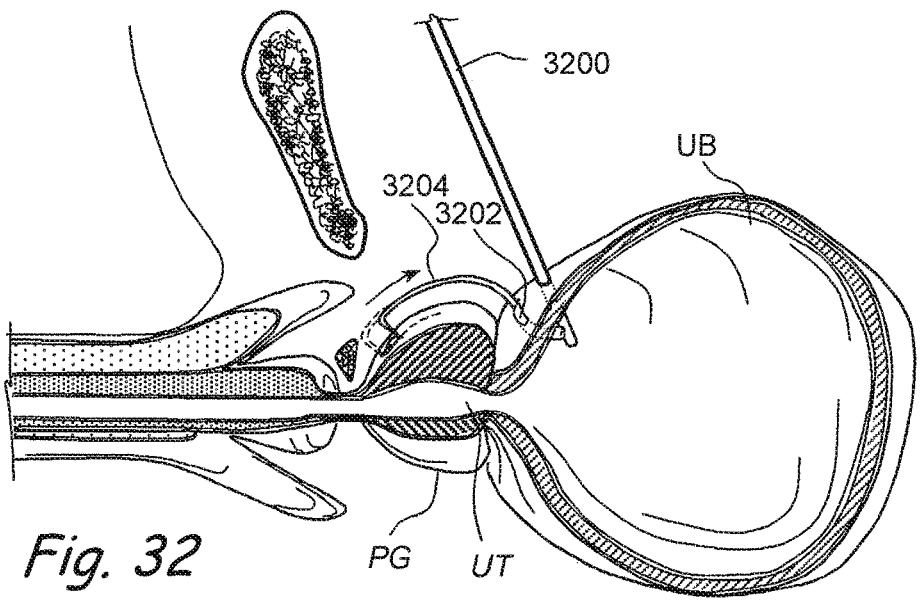

FIG. 32 shows a coronal section of a region of the male urinary system showing the general working environment of a method of treating prostate disorders by cutting prostrate tissue by a percutaneous device that penetrates the urinary bladder and accesses the outer surface of the prostate gland PG through an incision in the urinary bladder. In this method, a cannula 3200 is introduced percutaneously into the lower abdomen. Cannula 3200 can be made of suitable biocompatible materials including, but not limited to metals e.g. stainless steel, Nickel-Titanium alloys, titanium etc.; polymers etc. Cannula 3200 is advanced into the abdomen such that it passes above the pubic bone. The distal end of cannula 3200 enters the urinary bladder. Thereafter, an access device 3202 is advanced through cannula 3200 such that access device 3202 penetrates the urinary bladder wall as shown in FIG. 4. Thereafter, a cutting device 3204 is advanced through distal end of access device 3202 to the outer surface of the prostate gland PG. Cutting device 3202 can be retracted back into access device 3202. Cutting device 3202 comprises one or more cutting modalities such as electrosurgical cutter, Laser cutter, mechanical cutter e.g. a knife edge etc. Cutting device 3202 is used to cut one or more regions of the prostate gland PG including prostatic capsule, peripheral zone, transition zone or central zone. Cutting device 3202 may be moved relative to prostate tissue by several mechanisms including one or more deflecting or bending elements located on cutting device 3202 or access device 3202; motion of cutting device 3202 along access device 3202 etc. In one method embodiment, cutting device 3202 cuts prostatic capsule while being withdrawn into access device 3202. After the desired region or regions of the prostate gland PG are cut, cutting device 3202 is withdrawn into access device 3202. Access device 3202 is then withdrawn into cannula 3200. Thereafter, cannula 3200 is withdrawn from the urinary bladder. In one device embodiment, cannula 3200 further comprises an endoscope or means for inserting an endoscope.

Figure 33:
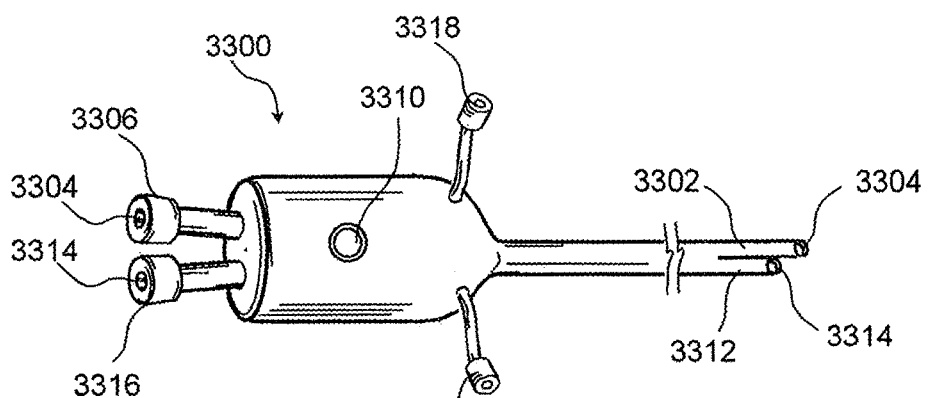
Figure 33:
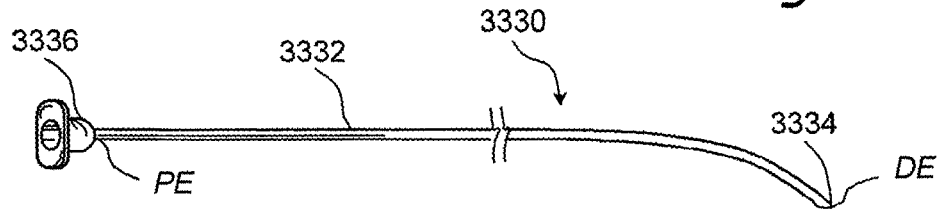
Figure 33:
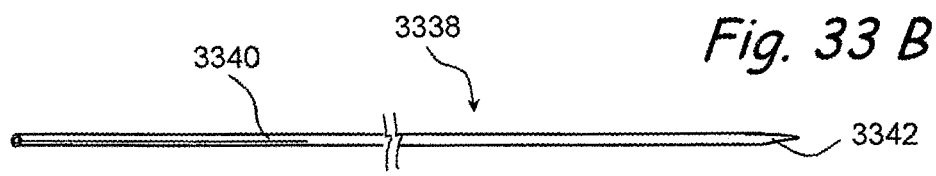
Figure 33:
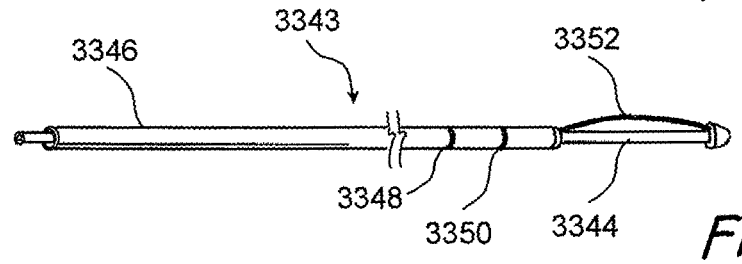
Figure 33:
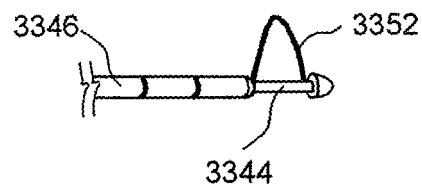
Figure 33:
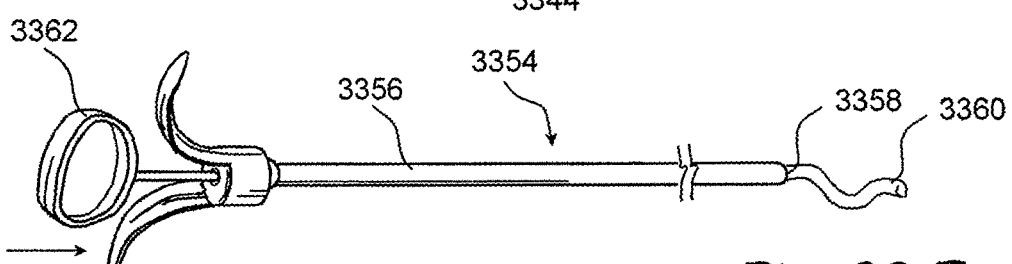
Figure 33:
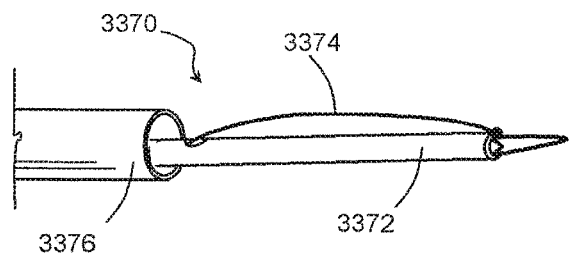
Figure 33:
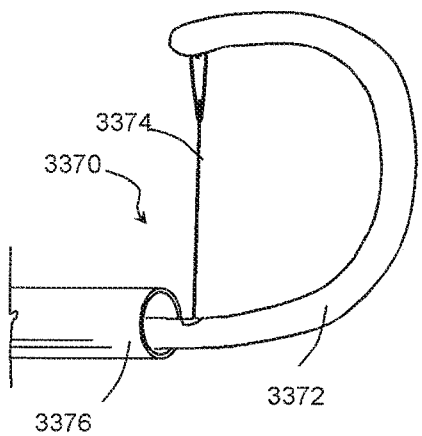
Figure 33:
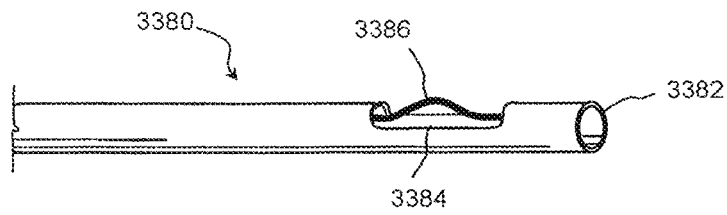
Figure 33:
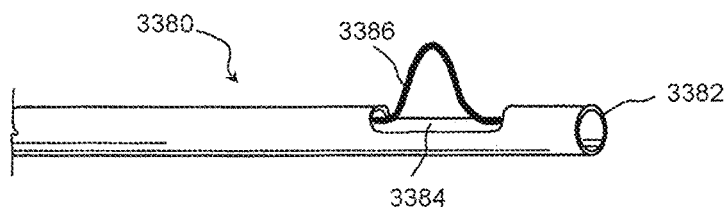
Figure 33:
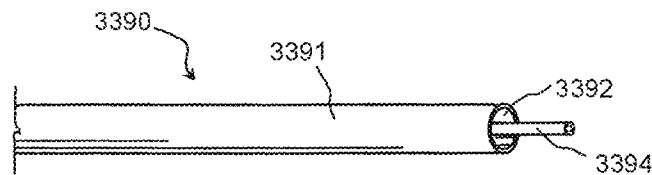
Figure 33:
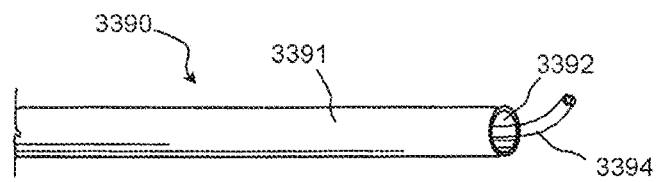
Figure 33:
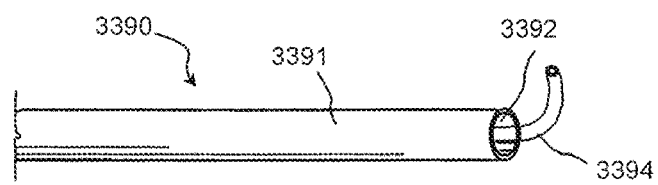
Figure 33:
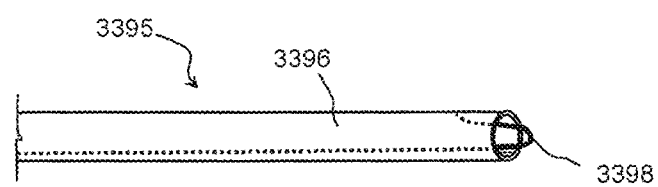
Figure 33:
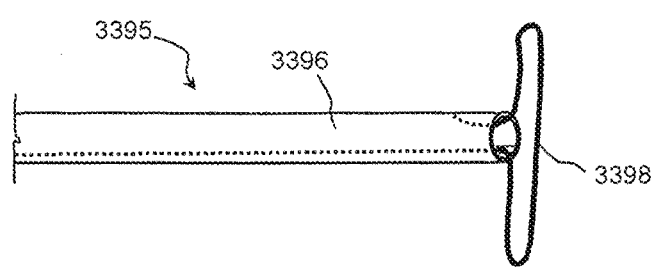

FIG. 33 series shows a perspective view of a prostate treatment kit to cut prostate tissue. FIG. 33A shows a perspective view of an introducer device. Introducer device 3300 comprises a first tubular element 3302 enclosing a working device lumen 3304. First tubular element 3302 can be made of suitable biocompatible materials such as Pebax, Polyimide, Braided Polyimide, Polyurethane, Nylon, PVC, Hytrel, HDPE, PEEK, metals like stainless steel and fluoropolymers like PTFE, PFA, FEP and EPTFE etc. The proximal end of working device lumen 3304 comprises a first stasis valve 3306. The distal end of working device lumen 3304 comprises a deflection mechanism. The deflection mechanism is used to bend the distal region of working device lumen 3304. One example of deflection mechanism is a pull wire and a deflection dial 3310 to adjust the magnitude and/or the direction of deflection caused by the pull wire. Similarly, other deflection mechanisms can be used in the introducer device instead of a pull wire. Introducer device 3300 further comprises a second tubular element 3312 which encloses a cystoscope lumen 3314. A cystoscope can be introduced through cystoscope lumen 3314 into the urethra. Typical examples of cystoscopes that can be used with introducer device are those manufactured by Olympus, Pentax, Storz, Wolf, Circon-ACMI, etc. These may have pre-set angles (i.e. 0, 30, 70, 120 degrees) or may be flexible scopes where in the tip may be deflectable. The proximal end of cystoscope lumen 3314 comprises a second stasis valve 3316. The cystoscope is inserted through the proximal end of cystoscope lumen 3314 and emerges out into the urethra from the distal end of cystoscope lumen 3314. The cystoscope can then be used to visualize the anatomy and various instruments during a procedure. Working device lumen 3314 may comprise one or more side ports e.g. a first side port 3318 for the introduction or removal of one or more fluids. Cystoscope lumen 3314 may comprise one or more side ports e.g. a second side port 3320 for the introduction or removal of one or more fluids.

FIG. 33B shows a perspective view of an injecting needle. Injecting needle 3330 is used for injecting one or more diagnostic or therapeutic agents in the anatomy. In one method embodiment, injecting needle 3330 is used to inject local anesthetic in the urethra and/or prostate gland PG. Specific examples of target areas for injecting local anesthetics are the neurovascular bundles, the genitourinary diaphragm, the region between the rectal wall and prostate, etc. Examples of local anesthetics that can be injected by injecting needle 3330 are anesthetic solutions e.g. 1% lidocaine solution; anesthetic gels e.g. lidocaine gels; combination of anesthetic agents e.g. combination of lidocaine and bupivacaine; etc. Injecting needle 3330 comprises a hollow shaft 3332 made of suitable biocompatible materials including, but not limited to stainless steel 304, stainless steel 306, Nickel-Titanium alloys, titanium etc. The length of hollow shaft 3332 can range from to centimeters. The distal end of hollow shaft 3332 comprises a sharp tip 3334. The proximal end of hollow shaft 3332 has a needle hub 3336 made of suitable biocompatible materials including, but not limited to metals e.g. like stainless steel 304, stainless steel 306, Nickel-Titanium alloys, titanium etc.; polymers e.g. polypropylene etc. In one embodiment, needle hub 3336 comprises a luer lock.

FIG. 33C shows a perspective view of a guiding device. Guiding device 3338 comprises an elongate body 3340 comprising a sharp distal tip 3342. In one embodiment, guiding device 3338 is a guidewire. Distal end of elongate body 3340 may comprise an anchoring element to reversibly anchor guiding device 3338 into tissue. Examples of suitable anchoring elements are barbs, multipronged arrowheads, balloons, other mechanically actuable members (e.g. bendable struts), screw tips, shape memory elements, or other suitable anchor designs disclosed elsewhere in this patent application.

FIG. 33D shows a perspective view of a RF cutting device. Cutting device 3343 comprises an inner sheath 3344 and an outer sheath 3346. Inner sheath 3344 comprises a lumen of a suitable dimension such that cutting device 3343 can be advanced over guiding device 538. Outer sheath 3346 can slide on inner sheath 3344. Outer sheath 3346 also comprises two marker bands: a proximal marker band 3348 and a distal marker band 3350. The marker bands can be seen by a cystoscope. In one embodiment, proximal marker band 3348 and distal marker band 3350 are radiopaque. The position of proximal marker band and distal marker band 3350 is such that after cutting device 3343 is placed in an optimum location in the anatomy, proximal marker band 3348 is located in the urethra where it can be seen by a cystoscope and distal marker band 3350 is located in the prostrate gland PG or in the wall of the urethra where it cannot be seen by the cystoscope. Cutting device 3343 further comprises a cutting wire 3352 that is capable of delivering electrical energy to the surrounding tissue. The distal end of cutting wire 3352 is fixed to the distal region of outer sheath 3344. The proximal end of cutting wire 3352 is connected to a distal region of outer sheath 3346 and is further connected to a source of electrical energy. In FIG. 33D, cutting wire 3352 is in an undeployed configuration. FIG. 33D' shows the distal region of cutting device 3343 when cutting wire 3352 is in a deployed configuration. To deploy cutting wire 3352, inner sheath 3344 is moved in the proximal direction with respect to outer sheath 546. This causes cutting wire 3352 to bend axially outward thus deploying cutting wire 3352 in the surrounding anatomy.

FIG. 33E shows a perspective view of an embodiment of a plugging device to plug an opening created during a procedure. Plugging device 3354 comprises a tubular shaft 3356 comprising a distal opening 3358. Distal opening 3358 is used to deliver one or more plugging materials 3360 in the adjacent anatomy. Plugging material 3360 may comprise a porous or non-porous matrix formed of a biodegradable or non-biodegradable material such as a flexible or rigid polymer foam, cotton wadding, gauze, hydrogels, etc. Examples of biodegradable polymers that may be foamed or otherwise rendered porous include but are not restricted to polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In one embodiment, plugging material 3360 comprises biocompatible sealants including but not limited to fibrin sealants, combination of natural proteins (e.g. collagen, albumin etc.) with aldehyde cross-linking agents (e.g. glutaraldehyde, formaldehyde) or other polymeric, biological or non-polymeric materials capable of being implanted with the body, etc. Plugging device 3354 may be introduced in the anatomy by various approaches including the approaches disclosed elsewhere in this patent application. Plugging device 3354 may be introduced in the anatomy through a cannula, over a guiding device such as a guidewire etc. In the embodiment shown in FIG. 33E, plugging material 3360 is preloaded in plugging device 3354. Plugging material 3360 is introduced through distal opening 3358 by pushing plunger 3362 in the distal direction. In another embodiment, plugging device 3354 comprises a lumen that extends from the proximal end to distal opening 3358. Plugging material 3360 may be injected through the proximal end of the lumen such that it emerges out through distal opening 3358.

FIGS. 33F through 33N show various alternate embodiments of the electrosurgical cutting device in FIG. 33D. FIGS. 33F and 33G show perspective views of the distal region of a first alternate embodiment of an electrosurgical cutting device in the undeployed and deployed states respectively. FIG. 33F show an electrosurgical cutting device 570 comprising an elongate shaft 3372. Shaft 3372 is made of an electrically insulating material. Electrosurgical cutting device 3370 further comprises an electrosurgical cutting wire 3374. Electrosurgical cutting wire 3374 can be made of a variety of materials including, but not limited to tungsten, stainless steel, etc. Distal end of cutting wire 3374 is attached to distal region of shaft 3372. The proximal region of cutting wire 3374 can be pulled in the proximal direction by an operator. In one embodiment, electrosurgical cutting device 3370 is introduced in the target anatomy through a sheath 3376. In FIG. 33F, electrosurgical cutting device 3370 is deployed by pulling cutting wire 3374 in the proximal direction. This causes distal region of shaft 3372 to bend. Thereafter, electrical energy is delivered through cutting wire 3374 to cut tissue. This may be accompanied by motion of electrosurgical cutting device 3370 along the proximal or distal direction.

FIGS. 33H and 33I show perspective views of the distal region of a second alternate embodiment of an electrosurgical cutting device in the undeployed and deployed states respectively. Electrosurgical cutting device 3380 comprises an elongate sheath 3382 comprising a lumen. Distal region of sheath 3382 has a window 3384. Electrosurgical cutting device 3380 further comprises an electrosurgical cutting wire 3386 located in the lumen. Distal end of cutting wire 3386 is fixed to the distal end of sheath 3384. Proximal end of cutting wire 3386 can be pushed in the distal direction by a user. In FIG. 33I, cutting wire 3386 is deployed by pushing cutting wire 3386 in the distal direction. This causes a region of cutting wire 3386 to bend in the radially outward direction and thus emerge out of window 3384. Thereafter, electrical energy is delivered through cutting wire 3386 to cut tissue. This may be accompanied by motion of electrosurgical cutting device 3380 along the proximal or distal direction.

FIGS. 33J through 33L show perspective views of the distal region of a second alternate embodiment of an electrosurgical cutting device showing the steps of deploying the electrosurgical cutting device. Electrosurgical cutting device 3390 comprises an elongate sheath 3391 comprising a lumen 3392. In FIG. 33J, an electrosurgical cutting wire 3394 is introduced through lumen 3392 such that it emerges out through the distal opening of lumen 3392. In FIG. 33K, cutting wire 3394 is further advanced in the distal direction. Distal end of cutting wire 3394 has a curved region so that cutting wire 3394 starts to bend as it emerges out of lumen 3392. In FIG. 33L, cutting wire 3394 is further advanced in the distal direction to fully deploy cutting wire 3394. Thereafter, electrical energy is delivered through cutting wire 3394 to cut tissue. This may be accompanied by motion of electrosurgical cutting device 3390 along the proximal or distal direction.

FIGS. 33M through 33N show perspective views of the distal region of a third alternate embodiment of an electrosurgical cutting device showing the steps of deploying the electrosurgical cutting device. Electrosurgical cutting device 3395 comprises an elongate sheath 3396 comprising a lumen. Cutting device 3395 further comprises a cutting wire 3398 located in the lumen of elongate sheath 3396. The proximal end of cutting wire 3398 is connected to a source of electrical energy. Distal end of cutting wire 3398 is connected to the inner surface of the distal region of elongate sheath 3396. Cutting wire 3398 may be made from suitable elastic, super-elastic or shape memory materials including but not limited to Nitinol, titanium, stainless steel etc. In FIG. 33N, Electrosurgical cutting device 3395 is deployed by pushing the proximal region of cutting wire 3398 in the distal direction. This causes a distal region of cutting wire 3398 to emerge from the distal end of elongate sheath 3396 as a loop. Thereafter, electrical energy is delivered through cutting wire 3398 to cut tissue. This may be accompanied by motion of electrosurgical cutting device 3395 along the proximal or distal direction. Electrosurgical cutting device 3395 can be used to cut multiple planes of tissue by withdrawing cutting wire 3398 in elongate sheath 3396, rotating elongate sheath 3396 to a new orientation, redeploying cutting wire 3398 and delivering electrical energy through cutting wire 3398. The devices 33H through 33N may be introduced by one or more access devices such as guidewires, sheaths etc.

FIG. 34 shows a perspective view of the distal region of a balloon catheter comprising a balloon with cutting blades. Balloon catheter 3400 can be introduced into a lumen or in the tissue of an organ to be treated using one or more of the introducing methods disclosed elsewhere in this patent application. Balloon catheter 3400 comprises a shaft 3402. Shaft 3402 may comprise a lumen to allow balloon catheter 3400 to be introduced over a guidewire. In one embodiment, shaft 3402 is torquable. Shaft 3402 comprises a balloon 3404 located on the distal end of shaft 3402. Balloon 3404 can be fabricated from materials including, but not limited to polyethylene terephthalate, Nylon, polyurethane, polyvinyl chloride, crosslinked polyethylene, polyolefins, HPTFE, HPE, HDPE, LDPE, EPTFE, block copolymers, latex and silicone. Balloon 3404 further comprises one or more cutter blades 3406. Balloon catheter 3400 is advanced with balloon 3404 deflated, into a natural or surgically created passageway and positioned adjacent to tissue or matter that is to be cut, dilated, or expanded. Thereafter, balloon 3404 is inflated to cause cutter blades 3406 to make one or more cuts in the adjacent tissue or matter. Thereafter balloon 3404 is deflated and balloon catheter 3400 is removed. Cutter blades 3406 may be energized with mono or bi-polar RF energy. Balloon catheter 3400 may comprise one or more navigation markers including, but not limited to radio-opaque markers, ultrasound markers, light source that can be detected visually etc.

FIG. 35 shows a perspective view of the distal region of a balloon catheter comprising a balloon with cutting wires. Balloon catheter 3500 can be introduced into a lumen or in the tissue of an organ to be treated using one or more of the introducing methods disclosed elsewhere in this patent application. Balloon catheter 3500 comprises a shaft 3502. Shaft 3502 may comprise a lumen to allow balloon catheter 3500 to be introduced over a guidewire. In one embodiment, shaft 3502 is torquable. Shaft 3502 comprises a balloon 3504 located on the distal end of shaft 3502. Balloon 3504 can be fabricated from materials including, but not limited to polyethylene terephthalate, Nylon, polyurethane, polyvinyl chloride, crosslinked polyethylene, polyolefins, HPTFE, HPE, HDPE, LDPE, EPTFE, block copolymers, latex and silicone. Balloon 3504 further comprises one or more radiofrequency wires 3506. Balloon catheter 3500 is advanced with balloon 3504 deflated, into a natural or surgically created passageway and positioned adjacent to tissue or matter that is to be cut, dilated, or expanded. Thereafter, balloon 3504 is inflated and an electrical current is delivered through radiofrequency wires 3506 to make one or more cuts in the adjacent tissue or matter. Thereafter the electrical current is stopped, balloon 3504 is deflated and balloon catheter 3500 is removed. Radiofrequency wires 3504 may be energized with mono or bi-polar RF energy. Balloon catheter 3500 may comprise one or more navigation markers including, but not limited to radio-opaque markers, ultrasound markers, light source that can be detected visually etc.

FIGS. 36A and 36B series show perspective views of an undeployed state and a deployed state respectively of a tissue displacement device. FIG. 36A shows a tissue anchoring device 3600 in the undeployed state. Anchoring device 3600 comprises an elongate body having a proximal end 3602 and a distal end 3604. Anchoring device 3600 may be made of a variety of elastic or super-elastic materials including, but not limited to Nitinol, stainless steel, titanium etc. Anchoring device 3600 is substantially straight in the undeployed state and has a tendency to become substantially curved in the deployed state. Anchoring device 3600 is maintained in the undeployed state by a variety of means including, but not limited to enclosing anchoring device 3600 in a cannula or sheath, etc. FIG. 36B shows tissue anchoring device 3600 in the deployed state. Anchoring device 3600 comprises a curved region. When anchoring device 3600 changes from an undeployed state to a deployed state, the anatomical tissue adjacent to the central region of anchoring device 3600 is displaced along the direction of motion of the central region. Anchoring device 3600 can be deployed by a variety of methods including, but not limited to removing anchoring device 3600 from a sheath or cannula, etc. In one embodiment, anchoring device 3600 is made from a shape memory material such as Nitinol. In this embodiment, anchoring device 3600 is maintained in the undeployed state by maintaining anchor device 3600 in a temperature lower than the transition temperature of the super-elastic material. Anchoring device 3600 is converted to the deployed state by implanting anchoring device 3600 in a patient such that the device is warmed to the body temperature which is above the transition temperature of the super-elastic material.

FIGS. 36C and 36D show a coronal view and a lateral view respectively of a pair of deployed tissue displacement devices of FIGS. 36A and 36B implanted in the prostate gland PG. In FIG. 36C, two anchoring devices are implanted in the prostate gland PG near the prostatic urethra in a patient with BPH. A first anchoring device 3600 is introduced on a first side of the urethra and is deployed there as shown. Similarly, a second anchoring device 3606 comprising a proximal end 3608 and a distal end 3610 is introduced on the other side of the urethra and is deployed there as shown. First anchoring device 3600 and second anchoring device 3606 change into the deployed curved configuration. This causes prostate gland PG tissue near the central regions of first anchoring device 3600 and second anchoring device 3606 to be displaced radially away from the urethra. This displacement of prostate gland PG tissue can be used to eliminate or reduce the compression of the urethra by an enlarged prostate gland PG. FIG. 36D shows a lateral view of the urethra enclosed by the prostate gland PG showing deployed first anchoring device 3600 and second anchoring device 3606.

The various cuts or punctures made by one ore more cutting devices disclosed in this patent application may be plugged or lined by a plugging or space filling substance. FIGS. 36E through 36H show an axial section through a prostate gland showing the various steps of a method of cutting or puncturing the prostate gland and lining or plugging the cut or puncture. FIG. 36E shows a section of the prostate gland showing the urethra, the lateral lobes and the middle lobe surrounded by the prostatic pseudocapsule. In FIG. 36F, one or more cuts are made in a region of the prostatic pseudocapsule. In addition, one or more cuts may be made in a region of between two lobes of the prostate gland. In FIG. 36G, a plugging material 3619 is introduced in the one or more regions of the prostate gland that are cut or punctured. Plugging material 3619 may be delivered through one or more delivery devices including, but not limited to the device disclosed in FIG. 33E. Plugging material 3619 may comprises a material such as plugging material 3360.

The various cuts or punctures made by one ore more cutting devices disclosed in this patent application may be spread open by a clipping device. For example, FIG. 36H shows an axial section through a prostate gland showing a clip for spreading open a cut or punctured region of the prostate gland. Spreading device 3620 comprises a body having a central region and two distal arms. Spreading device 3620 may be made of a variety of elastic or super-elastic materials including, but not limited to Nitinol, stainless steel, titanium etc. Spreading device 3620 has a reduced profile in the undeployed state by maintaining distal arms close to each other. Spreading device 5000 is maintained in the undeployed state by a variety of means including, but not limited to enclosing spreading device 3620 in a cannula or sheath, etc. When spreading device 3620 changes from an undeployed state to a deployed state, the distance between the two distal arms increases. This causes any anatomical tissue between two distal arms to spread along the straight line between two distal arms Spreading device 3620 can be deployed by a variety of methods including, but not limited to removing spreading device 3620 from a sheath or cannula, etc. In one embodiment, spreading device 3620 is made from a shape memory material such as Nitinol. In this embodiment, spreading device 3620 is maintained in the undeployed state by maintaining anchor device 3620 in a temperature lower than the transition temperature of the super-elastic material. Spreading device 3620 is converted to the deployed state by implanting spreading device 3620 in a patient such that the device is warmed to the body temperature which is above the transition temperature of the super-elastic material. Stretching of prostate gland tissue can be used to eliminate or reduce the compression of the urethra by an enlarged prostate gland or to prevent cut edges of a cut from rejoining.

More than one spreading device 3620 may be used to treat the effects of an enlarged prostate or to eliminate or reduce the compression of the urethra by an enlarged prostate gland or to prevent cut edges of a cut from rejoining.

FIGS. 37A through 37K show an embodiment of a method of treating prostate gland disorders by cutting a region of the prostate gland using the devices described in FIG. 33A through 33E. In FIG. 37A, introducer device 3300 is introduced in the urethra. It is advanced through the urethra such that the distal tip of introducer device 3300 is located in the prostatic urethra. Thereafter, injecting needle 3330 is introduced through introducer device 3300. The distal tip of injecting needle 3330 is advanced such that injecting needle 3330 penetrates the prostate gland. Injecting needle 3330 is then used to inject a substance such as an anesthetic in the prostate gland. Thereafter, in FIG. 37B, injecting needle 3330 is withdrawn from the anatomy. The distal region of introducer device 3300 is positioned near a region of the prostate gland to be punctured. Thereafter, in FIG. 37C, first tubular element 3302 is bent or deflected with a bending or deflecting mechanism such as the bending mechanism in FIGS. 37C'' and 37C''' to align the distal region of first tubular element 3302 along a desired trajectory of puncturing the prostate gland.

FIG. 37C' shows the proximal region of introducer device 3300. A cystoscope 3700 is introduced through second stasis valve 3316 such that the distal end of cystoscope 3700 emerges through the distal end of introducer device 3300. Cystoscope 3700 is then used to visualize the anatomy to facilitate the method of treating prostate gland disorders.

FIG. 37C'' shows a perspective view of the distal region of an embodiment of introducer device 3300 comprising a bending or deflecting mechanism. In this embodiment, first tubular element 3302 comprises a spiral cut distal end and a pull wire. In FIG. 37C''', the pull wire is pulled by deflection dial 3310. This deflects the distal tip of first tubular element 3302 as shown.

After the step in FIG. 37C, guiding device 3338 is introduced through first tubular element 3302. Guiding device 3338 is advanced through first tubular element 3302 such that the distal tip of guiding device 3338 penetrates into the prostate gland. In one method embodiment, guiding device 3338 is further advanced such that the distal tip of guiding device 3338 penetrates through the prostate gland and enters the urinary bladder. In one embodiment, distal region of guiding device 3338 comprises an anchoring element 3702. Anchoring element 3702 is deployed as shown in FIG. 37E. Thereafter, guiding device 3338 is pulled in the proximal direction till anchoring element 3702 is snug against the wall of the urinary bladder. Cystoscope 3700 can be used to visualize the steps of penetrating the prostate gland by guiding device 3338 and deploying anchoring element 3702. If guiding device 3338 is not positioned in a satisfactory position, guiding device 3338 is pulled back in introducer device 3300. The deflection angle of distal end of first tubular lumen 3302 is changed and guiding device 3338 is re-advanced into the urinary bladder. FIG. 37E' shows a perspective view of an embodiment of anchoring element 3702. Anchoring element comprises a hollow sheath 3704. Distal region of hollow sheath 3704 is attached to distal region of guiding device 3338. A number of windows are cut in the distal region of hollow sheath 3704 such that several thin, splayable strips are formed between adjacent windows. Pushing hollow sheath 3704 in the distal direction causes splayable strips to splay in the radially outward direction to form an anchoring element. In FIG. 37F, cutting device 3343 is advanced over guiding device 3338 into the prostate gland. In FIG. 37G, cutting device 3343 is positioned in the prostate gland such that proximal marker band 3348 can be seen by cystoscope 3700 but distal marker band 3350 cannot be seen.

Thereafter, in FIG. 37H, relative motion between outer sheath 3343 and inner sheath 3344 causes cutting wire 3352 to deploy outward in the axial direction. In one embodiment, this step is carried out by moving outer sheath 3343 in the distal direction while the inner sheath 3344 is stationary. In another embodiment, this step is carried out by moving inner sheath 3344 in the proximal direction while outer sheath 3343 is kept stationary. Also during step, electrical energy is delivered through cutting wire 3352 to cut tissue. In FIG. 37I, cutting device 3343 is pulled in the proximal direction such that the deployed cutting wire 3352 slices through tissue. Thereafter, cutting wire 3352 is withdrawn again in cutting device 3343. Cutting device 3343 is then removed from the anatomy.

In FIG. 37J, plugging device 3354 is introduced over guiding device 3338 through the puncture or opening in the prostate gland. Thereafter, in FIG. 37K, anchoring element 3702 is undeployed and guiding device 3343 is withdrawn from the anatomy. Thereafter, plugging device 3354 is used to deliver one or more plugging materials in the adjacent anatomy. The plugging materials can be used to plug or line some or all of the cuts or punctures created during the method.

FIGS. 38A to 38D show various components of a kit for treating prostate gland disorders by compressing a region of the prostate gland. FIG. 38A shows the perspective view of an introducer device 3800. Introducer device 3800 comprises an outer body 3801 constructed from suitable biocompatible materials including, but not limited to metals like stainless steel, Nichol plated brass, polymers like Pebax, Polyimide, Braided Polyimide, Polyurethane, Nylon, PVC, Hytrel, HDPE, PEEK and fluoropolymers like PTFE, PFA, FEP, EPTFE etc. Body 3801 comprises a working device lumen 3802. Distal end of working device lumen 3802 emerges out of the distal end of body 3801. Proximal end of working device lumen 3802 incorporates lock thread 3803 such that introducer device may join with other devices. Device lumen 3802 may comprise one or more side ports e.g. a first side port 3804 and a second side port 3805 for the introduction or removal of one or more fluids.

FIG. 38B shows a perspective view of a bridge device 3806 constructed from suitable biocompatible materials including, but not limited to metals like stainless steel, Nichol plated brass, polymers like Pebax, Polyimide, Braided Polyimide, Polyurethane, Nylon, PVC, Hytrel, HDPE, PEEK and fluoropolymers like PTFE, PFA, FEP, EPTFE etc. Bridge device may insert into introducer lumen 3802 and lock into place by threadably mating thread lock 3807 with thread 3803. Bridge may incorporate port 3808 for cystoscope with locking means 3809 that joins to cystoscope when inserted. Bridge device may incorporate one or more working lumens. Working lumen 3810 emerges out of the distal end of body 3806. In one embodiment, distal end of working device lumen 3810 has a bent or curved region. Proximal end of lumen 3810 emerges from port 3811 that may incorporate fluid stasis valve 3812 and a luer lock. Working lumen 3813 emerges distally in straight fashion through blunt obturator 3814 at distal end of body 3806 and emerges proximally through second port that may incorporate fluid stasis valve and luer lock.

FIG. 38C shows a perspective view of a distal anchor deployment device 3815 constructed from suitable biocompatible materials including, but not limited to polymers like Polycarbonate, PVC, Pebax, Polyimide, Braided Pebax, Polyurethane, Nylon, PVC, Hytrel, HDPE, PEEK, metals like stainless steel, Nichol plated brass, and fluoropolymers like PTFE, PFA, FEP, EPTFE etc. Deployment device 3815 comprises handle 3816, which incorporates movable thumb ring pusher 3817 and anchor deployment latch 3818; and distal shaft 3819 which has trocar point 3820 at distal end. Mounted on distal shaft 3819 is distal anchor 3821 that incorporates tether 3822. Tether 3822 can be made of suitable elastic or non-elastic materials including, but not limited to metals e.g. stainless steel 304, stainless steel 306, Nickel-Titanium alloys, suture materials, titanium etc. or polymers such as silicone, nylon, polyamide, polyglycolic acid, polypropylene, Pebax, PTFE, ePTFE, silk, gut, or any other monofilament or any braided or mono-filament material. Proximal end of tether 3822 may incorporate hypotube 3823. Distal anchor 3821 is constructed from suitable biocompatible materials including, but not limited to metals e.g. stainless steel 304, stainless steel 306, Nickel-Titanium alloys, titanium etc. or polymers e.g. Pebax, Braided Pebax, Polyimide, Braided Polyimide, Polyurethane, Nylon, PVC, Hytrel, HDPE, PEEK, PTFE, PFA, FEP, EPTFE etc. Deployment device 3815 is inserted into bridge working lumen 3810. Advancement of thumb ring 3817 extends distal shaft 3819 through distal end of working lumen 3810, preferably into tissue for deployment of distal anchor 3821. Depth of distal shaft deployment can be monitored on cystoscope by visualizing depth markers 3824. Once distal shaft 3819 is deployed to desired depth, anchor deployment latch 3818 is rotated to release distal anchor 3821. Refraction of thumb ring 3817 then refracts distal shaft 3819 while leaving distal anchor 3821 in tissue. Bridge 3806 is then disconnected from introducer device 3800 and removed.

FIG. 38D shows the proximal anchor delivery tool 3825 constructed from suitable biocompatible materials including, but not limited to polymers like Polycarbonate, PVC, Pebax, Polyimide, Braided Pebax, Polyurethane, Nylon, PVC, Hytrel, HDPE, PEEK, metals like stainless steel, Nichol plated brass, and fluoropolymers like PTFE, PFA, FEP, EPTFE etc. Proximal anchor delivery tool 3825 comprises handle 3826, which incorporates anchor deployment switch 3827 in slot 3828 and tether cut switch 3829; and distal shaft 3830 which houses hypotube 3831. Lumen of hypotube 3831 emerges proximally at port 3832 which may incorporate a luer lock. Mounted on the hypotube and distal shaft is the proximal anchor 3833 with cinching hub 3834. Proximal anchor 3833 is constructed from suitable biocompatible materials including, but not limited to metals e.g. stainless steel 304, stainless steel 306, Nickel-Titanium alloys, titanium etc. or polymers e.g. Pebax, Braided Pebax, Polyimide, Braided Polyimide, Polyurethane, Nylon, PVC, Hytrel, HDPE, PEEK, PTFE, PFA, FEP, EPTFE or biodegradable polymers e.g. polyglycolic acid, poly(dioxanone), poly(trimethylene carbonate) copolymers, and poly (.epsilon.-caprolactone) homopolymers and copolymers etc. FIG. 38E shows a close-up perspective view of proximal anchor 3833 mounted on hypotube 3831 and distal shaft 3830 of proximal anchor delivery tool 3825. Hypotube 3831 biases open the cinching lock 3835 of cinching hub 3834. In order to deploy proximal anchor 3833, hypotube 3823 is loaded into hypotube 3831 until it exits proximal port 3832. Hypotube 3823 is then stabilized while proximal anchor delivery tool 3825 is advanced into introducer device lumen 3802 and advanced to tissue target. Because hypotube 3831 biases open cinching lock 3835, the proximal anchor delivery tool travels freely along tether 3822. Once proximal anchor 3833 is adequately apposed to urethral wall of prostate, anchor deployment switch 3827 is retracted. During retraction of switch 3827, hypotube 3831 is retracted proximal to cinching hub 3834 and tether 3822 is tightened. When switch 3827 is fully retracted or desired tension is accomplished, tether 3822 is cut within cinching hub 3834 by advancing cutting switch 3829.

Any of the anchoring devices disclosed herein may comprise one or more sharp distal tips, barbs, hooks etc. to attach to tissue.

Various types of endoscopes can be used in conjunction with the devices disclosed herein such as flexible scopes that are thin, flexible, fibre-optic endoscopes and rigid scopes that are thin, solid, straight endoscopes. The scopes may have one or more side channels for insertion of various instruments. Further they may be used with in conjunction with standard and modified sheaths intended for endoscopic and transurethral use.

Local or general anesthesia may be used while performing the procedures disclosed herein. Examples of local anesthetics that can be used are anesthetic gels e.g. lidocaine gels in the urethra; combination of anesthetic agents e.g. combination of lidocaine and bupivacaine in the urethra; spinal anesthetics e.g. ropivacaine, fentanyl etc.; injectable anesthetics e.g. 1% lidocaine solution injected into the neurovascular bundles, the genitourinary diaphragm, and between the rectal wall and prostate; etc.

An optional trans-rectal ultrasound exam may be performed before and/or during the procedures disclosed herein. In this exam, a device called ultrasound transducer is inserted into the rectum. The ultrasound transducer is then used to image the prostate gland PG using ultrasound waves. The devices may be modified so that they are more visible under ultrasound such as etched surfaces. Other imaging devices may also be optionally used such as MRI, RF, electromagnetic and fluoroscopic or X-ray guidance. The anchoring devices or delivery devices may contain sensors or transmitters so that certain elements may be tracked and located within the body. The tethering devices may be used as cables to temporarily transmit energy to the distal and/or proximal anchors during deployment.

The invention has been described hereabove with reference to certain examples or embodiments of the invention but various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example un-novel, obvious to a person of ordinary skill in the relevant art or unsuitable for its intended use. All reasonable additions, deletions, modifications and alterations are to be considered equivalents of the described examples and embodiments and are to be included within the scope of the following claims.

We claim:

1. A method of treating an anatomical region within a urinary tract of a patient, comprising:
   providing a device comprising two or more spreading arms connected by a heel region, wherein the device has an undeployed configuration in which the spreading arms are held close to each other and a deployed configuration in which the spreading arms expand away from each other;
   inserting the device into the urinary tract of the patient in the undeployed configuration;
   positioning the device such that the spreading arms are near an anterior commissure of the patient;
   deploying the device from the undeployed configuration to the deployed configuration to spread apart two lateral lobes of a prostate gland of the patient wherein a portion of the heel region penetrates into tissue when the device is in the deployed configuration.

2. The method of claim 1, wherein a portion of the spreading arms penetrates into tissue.

3. The method of claim 1, wherein a portion of at least one of the spreading arms comprises a flattened region.

4. The method of claim 1, wherein at least one of the spreading arms is curved.

5. The method of claim 1, wherein at least one of the spreading arms is straight.

6. The method of claim 1, wherein the spreading arms are configured to have a biasing force that tends to spread the spreading arms away from each other in the deployed configuration.

7. The method of claim 6, wherein the force causes cutting of the anterior commissure.

8. The method of claim 1, further comprising making an opening in the anterior commissure prior to deploying the device.

9. The method of claim 1, wherein a portion of the device penetrates into tissue of a prostate gland of the patient.

10. The method of claim 1, wherein a portion of the device penetrates into tissue of a urethra of the patient.

11. The method of claim 1, wherein the spreading arms are joined by the heel and the heel is positioned near an anterior commissure of the patient.

12. The method of claim 1, wherein the spreading arms are joined by the heel and the heel is positioned within an anterior commissure of the patient.

13. A method of treating a prostate gland within a urinary tract of a patient, comprising:
providing a device comprising two or more spreading arms connected by a heel region, wherein the device has an undeployed configuration in which the spreading arms are held close to each other and a deployed configuration in which the spreading arms expand away from each other via a biasing force that tends to spread the spreading arms away from each other;
inserting the device via a delivery tool into the urinary tract of the patient in the undeployed configuration;
positioning the device such that the spreading arms are near an anterior commissure with the prostate gland of the patient;
deploying the device from the undeployed configuration to the deployed configuration wherein the biasing force causes separation of the two lateral lobes near the anterior commissure when the device is placed within a prostate gland of a patient.

14. The method of claim 13, wherein the spreading arms are joined by the heel and the heel is positioned near an anterior commissure of the patient.

15. The method of claim 13, wherein the spreading arms are joined by the heel and the heel is positioned within an anterior commissure of the patient.

16. The method of claim 13, wherein a portion of at least one of the spreading arms comprises a flattened region.

17. The method of claim 13, wherein at least one of the spreading arms is curved.

18. The method of claim 13, wherein at least one of the spreading arms is straight.

19. The method of claim 13, wherein the device is delivered by pushing the device out of a portion of a lumen of the delivery tool.

20. The method of claim 19, wherein the spreading arms of the device spread expand away from each other as the spreading arms emerge from the portion of the lumen.

21. The method of claim 13, wherein the device is detachably attached to the delivery tool by a detaching mechanism.

* * * * *

UNITED STATES PATENT AND TRADEMARK OFFICE
CERTIFICATE OF CORRECTION

PATENT NO. : 10,575,844 B2
APPLICATION NO. : 16/433018
DATED : March 3, 2020
INVENTOR(S) : Lamson et al.

Page 1 of 1

It is certified that error appears in the above-identified patent and that said Letters Patent is hereby corrected as shown below:

On the Title Page

Item (72), the fourth inventor's name is misspelled. Please replace "Jacqueline Nemey Welch" with -- Jacqueline Nerney Welch --.

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*